US006376210B1

(12) United States Patent
Yuan

(10) Patent No.: US 6,376,210 B1
(45) Date of Patent: Apr. 23, 2002

(54) METHODS AND COMPOSITIONS FOR ASSAYING ANALYTES

(75) Inventor: Chong-Sheng Yuan, San Diego, CA (US)

(73) Assignee: General Atomics, San Diego, CA (US)

( * ) Notice: Subject to any disclaimer, the term of this patent is extended or adjusted under 35 U.S.C. 154(b) by 0 days.

(21) Appl. No.: 09/347,878

(22) Filed: Jul. 6, 1999

(51) Int. Cl.[7] ............................ C12Q 1/34; C12N 9/14; C12N 1/20; C12N 15/00; C07H 21/04

(52) U.S. Cl. ...................... 435/18; 435/195; 435/252.3; 435/320.1; 435/455; 435/536; 435/23.2

(58) Field of Search ....................... 435/18, 195, 252.3, 435/320.1, 455; 536/23.2; 436/69.2

(56) References Cited

U.S. PATENT DOCUMENTS

| | | | | |
|---|---|---|---|---|
| 3,464,890 | A | 9/1969 | Weichselbaum | 195/66 |
| 3,647,070 | A | 3/1972 | Adler | 210/83 |
| 3,780,935 | A | 12/1973 | Lukacs et al. | 233/1 A |
| 3,852,194 | A | 12/1974 | Zine, Jr. | 210/83 |
| 4,140,631 | A | 2/1979 | Okuda et al. | 210/83 |
| 4,161,425 | A | 7/1979 | Perry | 435/11 |
| 4,164,448 | A | 8/1979 | Röeschlau et al. | 435/11 |
| 4,188,188 | A | 2/1980 | Willner et al. | 23/230 |
| 4,211,531 | A | 7/1980 | Das | 23/230 |
| 4,276,280 | A | 6/1981 | Akerkar et al. | 424/1 |
| 4,336,185 | A | 6/1982 | Niswender | 260/112 |
| 4,337,339 | A | 6/1982 | Farina et al. | 544/257 |
| 4,477,575 | A | 10/1984 | Vogel et al. | 436/170 |
| 4,795,699 | A | 1/1989 | Tabor et al. | 435/5 |
| 4,803,153 | A | 2/1989 | Shibata et al. | 435/2 |
| 5,034,332 | A | 7/1991 | Rapacz et al. | 436/71 |
| 5,047,327 | A | 9/1991 | Caris et al. | 435/11 |
| 5,162,516 | A | 11/1992 | Ingram et al. | 536/27 |
| 5,215,899 | A | 6/1993 | Dattagupta | 435/6 |
| 5,217,873 | A | 6/1993 | Caris et al. | 435/11 |
| 5,342,767 | A | 8/1994 | Wong et al. | 435/122 |
| 5,344,777 | A | 9/1994 | Tamaki et al. | 435/252.3 |
| 5,364,533 | A | 11/1994 | Ogura et al. | 210/645 |
| 5,374,560 | A | 12/1994 | Allen et al. | 436/129 |
| 5,385,833 | A | 1/1995 | Bradshaw et al. | 435/156 |
| 5,523,225 | A | 6/1996 | Kraus | |
| 5,541,098 | A | 7/1996 | Caput et al. | 435/191 |
| 5,593,894 | A | 1/1997 | Purdie | 436/71 |
| 5,624,836 | A | 4/1997 | Lange, III et al. | 435/325 |
| 5,631,127 | A | 5/1997 | Sundrehagen | 435/4 |
| 5,665,560 | A | 9/1997 | Fujishiro et al. | 435/11 |
| 5,679,548 | A | 10/1997 | Barbas et al. | 435/69.6 |
| 5,728,562 | A | 3/1998 | Shigyo et al. | 435/191 |
| 5,800,979 | A | 9/1998 | Kolhouse et al. | 435/4 |
| 5,854,023 | A | 12/1998 | Hillman et al. | 435/69.1 |
| 5,855,881 | A | 1/1999 | Loike et al. | 424/94.2 |
| 5,879,921 | A | 3/1999 | Cherry et al. | 435/190 |
| 5,885,767 | A | 3/1999 | Rozzell, Jr. | 435/4 |
| 5,891,704 | A | 4/1999 | Yuying | 435/232 |
| 5,908,924 | A | 6/1999 | Burdette et al. | 536/23.2 |

FOREIGN PATENT DOCUMENTS

| | | |
|---|---|---|
| DE | 197 57571 | 6/1999 |
| WO | WO 88/08137 | 10/1988 |
| WO | WO 93/15220 | 8/1993 |
| WO | WO 98/20156 | 5/1998 |

OTHER PUBLICATIONS

Adlt–Riche et al. (1994) FASEB Journal vol., No. 7, pp. A1412, AMABMB, Washington, May 21–25, 1994.*

Yuan et al. J. Biol. Chem. 271 (45): 28009–28016 (1996).*

"IUPAC–IUB Commission on Biochemical Nomenclature Symbols for Amino–Acid Derivatives and Peptides Recommendations", *Biochem. 11*(9):1726 (1972).

Amaratunga, et al., A synthetic module for the metH gene permits facile mutagenesis of the cobalamin–binding region of *escherichia coli* methionine synthase: initial characterization of seven mutant proteins, *Biochemistry*, 35(7):2453–63 (1996).

Araki, et al., Determination of free and total homocysteine in human plasma by high–performance liquid chromatography with fluorescence detection, *J. Chromatog.*, 422:43–52 (1987).

Ault–Richié et al., A single mutation at lysine 426 of human placental s–adenosylhomocysteine by hydrolase inactivates the enzyme, *J. Biol. Chem. 269*:31472–31478 (1994).

Bahnson et al., A link between protein structure and enzyme catalyzed hydrogen tunneling, *Proc. Natl. Acad. Sci.*, 94(24):12797–802 (1997).

Ballal, R.J., et al., Homocysteine: Update on a new risk factor, *Cleveland Clinic Journal of Medicine*, 64(10):543–549 (1997).

(List continued on next page.)

*Primary Examiner*—Ponnathapu Achutamurthy
*Assistant Examiner*—Tekchand Saidha
(74) *Attorney, Agent, or Firm*—Morrison & Foerster LLP

(57) ABSTRACT

Compositions and methods for assaying analytes, preferably, small molecule analytes. Assay methods that employ, in place of antibodies or molecules that bind to target analytes or substrates, modified enzymes, called substrate trapping enzymes. These modified enzymes retain binding affinity or have enhanced binding affinity for a target substrate or analyte, but have attenuated catalytic activity with respect to that substrate or analyte. The modified enzymes are also provided. In particular, a mutant S-adenosylhomocysteine (SAH) hydrolases, substantially retaining binding affinity or having enhanced binding affinity for Hcy or SAH but having attenuated catalytic activity, are provided. Also provided are methods, combinations, kits and articles of manufacture for assaying analytes, preferably small molecule analytes such as inorganic ions, amino acids (e.g., homocysteine), peptides, nucleosides, nucleotides, oligonucleotides, vitamins, monosaccharides (e.g., glucose), oligosaccharides, lipids (e.g., cholesterol), organic acids (e.g., folate species, bile acids and uric acids).

16 Claims, 4 Drawing Sheets

OTHER PUBLICATIONS

Basran et al., Effect of single–residue substitutions on negative cooperativity in ligand binding to dihydrofolate reductase, *Protein Eng.*, 10(7):815–26 (1997).
Benoist, C., et al., In vivo sequence requirements of the SV40 early promoter region, *Nature 290*:304–310 (1981).
Boers, G.H.J., The case for mild hyperhomocysteinaemia as a risk factor, *J. Inher. Metab. Dis.*, 20:301–306 (1997).
Bognar et al., Primary structure of the *Escherichia coli* folC gene and its folypolyglutamate synthetase–dihydrofolate synthetase product and regulation of expression by an upstream gene, *J. Biol. Chem.*, 262(25):12337–43 (1987).
Boushev, et al., A quantitative assessment of plasma homocysteine as a risk factor for vascular disease, *JAMA*, 274:1049–1057 (1995).
Brinster et al., Regulation of metallothionein–thymidine kinase fusion plasmids injected into mouse eggs, *Nature 296*:39–42 (1982).
Carreras et al., Thymidylate synthase with a C–terminal delection catalyzes partial reactions but is unable to catalyze thymidylate formation, *Biochemistry*, 31(26):6038–44 (1992).
Chu et al., Mutational analysis of the putative copper–binding site of rat urate oxidase[a], *Ann. N.Y. Acad. Sci.*, 804:781–6 (1996).
Clarke et al., Hyperhomecysteinemia: An independent risk factor for vascular disease, New Eng. J. Med. 324:1149–1155 (1991).
Colby et al., Active site modifications in a double mutant of liver alcohol dehydrogenase: Structural studies of two enzyme—ligand complexes, *Biochemistry*, 37(26):9295–304 (1998).
Corbin et al., Cloning of an insecticidal cholesterol oxidase gene and its expression in bacteria and in plant protoplasts, *Appl. Environ. Microbiol.*, 60(12):4239–44 (1994).
Cornell and Riscoe, Cloning and expression of *Escherichia coli* 5'–methylthioadenosine/S–adenosylhomocystein nucleosidase: Identification of te pfs gene product, *Biochim. Biophys. Acta*, 1396(1):8–14 (1998).
Costi, et al., Asparagine 229 mutants of thymidylate synthase catalyze the methylation of 3–methyl–2'–deoxyuridine 5'–monophosphate, *Biochemistry 35*:3944–3949 (1996).
Coulter–Karis and Hershfield, Sequence of full length cDNA for human S–adenosylhomocysteine hydrolase, *Ann. Hum. Genet.*, 53(2):169–175 (1989).
DeBoer, et al., The tac promoter: A functional hybrid derived from the trp and lac promoters, *Proc. Natl. Acad. Sci. U.S.A. 80*:21–25 (1983).
Diaz–Arrastia, et al., Hyperhomocysteinemia: A new risk factor for alzheimer disease?, *Arch. Neurol.*, 55:1407–1408 (1998).
Dicker et al., Identification and characterization of a mutation in the dihydrofolate reductase gene from the methotrexate–resistant chinese hamster ovary cell line Pro$^{-}$3 Mtx$^{RIII}$, *J. Biol. Chem.*, 265(14):8317–21 (1990).
DiPersio et al., Identification of the active site serine in pancreatic cholesterol esterase by chemical modification and site–specific mutagenesis, *J. Biol. Chem.*, 265(28):16801–6 (1990).
Dixon et al., The structure of the C–terminal domain of methione synthase: presenting S–adenosylmethionine for reductive methylation of $B_{12}$, *Structure*, 4(11):1263–75 (1996).
Ducloux, et al., Prevalence, determinants, and clinical significance of hyperhomecyst(e)inaemia in renal–transplant recipients, *Nephrol. Dial. Transplantl*, 13:2890–2893 (1998).
Ehrig et al., General base catalysis in a glutamine for histidine mutant at position 51 of human liver alcohol dehydrogenase, *Biochemistry*, 30(4):1062–8 (1991).
Finer–Moore et al., Contributions of orientation and hydrogen bionding to catalysis in Asn229 mutants of thymidylate synthase, *J. Mol. Biol.*, 276(1):113–29 (1998).
Finer–Moore et al., Partitioning roles of side chains in affinity, orientation, and catalysis with structures for mutant complexes: Asparagine–229 in thymidylate synthase, *Biochemistry*, 35(16):5125–36 (1996).
Foody, et al., Homocystein discovering a new predictor of coronary disease, *Clinician Reviews*, 8:203–210 (1998).
Frederick et al., Glucose oxidase from *aspergillus niger, J. Biol. Chem.*, 265(7):3793–802 (1990).
Garrow, Purification, kinetic properties, and cDNA cloning of mammalian betaine–homecystein, methyltransferase, *J. Biol. Chem.*, 271(37):22831–8 (1996).
Gilbert, W., et al., Useful proteins from recombinant bacteria, *Scientific American*, 242:74–94 (1980).
Goyette, et al., Gene structure of human and mouse methylenetetrahydrofolate reductase (MTHFR), *Mamm. Genome.*, 9(8):652–6 (1998).
Graves et al., Roles of $Cys^{148}$ and $Asp^{179}$ in catalysis by deoxycytidylate hydroxymethylase from bacteriophase T4 examined by site–directed mutagenesis, *Biochemistry 31*:15–21 (1992).
Grunstein, M. And Hogness, D., Colony hybridization: A method for the isolation of cloned DNAs that contain a specific gene, *Proc. Natl. Acad. Sci. U.S.A. 72*:3961 (1975).
Hori et al., Gene cloning and characterization of *pseudomonas putida* L–Methionine–α–deamino–λ–mercaptomethane–lyase[1], *Cancer Res.*, 56(9):2116–22 (1996).
Hornberger, et al., A cost–benefit analysis of a carbiovascular disease prevention trial, using folate supplementation as an example, *American J. of Public Health*, 88:61–67 (1998).
Hutchinson, et al., Mutagenesis at a specific position in a DNA sequence, *J. Biol. Chem 253*:6551 (1978).
Ikuta, et al., Molecular cloning of a full–length cDNA for human alcohol dehydrogenase, *Proc. Natl. Acad. Sci.*, 82(9):2703–7 (1985).
Ito, et al., Exchange reactions catalyzed by methioninase from *pseudomonas putida, J. Biochem.*, (Tokyo) 80(6):1327–34 (1976).
Jacobsen, et al., Acquired hyperhomocysteinemia in heart transplant recipients, *Clin. Chem.*, 44:2238–2239 (1998).
Kaneda, et al., Structural and functional analysis of the human thymidylate synthase gene, *J. Biol. Chem.*, 265(33):20277–84 (1990).
Kedishvili, et al., Expression and kinetic characterization of recombinant human stomach alcohol dehydrogenase, *J. Biol. Chem.*, 270(8):3625–30 (1995).
Kery, et al., Binding of pyridoxal 5'–phosphate to the heme protein human cystathionine β–synthase, *Biochemistry*, 38(9):2716–24 (1999).
Kim, et al., On the mechanism of pyridoxine responsive homocystinuria. II. Properties of normal and mutant cystathione β–synthase from cultured fibroblasts, *Proc. Nat. Acad. Sci.*, 71(2):4821–3825 (1974).
Koranyi, et al., Human islet glucokinase gene, *Diabetes*, 41(7):807–11 (1992).
Kozak, Structural features in eukaryotic mRNAs that modulate the initiation of translation, *J. Biol. Chem.*, 266:19867–19870 (1991).
Kunst et al., The complete genome sequence of the gram–positive bacterium *bacillus subtilis, Nature*, 390(6657):249–56 (1997).

Lai, et al., Editing of glutamate receptor B subunit ion channel RNAs by four alternatively spliced DRADA2 double–stranded RNA adenosine deaminase, *Mol. Cell. Biol.*, 17(5):2413–24 (1997).
Lal and Sachs, et al., Cloning and characterization of an anaerobically induced cDNA encoding glucose–6–phosphate isomerase from maize[1], *Plant Physiol.*, 108(3):1295–6 (1995).
Lee et al., Catalytic mechanism of xylose (glucose) isomerase from *clostridium thermosulfurogenes, J. Biol. Chem.*, 265(31):19082–90 (1990).
Mansoor, et al., Determination of the in vivo redox status of cystein, cysteinylglycine, homocystein, and glutathione in human plasma, *Anal. BioChem.*, 200:218–229 (1992).
Maxam and Gilbert, Sequencing end–labeled DNA with base–specific chemical cleavages[1], *Meth. Enzymol. 65*:499–560 (1980).
Millian and Garrow, Human betaine–homocystein methyltransferase is a zinc metalloenzyme[1], *Arch. Biochem. Biophys.*, 356(1):93–8 (1998).
Moghadasian, et al., Homocyst(e)ine and coronary artery disease, *Arch. Intern. Med.*, 157:2299–2307 (1997).
Mudd, SH., Homocystinuria, *Homocysteine: Selected aspects in Nyham W.L. ed. Hertable disorders of amino acid metabolism*. (ed) Perry, T. New York, John Wiley & Sons, pp. 419–451 (1974).
Refsum, et al., Homocystein and cardiovascular disease, *Annu. Rev. Medicine*, 49:31–62 (1998).
Refsum, et al., Radioenzyme determination of homocysteine in plasma and urine, *Clin. Chem.*, 31:624–628 (1985).
Saksela and Raivio, Cloning and expression in vitro of human xanthine dehydrogenase/oxidase, *Biochem. J.*, 315(1):235–9 (1996).
Sambrook, et al., 1989, Table of contents, *Molecular Cloning, A Laboratory Manual*, 2d Ed., Cold Spring Harbor Laboratory Press, Cold Spring Harbor, New York; Glover, D.M. (ed.), 1985.
Sanger, F., et al., DNA sequencing with chain–terminating inhibitors, *Proc. Natl. Acad. Sci. U.S.A.*, 74:5463 (1977).
Schiffer, et al., Crystal structure of human thymidylate synthase: A structural mechanism for guiding substrates into the active site, *Biochemistry*, 34(50):16279–87 (1995).
Scott et al., "The etiology of neural tube defects" in Graham, I., Refsum, H., Rosengerg, I.H., and Ureland P.M. ed. "Homocystein metabolism: from basic science to clinical medicine" Kluwer Academic Publishers, Boston, pp. 133–136 (1995).
Sharma et al., cDNA sequence of humn class III alcohol dehydrogenase, *Biochem. Biophys. Res. Commun.*, 164(2):631–7 (1989).
Shilo and Weinberg, DNA sequences homologous to vertebrate oncogenes are conserved in *Dsorphila melanogaster, Proc. Natl. Acad. Sci. USA 78*:6789–6792 (1981).
Smith and Johnson, Single–step purification of polypeptides expressed in *Escherichia coli* as fusions with glutathione S–transferase, *Gene 7*:31–40 (1988).
Stabler, et al., Elevation of total homocystein in the serum of patients with cobalamin or folate deficiency detected by capillary gas chromatography—mass spectrometry, *J. Clin. Invest.*, 81:466–474 (1988).
Steadman, et al., A structural role for glutamine 214 in human thymidylate synthase, *Biochemistry*, 37:7089–7095 (1998).
Stehouwer, et al., Plasma homocysteine concentration predicts mortality in non–insulin–dependent diabetic patients with and without albuminuria, *Kidney International*, 55308–314 (1999).
Stein, et al., Hyperhomocysteinemia and atheroslerotic vascular disease, *Arch. Intern. Med.*, 158:1301–1306 (1998).
Strop et al., Crystal structures of a marginally active thymidylate synthase mutant, Arg 126 → Glu, *Protein Sci.*, 6(12):2504–11 (1997).
Taylor et al., The rapid generation of oligonucleotide–directed mutations at high frequency using phosphorothioate–modified DNA, *Nucleic Acids Res.*, 13:8765–8785 (1985).
The, et al., Full length cDNA structure and deduced amino acid sequence of human 3⊕–hydroxy–5–ene steroid dehydrogenase, *Mol. Endocrinol.*, 3(8):1310–2 (1989).
Turner et al., Structure determination of selenomethionyl S–adenosylhomocystein hydrolase using data at a single wavelength, *Nature Structural Biology*, 5:369–376 (1998).
Ueland, et al., "Plasma homocysteine and cardiovascular disease" in Francis, R.B.Jr.eds. *Atherosclerotic Cardiovascular Disease, Hemostasis, and Endothelial Function*. New York, Marcel Dokker, pp. 182–236 (1992).
Ueland, et al., Plasma homocystein, a risk factor for vascular disease: Plasma levels in health, disease, and drug therapy, *J. Lab. Clin. Med.*, 114:473–501 (1989).
Ueland, et al., Total homocystein in plasma or serum: methods and clinical applications, *Clin. Chem.*, 39:1764–1779 (1993).
Villa–Kamaroff, et al., A bacterial clone synthesizing proinsulin, *Proc. Natl. Acad. Sci. U.S.A. 75*:3727–3731 (1978).
Wagner et al., Nucleotide sequence of the thymidine kinase gene of herpes simplex virus type 1, *Proc. Natl. Acad. Sci. U.S.A 78*:1441–1445 (1981).
Watson, et al., *Molecular Biology of the Gene*, 4th Edition, 1987, The Bejacmin/Cummings Pub. co., p. 224.
Williams, et al., A hydroxyl group at residue 216 is essential for catalysis by human thymidylate synthase, *Biochemistry*, 37(20):7096–102 (1998).
Wu, et al., Urate oxidase: Primary structure and evolutionary implications, *Proc. Natl. Acad. Sci.*, 86(23):9412–6 (1989).
Xu, et al., Genotyping of human alcohol dehydrogenase at the ADH2 and ADH3 Loci following DNA sequence amplification, *Genomics*, 2(3):209–14 (1988).
Yamamoto, et al., Identification of a functional promoter in the long terminal repeat of rous sarcoma virus, *Cell 22*:787–797 (1980).
Yuan et al., Chemical modification and site–directed mutagenesis of cysteine residues in human placental S–adenosylhomocystein hydrolase, *J. Biol. Chem.*, 268:17030–17037 (1993).
Yuan, et al., Mechanism of inactivation of S–adenosylhomocystein hydrolase by (Z)–4', 5'–didehydro–5'–deoxy–5'–fluoroadenosine, *J. Biol. Chem.*, 271:28008–28016 (1996).
Yue et al., Crystal structure determination of cholesterol oxidase from streptomyces and structural characterization of key active site mutants, *Biochemistry*, 38(14):4277–86 (1999).

* cited by examiner

SEQUENCE LISTING

```
<160> NUMBER OF SEQ ID NOS: 75

<210> SEQ ID NO 1
<211> LENGTH: 432
<212> TYPE: PRT
<213> ORGANISM: Homo sapiens
<220> FEATURE:
<223> OTHER INFORMATION: Human S-adenosylhomocysteine hydrolase protein
      sequence
<300> PUBLICATION INFORMATION:
<308> DATABASE ACCESSION NUMBER: M61831/GenBank

<400> SEQUENCE: 1

Met Ser Asp Lys Leu Pro Tyr Lys Val Ala Asp Ile Gly Leu Ala Ala
  1               5                  10                  15

Trp Gly Arg Lys Ala Leu Asp Ile Ala Glu Asn Glu Met Pro Gly Leu
             20                  25                  30

Met Arg Met Arg Glu Arg Tyr Ser Ala Ser Lys Pro Leu Lys Gly Ala
         35                  40                  45

Arg Ile Ala Gly Cys Leu His Met Thr Val Glu Thr Ala Val Leu Ile
     50                  55                  60

Glu Thr Leu Val Thr Leu Gly Ala Glu Val Gln Trp Ser Ser Cys Asn
 65                  70                  75                  80

Ile Phe Ser Thr Gln Asn His Ala Ala Ala Ala Ile Ala Lys Ala Gly
                 85                  90                  95

Ile Pro Val Tyr Ala Trp Lys Gly Glu Thr Asp Glu Glu Tyr Leu Trp
            100                 105                 110

Cys Ile Glu Gln Thr Leu Tyr Phe Lys Asp Gly Pro Leu Asn Met Ile
        115                 120                 125

Leu Asp Asp Gly Gly Asp Leu Thr Asn Leu Ile His Thr Lys Tyr Pro
    130                 135                 140

Gln Leu Leu Pro Gly Ile Arg Gly Ile Ser Glu Glu Thr Thr Thr Gly
145                 150                 155                 160

Val His Asn Leu Tyr Lys Met Met Ala Asn Gly Ile Leu Lys Val Pro
                165                 170                 175

Ala Ile Asn Val Asn Asp Ser Val Thr Lys Ser Lys Phe Asp Asn Leu
            180                 185                 190

Tyr Gly Cys Arg Glu Ser Leu Ile Asp Gly Ile Lys Arg Ala Thr Asp
```

-continued

```
        195                 200                 205

Val Met Ile Ala Gly Lys Val Ala Val Val Ala Gly Tyr Gly Asp Val
    210                 215                 220

Gly Lys Gly Cys Ala Gln Ala Leu Arg Gly Phe Gly Ala Arg Val Ile
225                 230                 235                 240

Ile Thr Glu Ile Asp Pro Ile Asn Ala Leu Gln Ala Ala Met Glu Gly
                245                 250                 255

Tyr Glu Val Thr Thr Met Asp Glu Ala Cys Gln Glu Gly Asn Ile Phe
            260                 265                 270

Val Thr Thr Thr Gly Cys Ile Asp Ile Ile Leu Gly Arg His Phe Glu
        275                 280                 285

Gln Met Lys Asp Asp Ala Ile Val Cys Asn Ile Gly His Phe Asp Val
    290                 295                 300

Glu Ile Asp Val Lys Trp Leu Asn Glu Asn Ala Val Glu Lys Val Asn
305                 310                 315                 320

Ile Lys Pro Gln Val Asp Arg Tyr Arg Leu Lys Asn Gly Arg Arg Ile
                325                 330                 335

Ile Leu Leu Ala Glu Gly Arg Leu Val Asn Leu Gly Cys Ala Met Gly
            340                 345                 350

His Pro Ser Phe Val Met Ser Asn Ser Phe Thr Asn Gln Val Met Ala
        355                 360                 365

Gln Ile Glu Leu Trp Thr His Pro Asp Lys Tyr Pro Val Gly Val His
    370                 375                 380

Phe Leu Pro Lys Lys Leu Asp Glu Ala Val Ala Glu Ala His Leu Gly
385                 390                 395                 400

Lys Leu Asn Val Lys Leu Thr Lys Leu Thr Glu Lys Gln Ala Gln Tyr
                405                 410                 415

Leu Gly Met Ser Cys Asp Gly Pro Phe Lys Pro Asp His Tyr Arg Tyr
            420                 425                 430
```

```
<210> SEQ ID NO 2
<211> LENGTH: 2211
<212> TYPE: DNA
<213> ORGANISM: Homo sapiens
<220> FEATURE:
<223> OTHER INFORMATION: Human S-adenosylhomocysteine hydrolase cDNA
<300> PUBLICATION INFORMATION:
<308> DATABASE ACCESSION NUMBER: M61831/GenBank

<400> SEQUENCE: 2

ctgaggccca gcccccttcg cccgtttcca tcacgagtgc cgccagcatg tctgacaaac     60

tgccctacaa agtcgccgac atcggcctgg ctgcctgggg acgcaaggcc ctggacattg    120

ctgagaacga gatgccgggc ctgatgcgta tgcgggagcg gtactcggcc tccaagccac    180

tgaagggcgc ccgcatcgct ggctgcctgc acatgaccgt ggagacggcc gtcctcattg    240

agaccctcgt caccctgggt gctgaggtgc agtggtccag ctgcaacatc ttctccaccc    300

agaaccatgc ggcggctgcc attgccaagg ctggcattcc ggtgtatgcc tggaagggcg    360

aaacggacga ggagtacctg tggtgcattg agcagaccct gtacttcaag gacgggcccc    420

tcaacatgat tctggacgac gggggcgacc tcaccaacct catccacacc aagtacccgc    480

agcttctgcc aggcatccga ggcatctctg aggagaccac gactggggtc cacaacctct    540

acaagatgat ggccaatggg atcctcaagg tgcctgccat caatgtcaat gactccgtca    600

ccaagagcaa gtttgacaac ctctatggct gccgggagtc cctcatagat ggcatcaagc    660

gggccacaga tgtgatgatt gccggcaagg tagcggtggt agcaggctat ggtgatgtgg    720
```

```
gcaagggctg tgcccaggcc ctgcggggtt tcggagcccg cgtcatcatc accgagattg    780

accccatcaa cgcactgcag gctgccatgg agggctatga ggtgaccacc atggatgagg    840

cctgtcagga gggcaacatc tttgtcacca ccacaggctg tattgacatc atccttggcc    900

ggtaggtgcc agatgggggg tcccggggag tgagggagga gggcagagtt gggacagctt    960

tctgtccctg acaatctccc acggtcttgg gctgcctgac aggcactttg agcagatgaa   1020

ggatgatgcc attgtgtgta acattggaca ctttgacgtg gagatcgatg tcaagtggct   1080

caacgagaac gccgtggaga aggtgaacat caagccgcag gtggaccggt atcggttgaa   1140

gaatgggcgc cgcatcatcc tgctggccga gggtcggctg gtcaacctgg gttgtgccat   1200

gggccacccc agcttcgtga tgagtaactc cttcaccaac caggtgatgg cgcagatcga   1260

gctgtggacc catccagaca agtaccccgt tggggttcat ttcctgccca agaagctgga   1320

tgaggcagtg gctgaagccc acctgggcaa gctgaatgtg aagttgacca agctaactga   1380

gaagcaagcc cagtacctgg gcatgtcctg tgatggcccc ttcaagccgg atcactaccg   1440

ctactgagag ccaggtctgc gtttcaccct ccagctgctg tccttgccca ggccccacct   1500

ctcctcccta agagctaatg gcaccaactt tgtgattggt ttgtcagtgt cccccatcga   1560

ctctctgggg ctgatcactt agtttttggc ctctgctgca gccgtcatac tgttccaaat   1620

gtggcagcgg gaacagagta ccctcttcaa gccccggtca tgatggaggt cccagccaca   1680

gggaaccatg agctcagtgg tcttggaaca gctcactaag tcagtccttc cttagcctgg   1740

aagtcagtag tggagtcaca aagcccatgt gttttgccat ctaggccttc acctggtctg   1800

tggacttata cctgtgtgct tggtttacag gtccagtggt tcttcagccc atgacagatg   1860

agaaggggct atattgaagg gcaaagagga actgttgttt gaattttcct gagagcctgg   1920

cttagtgctg ggccttctct taaacctcat tacaatgagg ttagtacttt tagtccctgt   1980

tttacagggg ttagaataga ctgttaaggg gcaactgaga aagaacagag aagtgacagc   2040

taggggttga gaggggccag aaaaacatga atgcaggcag atttcgtgaa atctgccacc   2100

actttataac cagatggttc ctttcacaac cctgggtcaa aaagagaata atttggccta   2160

taatgttaaa agaaagcagg aaggtgggta aataaaaatc ttggtgcctg g            2211

<210> SEQ ID NO 3
<211> LENGTH: 2226
<212> TYPE: DNA
<213> ORGANISM: Homo sapiens
<220> FEATURE:
<221> NAME/KEY: misc_feature
<222> LOCATION: (1)..(2226)
<223> OTHER INFORMATION: Polynucleotide encoding human
      S-adenosyl-5-homocysteine hydrolase (SAHH) derived
      from bladder; n=a, c, g, or t
<300> PUBLICATION INFORMATION:
<310> PATENT DOCUMENT NUMBER: 08/896,005
<311> PATENT FILING DATE: 1997-07-17
<312> PUBLICATION DATE: 1998-12-29

<400> SEQUENCE: 3

gttgccagct tgcatctgcc atcatttgat gcccacctta cagagctgac agatgaccaa     60

gcaaaatatc tgggactcaa caaaaatggg ccattcaaac ctaattatta cagatactaa    120

tggaccatac taccaaggac cagtccacct gaaccacaca ctctaaagaa atattttta     180

agataacttt tattttcttc ttactccttt cctcttgatt tttttcctat aatttcattc    240

ttgtttttc atctcattat ccaagttctg cagaccacac aggaacttgc ttcatggctc     300
```

```
tttagatgaa atagaagttc agggttcctc actctagtca ctaaagaagg attttactct    360

cccagcccag aaaggtgatt ctttctttac catttctggg gactttagtc ttaattaggt    420

accttattaa caggaaatgc taaggtacct tctctgtgga acaatctgca atgtctaaat    480

cgccttaaaa gagcccattt cttagctgct gaaatcagtg ctctttcact tcttcagaga    540

agcagggatg gtacctaccc ggcaggtagg ttagatgtgg gtggtgcatg ttaatttccc    600

ttagaagttc caagccctgt ttcctgcgta aaggtggtat gtccagttca gagatgtgta    660

taatgagcat ggcttgttaa gatcaggagg cccacttgga tttatagtat agcccttcct    720

ccactcccac cagacttgct catttttcga gtttttaact agactacact ctattgagtt    780

taattttgtc ctctaggatt tatttctgtt gtccaaaaaa aaaanaaaag aaaagaaaaa    840

ttaaggagaa tttttggtgt taatgctgag gaattgcttg agtggttagt tgttaccaat    900

ttctcttttg aacctttgga gctaaggatg ctgagtctag agaaatgcta gtctcaagcc    960

ctgttaagtc cctctgtttc tagcccgtag ttcatagcat cagtgaactg gagccacaac   1020

agcaaattct atcagctgtg taccatacag cttgtgctga aggcgaattt cttgagccat   1080

tactcagtat aaagcactga gttctatctt taggatttat ctttaagagc aaatttctgg   1140

tcagctgtgc ttctgcaacc taaaatattt aaagggaggt aggtgtgggc aggaggagga   1200

atgataaatt gggccagggc aagaaaaatc tagcttcata taatttgtct gggactatac   1260

accctatata atgttagttt tacagaagta atatgacttt tgattgctac ataccacaaa   1320

gagtttatga actgagatca taaagggcaa ctgatgtgtg aagaaagtag tcagtacatc   1380

ctggctcatg ctctgaaaga atatccagag aggctctctc aaagatcagg gagatgtatt   1440

cccatgccat gcaccctgct tcccagcatt tctgcatggt caagtgagct ttatgctcat   1500

gagctttaag tatataatta tccaggattt taaatcctca acttgttcta gcttgtgatc   1560

cctcaaagtt gggtcatacg ttagtgctag atactagaaa ttttcacttt tccactgatc   1620

agagagacag acattaaaaa caaaaataga agaaaggaaa gctttcaccc tgcagcttct   1680

tagcagggaa caattgtctt gccaaaactt ttttcccttt tctctcccat tttcttttac   1740

ccaatccctt cttactcctt gccagtgtga ccatgctttc ttctctgtag atgttaacag   1800

ttaaggccta ttttcctcgg gcacttaacc aaccaatcag aacaccacat ctgttagggg   1860

aggtaacctg gccaacagtg tatccatcac gttagccctg ctggagggaa gggacccaca   1920

ttcacctgcc ctctgacctg ccccttgatc ccatatctat taccgtgtcc ataggaataa   1980

taggtaaggg ctctgtctct gtcaagccat gtaacaaagg acactgttaa aaaaaaaaaa   2040

aagtctggca tcagagggag catgtggaga gcaacttggg aagaacaagt tcattttgta   2100

ttgaatgatt tttaatgaat gcaatattaa tccttgcaga tgagcaataa tcattaaaat   2160

cgattaaaat grtaagrcct taaaaaaaaa aaanaaaggnn gagaaggang gnngggggtg   2220

nngngg                                                              2226
```

<210> SEQ ID NO 4
<211> LENGTH: 7122
<212> TYPE: DNA
<213> ORGANISM: Homo sapiens
<220> FEATURE:
<221> NAME/KEY: CDS
<222> LOCATION: (287)..(4084)
<223> OTHER INFORMATION: Human methionine synthase cDNA
<300> PUBLICATION INFORMATION:
<308> DATABASE ACCESSION NUMBER: U75743/GenBank

<400> SEQUENCE: 4

-continued

```
gcgcgtgtct ggctgctagg ccgacaccaa ggactggccg ggtacccggg aagaaagcac     60

gtgctccagc agttgccgcg cccagccccg agagaggccc tagggcgctg cgggctttcg    120

gggtccgcag tccccccgcg acgcgagcca acgggaggcg tcaaaagacc cgggccttgt    180

gtggcaggct cgcctggcgc tggctggcgt ggcccttggc cgtcgtcacc tgtggagagc    240

acgtcttctc tgccgcgccc tctgcgcaag gaggagactc gacaac atg tca ccc       295
                                                   Met Ser Pro
                                                     1

gcg ctc caa gac ctg tcg caa ccc gaa ggt ctg aag aaa acc ctg cgg      343
Ala Leu Gln Asp Leu Ser Gln Pro Glu Gly Leu Lys Lys Thr Leu Arg
      5                  10                  15

gat gag atc aat gcc att ctg cag aag agg att atg gtg ctg gat gga      391
Asp Glu Ile Asn Ala Ile Leu Gln Lys Arg Ile Met Val Leu Asp Gly
 20                  25                  30                  35

ggg atg ggg acc atg atc cag cgg gag aag cta aac gaa gaa cac ttc      439
Gly Met Gly Thr Met Ile Gln Arg Glu Lys Leu Asn Glu Glu His Phe
                 40                  45                  50

cga ggt cag gaa ttt aaa gat cat gcc agg ccg ctg aaa ggc aac aat      487
Arg Gly Gln Glu Phe Lys Asp His Ala Arg Pro Leu Lys Gly Asn Asn
             55                  60                  65

gac att tta agt ata act cag cct gat gtc att tac caa atc cat aag      535
Asp Ile Leu Ser Ile Thr Gln Pro Asp Val Ile Tyr Gln Ile His Lys
         70                  75                  80

gaa tac ttg ctg gct ggg gca gat atc att gaa aca aat act ttt agc      583
Glu Tyr Leu Leu Ala Gly Ala Asp Ile Ile Glu Thr Asn Thr Phe Ser
     85                  90                  95

agc act agt att gcc caa gct gac tat ggc ctt gaa cac ttg gcc tac      631
Ser Thr Ser Ile Ala Gln Ala Asp Tyr Gly Leu Glu His Leu Ala Tyr
100                 105                 110                 115

cgg atg aac atg tgc tct gca gga gtg gcc aga aaa gct gcc gag gag      679
Arg Met Asn Met Cys Ser Ala Gly Val Ala Arg Lys Ala Ala Glu Glu
                120                 125                 130

gta act ctc cag aca gga att aag agg ttt gtg gca ggg gct ctg ggt      727
Val Thr Leu Gln Thr Gly Ile Lys Arg Phe Val Ala Gly Ala Leu Gly
            135                 140                 145

ccg act aat aag aca ctc tct gtg tcc cca tct gtg gaa agg ccg gat      775
Pro Thr Asn Lys Thr Leu Ser Val Ser Pro Ser Val Glu Arg Pro Asp
        150                 155                 160

tat agg aac atc aca ttt gat gag ctt gtt gaa gca tac caa gag cag      823
Tyr Arg Asn Ile Thr Phe Asp Glu Leu Val Glu Ala Tyr Gln Glu Gln
    165                 170                 175

gcc aaa gga ctt ctg gat ggc ggg gtt gat atc tta ctc att gaa act      871
Ala Lys Gly Leu Leu Asp Gly Gly Val Asp Ile Leu Leu Ile Glu Thr
180                 185                 190                 195

att ttt gat act gcc aat gcc aag gca gcc ttg ttt gca ctc caa aat      919
Ile Phe Asp Thr Ala Asn Ala Lys Ala Ala Leu Phe Ala Leu Gln Asn
                200                 205                 210

ctt ttt gag gag aaa tat gct ccc cgg cct atc ttt att tca ggg acg      967
Leu Phe Glu Glu Lys Tyr Ala Pro Arg Pro Ile Phe Ile Ser Gly Thr
            215                 220                 225

atc gtt gat aaa agt ggg cgg act ctt tcc gga cag aca gga gag gga     1015
Ile Val Asp Lys Ser Gly Arg Thr Leu Ser Gly Gln Thr Gly Glu Gly
        230                 235                 240

ttt gtc atc agc gtg tct cat gga gaa cca ctc tac att gga tta aat     1063
Phe Val Ile Ser Val Ser His Gly Glu Pro Leu Tyr Ile Gly Leu Asn
    245                 250                 255

tgt gct ttg ggt gca gct gaa atg aga cct ttt att gaa ata att gga     1111
Cys Ala Leu Gly Ala Ala Glu Met Arg Pro Phe Ile Glu Ile Ile Gly
```

-continued

```
260                 265                 270                 275

aaa tgt aca aca gcc tat gtc ctc tgt tat ccc aat gca ggt ctt ccc     1159
Lys Cys Thr Thr Ala Tyr Val Leu Cys Tyr Pro Asn Ala Gly Leu Pro
                280                 285                 290

aac acc ttt ggt gac tat gat gaa acg cct tct atg atg gcc aag cac     1207
Asn Thr Phe Gly Asp Tyr Asp Glu Thr Pro Ser Met Met Ala Lys His
            295                 300                 305

cta aag gat ttt gct atg gat ggc ttg gtc aat ata gtt gga gga tgc     1255
Leu Lys Asp Phe Ala Met Asp Gly Leu Val Asn Ile Val Gly Gly Cys
        310                 315                 320

tgt ggg tca aca cca gat cat atc agg gaa att gct gaa gct gtg aaa     1303
Cys Gly Ser Thr Pro Asp His Ile Arg Glu Ile Ala Glu Ala Val Lys
    325                 330                 335

aat tgt aag cct aga gtt cca cct gcc act gct ttt gaa gga cat atg     1351
Asn Cys Lys Pro Arg Val Pro Pro Ala Thr Ala Phe Glu Gly His Met
340                 345                 350                 355

tta ctg tct ggt cta gag ccc ttc agg att gga ccg tac acc aac ttt     1399
Leu Leu Ser Gly Leu Glu Pro Phe Arg Ile Gly Pro Tyr Thr Asn Phe
                360                 365                 370

gtt aac att gga gag cgc tgt aat gtt gca gga tca agg aag ttt gct     1447
Val Asn Ile Gly Glu Arg Cys Asn Val Ala Gly Ser Arg Lys Phe Ala
            375                 380                 385

aaa ctc atc atg gca gga aac tat gaa gaa gcc ttg tgt gtt gcc aaa     1495
Lys Leu Ile Met Ala Gly Asn Tyr Glu Glu Ala Leu Cys Val Ala Lys
        390                 395                 400

gtg cag gtg gaa atg gga gcc cag gtg ttg gat gtc aac atg gat gat     1543
Val Gln Val Glu Met Gly Ala Gln Val Leu Asp Val Asn Met Asp Asp
    405                 410                 415

ggc atg cta gat ggt cca agt gca atg acc aga ttt tgc aac tta att     1591
Gly Met Leu Asp Gly Pro Ser Ala Met Thr Arg Phe Cys Asn Leu Ile
420                 425                 430                 435

gct tcc gag cca gac atc gca aag gta cct ttg tgc atc gac tcc tcc     1639
Ala Ser Glu Pro Asp Ile Ala Lys Val Pro Leu Cys Ile Asp Ser Ser
                440                 445                 450

aat ttt gct gtg att gaa gct ggg tta aag tgc tgc caa ggg aag tgc     1687
Asn Phe Ala Val Ile Glu Ala Gly Leu Lys Cys Cys Gln Gly Lys Cys
            455                 460                 465

att gtc aat agc att agt ctg aag gaa gga gag gac gac ttc ttg gag     1735
Ile Val Asn Ser Ile Ser Leu Lys Glu Gly Glu Asp Asp Phe Leu Glu
        470                 475                 480

aag gcc agg aag att aaa aag tat gga gct gct atg gtg gtc atg gct     1783
Lys Ala Arg Lys Ile Lys Lys Tyr Gly Ala Ala Met Val Val Met Ala
    485                 490                 495

ttt gat gaa gaa gga cag gca aca gaa aca gac aca aaa atc aga gtg     1831
Phe Asp Glu Glu Gly Gln Ala Thr Glu Thr Asp Thr Lys Ile Arg Val
500                 505                 510                 515

tgc acc cgg gcc tac cat ctg ctt gtg aaa aaa ctg ggc ttt aat cca     1879
Cys Thr Arg Ala Tyr His Leu Leu Val Lys Lys Leu Gly Phe Asn Pro
                520                 525                 530

aat gac att att ttt gac cct aat atc cta acc att ggg act gga atg     1927
Asn Asp Ile Ile Phe Asp Pro Asn Ile Leu Thr Ile Gly Thr Gly Met
            535                 540                 545

gag gaa cac aac ttg tat gcc att aat ttt atc cat gca aca aaa gtc     1975
Glu Glu His Asn Leu Tyr Ala Ile Asn Phe Ile His Ala Thr Lys Val
        550                 555                 560

att aaa gaa aca tta cct gga gcc aga ata agt gga ggt ctt tcc aac     2023
Ile Lys Glu Thr Leu Pro Gly Ala Arg Ile Ser Gly Gly Leu Ser Asn
    565                 570                 575

ttg tcc ttc tcc ttc cga gga atg gaa gcc att cga gaa gca atg cat     2071
```

-continued

```
Leu Ser Phe Ser Phe Arg Gly Met Glu Ala Ile Arg Glu Ala Met His
580                 585                 590                 595

ggg gtt ttc ctt tac cat gca atc aag tct ggc atg gac atg ggg ata      2119
Gly Val Phe Leu Tyr His Ala Ile Lys Ser Gly Met Asp Met Gly Ile
                600                 605                 610

gtg aat gct gga aac ctc cct gtg tat gat gat atc cat aag gaa ctt      2167
Val Asn Ala Gly Asn Leu Pro Val Tyr Asp Asp Ile His Lys Glu Leu
            615                 620                 625

ctg cag ctc tgt gaa gat ctc atc tgg aat aaa gac cct gag gcc act      2215
Leu Gln Leu Cys Glu Asp Leu Ile Trp Asn Lys Asp Pro Glu Ala Thr
        630                 635                 640

gag aag ctc tta cgt tat gcc cag act caa ggc aca gga ggg aag aaa      2263
Glu Lys Leu Leu Arg Tyr Ala Gln Thr Gln Gly Thr Gly Gly Lys Lys
    645                 650                 655

gtc att cag act gat gag tgg aga aat ggc cct gtc gaa gaa cgc ctt      2311
Val Ile Gln Thr Asp Glu Trp Arg Asn Gly Pro Val Glu Glu Arg Leu
660                 665                 670                 675

gag tat gcc ctt gtg aag ggc att gaa aaa cat att att gag gat act      2359
Glu Tyr Ala Leu Val Lys Gly Ile Glu Lys His Ile Ile Glu Asp Thr
                680                 685                 690

gag gaa gcc agg tta aac caa aaa aaa tat ccc cga cct ctc aat ata      2407
Glu Glu Ala Arg Leu Asn Gln Lys Lys Tyr Pro Arg Pro Leu Asn Ile
            695                 700                 705

att gaa gga ccc ctg atg aat gga atg aaa att gtt ggt gat ctt ttt      2455
Ile Glu Gly Pro Leu Met Asn Gly Met Lys Ile Val Gly Asp Leu Phe
        710                 715                 720

gga gct gga aaa atg ttt cta cct cag gtt ata aag tca gcc cgg gtt      2503
Gly Ala Gly Lys Met Phe Leu Pro Gln Val Ile Lys Ser Ala Arg Val
    725                 730                 735

atg aag aag gct gtt ggc cac ctt atc cct ttc atg gaa aaa gaa aga      2551
Met Lys Lys Ala Val Gly His Leu Ile Pro Phe Met Glu Lys Glu Arg
740                 745                 750                 755

gaa gaa acc aga gtg ctt aac ggc aca gta gaa gaa gag gac cct tac      2599
Glu Glu Thr Arg Val Leu Asn Gly Thr Val Glu Glu Glu Asp Pro Tyr
                760                 765                 770

cag ggc acc atc gtg ctg gcc act gtt aaa ggc gac gtg cac gac ata      2647
Gln Gly Thr Ile Val Leu Ala Thr Val Lys Gly Asp Val His Asp Ile
            775                 780                 785

ggc aag aac ata gtt gga gta gtc ctt ggc tgc aat aat ttc cga gtt      2695
Gly Lys Asn Ile Val Gly Val Val Leu Gly Cys Asn Asn Phe Arg Val
        790                 795                 800

att gat tta gga gtc atg act cca tgt gat aag ata ctg aaa gct gct      2743
Ile Asp Leu Gly Val Met Thr Pro Cys Asp Lys Ile Leu Lys Ala Ala
    805                 810                 815

ctt gac cac aaa gca gat ata att ggc ctg tca gga ctc atc act cct      2791
Leu Asp His Lys Ala Asp Ile Ile Gly Leu Ser Gly Leu Ile Thr Pro
820                 825                 830                 835

tcc ctg gat gaa atg att ttt gtt gcc aag gaa atg gag aga tta gct      2839
Ser Leu Asp Glu Met Ile Phe Val Ala Lys Glu Met Glu Arg Leu Ala
                840                 845                 850

ata agg att cca ttg ttg att gga gga gca acc act tca aaa acc cac      2887
Ile Arg Ile Pro Leu Leu Ile Gly Gly Ala Thr Thr Ser Lys Thr His
            855                 860                 865

aca gca gtt aaa ata gct ccg aga tac agt gca cct gta atc cat gtc      2935
Thr Ala Val Lys Ile Ala Pro Arg Tyr Ser Ala Pro Val Ile His Val
        870                 875                 880

ctg gac gcg tcc aag agt gtg gtg gtg tgt tcc cag ctg tta gat gaa      2983
Leu Asp Ala Ser Lys Ser Val Val Val Cys Ser Gln Leu Leu Asp Glu
    885                 890                 895
```

-continued

```
aat cta aag gat gaa tac ttt gag gaa atc atg gaa gaa tat gaa gat      3031
Asn Leu Lys Asp Glu Tyr Phe Glu Glu Ile Met Glu Glu Tyr Glu Asp
900                 905                 910                 915

att aga cag gac cat tat gag tct ctc aag gag agg aga tac tta ccc      3079
Ile Arg Gln Asp His Tyr Glu Ser Leu Lys Glu Arg Arg Tyr Leu Pro
                920                 925                 930

tta agt caa gcc aga aaa agt ggt ttc caa atg gat tgg ctg tct gaa      3127
Leu Ser Gln Ala Arg Lys Ser Gly Phe Gln Met Asp Trp Leu Ser Glu
            935                 940                 945

cct cac cca gtg aag ccc acg ttt att ggg acc cag gtc ttt gaa gac      3175
Pro His Pro Val Lys Pro Thr Phe Ile Gly Thr Gln Val Phe Glu Asp
        950                 955                 960

tat gac ctg cag aag ctg gtg gac tac att gac tgg aag cct ttc ttt      3223
Tyr Asp Leu Gln Lys Leu Val Asp Tyr Ile Asp Trp Lys Pro Phe Phe
    965                 970                 975

gat gtc tgg cag ctc cgg ggc aag tac ccg aat cga ggc ttt ccc aag      3271
Asp Val Trp Gln Leu Arg Gly Lys Tyr Pro Asn Arg Gly Phe Pro Lys
980                 985                 990                 995

ata ttt aac gac aaa aca gta ggt gga gag gcc agg aag gtc tac gat      3319
Ile Phe Asn Asp Lys Thr Val Gly Gly Glu Ala Arg Lys Val Tyr Asp
                1000                1005                1010

gat gcc cac aat atg ctg aac aca ctg att agt caa aag aaa ctc cgg      3367
Asp Ala His Asn Met Leu Asn Thr Leu Ile Ser Gln Lys Lys Leu Arg
            1015                1020                1025

gcc cgg ggt gtg gtt ggg ttc tgg cca gca cag agt atc caa gac gac      3415
Ala Arg Gly Val Val Gly Phe Trp Pro Ala Gln Ser Ile Gln Asp Asp
        1030                1035                1040

att cac ctg tac gca gag gct gct gtg ccc cag gct gca gag ccc ata      3463
Ile His Leu Tyr Ala Glu Ala Ala Val Pro Gln Ala Ala Glu Pro Ile
    1045                1050                1055

gcc acc ttc tat ggg tta agg caa cag gct gag aag gac tct gcc agc      3511
Ala Thr Phe Tyr Gly Leu Arg Gln Gln Ala Glu Lys Asp Ser Ala Ser
1060                1065                1070                1075

acg gag cca tac tac tgc ctc tca gac ttc atc gct ccc ttg cat tct      3559
Thr Glu Pro Tyr Tyr Cys Leu Ser Asp Phe Ile Ala Pro Leu His Ser
                1080                1085                1090

ggc atc cgt gac tac ctg ggc ctg ttt gcc gtt gcc tgc ttt ggg gta      3607
Gly Ile Arg Asp Tyr Leu Gly Leu Phe Ala Val Ala Cys Phe Gly Val
            1095                1100                1105

gaa gag ctg agc aag gcc tat gag gat gat ggt gac gac tac agc agc      3655
Glu Glu Leu Ser Lys Ala Tyr Glu Asp Asp Gly Asp Asp Tyr Ser Ser
        1110                1115                1120

atc atg gtc aag gcg ctg ggg gac cgg ctg gca gag gcc ttt gca gaa      3703
Ile Met Val Lys Ala Leu Gly Asp Arg Leu Ala Glu Ala Phe Ala Glu
    1125                1130                1135

gag ctc cat gaa aga gtt cgc cga gaa ctg tgg gcc tac tgt ggc agt      3751
Glu Leu His Glu Arg Val Arg Arg Glu Leu Trp Ala Tyr Cys Gly Ser
1140                1145                1150                1155

gag cag ctg gac gtc gca gac ctg cgc agg ctg cgg tac aag ggc atc      3799
Glu Gln Leu Asp Val Ala Asp Leu Arg Arg Leu Arg Tyr Lys Gly Ile
                1160                1165                1170

cgc ccg gct cct ggc tac ccc agc cag ccc gac cac acc gag aag ctc      3847
Arg Pro Ala Pro Gly Tyr Pro Ser Gln Pro Asp His Thr Glu Lys Leu
            1175                1180                1185

acc atg tgg aga ctc gca gac atc gag cag tct aca ggc att agg tta      3895
Thr Met Trp Arg Leu Ala Asp Ile Glu Gln Ser Thr Gly Ile Arg Leu
        1190                1195                1200

aca gaa tca tta gca atg gca cct gct tca gca gtc tca ggc ctc tac      3943
Thr Glu Ser Leu Ala Met Ala Pro Ala Ser Ala Val Ser Gly Leu Tyr
    1205                1210                1215
```

-continued

```
ttc tcc aat ttg aag tcc aaa tat ttt gct gtg ggg aag att tcc aag     3991
Phe Ser Asn Leu Lys Ser Lys Tyr Phe Ala Val Gly Lys Ile Ser Lys
1220                1225                1230                1235

gat cag gtt gag gat tat gca ttg agg aag aac ata tct gtg gct gag     4039
Asp Gln Val Glu Asp Tyr Ala Leu Arg Lys Asn Ile Ser Val Ala Glu
               1240                1245                1250

gtt gag aaa tgg ctt gga ccc att ttg gga tat gat aca gac taa         4084
Val Glu Lys Trp Leu Gly Pro Ile Leu Gly Tyr Asp Thr Asp
           1255                1260                1265

ctttttttt ttttgccttt tttattcttg atgatcctca aggaaataca acctagggtg   4144

ccttaaaaat aacaacaaca aaaaacctgt gtgcatctgg ctgacactta cctgcttctg   4204

gttttcgaag actatttagt ggaaccttgt agaggagcag ggtcttcctg cagtgcctgg   4264

aaaacaggcg ctgttttttt gggaccttgc gtgaagagca gtgagcaggg ttcctgtggt   4324

ttccctggtc cctctgagat ggggacagac tgaagacaga ggtcgtttga tttcaaagca   4384

agtcaacctg ctttttctg tttttacagt ggaatctagg aggccactta gtcgtctttt   4444

tttcctctta gaagaaaagc ctgaaactga gttgaataga gaagtgtgac cctgtgacaa   4504

aatgatactg tgaaaaatgg ggcattttaa tctaagtggt tataacagtg gattctgacg   4564

gggaaggtgt agctctgttc tcttcggaag acctcgtttt ctaaaggctg gactaaatgg   4624

ctgcagaact ccctttggca aaaggcatgc gctcactgct tgcttgtcag aaacactgaa   4684

gccatttgcc ccagtgtggt caagcagcca tgctttctgg gcattttcgt cctcccataa   4744

tttcatattt ccgtacccct gaggaaacaa aaaggaaatg aggagagaaa gttactgtta   4804

agggtggtta acattttttt tgttttgttt tgttttggtt tttttttttt gagacagagt   4864

ctggctctgt cgcccaggct ggagtgcagg ggcgcaatct cggctcatag caagctccgc   4924

ctcctgggtt catgccattc tcctgcctca gcctccagag tagctgggac tacaggtgcc   4984

caccaccaca cccggctaat tttttgtgtt tttacaaaat acaaaaaagt agagacagga   5044

tttcactgtg ttagccagga tggtcttgat ctcccgacct cgtgatctgc ccacctcagc   5104

ctcccaaaat gctgggatta caggcgtgag ccaccgagcc tggccggtta acatctttta   5164

attgtttcca ggattgagca ggttctcagc tgggctctga tatcccgtgc ggagttggac   5224

aagtgggcag cataaagtca ctcatttctt accattttat tcccctcaat tctcaatata   5284

ttcagtaatg aagaatggtg ccaccactca agcaacaagc ctcaaactca accatgtcat   5344

ctttttcttg gatgattgca gttatttcaa aaatttgcat gcaaaatata cactcatcct   5404

acttcaagat ggtggtggca atagtcagga gaaggtaaca ttggagtcct ggtttgattc   5464

gaaggatgaa gacgaagaag caagggagga acaaatgaag aaccatcttt gttcatgaat   5524

aggaatattc aagattataa aggtatcagg tctcctaaaa ttgatctatg gatttaatac   5584

cattttcaat ggaaattcca acagatttta ttgaatgaaa caagcaggtg tttatatgga   5644

gtagcaaagg acttaaaatt accaaatgct tctaaatatg aaggagaggt tggggacacg   5704

caccctatgt gataccaagt tttattgtca agacagtgtc atggtgcaga ggtaggcatt   5764

ctgagcaggg gaacaaaata agggcctaga aactcacccg tgcatatgtt gacctttgca   5824

aaatgacctg gtgacatggc aagtcagtgg ggacaggaag gaccactccc taagtaatcc   5884

cagaacaatg gctattcatg tgggaaaaaa agaaatttta ctttctctca ccttacctgg   5944

tgataagttc caaatatgtt aagggcttta atacaaaaag caaaaattgt cagtgtttgg   6004

atgaaaaaag ccttagggca ggaaagaatc tcttgagaca taaagtagta atcataaagg   6064
```

-continued

```
acaagatggt taagtcaatt ctgttaaaac tcaaggctta tattaagcaa acacttgaag   6124

tgagaagatg atccacaact tgagaagaca tttataatac aaataactga tgaaggattc   6184

ataatcacaa atatagagaa ttcctattta aaaaaataga aaaatagtga agactacaca   6244

agaggaaata gggcttttaa ataaatagat gttctgtagc attggtcagg gaaatatgaa   6304

ttaggaccac aatgagattc cattttatat ccataagatt tgcaaaggtt gggtctgaca   6364

gtaccagttg ttagatctgt agggacttgt acaacattgt ggatgtgtaa acaggcacca   6424

ctgctttaaa aaacaattat cccttacaga cttgaacatt tgcagacgtt atgatcttgc   6484

ttccaactcc cacctgtatg tccagcaaac tcttgcatgt ggccactagg aggaatgtgt   6544

aagaatgttc atagttacat atttataata gttaataact ggaaaaagtg aaatgtatgt   6604

ctgtctacag gaaaataggt gaataattag atatatatat tcattctacg ggatattatt   6664

cagtagtgga aatgagtgaa ctacagctat acctcacaat aagaatgaat ctcagaaaat   6724

attaaggaaa aaagcaagtt tgaagagacc acatggggcg tactattttt attgggccca   6784

aaaacaagca aaaccaaaga atatgtagtc taagcatacg tatacaataa aactatgcta   6844

ttaaaaaaaa aaggtaactg ataaaccaaa attgagcata gtaattaccc acagaaggag   6904

gaagtggaag ggacaggagc acataggtag atgccaagtt atgcagctgt tctggttcct   6964

cctggtaggc ttacaagtgt ttactatatg ctattaatac attatacttt ataactaata   7024

gataacagtt ttttacatat taaatatgtt ctacttaaat atattataaa aaataaaggc   7084

aaagtggaat gtttaaaaaa aaaaaaaaaa aaaaaaaa                           7122
```

```
<210> SEQ ID NO 5
<211> LENGTH: 1265
<212> TYPE: PRT
<213> ORGANISM: Homo sapiens

<400> SEQUENCE: 5

Met Ser Pro Ala Leu Gln Asp Leu Ser Gln Pro Glu Gly Leu Lys Lys
  1               5                  10                  15

Thr Leu Arg Asp Glu Ile Asn Ala Ile Leu Gln Lys Arg Ile Met Val
             20                  25                  30

Leu Asp Gly Gly Met Gly Thr Met Ile Gln Arg Glu Lys Leu Asn Glu
         35                  40                  45

Glu His Phe Arg Gly Gln Glu Phe Lys Asp His Ala Arg Pro Leu Lys
     50                  55                  60

Gly Asn Asn Asp Ile Leu Ser Ile Thr Gln Pro Asp Val Ile Tyr Gln
 65                  70                  75                  80

Ile His Lys Glu Tyr Leu Leu Ala Gly Ala Asp Ile Ile Glu Thr Asn
                 85                  90                  95

Thr Phe Ser Ser Thr Ser Ile Ala Gln Ala Asp Tyr Gly Leu Glu His
            100                 105                 110

Leu Ala Tyr Arg Met Asn Met Cys Ser Ala Gly Val Ala Arg Lys Ala
        115                 120                 125

Ala Glu Glu Val Thr Leu Gln Thr Gly Ile Lys Arg Phe Val Ala Gly
    130                 135                 140

Ala Leu Gly Pro Thr Asn Lys Thr Leu Ser Val Ser Pro Ser Val Glu
145                 150                 155                 160

Arg Pro Asp Tyr Arg Asn Ile Thr Phe Asp Glu Leu Val Glu Ala Tyr
                165                 170                 175

Gln Glu Gln Ala Lys Gly Leu Leu Asp Gly Gly Val Asp Ile Leu Leu
            180                 185                 190
```

-continued

```
Ile Glu Thr Ile Phe Asp Thr Ala Asn Ala Lys Ala Ala Leu Phe Ala
        195                 200                 205

Leu Gln Asn Leu Phe Glu Glu Lys Tyr Ala Pro Arg Pro Ile Phe Ile
    210                 215                 220

Ser Gly Thr Ile Val Asp Lys Ser Gly Arg Thr Leu Ser Gly Gln Thr
225                 230                 235                 240

Gly Glu Gly Phe Val Ile Ser Val Ser His Gly Glu Pro Leu Tyr Ile
                245                 250                 255

Gly Leu Asn Cys Ala Leu Gly Ala Ala Glu Met Arg Pro Phe Ile Glu
            260                 265                 270

Ile Ile Gly Lys Cys Thr Thr Ala Tyr Val Leu Cys Tyr Pro Asn Ala
        275                 280                 285

Gly Leu Pro Asn Thr Phe Gly Asp Tyr Asp Glu Thr Pro Ser Met Met
    290                 295                 300

Ala Lys His Leu Lys Asp Phe Ala Met Asp Gly Leu Val Asn Ile Val
305                 310                 315                 320

Gly Gly Cys Cys Gly Ser Thr Pro Asp His Ile Arg Glu Ile Ala Glu
                325                 330                 335

Ala Val Lys Asn Cys Lys Pro Arg Val Pro Pro Ala Thr Ala Phe Glu
            340                 345                 350

Gly His Met Leu Leu Ser Gly Leu Glu Pro Phe Arg Ile Gly Pro Tyr
        355                 360                 365

Thr Asn Phe Val Asn Ile Gly Glu Arg Cys Asn Val Ala Gly Ser Arg
    370                 375                 380

Lys Phe Ala Lys Leu Ile Met Ala Gly Asn Tyr Glu Glu Ala Leu Cys
385                 390                 395                 400

Val Ala Lys Val Gln Val Glu Met Gly Ala Gln Val Leu Asp Val Asn
                405                 410                 415

Met Asp Asp Gly Met Leu Asp Gly Pro Ser Ala Met Thr Arg Phe Cys
            420                 425                 430

Asn Leu Ile Ala Ser Glu Pro Asp Ile Ala Lys Val Pro Leu Cys Ile
        435                 440                 445

Asp Ser Ser Asn Phe Ala Val Ile Glu Ala Gly Leu Lys Cys Cys Gln
    450                 455                 460

Gly Lys Cys Ile Val Asn Ser Ile Ser Leu Lys Glu Gly Glu Asp Asp
465                 470                 475                 480

Phe Leu Glu Lys Ala Arg Lys Ile Lys Lys Tyr Gly Ala Ala Met Val
                485                 490                 495

Val Met Ala Phe Asp Glu Glu Gly Gln Ala Thr Glu Thr Asp Thr Lys
            500                 505                 510

Ile Arg Val Cys Thr Arg Ala Tyr His Leu Leu Val Lys Lys Leu Gly
        515                 520                 525

Phe Asn Pro Asn Asp Ile Ile Phe Asp Pro Asn Ile Leu Thr Ile Gly
    530                 535                 540

Thr Gly Met Glu Glu His Asn Leu Tyr Ala Ile Asn Phe Ile His Ala
545                 550                 555                 560

Thr Lys Val Ile Lys Glu Thr Leu Pro Gly Ala Arg Ile Ser Gly Gly
                565                 570                 575

Leu Ser Asn Leu Ser Phe Ser Phe Arg Gly Met Glu Ala Ile Arg Glu
            580                 585                 590

Ala Met His Gly Val Phe Leu Tyr His Ala Ile Lys Ser Gly Met Asp
        595                 600                 605
```

-continued

```
Met Gly Ile Val Asn Ala Gly Asn Leu Pro Val Tyr Asp Asp Ile His
    610                 615                 620

Lys Glu Leu Leu Gln Leu Cys Glu Asp Leu Ile Trp Asn Lys Asp Pro
625                 630                 635                 640

Glu Ala Thr Glu Lys Leu Leu Arg Tyr Ala Gln Thr Gln Gly Thr Gly
                645                 650                 655

Gly Lys Lys Val Ile Gln Thr Asp Glu Trp Arg Asn Gly Pro Val Glu
            660                 665                 670

Glu Arg Leu Glu Tyr Ala Leu Val Lys Gly Ile Glu Lys His Ile Ile
        675                 680                 685

Glu Asp Thr Glu Glu Ala Arg Leu Asn Gln Lys Lys Tyr Pro Arg Pro
    690                 695                 700

Leu Asn Ile Ile Glu Gly Pro Leu Met Asn Gly Met Lys Ile Val Gly
705                 710                 715                 720

Asp Leu Phe Gly Ala Gly Lys Met Phe Leu Pro Gln Val Ile Lys Ser
                725                 730                 735

Ala Arg Val Met Lys Lys Ala Val Gly His Leu Ile Pro Phe Met Glu
            740                 745                 750

Lys Glu Arg Glu Glu Thr Arg Val Leu Asn Gly Thr Val Glu Glu Glu
        755                 760                 765

Asp Pro Tyr Gln Gly Thr Ile Val Leu Ala Thr Val Lys Gly Asp Val
    770                 775                 780

His Asp Ile Gly Lys Asn Ile Val Gly Val Val Leu Gly Cys Asn Asn
785                 790                 795                 800

Phe Arg Val Ile Asp Leu Gly Val Met Thr Pro Cys Asp Lys Ile Leu
                805                 810                 815

Lys Ala Ala Leu Asp His Lys Ala Asp Ile Ile Gly Leu Ser Gly Leu
            820                 825                 830

Ile Thr Pro Ser Leu Asp Glu Met Ile Phe Val Ala Lys Glu Met Glu
        835                 840                 845

Arg Leu Ala Ile Arg Ile Pro Leu Leu Ile Gly Gly Ala Thr Thr Ser
    850                 855                 860

Lys Thr His Thr Ala Val Lys Ile Ala Pro Arg Tyr Ser Ala Pro Val
865                 870                 875                 880

Ile His Val Leu Asp Ala Ser Lys Ser Val Val Val Cys Ser Gln Leu
                885                 890                 895

Leu Asp Glu Asn Leu Lys Asp Glu Tyr Phe Glu Glu Ile Met Glu Glu
            900                 905                 910

Tyr Glu Asp Ile Arg Gln Asp His Tyr Glu Ser Leu Lys Glu Arg Arg
        915                 920                 925

Tyr Leu Pro Leu Ser Gln Ala Arg Lys Ser Gly Phe Gln Met Asp Trp
    930                 935                 940

Leu Ser Glu Pro His Pro Val Lys Pro Thr Phe Ile Gly Thr Gln Val
945                 950                 955                 960

Phe Glu Asp Tyr Asp Leu Gln Lys Leu Val Asp Tyr Ile Asp Trp Lys
                965                 970                 975

Pro Phe Phe Asp Val Trp Gln Leu Arg Gly Lys Tyr Pro Asn Arg Gly
            980                 985                 990

Phe Pro Lys Ile Phe Asn Asp Lys Thr Val Gly Gly Glu Ala Arg Lys
        995                 1000                1005

Val Tyr Asp Asp Ala His Asn Met Leu Asn Thr Leu Ile Ser Gln Lys
   1010                1015                1020

Lys Leu Arg Ala Arg Gly Val Val Gly Phe Trp Pro Ala Gln Ser Ile
```

-continued

```
1025                1030                1035                1040

Gln Asp Asp Ile His Leu Tyr Ala Glu Ala Ala Val Pro Gln Ala Ala
               1045                1050                1055

Glu Pro Ile Ala Thr Phe Tyr Gly Leu Arg Gln Gln Ala Glu Lys Asp
           1060                1065                1070

Ser Ala Ser Thr Glu Pro Tyr Tyr Cys Leu Ser Asp Phe Ile Ala Pro
       1075                1080                1085

Leu His Ser Gly Ile Arg Asp Tyr Leu Gly Leu Phe Ala Val Ala Cys
   1090                1095                1100

Phe Gly Val Glu Glu Leu Ser Lys Ala Tyr Glu Asp Asp Gly Asp Asp
1105                1110                1115                1120

Tyr Ser Ser Ile Met Val Lys Ala Leu Gly Asp Arg Leu Ala Glu Ala
               1125                1130                1135

Phe Ala Glu Glu Leu His Glu Arg Val Arg Arg Glu Leu Trp Ala Tyr
           1140                1145                1150

Cys Gly Ser Glu Gln Leu Asp Val Ala Asp Leu Arg Arg Leu Arg Tyr
       1155                1160                1165

Lys Gly Ile Arg Pro Ala Pro Gly Tyr Pro Ser Gln Pro Asp His Thr
   1170                1175                1180

Glu Lys Leu Thr Met Trp Arg Leu Ala Asp Ile Glu Gln Ser Thr Gly
1185                1190                1195                1200

Ile Arg Leu Thr Glu Ser Leu Ala Met Ala Pro Ala Ser Ala Val Ser
               1205                1210                1215

Gly Leu Tyr Phe Ser Asn Leu Lys Ser Lys Tyr Phe Ala Val Gly Lys
           1220                1225                1230

Ile Ser Lys Asp Gln Val Glu Asp Tyr Ala Leu Arg Lys Asn Ile Ser
       1235                1240                1245

Val Ala Glu Val Glu Lys Trp Leu Gly Pro Ile Leu Gly Tyr Asp Thr
   1250                1255                1260

Asp
1265


<210> SEQ ID NO 6
<211> LENGTH: 7224
<212> TYPE: DNA
<213> ORGANISM: Homo sapiens
<220> FEATURE:
<221> NAME/KEY: CDS
<222> LOCATION: (395)..(4192)
<220> FEATURE:
<223> OTHER INFORMATION: Human methionine synthase
<300> PUBLICATION INFORMATION:
<308> DATABASE ACCESSION NUMBER: U73338/GenBank

<400> SEQUENCE: 6

aaaggttcta aatgtctgcg gggctcagag ccggatgtca cgtcgtcctc ctctgccggt     60

tttctcttgg gtccttttcc gtgccgtccc gcgactccgc ctctggccgc gcgtgtctgg    120

ctgctaggcc gacaccaagg actggccggg tacccgggaa gaaagcacgt gctccagcag    180

ttgccgcgcc cagccccgag agaggcccta gggcgctgcg ggctttcggg gtccgcagtc    240

cccccgcgac gcgagccaac gggaggcgtc aaaagacccg ggccttgtgt ggcaggctcg    300

cctggcgctg gctggcgtgg cccttggccg tcgtcacctg tggagagcac gtcttctctg    360

ccgcgccctc tgcgcaagga ggagactcga caac atg tca ccc gcg ctc caa gac    415
                                     Met Ser Pro Ala Leu Gln Asp
                                       1               5

ctg tcg caa ccc gaa ggt ctg aag aaa acc ctg cgg gat gag atc aat      463
```

-continued

```
Leu Ser Gln Pro Glu Gly Leu Lys Lys Thr Leu Arg Asp Glu Ile Asn
        10                  15                  20

gcc att ctg cag aag agg att atg gtg ctg gat gga ggg atg ggg acc      511
Ala Ile Leu Gln Lys Arg Ile Met Val Leu Asp Gly Gly Met Gly Thr
    25                  30                  35

atg atc cag cgg gag aag cta aac gaa gaa cac ttc cga ggt cag gaa      559
Met Ile Gln Arg Glu Lys Leu Asn Glu Glu His Phe Arg Gly Gln Glu
 40                  45                  50                  55

ttt aaa gat cat gcc agg ccg ctg aaa ggc aac aat gac att tta agt      607
Phe Lys Asp His Ala Arg Pro Leu Lys Gly Asn Asn Asp Ile Leu Ser
                60                  65                  70

ata act cag cct gat gtc att tac caa atc cat aag gaa tac ttg ctg      655
Ile Thr Gln Pro Asp Val Ile Tyr Gln Ile His Lys Glu Tyr Leu Leu
            75                  80                  85

gct ggg gca gat atc att gaa aca aat act ttt agc agc act agt att      703
Ala Gly Ala Asp Ile Ile Glu Thr Asn Thr Phe Ser Ser Thr Ser Ile
        90                  95                 100

gcc caa gct gac tat ggc ctt gaa cac ttg gcc tac cgg atg aac atg      751
Ala Gln Ala Asp Tyr Gly Leu Glu His Leu Ala Tyr Arg Met Asn Met
    105                 110                 115

tgc tct gca gga gtg gcc aga aaa gct gcc gag gag gta act ctc cag      799
Cys Ser Ala Gly Val Ala Arg Lys Ala Ala Glu Glu Val Thr Leu Gln
120                 125                 130                 135

aca gga att aag agg ttt gtg gca ggg gct ctg ggt ccg act aat aag      847
Thr Gly Ile Lys Arg Phe Val Ala Gly Ala Leu Gly Pro Thr Asn Lys
                140                 145                 150

aca ctc tct gtg tcc cca tct gtg gaa agg ccg gat tat agg aac atc      895
Thr Leu Ser Val Ser Pro Ser Val Glu Arg Pro Asp Tyr Arg Asn Ile
            155                 160                 165

aca ttt gat gag ctt gtt gaa gca tac caa gag cag gcc aaa gga ctt      943
Thr Phe Asp Glu Leu Val Glu Ala Tyr Gln Glu Gln Ala Lys Gly Leu
        170                 175                 180

ctg gat ggc ggg gtt gat atc tta ctc att gaa act att ttt gat act      991
Leu Asp Gly Gly Val Asp Ile Leu Leu Ile Glu Thr Ile Phe Asp Thr
    185                 190                 195

gcc aat gcc aag gca gcc ttg ttt gca ctc caa aat ctt ttt gag gag     1039
Ala Asn Ala Lys Ala Ala Leu Phe Ala Leu Gln Asn Leu Phe Glu Glu
200                 205                 210                 215

aaa tat gct ccc cgg cct atc ttt att tca ggg acg atc gtt gat aaa     1087
Lys Tyr Ala Pro Arg Pro Ile Phe Ile Ser Gly Thr Ile Val Asp Lys
                220                 225                 230

agt ggg cgg act ctt tcc gga cag aca gga gag gga ttt gtc atc agc     1135
Ser Gly Arg Thr Leu Ser Gly Gln Thr Gly Glu Gly Phe Val Ile Ser
            235                 240                 245

gtg tct cat gga gaa cca ctc tgc att gga tta aat tgt gct ttg ggt     1183
Val Ser His Gly Glu Pro Leu Cys Ile Gly Leu Asn Cys Ala Leu Gly
        250                 255                 260

gca gct gaa atg aga cct ttt att gaa ata att gga aaa tgt aca aca     1231
Ala Ala Glu Met Arg Pro Phe Ile Glu Ile Ile Gly Lys Cys Thr Thr
    265                 270                 275

gcc tat gtc ctc tgt tat ccc aat gca ggt ctt ccc aac acc ttt ggt     1279
Ala Tyr Val Leu Cys Tyr Pro Asn Ala Gly Leu Pro Asn Thr Phe Gly
280                 285                 290                 295

gac tat gat gaa acg cct tct atg atg gcc aag cac cta aag gat ttt     1327
Asp Tyr Asp Glu Thr Pro Ser Met Met Ala Lys His Leu Lys Asp Phe
                300                 305                 310

gct atg gat ggc ttg gtc aat ata gtt gga gga tgc tgt ggg tca aca     1375
Ala Met Asp Gly Leu Val Asn Ile Val Gly Gly Cys Cys Gly Ser Thr
            315                 320                 325
```

-continued

```
cca gat cat atc agg gaa att gct gaa gct gtg aaa aat tgt aag cct      1423
Pro Asp His Ile Arg Glu Ile Ala Glu Ala Val Lys Asn Cys Lys Pro
        330                 335                 340

aga gtt cca cct gcc act gct ttt gaa gga cat atg tta ctg tct ggt      1471
Arg Val Pro Pro Ala Thr Ala Phe Glu Gly His Met Leu Leu Ser Gly
    345                 350                 355

cta gag ccc ttc agg att gga ccg tac acc aac ttt gtt aac att gga      1519
Leu Glu Pro Phe Arg Ile Gly Pro Tyr Thr Asn Phe Val Asn Ile Gly
360                 365                 370                 375

gag cgc tgt aat gtt gca gga tca agg aag ttt gct aaa ctc atc atg      1567
Glu Arg Cys Asn Val Ala Gly Ser Arg Lys Phe Ala Lys Leu Ile Met
            380                 385                 390

gca gga aac tat gaa gaa gcc ttg tgt gtt gcc aaa gtg cag gtg gaa      1615
Ala Gly Asn Tyr Glu Glu Ala Leu Cys Val Ala Lys Val Gln Val Glu
            395                 400                 405

atg gga gcc cag gtg ttg gat gtc aac atg gat gat ggc atg cta gat      1663
Met Gly Ala Gln Val Leu Asp Val Asn Met Asp Asp Gly Met Leu Asp
        410                 415                 420

ggt cca agt gca atg acc aga ttt tgc aac tta att gct tcc gag cca      1711
Gly Pro Ser Ala Met Thr Arg Phe Cys Asn Leu Ile Ala Ser Glu Pro
    425                 430                 435

gac atc gca aag gta cct ttg tgc atc gac tcc tcc aat ttt gct gtg      1759
Asp Ile Ala Lys Val Pro Leu Cys Ile Asp Ser Ser Asn Phe Ala Val
440                 445                 450                 455

att gaa gct ggg tta aag tgc tgc caa ggg aag tgc att gtc aat agc      1807
Ile Glu Ala Gly Leu Lys Cys Cys Gln Gly Lys Cys Ile Val Asn Ser
            460                 465                 470

att agt ctg aag gaa gga gag gac gac ttc ttg gag aag gcc agg aag      1855
Ile Ser Leu Lys Glu Gly Glu Asp Asp Phe Leu Glu Lys Ala Arg Lys
            475                 480                 485

att aaa aag tat gga gct gct atg gtg gtc atg gct ttt gat gaa gaa      1903
Ile Lys Lys Tyr Gly Ala Ala Met Val Val Met Ala Phe Asp Glu Glu
        490                 495                 500

gga cag gca aca gaa aca gac aca aaa atc aga gtg tgc acc cgg gcc      1951
Gly Gln Ala Thr Glu Thr Asp Thr Lys Ile Arg Val Cys Thr Arg Ala
    505                 510                 515

tac cat ctg ctt gtg aaa aaa ctg ggc ttt aat cca aat gac att att      1999
Tyr His Leu Leu Val Lys Lys Leu Gly Phe Asn Pro Asn Asp Ile Ile
520                 525                 530                 535

ttt gac cct aat atc cta acc att ggg act gga atg gag gaa cac aac      2047
Phe Asp Pro Asn Ile Leu Thr Ile Gly Thr Gly Met Glu Glu His Asn
            540                 545                 550

ttg tat gcc att aat ttt atc cat gca aca aaa gtc att aaa gaa aca      2095
Leu Tyr Ala Ile Asn Phe Ile His Ala Thr Lys Val Ile Lys Glu Thr
            555                 560                 565

tta cct gga gcc aga ata agt gga ggt ctt tcc aac ttg tcc ttc tcc      2143
Leu Pro Gly Ala Arg Ile Ser Gly Gly Leu Ser Asn Leu Ser Phe Ser
        570                 575                 580

ttc cga gga atg gaa gcc att cga gaa gca atg cat ggg gtt ttc ctt      2191
Phe Arg Gly Met Glu Ala Ile Arg Glu Ala Met His Gly Val Phe Leu
    585                 590                 595

tac cat gca atc aag tct ggc atg gac atg ggg ata gtg aat gct gga      2239
Tyr His Ala Ile Lys Ser Gly Met Asp Met Gly Ile Val Asn Ala Gly
600                 605                 610                 615

aac ctc cct gtg tat gat gat atc cat aag gaa ctt ctg cag ctc tgt      2287
Asn Leu Pro Val Tyr Asp Asp Ile His Lys Glu Leu Leu Gln Leu Cys
            620                 625                 630

gaa gat ctc atc tgg aat aaa gac cct gag gcc act gag aag ctc tta      2335
Glu Asp Leu Ile Trp Asn Lys Asp Pro Glu Ala Thr Glu Lys Leu Leu
            635                 640                 645
```

-continued

```
cgt tat gcc cag act caa ggc aca gga ggg aag aaa gtc att cag act      2383
Arg Tyr Ala Gln Thr Gln Gly Thr Gly Gly Lys Lys Val Ile Gln Thr
        650                 655                 660

gat gag tgg aga aat ggc cct gtc gaa gaa cgc ctt gag tat gcc ctt      2431
Asp Glu Trp Arg Asn Gly Pro Val Glu Glu Arg Leu Glu Tyr Ala Leu
    665                 670                 675

gtg aag ggc att gaa aaa cat att att gag gat act gag gaa gcc agg      2479
Val Lys Gly Ile Glu Lys His Ile Ile Glu Asp Thr Glu Glu Ala Arg
680                 685                 690                 695

tta aac caa aaa aaa tat ccc cga cct ctc aat ata att gaa gga ccc      2527
Leu Asn Gln Lys Lys Tyr Pro Arg Pro Leu Asn Ile Ile Glu Gly Pro
                700                 705                 710

ctg atg aat gga atg aaa att gtt ggt gat ctt ttt gga gct gga aaa      2575
Leu Met Asn Gly Met Lys Ile Val Gly Asp Leu Phe Gly Ala Gly Lys
            715                 720                 725

atg ttt cta cct cag gtt ata aag tca gcc cgg gtt atg aag aag gct      2623
Met Phe Leu Pro Gln Val Ile Lys Ser Ala Arg Val Met Lys Lys Ala
        730                 735                 740

gtt ggc cac ctt atc cct ttc atg gaa aaa gaa aga gaa gaa acc aga      2671
Val Gly His Leu Ile Pro Phe Met Glu Lys Glu Arg Glu Glu Thr Arg
    745                 750                 755

gtg ctt aac ggc aca gta gaa gaa gag gac cct tac cag ggc acc atc      2719
Val Leu Asn Gly Thr Val Glu Glu Glu Asp Pro Tyr Gln Gly Thr Ile
760                 765                 770                 775

gtg ctg gcc act gtt aaa ggc gac gtg cac gac ata ggc aag aac ata      2767
Val Leu Ala Thr Val Lys Gly Asp Val His Asp Ile Gly Lys Asn Ile
                780                 785                 790

gtt gga gta gtc ctt ggc tgc aat aat ttc cga gtt att gat tta gga      2815
Val Gly Val Val Leu Gly Cys Asn Asn Phe Arg Val Ile Asp Leu Gly
            795                 800                 805

gtc atg act cca tgt gat aag ata ctg aaa gct gct ctt gac cac aaa      2863
Val Met Thr Pro Cys Asp Lys Ile Leu Lys Ala Ala Leu Asp His Lys
        810                 815                 820

gca gat ata att ggc ctg tca gga ctc atc act cct tcc ctg gat gaa      2911
Ala Asp Ile Ile Gly Leu Ser Gly Leu Ile Thr Pro Ser Leu Asp Glu
    825                 830                 835

atg att ttt gtt gcc aag gaa atg gag aga tta gct ata agg att cca      2959
Met Ile Phe Val Ala Lys Glu Met Glu Arg Leu Ala Ile Arg Ile Pro
840                 845                 850                 855

ttg ttg att gga gga gca acc act tca aaa acc cac aca gca gtt aaa      3007
Leu Leu Ile Gly Gly Ala Thr Thr Ser Lys Thr His Thr Ala Val Lys
                860                 865                 870

ata gct ccg aga tac agt gca cct gta atc cat gtc ctg gac gcg tcc      3055
Ile Ala Pro Arg Tyr Ser Ala Pro Val Ile His Val Leu Asp Ala Ser
            875                 880                 885

aag agt gtg gtg gtg tgt tcc cag ctg tta gat gaa aat cta aag gat      3103
Lys Ser Val Val Val Cys Ser Gln Leu Leu Asp Glu Asn Leu Lys Asp
        890                 895                 900

gaa tac ttt gag gaa atc atg gaa gaa tat gaa gat att aga cag gac      3151
Glu Tyr Phe Glu Glu Ile Met Glu Glu Tyr Glu Asp Ile Arg Gln Asp
    905                 910                 915

cat tat gag tct ctc aag gag agg aga tac tta ccc tta agt caa gcc      3199
His Tyr Glu Ser Leu Lys Glu Arg Arg Tyr Leu Pro Leu Ser Gln Ala
920                 925                 930                 935

aga aaa agt ggt ttc caa atg gat tgg ctg tct gaa cct cac cca gtg      3247
Arg Lys Ser Gly Phe Gln Met Asp Trp Leu Ser Glu Pro His Pro Val
                940                 945                 950

aag ccc acg ttt att ggg acc cag gtc ttt gaa gac tat gac ctg cag      3295
Lys Pro Thr Phe Ile Gly Thr Gln Val Phe Glu Asp Tyr Asp Leu Gln
```

-continued

```
            955                 960                 965

aag ctg gtg gac tac att gac tgg aag cct ttc ttt gat gtc tgg cag     3343
Lys Leu Val Asp Tyr Ile Asp Trp Lys Pro Phe Phe Asp Val Trp Gln
        970                 975                 980

ctc cgg ggc aag tac ccg aat cga ggc ttt ccc aag ata ttt aac gac     3391
Leu Arg Gly Lys Tyr Pro Asn Arg Gly Phe Pro Lys Ile Phe Asn Asp
    985                 990                 995

aaa aca gta ggt gga gag gcc agg aag gtc tac gat gat gcc cac aat     3439
Lys Thr Val Gly Gly Glu Ala Arg Lys Val Tyr Asp Asp Ala His Asn
1000                1005                1010                1015

atg ctg aac aca ctg att agt caa aag aaa ctc cgg gcc cgg ggt gtg     3487
Met Leu Asn Thr Leu Ile Ser Gln Lys Lys Leu Arg Ala Arg Gly Val
                1020                1025                1030

gtt ggg ttc tgg cca gca cag agt atc caa gac gac att cac ctg tac     3535
Val Gly Phe Trp Pro Ala Gln Ser Ile Gln Asp Asp Ile His Leu Tyr
            1035                1040                1045

gcg gag gct gct gtg ccc cag gct gca gag ccc ata gcc acc ttc tat     3583
Ala Glu Ala Ala Val Pro Gln Ala Ala Glu Pro Ile Ala Thr Phe Tyr
        1050                1055                1060

ggg tta agg caa cag gct gag aag gac tct gcc agc acg gag cca tac     3631
Gly Leu Arg Gln Gln Ala Glu Lys Asp Ser Ala Ser Thr Glu Pro Tyr
    1065                1070                1075

tac tgc ctc tca gac ttc atc gct ccc ttg cat tct ggc atc cgt gac     3679
Tyr Cys Leu Ser Asp Phe Ile Ala Pro Leu His Ser Gly Ile Arg Asp
1080                1085                1090                1095

tac ctg ggc ctg ttt gcc gtt gcc tgc ttt ggg gta gaa gag ctg agc     3727
Tyr Leu Gly Leu Phe Ala Val Ala Cys Phe Gly Val Glu Glu Leu Ser
                1100                1105                1110

aag gcc tat gag gat gat ggt gac gac tac agc agc atc atg gtc aag     3775
Lys Ala Tyr Glu Asp Asp Gly Asp Asp Tyr Ser Ser Ile Met Val Lys
            1115                1120                1125

gcg ctg ggg gac cgg ctg gca gag gcc ttt gca gaa gag ctc cat gaa     3823
Ala Leu Gly Asp Arg Leu Ala Glu Ala Phe Ala Glu Glu Leu His Glu
        1130                1135                1140

aga gtt cgc cga gaa ctg tgg gcc tac tgt ggc agt gag cag ctg gac     3871
Arg Val Arg Arg Glu Leu Trp Ala Tyr Cys Gly Ser Glu Gln Leu Asp
    1145                1150                1155

gtc gca gac ctg cgc agg ctg cgg tac aag ggc atc cgc ccg gct cct     3919
Val Ala Asp Leu Arg Arg Leu Arg Tyr Lys Gly Ile Arg Pro Ala Pro
1160                1165                1170                1175

ggc tac ccc agc cag ccc gac cac acc gag aag ctc acc atg tgg aga     3967
Gly Tyr Pro Ser Gln Pro Asp His Thr Glu Lys Leu Thr Met Trp Arg
                1180                1185                1190

ctt gca gac atc gag cag tct aca ggc att agg tta aca gaa tca tta     4015
Leu Ala Asp Ile Glu Gln Ser Thr Gly Ile Arg Leu Thr Glu Ser Leu
            1195                1200                1205

gca atg gca cct gct tca gca gtc tca ggc ctc tac ttc tcc aat ttg     4063
Ala Met Ala Pro Ala Ser Ala Val Ser Gly Leu Tyr Phe Ser Asn Leu
        1210                1215                1220

aag tcc aaa tat ttt gct gtg ggg aag att tcc aag gat cag gtt gag     4111
Lys Ser Lys Tyr Phe Ala Val Gly Lys Ile Ser Lys Asp Gln Val Glu
    1225                1230                1235

gat tat gca ttg agg aag aac ata tct gtg gct gag gtt gag aaa tgg     4159
Asp Tyr Ala Leu Arg Lys Asn Ile Ser Val Ala Glu Val Glu Lys Trp
1240                1245                1250                1255

ctt gga ccc att ttg gga tat gat aca gac taa cttttttttt ttttgccttt   4212
Leu Gly Pro Ile Leu Gly Tyr Asp Thr Asp
                1260                1265

tttattcttg atgatcctca aggaaataca acctagggtg ccttaaaaat aacaacaaca   4272
```

-continued

```
aaaaacctgt gtgcatctgg ctgacacttc cctgcttctg gttttcgaag actatttagt   4332
ggaaccttgt agaggagcag ggtcttcctg cagtgcctgg aaaacaggcg ctgttttttt   4392
gggaccttgc gtgaagagca gtgagcaggg ttcctgtggt ttccctggtc cctctgagat   4452
ggggacagac tgaagacaga ggtcgtttga tttcaaagca agtcaacctg ctttttttctg  4512
tttttacagt ggaatctagg aggccactta gtcgtctttt tttcctctta gaagaaaagc   4572
ctgaaactga gttgaataga gaagtgtgac cctgtgacaa aatgatactg tgagaaatgg   4632
ggcattttaa tctaagtggt tataacagtg gattctgacg gggaaggtgt agctctgttc   4692
tcttcggaag acctcgtttt ctaaaggctg gactaaatgg ctgcagaact ccctttggca   4752
aaaggcatgc gctcactgct tgcttgtcag aaacactgaa gccatttgcc ccagtgtggt   4812
caagcagcca tgctttctgg gcattttcgt cctcccataa tttcatattt ccgtacccct   4872
gaggaaacaa aaaggaaatg aggagagaaa gttactgtta agggtggtta acattttttt   4932
tgttttgttt tgttttggtt tttttttttt tgagacagag tctggctctg tcgcccaggc   4992
tggagtgcag gggcgcaatc tcggctcata gcaagctccg cctcctgggt tcatgccatt   5052
ctcctgcctc agcctccaga gtagctggga ctacaggtgc ccgccaccac acccggctaa   5112
ttttttgtgt ttttacaaaa tacaaaaaag tagagacagg atttcactgt gttagccagg   5172
atggtcttga tctcccgacc tcgtgatctg cccacctcag cctcccaaaa tgctgggatt   5232
acaggcgtga gccaccgagc ctggccggtt aacatctttt aattgtttcc aggattgagc   5292
aggttctcag ctgggctctg atatcccgtg cggagttgga caagtgggca gcataaagtc   5352
actcatttct taccatttta ttcccctcaa ttctcaatat attcagtaat gaagaatggt   5412
gccaccactc aagcaacaag cctcaaactc acccatgtca tctttttctt ggatgattgc   5472
agttatttca aaaatttgca tgcaaaatat acactcatcc tacttcaaga tggtggtggc   5532
aatagtcagg agaaggtagc attggagtcc tggtttgatt cgaaggatga agacgaagaa   5592
gcaagggagg aacaaatgaa gaaccatctt tgttcatgaa taggaatatt caagattata   5652
aaggtatcag gtctcctaaa attgatctat ggatttaata ccattttcaa tggaaattcc   5712
aacagatttt attgaatgaa acaagcaggt gtttatatgg agtagcaaag gacttaaaat   5772
taccaaatgc ttctaaatat gaaggagagg ttggggacac gcaccctatg tgataccaag   5832
ttttattgtc aagacagtgt catggtgcag aggtaggcat tctgagcagg ggaacaaaat   5892
aagggcctag aaactcaccc gtgcatatgt tgacctttgc aaaatgacct ggtgacatgg   5952
caagtcagtg gggacaggaa ggaccactcc ctaagtaatc ccagaacaat ggctattcat   6012
gtgggaaaaa aagaaatttt actttctctc accttacctg gtgataagtt ccaaatatgt   6072
taagggcttt aatacaaaaa gcaaaaattg tcagtgtttg gatgaaaaaa gccttagggc   6132
aggaaagaat ctcttgagac ataaagtagt aatcataaag gacaagatgg ttaagtcaat   6192
tctgttaaaa ctcaaggctt atattaagca aacacttgaa gtgagaagat gatccacaac   6252
ttgagaagac atttataata caaataactg atgaaggatt cataatcaca aatatagaga   6312
attcctattt aaaaaaatag aaaaatagtg aagactacac aagaggaaat agggctttta   6372
aataaataga tgttctgtag cattggtcag ggaaatatga attaggacca caatgagatt   6432
ccattttata tccataagat ttgcaaaggt tgggtctgac agtaccagtt gttagatctg   6492
tagggacttg tacaacattg tggatgtgta aacaggcacc actgctttaa aaaacaatta   6552
tcccttacag acttgaacat ttgcagacct tatgatcttg cttccaactc ccacctgtat   6612
```

-continued

```
gtccagcaaa ctcttgcatg tggccactag gaggaatgtg taagaatgtt catagttaca   6672

tatttataat agttaataac tggaaaaagt gaaatgtatg tctgtctaca ggaaaatagg   6732

tgaataatta gatatatgta ttcattctac gggatattat tcagtagtgg aaatgagtga   6792

actacagcta tacctcacaa taagaatgaa tctcagaaaa tattaaggaa aaaagcaagt   6852

ttgaagagac cacatggggc gtactatttt tattgagccc aaaaacaagc aaaaccaaag   6912

aatatgtagt ctaagcatac gtatacaata aaactatgct attaaaaaaa aaggtaactg   6972

ataaaccaaa attgagcata gtaattaccc acagaaggag gaagtggaag ggacaggagc   7032

acataggtag atgccaagtt atgcagctgt tctggttcct cctggtaggc ttacaagtgt   7092

ttactatatg ctattaatac attatacttt ataactaata gataacagtt ttttacatat   7152

taaatatgtt ctacttaaat atattataaa aaataaaggc aaagtggaat gataacctaa   7212

aaaaaaaaaa aa                                                        7224


<210> SEQ ID NO 7
<211> LENGTH: 1265
<212> TYPE: PRT
<213> ORGANISM: Homo sapiens

<400> SEQUENCE: 7

Met Ser Pro Ala Leu Gln Asp Leu Ser Gln Pro Glu Gly Leu Lys Lys
  1               5                  10                  15

Thr Leu Arg Asp Glu Ile Asn Ala Ile Leu Gln Lys Arg Ile Met Val
             20                  25                  30

Leu Asp Gly Gly Met Gly Thr Met Ile Gln Arg Glu Lys Leu Asn Glu
         35                  40                  45

Glu His Phe Arg Gly Gln Glu Phe Lys Asp His Ala Arg Pro Leu Lys
     50                  55                  60

Gly Asn Asn Asp Ile Leu Ser Ile Thr Gln Pro Asp Val Ile Tyr Gln
 65                  70                  75                  80

Ile His Lys Glu Tyr Leu Leu Ala Gly Ala Asp Ile Ile Glu Thr Asn
                 85                  90                  95

Thr Phe Ser Ser Thr Ser Ile Ala Gln Ala Asp Tyr Gly Leu Glu His
            100                 105                 110

Leu Ala Tyr Arg Met Asn Met Cys Ser Ala Gly Val Ala Arg Lys Ala
        115                 120                 125

Ala Glu Glu Val Thr Leu Gln Thr Gly Ile Lys Arg Phe Val Ala Gly
    130                 135                 140

Ala Leu Gly Pro Thr Asn Lys Thr Leu Ser Val Ser Pro Ser Val Glu
145                 150                 155                 160

Arg Pro Asp Tyr Arg Asn Ile Thr Phe Asp Glu Leu Val Glu Ala Tyr
                165                 170                 175

Gln Glu Gln Ala Lys Gly Leu Leu Asp Gly Gly Val Asp Ile Leu Leu
            180                 185                 190

Ile Glu Thr Ile Phe Asp Thr Ala Asn Ala Lys Ala Ala Leu Phe Ala
        195                 200                 205

Leu Gln Asn Leu Phe Glu Glu Lys Tyr Ala Pro Arg Pro Ile Phe Ile
    210                 215                 220

Ser Gly Thr Ile Val Asp Lys Ser Gly Arg Thr Leu Ser Gly Gln Thr
225                 230                 235                 240

Gly Glu Gly Phe Val Ile Ser Val Ser His Gly Glu Pro Leu Cys Ile
                245                 250                 255

Gly Leu Asn Cys Ala Leu Gly Ala Ala Glu Met Arg Pro Phe Ile Glu
```

-continued

```
            260                 265                 270

Ile Ile Gly Lys Cys Thr Thr Ala Tyr Val Leu Cys Tyr Pro Asn Ala
        275                 280                 285

Gly Leu Pro Asn Thr Phe Gly Asp Tyr Asp Glu Thr Pro Ser Met Met
    290                 295                 300

Ala Lys His Leu Lys Asp Phe Ala Met Asp Gly Leu Val Asn Ile Val
305                 310                 315                 320

Gly Gly Cys Cys Gly Ser Thr Pro Asp His Ile Arg Glu Ile Ala Glu
                325                 330                 335

Ala Val Lys Asn Cys Lys Pro Arg Val Pro Pro Ala Thr Ala Phe Glu
            340                 345                 350

Gly His Met Leu Leu Ser Gly Leu Glu Pro Phe Arg Ile Gly Pro Tyr
        355                 360                 365

Thr Asn Phe Val Asn Ile Gly Glu Arg Cys Asn Val Ala Gly Ser Arg
    370                 375                 380

Lys Phe Ala Lys Leu Ile Met Ala Gly Asn Tyr Glu Glu Ala Leu Cys
385                 390                 395                 400

Val Ala Lys Val Gln Val Glu Met Gly Ala Gln Val Leu Asp Val Asn
                405                 410                 415

Met Asp Asp Gly Met Leu Asp Gly Pro Ser Ala Met Thr Arg Phe Cys
            420                 425                 430

Asn Leu Ile Ala Ser Glu Pro Asp Ile Ala Lys Val Pro Leu Cys Ile
        435                 440                 445

Asp Ser Ser Asn Phe Ala Val Ile Glu Ala Gly Leu Lys Cys Cys Gln
    450                 455                 460

Gly Lys Cys Ile Val Asn Ser Ile Ser Leu Lys Glu Gly Glu Asp Asp
465                 470                 475                 480

Phe Leu Glu Lys Ala Arg Lys Ile Lys Lys Tyr Gly Ala Ala Met Val
                485                 490                 495

Val Met Ala Phe Asp Glu Glu Gly Gln Ala Thr Glu Thr Asp Thr Lys
            500                 505                 510

Ile Arg Val Cys Thr Arg Ala Tyr His Leu Leu Val Lys Lys Leu Gly
        515                 520                 525

Phe Asn Pro Asn Asp Ile Ile Phe Asp Pro Asn Ile Leu Thr Ile Gly
    530                 535                 540

Thr Gly Met Glu Glu His Asn Leu Tyr Ala Ile Asn Phe Ile His Ala
545                 550                 555                 560

Thr Lys Val Ile Lys Glu Thr Leu Pro Gly Ala Arg Ile Ser Gly Gly
                565                 570                 575

Leu Ser Asn Leu Ser Phe Ser Phe Arg Gly Met Glu Ala Ile Arg Glu
            580                 585                 590

Ala Met His Gly Val Phe Leu Tyr His Ala Ile Lys Ser Gly Met Asp
        595                 600                 605

Met Gly Ile Val Asn Ala Gly Asn Leu Pro Val Tyr Asp Asp Ile His
    610                 615                 620

Lys Glu Leu Leu Gln Leu Cys Glu Asp Leu Ile Trp Asn Lys Asp Pro
625                 630                 635                 640

Glu Ala Thr Glu Lys Leu Leu Arg Tyr Ala Gln Thr Gln Gly Thr Gly
                645                 650                 655

Gly Lys Lys Val Ile Gln Thr Asp Glu Trp Arg Asn Gly Pro Val Glu
            660                 665                 670

Glu Arg Leu Glu Tyr Ala Leu Val Lys Gly Ile Glu Lys His Ile Ile
        675                 680                 685
```

-continued

```
Glu Asp Thr Glu Glu Ala Arg Leu Asn Gln Lys Lys Tyr Pro Arg Pro
    690                 695                 700

Leu Asn Ile Ile Glu Gly Pro Leu Met Asn Gly Met Lys Ile Val Gly
705                 710                 715                 720

Asp Leu Phe Gly Ala Gly Lys Met Phe Leu Pro Gln Val Ile Lys Ser
                725                 730                 735

Ala Arg Val Met Lys Lys Ala Val Gly His Leu Ile Pro Phe Met Glu
            740                 745                 750

Lys Glu Arg Glu Glu Thr Arg Val Leu Asn Gly Thr Val Glu Glu Glu
        755                 760                 765

Asp Pro Tyr Gln Gly Thr Ile Val Leu Ala Thr Val Lys Gly Asp Val
    770                 775                 780

His Asp Ile Gly Lys Asn Ile Val Gly Val Val Leu Gly Cys Asn Asn
785                 790                 795                 800

Phe Arg Val Ile Asp Leu Gly Val Met Thr Pro Cys Asp Lys Ile Leu
                805                 810                 815

Lys Ala Ala Leu Asp His Lys Ala Asp Ile Ile Gly Leu Ser Gly Leu
            820                 825                 830

Ile Thr Pro Ser Leu Asp Glu Met Ile Phe Val Ala Lys Glu Met Glu
        835                 840                 845

Arg Leu Ala Ile Arg Ile Pro Leu Leu Ile Gly Gly Ala Thr Thr Ser
    850                 855                 860

Lys Thr His Thr Ala Val Lys Ile Ala Pro Arg Tyr Ser Ala Pro Val
865                 870                 875                 880

Ile His Val Leu Asp Ala Ser Lys Ser Val Val Val Cys Ser Gln Leu
                885                 890                 895

Leu Asp Glu Asn Leu Lys Asp Glu Tyr Phe Glu Glu Ile Met Glu Glu
            900                 905                 910

Tyr Glu Asp Ile Arg Gln Asp His Tyr Glu Ser Leu Lys Glu Arg Arg
        915                 920                 925

Tyr Leu Pro Leu Ser Gln Ala Arg Lys Ser Gly Phe Gln Met Asp Trp
    930                 935                 940

Leu Ser Glu Pro His Pro Val Lys Pro Thr Phe Ile Gly Thr Gln Val
945                 950                 955                 960

Phe Glu Asp Tyr Asp Leu Gln Lys Leu Val Asp Tyr Ile Asp Trp Lys
                965                 970                 975

Pro Phe Phe Asp Val Trp Gln Leu Arg Gly Lys Tyr Pro Asn Arg Gly
            980                 985                 990

Phe Pro Lys Ile Phe Asn Asp Lys Thr Val Gly Gly Glu Ala Arg Lys
        995                1000                1005

Val Tyr Asp Asp Ala His Asn Met Leu Asn Thr Leu Ile Ser Gln Lys
   1010                1015                1020

Lys Leu Arg Ala Arg Gly Val Val Gly Phe Trp Pro Ala Gln Ser Ile
1025                1030                1035                1040

Gln Asp Asp Ile His Leu Tyr Ala Glu Ala Ala Val Pro Gln Ala Ala
               1045                1050                1055

Glu Pro Ile Ala Thr Phe Tyr Gly Leu Arg Gln Gln Ala Glu Lys Asp
           1060                1065                1070

Ser Ala Ser Thr Glu Pro Tyr Tyr Cys Leu Ser Asp Phe Ile Ala Pro
       1075                1080                1085

Leu His Ser Gly Ile Arg Asp Tyr Leu Gly Leu Phe Ala Val Ala Cys
   1090                1095                1100
```

-continued

```
Phe Gly Val Glu Glu Leu Ser Lys Ala Tyr Glu Asp Asp Gly Asp Asp
1105                1110                1115                1120

Tyr Ser Ser Ile Met Val Lys Ala Leu Gly Asp Arg Leu Ala Glu Ala
                1125                1130                1135

Phe Ala Glu Glu Leu His Glu Arg Val Arg Arg Glu Leu Trp Ala Tyr
            1140                1145                1150

Cys Gly Ser Glu Gln Leu Asp Val Ala Asp Leu Arg Arg Leu Arg Tyr
        1155                1160                1165

Lys Gly Ile Arg Pro Ala Pro Gly Tyr Pro Ser Gln Pro Asp His Thr
    1170                1175                1180

Glu Lys Leu Thr Met Trp Arg Leu Ala Asp Ile Glu Gln Ser Thr Gly
1185                1190                1195                1200

Ile Arg Leu Thr Glu Ser Leu Ala Met Ala Pro Ala Ser Ala Val Ser
                1205                1210                1215

Gly Leu Tyr Phe Ser Asn Leu Lys Ser Lys Tyr Phe Ala Val Gly Lys
            1220                1225                1230

Ile Ser Lys Asp Gln Val Glu Asp Tyr Ala Leu Arg Lys Asn Ile Ser
        1235                1240                1245

Val Ala Glu Val Glu Lys Trp Leu Gly Pro Ile Leu Gly Tyr Asp Thr
    1250                1255                1260

Asp
1265


<210> SEQ ID NO 8
<211> LENGTH: 2542
<212> TYPE: DNA
<213> ORGANISM: Homo sapiens
<220> FEATURE:
<221> NAME/KEY: CDS
<222> LOCATION: (181)..(1833)
<220> FEATURE:
<223> OTHER INFORMATION: Polynucleotide encoding human cystathionine
      beta-synthase
<300> PUBLICATION INFORMATION:
<310> PATENT DOCUMENT NUMBER: 08/120,960
<311> PATENT FILING DATE: 1993-09-13
<312> PUBLICATION DATE: 1996-07-04

<400> SEQUENCE: 8

tgcagggcca ggacgcacgt ttcaagctca tcagtaaagg ttccttaaat tcccgaagca      60

agaagttaac caagtaaaac agcatcggaa caccaggatc ccatgacaga ttctgttgtc     120

acgtctcctt acagagtttg agcggtgctg aactgtcagc accatctgtc cggtcccagc     180

atg cct tct gag acc ccc cag gca gaa gtg ggg ccc aca ggc tgc ccc       228
Met Pro Ser Glu Thr Pro Gln Ala Glu Val Gly Pro Thr Gly Cys Pro
  1               5                  10                  15

cac cgc tca ggg cca cac tcg gcg aag ggg agc ctg gag aag ggg tcc       276
His Arg Ser Gly Pro His Ser Ala Lys Gly Ser Leu Glu Lys Gly Ser
             20                  25                  30

cca gag gat aag gaa gcc aag gag ccc ctg tgg atc cgg ccc gat gct       324
Pro Glu Asp Lys Glu Ala Lys Glu Pro Leu Trp Ile Arg Pro Asp Ala
         35                  40                  45

ccg agc agg tgc acc tgg cag ctg ggc cgg cct gcc tcc gag tcc cca       372
Pro Ser Arg Cys Thr Trp Gln Leu Gly Arg Pro Ala Ser Glu Ser Pro
     50                  55                  60

cat cac cac act gcc ccg gca aaa tct cca aaa atc ttg cca gat att       420
His His His Thr Ala Pro Ala Lys Ser Pro Lys Ile Leu Pro Asp Ile
 65                  70                  75                  80

ctg aag aaa atc ggg gac acc cct atg gtc aga atc aac aag att ggg       468
Leu Lys Lys Ile Gly Asp Thr Pro Met Val Arg Ile Asn Lys Ile Gly
```

-continued

```
                 85                  90                  95

aag aag ttc ggc ctg aag tgt gag ctc ttg gcc aag tgt gag ttc ttc      516
Lys Lys Phe Gly Leu Lys Cys Glu Leu Leu Ala Lys Cys Glu Phe Phe
            100                 105                 110

aac gcg ggc ggg agc gtg aag gac cgc atc agc ctg cgg atg att gag      564
Asn Ala Gly Gly Ser Val Lys Asp Arg Ile Ser Leu Arg Met Ile Glu
        115                 120                 125

gat gct gag cgc gac ggg acg ctg aag ccc ggg gac acg att atc gag      612
Asp Ala Glu Arg Asp Gly Thr Leu Lys Pro Gly Asp Thr Ile Ile Glu
    130                 135                 140

ccg aca tcc ggg aac acc ggg atc ggg ctg gcc ctg gct gcg gca gtg      660
Pro Thr Ser Gly Asn Thr Gly Ile Gly Leu Ala Leu Ala Ala Ala Val
145                 150                 155                 160

agg ggc tat cgc tgc atc atc gtg atg cca gag aag atg agc tcc gag      708
Arg Gly Tyr Arg Cys Ile Ile Val Met Pro Glu Lys Met Ser Ser Glu
                165                 170                 175

aag gtg gac gtg ctg cgg gca ctg ggg gct gag att gtg agg acg ccc      756
Lys Val Asp Val Leu Arg Ala Leu Gly Ala Glu Ile Val Arg Thr Pro
            180                 185                 190

acc aat gcc agg ttc gac tcc ccg gag tca cac gtg ggg gtg gcc tgg      804
Thr Asn Ala Arg Phe Asp Ser Pro Glu Ser His Val Gly Val Ala Trp
        195                 200                 205

cgg ctg aag aac gaa atc ccc aat tct cac atc cta gac cag tac cgc      852
Arg Leu Lys Asn Glu Ile Pro Asn Ser His Ile Leu Asp Gln Tyr Arg
    210                 215                 220

aac gcc agc aac ccc ctg gct cac tac gac acc acc gct gat gag atc      900
Asn Ala Ser Asn Pro Leu Ala His Tyr Asp Thr Thr Ala Asp Glu Ile
225                 230                 235                 240

ctg cag cag tgt gat ggg aag ctg gac atg ctg gtg gct tca gtg ggc      948
Leu Gln Gln Cys Asp Gly Lys Leu Asp Met Leu Val Ala Ser Val Gly
                245                 250                 255

acg ggc ggc acc atc acg ggc att gcc agg aag ctg aag gag aag tgt      996
Thr Gly Gly Thr Ile Thr Gly Ile Ala Arg Lys Leu Lys Glu Lys Cys
            260                 265                 270

cct gga tgc agg atc att ggg gtg gat ccc gaa ggg tcc atc ctc gca     1044
Pro Gly Cys Arg Ile Ile Gly Val Asp Pro Glu Gly Ser Ile Leu Ala
        275                 280                 285

gag ccg gag gag ctg aac cag acg gag cag aca acc tac gag gtg gaa     1092
Glu Pro Glu Glu Leu Asn Gln Thr Glu Gln Thr Thr Tyr Glu Val Glu
    290                 295                 300

ggg atc ggc tac gac ttc atc ccc acg gtg ctg gac agg acg gtg gtg     1140
Gly Ile Gly Tyr Asp Phe Ile Pro Thr Val Leu Asp Arg Thr Val Val
305                 310                 315                 320

gac aag tgg ttc aag agc aac gat gag gag gcg ttc acc ttt gcc cgc     1188
Asp Lys Trp Phe Lys Ser Asn Asp Glu Glu Ala Phe Thr Phe Ala Arg
                325                 330                 335

atg ctg atc gcg caa gag ggg ctg ctg tgc ggt ggc agt gct ggc agc     1236
Met Leu Ile Ala Gln Glu Gly Leu Leu Cys Gly Gly Ser Ala Gly Ser
            340                 345                 350

acg gtg gcg gtg gcc gtg aag gct gcg cag gag ctg cag gag ggc cag     1284
Thr Val Ala Val Ala Val Lys Ala Ala Gln Glu Leu Gln Glu Gly Gln
        355                 360                 365

cgc tgc gtg gtc att ctg ccc gac tca gtg cgg aac tac atg acc aag     1332
Arg Cys Val Val Ile Leu Pro Asp Ser Val Arg Asn Tyr Met Thr Lys
    370                 375                 380

ttc ctg agc gac agg tgg atg ctg cag aag ggc ttt ctg aag gag gag     1380
Phe Leu Ser Asp Arg Trp Met Leu Gln Lys Gly Phe Leu Lys Glu Glu
385                 390                 395                 400

gac ctc acg gag aag aag ccc tgg tgg tgg cac ctc cgt gtt cag gag     1428
```

-continued

Asp Leu Thr Glu Lys Lys Pro Trp Trp Trp His Leu Arg Val Gln Glu
405 410 415 ctg ggc ctg tca gcc ccg ctg acc gtg ctc ccg acc atc acc tgt ggg 1476
Leu Gly Leu Ser Ala Pro Leu Thr Val Leu Pro Thr Ile Thr Cys Gly
420 425 430 cac acc atc gag atc ctc cgg gag aag ggc ttc gac cag gcg ccc gtg 1524
His Thr Ile Glu Ile Leu Arg Glu Lys Gly Phe Asp Gln Ala Pro Val
435 440 445 gtg gat gag gcg ggg gta atc ctg gga atg gtg acg ctt ggg aac atg 1572
Val Asp Glu Ala Gly Val Ile Leu Gly Met Val Thr Leu Gly Asn Met
450 455 460 ctc tcg tcc ctg ctt gcc ggg aag gtg cag ccg tca gac caa gtt ggc 1620
Leu Ser Ser Leu Leu Ala Gly Lys Val Gln Pro Ser Asp Gln Val Gly
465 470 475 480 aaa gtc atc tac aag cag ttc aaa cag atc cgc ctc acg gac acg ctg 1668
Lys Val Ile Tyr Lys Gln Phe Lys Gln Ile Arg Leu Thr Asp Thr Leu
485 490 495 ggc agg ctc tcg cac atc ctg gag atg gac cac ttc gcc ctg gtg gtg 1716
Gly Arg Leu Ser His Ile Leu Glu Met Asp His Phe Ala Leu Val Val
500 505 510 cac gag cag atc cag tac cac agc acc ggg aag tcc agt cag cgg cag 1764
His Glu Gln Ile Gln Tyr His Ser Thr Gly Lys Ser Ser Gln Arg Gln
515 520 525 atg gtg ttc ggg gtg gtc acc gcc att gac ttg ctg aac ttc gtg gcc 1812
Met Val Phe Gly Val Val Thr Ala Ile Asp Leu Leu Asn Phe Val Ala
530 535 540 gcc cag gag cgg gac cag aag tgaagtccgg agcgctgggc ggtgtggagc 1863
Ala Gln Glu Arg Asp Gln Lys
545 550 gggcccgcca cccttgccca cttctccttc gctttcctga gccctaaaca cacgcgtgat 1923 tggtaactgc ctggcctggc accgttatcc ctgcacacgg cacagagcat ccgtctcccc 1983 tcgttaacac atggcttcct aaatggccct gtttacggcc tatgagatga aatatgtgat 2043 tttctctaat gtaacttcct cttaggatgt ttcaccaagg aaatattgag agagaagtcg 2103 gccaggtagg atgaacacag gcaatgactg cgcagagtgg attaaaggca aaagagagaa 2163 gagtccagga aggggcgggg agaagcctgg gtggctcagc atcctccacg ggctgcgcgt 2223 ctgctcgggg ctgagctggc gggacgagtt tgcgtgtttg ggttttttaa ttgagatgaa 2283 attcaaataa cctaaaaatc aatcacttga aagtgaacaa tcagcggcat ttagtacatc 2343 cagaaagttg tgtaggcacc acctctgtca cgttctggaa cattctgtca tcaccccgtg 2403 aagcaatcat ttcccctccc gtcttcctcc tcccctggca actgctgtcg actttgtgtc 2463 tctgttgtct aaaataggtt ttccctgttc tggacatttc atataaatgg aatcacacaa 2523 aaaaaaaaaa aaaaaaaaa 2542

<210> SEQ ID NO 9
<211> LENGTH: 551
<212> TYPE: PRT
<213> ORGANISM: Homo sapiens

<400> SEQUENCE: 9

Met Pro Ser Glu Thr Pro Gln Ala Glu Val Gly Pro Thr Gly Cys Pro
1 5 10 15

His Arg Ser Gly Pro His Ser Ala Lys Gly Ser Leu Glu Lys Gly Ser
20 25 30

Pro Glu Asp Lys Glu Ala Lys Glu Pro Leu Trp Ile Arg Pro Asp Ala
35 40 45

-continued

```
Pro Ser Arg Cys Thr Trp Gln Leu Gly Arg Pro Ala Ser Glu Ser Pro
     50                  55                  60

His His His Thr Ala Pro Ala Lys Ser Pro Lys Ile Leu Pro Asp Ile
 65                  70                  75                  80

Leu Lys Lys Ile Gly Asp Thr Pro Met Val Arg Ile Asn Lys Ile Gly
                 85                  90                  95

Lys Lys Phe Gly Leu Lys Cys Glu Leu Leu Ala Lys Cys Glu Phe Phe
            100                 105                 110

Asn Ala Gly Gly Ser Val Lys Asp Arg Ile Ser Leu Arg Met Ile Glu
        115                 120                 125

Asp Ala Glu Arg Asp Gly Thr Leu Lys Pro Gly Asp Thr Ile Ile Glu
    130                 135                 140

Pro Thr Ser Gly Asn Thr Gly Ile Gly Leu Ala Leu Ala Ala Ala Val
145                 150                 155                 160

Arg Gly Tyr Arg Cys Ile Ile Val Met Pro Glu Lys Met Ser Ser Glu
                165                 170                 175

Lys Val Asp Val Leu Arg Ala Leu Gly Ala Glu Ile Val Arg Thr Pro
            180                 185                 190

Thr Asn Ala Arg Phe Asp Ser Pro Glu Ser His Val Gly Val Ala Trp
        195                 200                 205

Arg Leu Lys Asn Glu Ile Pro Asn Ser His Ile Leu Asp Gln Tyr Arg
    210                 215                 220

Asn Ala Ser Asn Pro Leu Ala His Tyr Asp Thr Thr Ala Asp Glu Ile
225                 230                 235                 240

Leu Gln Gln Cys Asp Gly Lys Leu Asp Met Leu Val Ala Ser Val Gly
                245                 250                 255

Thr Gly Gly Thr Ile Thr Gly Ile Ala Arg Lys Leu Lys Glu Lys Cys
            260                 265                 270

Pro Gly Cys Arg Ile Ile Gly Val Asp Pro Glu Gly Ser Ile Leu Ala
        275                 280                 285

Glu Pro Glu Glu Leu Asn Gln Thr Glu Gln Thr Thr Tyr Glu Val Glu
    290                 295                 300

Gly Ile Gly Tyr Asp Phe Ile Pro Thr Val Leu Asp Arg Thr Val Val
305                 310                 315                 320

Asp Lys Trp Phe Lys Ser Asn Asp Glu Glu Ala Phe Thr Phe Ala Arg
                325                 330                 335

Met Leu Ile Ala Gln Glu Gly Leu Leu Cys Gly Gly Ser Ala Gly Ser
            340                 345                 350

Thr Val Ala Val Ala Val Lys Ala Ala Gln Glu Leu Gln Glu Gly Gln
        355                 360                 365

Arg Cys Val Val Ile Leu Pro Asp Ser Val Arg Asn Tyr Met Thr Lys
    370                 375                 380

Phe Leu Ser Asp Arg Trp Met Leu Gln Lys Gly Phe Leu Lys Glu Glu
385                 390                 395                 400

Asp Leu Thr Glu Lys Lys Pro Trp Trp Trp His Leu Arg Val Gln Glu
                405                 410                 415

Leu Gly Leu Ser Ala Pro Leu Thr Val Leu Pro Thr Ile Thr Cys Gly
            420                 425                 430

His Thr Ile Glu Ile Leu Arg Glu Lys Gly Phe Asp Gln Ala Pro Val
        435                 440                 445

Val Asp Glu Ala Gly Val Ile Leu Gly Met Val Thr Leu Gly Asn Met
    450                 455                 460
```

-continued

```
Leu Ser Ser Leu Leu Ala Gly Lys Val Gln Pro Ser Asp Gln Val Gly
465                 470                 475                 480

Lys Val Ile Tyr Lys Gln Phe Lys Gln Ile Arg Leu Thr Asp Thr Leu
                485                 490                 495

Gly Arg Leu Ser His Ile Leu Glu Met Asp His Phe Ala Leu Val Val
            500                 505                 510

His Glu Gln Ile Gln Tyr His Ser Thr Gly Lys Ser Ser Gln Arg Gln
        515                 520                 525

Met Val Phe Gly Val Val Thr Ala Ile Asp Leu Leu Asn Phe Val Ala
    530                 535                 540

Ala Gln Glu Arg Asp Gln Lys
545                 550


<210> SEQ ID NO 10
<211> LENGTH: 1221
<212> TYPE: DNA
<213> ORGANISM: Homo sapiens
<220> FEATURE:
<223> OTHER INFORMATION: Human betaine-homocysteine methyltransferase
      gene: exons 1-8
<300> PUBLICATION INFORMATION:
<308> DATABASE ACCESSION NUMBER: AF118371-8/GenBank

<400> SEQUENCE: 10

atgccacccg ttgggggcaa aaaggccaag aagggcatcc tagaacgttt aaatgctgga     60

gagattgtga ttggagatgg agggtttgtc tttgcactgg agaagagggg ctacgtaaag    120

gcaggaccct ggactcctga agctgctgtg gagcacccag aagcagttcg ccagcttcat    180

cgagagttcc tcagagctgg ctcaaacgtc atgcagacct tcaccttcta tgcgagtgaa    240

gacaagctgg agaacagggg caactatgtc ttagagaaga tatctgggca ggaagtcaat    300

gaagctgctt gcgacatcgc ccgacaagtg gctgatgaag gagatgcttt ggtagcagga    360

ggagtgagtc agacaccttc ataccttagc tgcaagagtg aaactgaagt caaaaaagta    420

tttctgcaac agttagaggt ctttatgaag aagaacgtgg acttcttgat tgcagagtat    480

tttgaacacg ttgaagaagc tgtgtgggca gttgaaacct tgatagcatc cggtaaacct    540

gtggcagcaa ccatgtgcat tggcccagaa ggagatttgc atggcgtgcc ccccggcgag    600

tgtgcagtgc gcctggtgaa agcaggagca tccatcattg gtgtgaactg ccactttgac    660

cccaccatta gtttaaaaac agtgaagctc atgaaggagg gcttggaggc tgcccgactg    720

aaagctcacc tgatgagcca gcccttggct taccacactc ctgactgcaa caagcaggga    780

ttcatcgatc tcccagaatt cccatttgga ctggaaccca gagttgccac cagatgggat    840

attcaaaaat acgccagaga ggcctacaac ctgggggtca ggtacattgg cgggtgctgt    900

ggatttgagc cctaccacat cagggcaatt gcagaggagc tggccccaga aaggggcttt    960

ttgccaccag cttcagaaaa acatggcagc tggggaagtg gtttggacat gcacaccaaa   1020

ccctgggtta gagcaagggc caggaaggaa tactgggaga atcttcggat agcctcaggc   1080

cggccataca acccttcaat gtcaaagcca gatggctggg gagtgaccaa aggaacagcc   1140

gagctgatgc agcagaaaga agccacaact gagcagcagc tgaaagagct ctttgaaaaa   1200

caaaaattca aatcacagta g                                             1221


<210> SEQ ID NO 11
<211> LENGTH: 1369
<212> TYPE: DNA
<213> ORGANISM: Pseudomonas putida
<220> FEATURE:
```

```
<221> NAME/KEY: CDS
<222> LOCATION: (48)..(1241)
<220> FEATURE:
<223> OTHER INFORMATION: Pseudomonas putida methioninase-encoding
      nucleic acid
<300> PUBLICATION INFORMATION:
<310> PATENT DOCUMENT NUMBER: 08/642,541
<311> PATENT FILING DATE: 1996-05-03
<312> PUBLICATION DATE: 1999-04-06

<400> SEQUENCE: 11

gccggtctgt ggaataagct tataacaaac cacaagaggc ggttgcc atg cac ggc       56
                                                    Met His Gly
                                                      1

tcc aac aag ctc cca gga ttt gcc acc cgc gcc att cac cat ggc tac      104
Ser Asn Lys Leu Pro Gly Phe Ala Thr Arg Ala Ile His His Gly Tyr
      5                  10                  15

gac ccc cag gac cac ggc ggc gca ctg gtg cca ccg gtc tac cag acc      152
Asp Pro Gln Asp His Gly Gly Ala Leu Val Pro Pro Val Tyr Gln Thr
 20                  25                  30                  35

gcg acg ttc acc ttc ccc acc gtg gaa tac ggc gct gcg tgc ttt gcc      200
Ala Thr Phe Thr Phe Pro Thr Val Glu Tyr Gly Ala Ala Cys Phe Ala
                 40                  45                  50

ggc gag cag gcc ggc cat ttc tac agc cgc atc tcc aac ccc acc ctc      248
Gly Glu Gln Ala Gly His Phe Tyr Ser Arg Ile Ser Asn Pro Thr Leu
             55                  60                  65

aac ctg ctg gaa gca cgc atg gcc tcg ctg gaa ggc ggc gag gcc ggg      296
Asn Leu Leu Glu Ala Arg Met Ala Ser Leu Glu Gly Gly Glu Ala Gly
         70                  75                  80

ctg gcg ctg gcc tcg ggc atg ggg gcg atc acg tcc acg cta tgg aca      344
Leu Ala Leu Ala Ser Gly Met Gly Ala Ile Thr Ser Thr Leu Trp Thr
     85                  90                  95

ctg ctg cgc ccc ggt gac gag gtg ctg ctg ggc aac acc ctg tac ggc      392
Leu Leu Arg Pro Gly Asp Glu Val Leu Leu Gly Asn Thr Leu Tyr Gly
100                 105                 110                 115

tgc acc ttt gcc ttc ctg cac cac ggc atc ggc gag ttc ggg gtc aag      440
Cys Thr Phe Ala Phe Leu His His Gly Ile Gly Glu Phe Gly Val Lys
                120                 125                 130

ctg cgc cat gtg gac atg gcc gac ctg cag gca ctg gag gcg gcc atg      488
Leu Arg His Val Asp Met Ala Asp Leu Gln Ala Leu Glu Ala Ala Met
            135                 140                 145

acg ccg gcc acc cgg gtg atc tat ttc gag tcg ccg gcc aac ccc aac      536
Thr Pro Ala Thr Arg Val Ile Tyr Phe Glu Ser Pro Ala Asn Pro Asn
        150                 155                 160

atg cac atg gcc gat atc gcc ggc gtg gcg aag att gca cgc aag cac      584
Met His Met Ala Asp Ile Ala Gly Val Ala Lys Ile Ala Arg Lys His
    165                 170                 175

ggc gcg acc gtg gtg gtc gac aac acc tac tgc acg ccg tac ctg caa      632
Gly Ala Thr Val Val Val Asp Asn Thr Tyr Cys Thr Pro Tyr Leu Gln
180                 185                 190                 195

cgg cca ctg gag ctg ggc gcc gac ctg gtg gtg cat tcg gcc acc aag      680
Arg Pro Leu Glu Leu Gly Ala Asp Leu Val Val His Ser Ala Thr Lys
                200                 205                 210

tac ctg agc ggc cat ggc gac atc act gct ggc att gtg gtg ggc agc      728
Tyr Leu Ser Gly His Gly Asp Ile Thr Ala Gly Ile Val Val Gly Ser
            215                 220                 225

cag gca ctg gtg gac cgt ata cgt ctg cag ggc ctc aag gac atg acc      776
Gln Ala Leu Val Asp Arg Ile Arg Leu Gln Gly Leu Lys Asp Met Thr
        230                 235                 240

ggt gcg gtg ctc tcg ccc cat gac gcc gca ctg ttg atg cgc ggc atc      824
Gly Ala Val Leu Ser Pro His Asp Ala Ala Leu Leu Met Arg Gly Ile
    245                 250                 255
```

-continued

```
aag acc ctc aac ctg cgc atg gac cgc cac tgc gcc aac gct cag gtg      872
Lys Thr Leu Asn Leu Arg Met Asp Arg His Cys Ala Asn Ala Gln Val
260                 265                 270                 275

ctg gcc gag ttc ctc gcc cgg cag ccg cag gtg gag ctg atc cat tac      920
Leu Ala Glu Phe Leu Ala Arg Gln Pro Gln Val Glu Leu Ile His Tyr
                280                 285                 290

ccg ggc ctg gcg agc ttc ccg cag tac acc ctg gcc cgc cag cag atg      968
Pro Gly Leu Ala Ser Phe Pro Gln Tyr Thr Leu Ala Arg Gln Gln Met
            295                 300                 305

agc cag ccg ggc ggc atg atc gcc ttc gaa ctc aag ggc ggc atc ggt     1016
Ser Gln Pro Gly Gly Met Ile Ala Phe Glu Leu Lys Gly Gly Ile Gly
        310                 315                 320

gcc ggg cgg cgg ttc atg aac gcc ctg caa ctg ttc agc cgc gcg gtg     1064
Ala Gly Arg Arg Phe Met Asn Ala Leu Gln Leu Phe Ser Arg Ala Val
    325                 330                 335

agc ctg ggc gat gcc gag tcg ctg gcg cag cac ccg gca agc atg act     1112
Ser Leu Gly Asp Ala Glu Ser Leu Ala Gln His Pro Ala Ser Met Thr
340                 345                 350                 355

cat tcc agc tat acc cca gag gag cgt gcg cat tac ggc atc tcc gag     1160
His Ser Ser Tyr Thr Pro Glu Glu Arg Ala His Tyr Gly Ile Ser Glu
                360                 365                 370

ggg ctg gtg cgg ttg tcg gtg ggg ctg gaa gac atc gac gac ctg ctg     1208
Gly Leu Val Arg Leu Ser Val Gly Leu Glu Asp Ile Asp Asp Leu Leu
            375                 380                 385

gcc gat gtg caa cag gca ctc aag gcg agt gcc tgaacccgtc acggatgagg   1261
Ala Asp Val Gln Gln Ala Leu Lys Ala Ser Ala
        390                 395

tcaatgcaat ggtggcaatg atgaaccttg tgcctggcga cggcgtgccc ggtgacagcg   1321

accctggcga aactgcagag tggctggagg cgctggagtc gaccctgg                1369


<210> SEQ ID NO 12
<211> LENGTH: 398
<212> TYPE: PRT
<213> ORGANISM: Pseudomonas putida

<400> SEQUENCE: 12

Met His Gly Ser Asn Lys Leu Pro Gly Phe Ala Thr Arg Ala Ile His
  1               5                  10                  15

His Gly Tyr Asp Pro Gln Asp His Gly Gly Ala Leu Val Pro Pro Val
             20                  25                  30

Tyr Gln Thr Ala Thr Phe Thr Phe Pro Thr Val Glu Tyr Gly Ala Ala
         35                  40                  45

Cys Phe Ala Gly Glu Gln Ala Gly His Phe Tyr Ser Arg Ile Ser Asn
     50                  55                  60

Pro Thr Leu Asn Leu Leu Glu Ala Arg Met Ala Ser Leu Glu Gly Gly
 65                  70                  75                  80

Glu Ala Gly Leu Ala Leu Ala Ser Gly Met Gly Ala Ile Thr Ser Thr
                85                  90                  95

Leu Trp Thr Leu Leu Arg Pro Gly Asp Glu Val Leu Leu Gly Asn Thr
            100                 105                 110

Leu Tyr Gly Cys Thr Phe Ala Phe Leu His His Gly Ile Gly Glu Phe
        115                 120                 125

Gly Val Lys Leu Arg His Val Asp Met Ala Asp Leu Gln Ala Leu Glu
    130                 135                 140

Ala Ala Met Thr Pro Ala Thr Arg Val Ile Tyr Phe Glu Ser Pro Ala
145                 150                 155                 160
```

-continued

```
Asn Pro Asn Met His Met Ala Asp Ile Ala Gly Val Ala Lys Ile Ala
                165                 170                 175

Arg Lys His Gly Ala Thr Val Val Val Asp Asn Thr Tyr Cys Thr Pro
            180                 185                 190

Tyr Leu Gln Arg Pro Leu Glu Leu Gly Ala Asp Leu Val Val His Ser
        195                 200                 205

Ala Thr Lys Tyr Leu Ser Gly His Gly Asp Ile Thr Ala Gly Ile Val
    210                 215                 220

Val Gly Ser Gln Ala Leu Val Asp Arg Ile Arg Leu Gln Gly Leu Lys
225                 230                 235                 240

Asp Met Thr Gly Ala Val Leu Ser Pro His Asp Ala Ala Leu Leu Met
                245                 250                 255

Arg Gly Ile Lys Thr Leu Asn Leu Arg Met Asp Arg His Cys Ala Asn
            260                 265                 270

Ala Gln Val Leu Ala Glu Phe Leu Ala Arg Gln Pro Gln Val Glu Leu
        275                 280                 285

Ile His Tyr Pro Gly Leu Ala Ser Phe Pro Gln Tyr Thr Leu Ala Arg
    290                 295                 300

Gln Gln Met Ser Gln Pro Gly Gly Met Ile Ala Phe Glu Leu Lys Gly
305                 310                 315                 320

Gly Ile Gly Ala Gly Arg Arg Phe Met Asn Ala Leu Gln Leu Phe Ser
                325                 330                 335

Arg Ala Val Ser Leu Gly Asp Ala Glu Ser Leu Ala Gln His Pro Ala
            340                 345                 350

Ser Met Thr His Ser Ser Tyr Thr Pro Glu Glu Arg Ala His Tyr Gly
        355                 360                 365

Ile Ser Glu Gly Leu Val Arg Leu Ser Val Gly Leu Glu Asp Ile Asp
    370                 375                 380

Asp Leu Leu Ala Asp Val Gln Gln Ala Leu Lys Ala Ser Ala
385                 390                 395


<210> SEQ ID NO 13
<211> LENGTH: 1615
<212> TYPE: DNA
<213> ORGANISM: Pseudomonas putida
<220> FEATURE:
<221> NAME/KEY: CDS
<222> LOCATION: (304)..(1500)
<223> OTHER INFORMATION: Pseudomonas putida methionine gamma-lyase
<300> PUBLICATION INFORMATION:
<308> DATABASE ACCESSION NUMBER: L43133/GenBank

<400> SEQUENCE: 13

ataggatggc ctggtagcca gtgatatagc cgttgtcttc cagcagcttg acccggcgcc      60

agcaggggcg aggtggtcaa tgccacctgg tcggcaagtt cggcgacggt taggcgggcg     120

ttgtcctgca aggcggcgag cagggcgcgg tcggtgcggt cgaggcttga aggcatgttt     180

tgccctcctg gtccgttaat tattgttttt gttccagcaa gcacgcagat gcgtgggcaa     240

ttttggaaaa aatcgggcag ctcggtggca taagcttata acaaaccaca agaggctgtt     300

gcc atg cgc gac tcc cat aac aac acc ggt ttt tcc aca cgg gcc att      348
    Met Arg Asp Ser His Asn Asn Thr Gly Phe Ser Thr Arg Ala Ile
      1               5                  10                  15

cac cac ggc tac gac ccg ctt tcc cac ggt ggt gcc ttg gtg cca ccg      396
His His Gly Tyr Asp Pro Leu Ser His Gly Gly Ala Leu Val Pro Pro
                 20                  25                  30

gtg tac cag acc gcg acc tat gcc ttc ccg act gtc gaa tac ggc gct      444
Val Tyr Gln Thr Ala Thr Tyr Ala Phe Pro Thr Val Glu Tyr Gly Ala
```

-continued

```
             35                  40                  45

gcg tgc ttc gcc ggg gag gag gcg ggg cac ttc tac agc cgc atc tcc      492
Ala Cys Phe Ala Gly Glu Glu Ala Gly His Phe Tyr Ser Arg Ile Ser
         50                  55                  60

aac ccc acc ctg gcc ttg ctc gag caa cgc atg gcc tcg ttg gag ggt      540
Asn Pro Thr Leu Ala Leu Leu Glu Gln Arg Met Ala Ser Leu Glu Gly
     65                  70                  75

ggt gag gcg gga ttg gcg ctg gcg tcg ggg atg gga gcc att act tcg      588
Gly Glu Ala Gly Leu Ala Leu Ala Ser Gly Met Gly Ala Ile Thr Ser
 80                  85                  90                  95

acc ctc tgg acc ctg ctg cgg cct ggt gat gag ctg atc gtg ggg cgc      636
Thr Leu Trp Thr Leu Leu Arg Pro Gly Asp Glu Leu Ile Val Gly Arg
                100                 105                 110

acc ttg tat ggc tgc acc ttt gcg ttc ctg cac cat ggc att ggc gag      684
Thr Leu Tyr Gly Cys Thr Phe Ala Phe Leu His His Gly Ile Gly Glu
            115                 120                 125

ttc ggg gtc aag atc cac cat gtc gac ctt aac gat gcc aag gcc ctg      732
Phe Gly Val Lys Ile His His Val Asp Leu Asn Asp Ala Lys Ala Leu
        130                 135                 140

aaa gcg gcg atc aac agc aaa acg cgg atg atc tac ttc gaa aca ccg      780
Lys Ala Ala Ile Asn Ser Lys Thr Arg Met Ile Tyr Phe Glu Thr Pro
    145                 150                 155

gcc aac ccc aac atg caa ctg gtg gat ata gcg gcg gtc gtc gag gca      828
Ala Asn Pro Asn Met Gln Leu Val Asp Ile Ala Ala Val Val Glu Ala
160                 165                 170                 175

gtg cgg ggg agt gat gtg ctt gtg gtg gtc gac aac acc tac tgc acg      876
Val Arg Gly Ser Asp Val Leu Val Val Val Asp Asn Thr Tyr Cys Thr
                180                 185                 190

ccc tac ctg cag cgg cca ctg gaa ctg ggg gca gac ctg gtg gtg cat      924
Pro Tyr Leu Gln Arg Pro Leu Glu Leu Gly Ala Asp Leu Val Val His
            195                 200                 205

tcg gca acc aag tac ctc agt ggc cat ggc gac atc act gcg ggc ctg      972
Ser Ala Thr Lys Tyr Leu Ser Gly His Gly Asp Ile Thr Ala Gly Leu
        210                 215                 220

gtg gtg ggg cgc aag gct ttg gtc gac cgc att cgg ctg gaa ggg ctg     1020
Val Val Gly Arg Lys Ala Leu Val Asp Arg Ile Arg Leu Glu Gly Leu
    225                 230                 235

aaa gac atg acc ggg gca gcc ttg tca ccg cat gac gct gcg ttg ttg     1068
Lys Asp Met Thr Gly Ala Ala Leu Ser Pro His Asp Ala Ala Leu Leu
240                 245                 250                 255

atg cgc ggc atc aag acc ctg gcg ctg cgc atg gac cgg cat tgc gcc     1116
Met Arg Gly Ile Lys Thr Leu Ala Leu Arg Met Asp Arg His Cys Ala
                260                 265                 270

aac gcc ctg gag gtc gcg cag ttc ctg gcc ggg cag ccc cag gtg gag     1164
Asn Ala Leu Glu Val Ala Gln Phe Leu Ala Gly Gln Pro Gln Val Glu
            275                 280                 285

ctg atc cac tac ccg ggc ttg ccg tcg ttt gcc cag tac gaa ctg gca     1212
Leu Ile His Tyr Pro Gly Leu Pro Ser Phe Ala Gln Tyr Glu Leu Ala
        290                 295                 300

cag cgg cag atg cgt ttg ccg ggc ggg atg att gcc ttt gag ctc aag     1260
Gln Arg Gln Met Arg Leu Pro Gly Gly Met Ile Ala Phe Glu Leu Lys
    305                 310                 315

ggc ggt atc gag gcc ggg cgc ggc ttc atg aat gcc ctg cag ctt ttt     1308
Gly Gly Ile Glu Ala Gly Arg Gly Phe Met Asn Ala Leu Gln Leu Phe
320                 325                 330                 335

gcc cgt gcg gtg agc ctg ggg gat gcc gag tcg ctg gca cag cac ccg     1356
Ala Arg Ala Val Ser Leu Gly Asp Ala Glu Ser Leu Ala Gln His Pro
                340                 345                 350

gcg agc atg acg cac tcc agt tac acg cca caa gag cgg gcg cat cac     1404
```

```
Ala Ser Met Thr His Ser Ser Tyr Thr Pro Gln Glu Arg Ala His His
            355                 360                 365

ggg ata tca gag ggg ctg gtg agg ttg tca gtg ggg ctg gag gat gtg     1452
Gly Ile Ser Glu Gly Leu Val Arg Leu Ser Val Gly Leu Glu Asp Val
        370                 375                 380

gag gac ctg ctg gca gat atc gag ttg gcg ttg gag gcg tgt gca tga     1500
Glu Asp Leu Leu Ala Asp Ile Glu Leu Ala Leu Glu Ala Cys Ala
    385                 390                 395

acttgccttg caggatcggg aacacttgcc caatgcctca cgggatcagg cgatggcact   1560

ttggatgagc tggtgaattg gccggcttat ccaagaggag tttaaaatga ccgta        1615


<210> SEQ ID NO 14
<211> LENGTH: 398
<212> TYPE: PRT
<213> ORGANISM: Pseudomonas putida

<400> SEQUENCE: 14

Met Arg Asp Ser His Asn Asn Thr Gly Phe Ser Thr Arg Ala Ile His
  1               5                  10                  15

His Gly Tyr Asp Pro Leu Ser His Gly Gly Ala Leu Val Pro Pro Val
            20                  25                  30

Tyr Gln Thr Ala Thr Tyr Ala Phe Pro Thr Val Glu Tyr Gly Ala Ala
        35                  40                  45

Cys Phe Ala Gly Glu Glu Ala Gly His Phe Tyr Ser Arg Ile Ser Asn
    50                  55                  60

Pro Thr Leu Ala Leu Leu Glu Gln Arg Met Ala Ser Leu Glu Gly Gly
 65                  70                  75                  80

Glu Ala Gly Leu Ala Leu Ala Ser Gly Met Gly Ala Ile Thr Ser Thr
                85                  90                  95

Leu Trp Thr Leu Leu Arg Pro Gly Asp Glu Leu Ile Val Gly Arg Thr
            100                 105                 110

Leu Tyr Gly Cys Thr Phe Ala Phe Leu His His Gly Ile Gly Glu Phe
        115                 120                 125

Gly Val Lys Ile His His Val Asp Leu Asn Asp Ala Lys Ala Leu Lys
    130                 135                 140

Ala Ala Ile Asn Ser Lys Thr Arg Met Ile Tyr Phe Glu Thr Pro Ala
145                 150                 155                 160

Asn Pro Asn Met Gln Leu Val Asp Ile Ala Ala Val Val Glu Ala Val
                165                 170                 175

Arg Gly Ser Asp Val Leu Val Val Val Asp Asn Thr Tyr Cys Thr Pro
            180                 185                 190

Tyr Leu Gln Arg Pro Leu Glu Leu Gly Ala Asp Leu Val Val His Ser
        195                 200                 205

Ala Thr Lys Tyr Leu Ser Gly His Gly Asp Ile Thr Ala Gly Leu Val
    210                 215                 220

Val Gly Arg Lys Ala Leu Val Asp Arg Ile Arg Leu Glu Gly Leu Lys
225                 230                 235                 240

Asp Met Thr Gly Ala Ala Leu Ser Pro His Asp Ala Ala Leu Leu Met
                245                 250                 255

Arg Gly Ile Lys Thr Leu Ala Leu Arg Met Asp Arg His Cys Ala Asn
            260                 265                 270

Ala Leu Glu Val Ala Gln Phe Leu Ala Gly Gln Pro Gln Val Glu Leu
        275                 280                 285

Ile His Tyr Pro Gly Leu Pro Ser Phe Ala Gln Tyr Glu Leu Ala Gln
    290                 295                 300
```

```
Arg Gln Met Arg Leu Pro Gly Gly Met Ile Ala Phe Glu Leu Lys Gly
305                 310                 315                 320

Gly Ile Glu Ala Gly Arg Gly Phe Met Asn Ala Leu Gln Leu Phe Ala
                325                 330                 335

Arg Ala Val Ser Leu Gly Asp Ala Glu Ser Leu Ala Gln His Pro Ala
            340                 345                 350

Ser Met Thr His Ser Ser Tyr Thr Pro Gln Glu Arg Ala His His Gly
        355                 360                 365

Ile Ser Glu Gly Leu Val Arg Leu Ser Val Gly Leu Glu Asp Val Glu
    370                 375                 380

Asp Leu Leu Ala Asp Ile Glu Leu Ala Leu Glu Ala Cys Ala
385                 390                 395


<210> SEQ ID NO 15
<211> LENGTH: 3564
<212> TYPE: DNA
<213> ORGANISM: Homo sapiens
<220> FEATURE:
<221> NAME/KEY: CDS
<222> LOCATION: (414)..(2558)
<220> FEATURE:
<223> OTHER INFORMATION: Human adenosine deaminase DRADA2c
<300> PUBLICATION INFORMATION:
<308> DATABASE ACCESSION NUMBER: U76422/GenBank

<400> SEQUENCE: 15

gcggcggcgg cggcggcggc ggcagcggcg gccaagcggc caggttggcg gccggggctc      60

cgggccgcgc gaggccacgg ccacgccgcg ccgctgcgca caaccaacga ggcagagcgc     120

cgcccggcgc gagactgcgg ccgaagcgtg ggcgcgcgt gcggaggacc aggcgcggcg     180

cggctgcggc tgagagtgga gcctttcagg ctggcatgga gagcttaagg ggcaactgaa     240

ggagacacac tggccaagcg cggagttctg cttacttcag tcctgctgag atactctctc     300

agtccgctcg caccgaagga agctgccttg ggatcagagc agacataaag ctagaaaaat     360

ttcaagacag aaacagtctc cgccagtcaa gaaaccctca aaagtatttt gcc atg        416
                                                           Met
                                                            1

gat ata gaa gat gaa gaa aac atg agt tcc agc agc act gat gtg aag       464
Asp Ile Glu Asp Glu Glu Asn Met Ser Ser Ser Ser Thr Asp Val Lys
            5                   10                  15

gaa aac cgc aat ctg gac aac gtg tcc ccc aag gat ggc agc aca cct       512
Glu Asn Arg Asn Leu Asp Asn Val Ser Pro Lys Asp Gly Ser Thr Pro
        20                  25                  30

ggg cct ggc gag ggc tct cag ctc tcc aat ggg ggt ggt ggt ggc ccc       560
Gly Pro Gly Glu Gly Ser Gln Leu Ser Asn Gly Gly Gly Gly Gly Pro
     35                  40                  45

ggc aga aag cgg ccc ctg gag gag ggc agc aat ggc cac tcc aag tac       608
Gly Arg Lys Arg Pro Leu Glu Glu Gly Ser Asn Gly His Ser Lys Tyr
 50                  55                  60                  65

cgc ctg aag aaa agg agg aaa aca cca ggg ccc gtc ctc ccc aag aac       656
Arg Leu Lys Lys Arg Arg Lys Thr Pro Gly Pro Val Leu Pro Lys Asn
                70                  75                  80

gcc ctg atg cag ctg aat gag atc aag cct ggt ttg cag tac aca ctc       704
Ala Leu Met Gln Leu Asn Glu Ile Lys Pro Gly Leu Gln Tyr Thr Leu
            85                  90                  95

ctg tcc cag act ggg ccc gtg cac gcg cct ttg ttt gtc atg tct gtg       752
Leu Ser Gln Thr Gly Pro Val His Ala Pro Leu Phe Val Met Ser Val
        100                 105                 110

gag gtg aat ggc cag gtt ttt gag ggc tct ggt ccc aca aag aaa aag       800
```

-continued

```
Glu Val Asn Gly Gln Val Phe Glu Gly Ser Gly Pro Thr Lys Lys Lys
    115                 120                 125

gca aaa ctc cat gct gct gag aag gcc ttg agg tct ttc gtt cag ttt      848
Ala Lys Leu His Ala Ala Glu Lys Ala Leu Arg Ser Phe Val Gln Phe
130                 135                 140                 145

cct aat gcc tct gag gcc cac ctg gcc atg ggg agg acc ctg tct gtc      896
Pro Asn Ala Ser Glu Ala His Leu Ala Met Gly Arg Thr Leu Ser Val
                150                 155                 160

aac acg gac ttc aca tct gac cag gcc gac ttc cct gac acg ctc ttc      944
Asn Thr Asp Phe Thr Ser Asp Gln Ala Asp Phe Pro Asp Thr Leu Phe
            165                 170                 175

aat ggt ttt gaa act cct gac aag gcg gag cct ccc ttt tac gtg ggc      992
Asn Gly Phe Glu Thr Pro Asp Lys Ala Glu Pro Pro Phe Tyr Val Gly
        180                 185                 190

tcc aat ggg gat gac tcc ttc agt tcc agc ggg gac ctc agc ttg tct     1040
Ser Asn Gly Asp Asp Ser Phe Ser Ser Ser Gly Asp Leu Ser Leu Ser
    195                 200                 205

gct tcc ccg gtg cct gcc agc cta gcc cag cct cct ctc cct gtc tta     1088
Ala Ser Pro Val Pro Ala Ser Leu Ala Gln Pro Pro Leu Pro Val Leu
210                 215                 220                 225

cca cca ttc cca ccc ccg agt ggg aag aat ccc gtg atg atc ttg aac     1136
Pro Pro Phe Pro Pro Pro Ser Gly Lys Asn Pro Val Met Ile Leu Asn
                230                 235                 240

gaa ctg cgc cca gga ctc aag tat gac ttc ctc tcc gag agc ggg gag     1184
Glu Leu Arg Pro Gly Leu Lys Tyr Asp Phe Leu Ser Glu Ser Gly Glu
            245                 250                 255

agc cat gcc aag agc ttc gtc atg tct gtg gtc gtg gat ggt cag ttc     1232
Ser His Ala Lys Ser Phe Val Met Ser Val Val Val Asp Gly Gln Phe
        260                 265                 270

ttt gaa ggc tcg ggg aga aac aag aag ctt gcc aag gcc cgg gct gcg     1280
Phe Glu Gly Ser Gly Arg Asn Lys Lys Leu Ala Lys Ala Arg Ala Ala
    275                 280                 285

cag tct gcc ctg gcc gcc att ttt aac ttg cac ttg gat cag acg cca     1328
Gln Ser Ala Leu Ala Ala Ile Phe Asn Leu His Leu Asp Gln Thr Pro
290                 295                 300                 305

tct cgc cag cct att ccc agt gag ggt ctt cag ctg cat tta ccg cag     1376
Ser Arg Gln Pro Ile Pro Ser Glu Gly Leu Gln Leu His Leu Pro Gln
                310                 315                 320

gtt tta gct gac gct gtc tca cgc ctg gtc ctg ggt aag ttt ggt gac     1424
Val Leu Ala Asp Ala Val Ser Arg Leu Val Leu Gly Lys Phe Gly Asp
            325                 330                 335

ctg acc gac aac ttc tcc tcc cct cac gct cgc aga aaa gtg ctg gct     1472
Leu Thr Asp Asn Phe Ser Ser Pro His Ala Arg Arg Lys Val Leu Ala
        340                 345                 350

gga gtc gtc atg aca aca ggc aca gat gtt aaa gat gcc aag gtg ata     1520
Gly Val Val Met Thr Thr Gly Thr Asp Val Lys Asp Ala Lys Val Ile
    355                 360                 365

agt gtt tct aca gga aca aaa tgt att aat ggt gaa tac atg agt gat     1568
Ser Val Ser Thr Gly Thr Lys Cys Ile Asn Gly Glu Tyr Met Ser Asp
370                 375                 380                 385

cgt ggc ctt gca tta aat gac tgc cat gca gaa ata ata tct cgg aga     1616
Arg Gly Leu Ala Leu Asn Asp Cys His Ala Glu Ile Ile Ser Arg Arg
                390                 395                 400

tcc ttg ctc aga ttt ctt tat aca caa ctt gag ctt tac tta aat aac     1664
Ser Leu Leu Arg Phe Leu Tyr Thr Gln Leu Glu Leu Tyr Leu Asn Asn
            405                 410                 415

aaa gat gat caa aaa aga tcc atc ttt cag aaa tca gag cga ggg ggg     1712
Lys Asp Asp Gln Lys Arg Ser Ile Phe Gln Lys Ser Glu Arg Gly Gly
        420                 425                 430
```

-continued

```
ttt agg ctg aag gag aat gtc cag ttt cat ctg tac atc agc acc tct      1760
Phe Arg Leu Lys Glu Asn Val Gln Phe His Leu Tyr Ile Ser Thr Ser
    435                 440                 445

ccc tgt gga gat gcc aga atc ttc tca cca cat gag cca atc ctg gaa      1808
Pro Cys Gly Asp Ala Arg Ile Phe Ser Pro His Glu Pro Ile Leu Glu
450                 455                 460                 465

ggg tct cgc tct tac acc cag gct gga gtg cag tgg tgc aat cat ggc      1856
Gly Ser Arg Ser Tyr Thr Gln Ala Gly Val Gln Trp Cys Asn His Gly
                470                 475                 480

tca ctg cag cct cga cct cct ggg ctc tta agc gat cct tcc acc tca      1904
Ser Leu Gln Pro Arg Pro Pro Gly Leu Leu Ser Asp Pro Ser Thr Ser
            485                 490                 495

acc ttc caa gga gct ggg act aca gaa cca gca gat aga cac cca aat      1952
Thr Phe Gln Gly Ala Gly Thr Thr Glu Pro Ala Asp Arg His Pro Asn
        500                 505                 510

cgt aaa gca aga gga cag cta cgg acc aaa ata gag tct ggt gag ggg      2000
Arg Lys Ala Arg Gly Gln Leu Arg Thr Lys Ile Glu Ser Gly Glu Gly
    515                 520                 525

acg att cca gtg cgc tcc aat gcg agc atc caa acg tgg gac ggg gtg      2048
Thr Ile Pro Val Arg Ser Asn Ala Ser Ile Gln Thr Trp Asp Gly Val
530                 535                 540                 545

ctg caa ggg gag cgg ctg ctc acc atg tcc tgc agt gac aag att gca      2096
Leu Gln Gly Glu Arg Leu Leu Thr Met Ser Cys Ser Asp Lys Ile Ala
                550                 555                 560

cgc tgg aac gtg gtg ggc atc cag gga tcc ctg ctc agc att ttc gtg      2144
Arg Trp Asn Val Val Gly Ile Gln Gly Ser Leu Leu Ser Ile Phe Val
            565                 570                 575

gag ccc att tac ttc tcg agc atc atc ctg ggc agc ctt tac cac ggg      2192
Glu Pro Ile Tyr Phe Ser Ser Ile Ile Leu Gly Ser Leu Tyr His Gly
        580                 585                 590

gac cac ctt tcc agg gcc atg tac cag cgg atc tcc aac ata gag gac      2240
Asp His Leu Ser Arg Ala Met Tyr Gln Arg Ile Ser Asn Ile Glu Asp
    595                 600                 605

ctg cca cct ctc tac acc ctc aac aag cct ttg ctc agt ggc atc agc      2288
Leu Pro Pro Leu Tyr Thr Leu Asn Lys Pro Leu Leu Ser Gly Ile Ser
610                 615                 620                 625

aat gca gaa gca cgg cag cca ggg aag gcc ccc aac ttc agt gtc aac      2336
Asn Ala Glu Ala Arg Gln Pro Gly Lys Ala Pro Asn Phe Ser Val Asn
                630                 635                 640

tgg acg gta ggc gac tcc gct att gag gtc atc aac gcc acg act ggg      2384
Trp Thr Val Gly Asp Ser Ala Ile Glu Val Ile Asn Ala Thr Thr Gly
            645                 650                 655

aag gat gag ctg ggc cgc gcg tcc cgc ctg tgt aag cac gcg ttg tac      2432
Lys Asp Glu Leu Gly Arg Ala Ser Arg Leu Cys Lys His Ala Leu Tyr
        660                 665                 670

tgt cgc tgg atg cgt gtg cac ggc aag gtt ccc tcc cac tta cta cgc      2480
Cys Arg Trp Met Arg Val His Gly Lys Val Pro Ser His Leu Leu Arg
    675                 680                 685

tcc aag att acc aag ccc aac gtg tac cat gag tcc aag ctg gcg gca      2528
Ser Lys Ile Thr Lys Pro Asn Val Tyr His Glu Ser Lys Leu Ala Ala
690                 695                 700                 705

aag gag tac cag gcc gcc aag gta cac tga ggaggggacg gctccgtctt        2578
Lys Glu Tyr Gln Ala Ala Lys Val His
                710

cacattgtgc acagatctga ggatgggatt agcgaagctg tggagactgc acatccggac   2638

ctgcccatgt ctcaaaacaa acacatgtac agtggctctt tttccttctc aaacacttta   2698

ccccagaagc aggtggtctg ccccaggcat aaagaaggaa aattggccat ctttcccacc   2758

tctaaattct gtaaaattat agacttgctc aaaagattcc tttttatcat ccccacgctg   2818
```

```
tgtaagtgga aagggcattg tgttccgtgt gtgtccagtt tacagcgtct ctgcccccta   2878

gcgtgttttg tgacaatctc ccctgggtga ggagtgggtg cacccagccc cgaggccagt   2938

ggttgctcgg ggccttccgt gtgagttcta gtgttcactt gatgccgggg aatagaatta   2998

gagaaaactc tgacctgccg ggttccaggg actggtggag gtggatggca ggtccgactc   3058

gaccatgact tagttgtaag ggtgtgtcgg ctttttcagt ctcatgtgaa aatcctcctg   3118

tctctggcag cactgtctgc actttcttgt ttactgtttg aagggacgag taccaagcca   3178

caaggaacac ttcttttggc cacagcataa gctgatggta tgtaaggaac cgatgggcca   3238

ttaaacatga actgaacggt taaaagcaca gtctatggaa cgctaatgga gtcagcccct   3298

aaagctgttt gctttttcag gctttggatt acatgctttt aatttgattt tagaatctgg   3358

acactttcta tgaatgtaat tcggctgaga aacatgttgc tgagatgcaa tcctcagtgt   3418

tctctgtatg taaatctgtg tatacaccac acgttacaac tgcatgagct tcctctcgca   3478

caagaccagc tggaactgag catgagacgc tgtcaaatac agacaaagga tttgagatgt   3538

tctcaataaa aagaaaatgt ttcact                                        3564
```

<210> SEQ ID NO 16
<211> LENGTH: 714
<212> TYPE: PRT
<213> ORGANISM: Homo sapiens

<400> SEQUENCE: 16

```
Met Asp Ile Glu Asp Glu Glu Asn Met Ser Ser Ser Ser Thr Asp Val
  1               5                  10                  15

Lys Glu Asn Arg Asn Leu Asp Asn Val Ser Pro Lys Asp Gly Ser Thr
             20                  25                  30

Pro Gly Pro Gly Glu Gly Ser Gln Leu Ser Asn Gly Gly Gly Gly Gly
         35                  40                  45

Pro Gly Arg Lys Arg Pro Leu Glu Glu Gly Ser Asn Gly His Ser Lys
     50                  55                  60

Tyr Arg Leu Lys Lys Arg Arg Lys Thr Pro Gly Pro Val Leu Pro Lys
 65                  70                  75                  80

Asn Ala Leu Met Gln Leu Asn Glu Ile Lys Pro Gly Leu Gln Tyr Thr
                 85                  90                  95

Leu Leu Ser Gln Thr Gly Pro Val His Ala Pro Leu Phe Val Met Ser
            100                 105                 110

Val Glu Val Asn Gly Gln Val Phe Glu Gly Ser Gly Pro Thr Lys Lys
        115                 120                 125

Lys Ala Lys Leu His Ala Ala Glu Lys Ala Leu Arg Ser Phe Val Gln
    130                 135                 140

Phe Pro Asn Ala Ser Glu Ala His Leu Ala Met Gly Arg Thr Leu Ser
145                 150                 155                 160

Val Asn Thr Asp Phe Thr Ser Asp Gln Ala Asp Phe Pro Asp Thr Leu
                165                 170                 175

Phe Asn Gly Phe Glu Thr Pro Asp Lys Ala Glu Pro Pro Phe Tyr Val
            180                 185                 190

Gly Ser Asn Gly Asp Asp Ser Phe Ser Ser Ser Gly Asp Leu Ser Leu
        195                 200                 205

Ser Ala Ser Pro Val Pro Ala Ser Leu Ala Gln Pro Pro Leu Pro Val
    210                 215                 220

Leu Pro Pro Phe Pro Pro Pro Ser Gly Lys Asn Pro Val Met Ile Leu
225                 230                 235                 240
```

-continued

```
Asn Glu Leu Arg Pro Gly Leu Lys Tyr Asp Phe Leu Ser Glu Ser Gly
                245                 250                 255

Glu Ser His Ala Lys Ser Phe Val Met Ser Val Val Val Asp Gly Gln
            260                 265                 270

Phe Phe Glu Gly Ser Gly Arg Asn Lys Lys Leu Ala Lys Ala Arg Ala
        275                 280                 285

Ala Gln Ser Ala Leu Ala Ala Ile Phe Asn Leu His Leu Asp Gln Thr
    290                 295                 300

Pro Ser Arg Gln Pro Ile Pro Ser Glu Gly Leu Gln Leu His Leu Pro
305                 310                 315                 320

Gln Val Leu Ala Asp Ala Val Ser Arg Leu Val Leu Gly Lys Phe Gly
                325                 330                 335

Asp Leu Thr Asp Asn Phe Ser Ser Pro His Ala Arg Arg Lys Val Leu
            340                 345                 350

Ala Gly Val Val Met Thr Thr Gly Thr Asp Val Lys Asp Ala Lys Val
        355                 360                 365

Ile Ser Val Ser Thr Gly Thr Lys Cys Ile Asn Gly Glu Tyr Met Ser
    370                 375                 380

Asp Arg Gly Leu Ala Leu Asn Asp Cys His Ala Glu Ile Ile Ser Arg
385                 390                 395                 400

Arg Ser Leu Leu Arg Phe Leu Tyr Thr Gln Leu Glu Leu Tyr Leu Asn
                405                 410                 415

Asn Lys Asp Asp Gln Lys Arg Ser Ile Phe Gln Lys Ser Glu Arg Gly
            420                 425                 430

Gly Phe Arg Leu Lys Glu Asn Val Gln Phe His Leu Tyr Ile Ser Thr
        435                 440                 445

Ser Pro Cys Gly Asp Ala Arg Ile Phe Ser Pro His Glu Pro Ile Leu
    450                 455                 460

Glu Gly Ser Arg Ser Tyr Thr Gln Ala Gly Val Gln Trp Cys Asn His
465                 470                 475                 480

Gly Ser Leu Gln Pro Arg Pro Pro Gly Leu Leu Ser Asp Pro Ser Thr
                485                 490                 495

Ser Thr Phe Gln Gly Ala Gly Thr Thr Glu Pro Ala Asp Arg His Pro
            500                 505                 510

Asn Arg Lys Ala Arg Gly Gln Leu Arg Thr Lys Ile Glu Ser Gly Glu
        515                 520                 525

Gly Thr Ile Pro Val Arg Ser Asn Ala Ser Ile Gln Thr Trp Asp Gly
    530                 535                 540

Val Leu Gln Gly Glu Arg Leu Leu Thr Met Ser Cys Ser Asp Lys Ile
545                 550                 555                 560

Ala Arg Trp Asn Val Val Gly Ile Gln Gly Ser Leu Leu Ser Ile Phe
                565                 570                 575

Val Glu Pro Ile Tyr Phe Ser Ser Ile Ile Leu Gly Ser Leu Tyr His
            580                 585                 590

Gly Asp His Leu Ser Arg Ala Met Tyr Gln Arg Ile Ser Asn Ile Glu
        595                 600                 605

Asp Leu Pro Pro Leu Tyr Thr Leu Asn Lys Pro Leu Leu Ser Gly Ile
    610                 615                 620

Ser Asn Ala Glu Ala Arg Gln Pro Gly Lys Ala Pro Asn Phe Ser Val
625                 630                 635                 640

Asn Trp Thr Val Gly Asp Ser Ala Ile Glu Val Ile Asn Ala Thr Thr
                645                 650                 655
```

-continued

```
Gly Lys Asp Glu Leu Gly Arg Ala Ser Arg Leu Cys Lys His Ala Leu
            660                 665                 670

Tyr Cys Arg Trp Met Arg Val His Gly Lys Val Pro Ser His Leu Leu
        675                 680                 685

Arg Ser Lys Ile Thr Lys Pro Asn Val Tyr His Glu Ser Lys Leu Ala
    690                 695                 700

Ala Lys Glu Tyr Gln Ala Ala Lys Val His
705                 710


<210> SEQ ID NO 17
<211> LENGTH: 699
<212> TYPE: DNA
<213> ORGANISM: Escherichia coli
<220> FEATURE:
<221> NAME/KEY: CDS
<222> LOCATION: (1)..(699)
<220> FEATURE:
<223> OTHER INFORMATION: Escherichia coli MTA/SAH nucleosidase
<300> PUBLICATION INFORMATION:
<308> DATABASE ACCESSION NUMBER: U24438/GenBank

<400> SEQUENCE: 17

atg aaa atc ggc atc att ggt gca atg gaa gaa gaa gtt acg ctg ctg       48
Met Lys Ile Gly Ile Ile Gly Ala Met Glu Glu Glu Val Thr Leu Leu
  1               5                  10                  15

cgt gac aaa atc gaa aac cgt caa act atc agt ctc ggc ggt tgc gaa       96
Arg Asp Lys Ile Glu Asn Arg Gln Thr Ile Ser Leu Gly Gly Cys Glu
             20                  25                  30

atc tat acc ggc caa ctg aat gga acc gag gtt gcg ctt ctg aaa tcg      144
Ile Tyr Thr Gly Gln Leu Asn Gly Thr Glu Val Ala Leu Leu Lys Ser
         35                  40                  45

ggc atc ggt aaa gtc gct gcg gcg ctg ggt gcc act ttg ctg ttg gaa      192
Gly Ile Gly Lys Val Ala Ala Ala Leu Gly Ala Thr Leu Leu Leu Glu
     50                  55                  60

cac tgc aag cca gat gtg att att aac acc ggt tct gcc ggt ggc ctg      240
His Cys Lys Pro Asp Val Ile Ile Asn Thr Gly Ser Ala Gly Gly Leu
 65                  70                  75                  80

gca cca acg ttg aaa gtg ggc gat atc gtt gtc tcg gac gaa gca cgt      288
Ala Pro Thr Leu Lys Val Gly Asp Ile Val Val Ser Asp Glu Ala Arg
                 85                  90                  95

tat cac gac gcg gat gtc acg gca ttt ggt tat gaa tac ggt cag tta      336
Tyr His Asp Ala Asp Val Thr Ala Phe Gly Tyr Glu Tyr Gly Gln Leu
            100                 105                 110

cca ggc tgt ccg gca ggc ttt aaa gct gac gat aaa ctg atc gct gcc      384
Pro Gly Cys Pro Ala Gly Phe Lys Ala Asp Asp Lys Leu Ile Ala Ala
        115                 120                 125

gct gag gcc tgc att gcc gaa ctg aat ctt aac gct gta cgt ggc ctg      432
Ala Glu Ala Cys Ile Ala Glu Leu Asn Leu Asn Ala Val Arg Gly Leu
    130                 135                 140

att gtt agc ggc gac gct ttc atc aac ggt tct gtt ggt ctg gcg aaa      480
Ile Val Ser Gly Asp Ala Phe Ile Asn Gly Ser Val Gly Leu Ala Lys
145                 150                 155                 160

atc cgc cac aac ttc cca cag gcc att gct gta gag atg gaa gcg acg      528
Ile Arg His Asn Phe Pro Gln Ala Ile Ala Val Glu Met Glu Ala Thr
                165                 170                 175

gca atc gcc cat gtc tgc cac aat ttc aac gtc ccg ttt gtt gtc gta      576
Ala Ile Ala His Val Cys His Asn Phe Asn Val Pro Phe Val Val Val
            180                 185                 190

cgc gcc atc tcc gac gtg gcc gat caa cag tct cat ctt agc ttc gat      624
Arg Ala Ile Ser Asp Val Ala Asp Gln Gln Ser His Leu Ser Phe Asp
        195                 200                 205
```

-continued

```
gag ttc ctg gct gtt gcc gct aaa cag tcc agc ctg atg gtt gag tca      672
Glu Phe Leu Ala Val Ala Ala Lys Gln Ser Ser Leu Met Val Glu Ser
    210                 215                 220

ctg gtg cag aaa ctt gca cat ggc taa                                  699
Leu Val Gln Lys Leu Ala His Gly
225                 230


<210> SEQ ID NO 18
<211> LENGTH: 232
<212> TYPE: PRT
<213> ORGANISM: Escherichia coli

<400> SEQUENCE: 18

Met Lys Ile Gly Ile Ile Gly Ala Met Glu Glu Glu Val Thr Leu Leu
  1               5                  10                  15

Arg Asp Lys Ile Glu Asn Arg Gln Thr Ile Ser Leu Gly Gly Cys Glu
             20                  25                  30

Ile Tyr Thr Gly Gln Leu Asn Gly Thr Glu Val Ala Leu Leu Lys Ser
         35                  40                  45

Gly Ile Gly Lys Val Ala Ala Ala Leu Gly Ala Thr Leu Leu Leu Glu
     50                  55                  60

His Cys Lys Pro Asp Val Ile Ile Asn Thr Gly Ser Ala Gly Gly Leu
 65                  70                  75                  80

Ala Pro Thr Leu Lys Val Gly Asp Ile Val Val Ser Asp Glu Ala Arg
                 85                  90                  95

Tyr His Asp Ala Asp Val Thr Ala Phe Gly Tyr Glu Tyr Gly Gln Leu
            100                 105                 110

Pro Gly Cys Pro Ala Gly Phe Lys Ala Asp Asp Lys Leu Ile Ala Ala
        115                 120                 125

Ala Glu Ala Cys Ile Ala Glu Leu Asn Leu Asn Ala Val Arg Gly Leu
    130                 135                 140

Ile Val Ser Gly Asp Ala Phe Ile Asn Gly Ser Val Gly Leu Ala Lys
145                 150                 155                 160

Ile Arg His Asn Phe Pro Gln Ala Ile Ala Val Glu Met Glu Ala Thr
                165                 170                 175

Ala Ile Ala His Val Cys His Asn Phe Asn Val Pro Phe Val Val Val
            180                 185                 190

Arg Ala Ile Ser Asp Val Ala Asp Gln Gln Ser His Leu Ser Phe Asp
        195                 200                 205

Glu Phe Leu Ala Val Ala Ala Lys Gln Ser Ser Leu Met Val Glu Ser
    210                 215                 220

Leu Val Gln Lys Leu Ala His Gly
225                 230


<210> SEQ ID NO 19
<211> LENGTH: 4381
<212> TYPE: DNA
<213> ORGANISM: Homo sapiens
<220> FEATURE:
<221> NAME/KEY: CDS
<222> LOCATION: (35)..(4036)
<220> FEATURE:
<223> OTHER INFORMATION: Human xanthine dehydrogenase/oxidase
<300> PUBLICATION INFORMATION:
<308> DATABASE ACCESSION NUMBER: U39487/GenBank

<400> SEQUENCE: 19

ggtacctgga gttcggggac cccaacctgt gaca atg aca gca gac aaa ttg gtt     55
                                      Met Thr Ala Asp Lys Leu Val
                                        1               5
```

-continued

```
ttc ttt gtg aat ggc aga aag gtg gtg gag aaa aat gca gat cca gag      103
Phe Phe Val Asn Gly Arg Lys Val Val Glu Lys Asn Ala Asp Pro Glu
         10                  15                  20

aca acc ctt ttg gcc tac ctg aga aga aag ttg ggg ctg agt gga acc      151
Thr Thr Leu Leu Ala Tyr Leu Arg Arg Lys Leu Gly Leu Ser Gly Thr
     25                  30                  35

aag ctc ggc tgt gga gag ggg ggc tgc ggg gct tgc aca gtg atg ctc      199
Lys Leu Gly Cys Gly Glu Gly Gly Cys Gly Ala Cys Thr Val Met Leu
 40                  45                  50                  55

tcc aag tat gat cgt ctg cag aac aag atc gtc cac ttt tct gcc aat      247
Ser Lys Tyr Asp Arg Leu Gln Asn Lys Ile Val His Phe Ser Ala Asn
                 60                  65                  70

gcc tgc ctg gcc ccc atc tgc tcc ttg cac cat gtt gca gtg aca act      295
Ala Cys Leu Ala Pro Ile Cys Ser Leu His His Val Ala Val Thr Thr
             75                  80                  85

gtg gaa gga ata gga agc acc aag acg agg ctg cat cct gtg cag gag      343
Val Glu Gly Ile Gly Ser Thr Lys Thr Arg Leu His Pro Val Gln Glu
         90                  95                 100

aga att gcc aaa agc cac ggc tcc cag tgc ggg ttc tgc acc cct ggc      391
Arg Ile Ala Lys Ser His Gly Ser Gln Cys Gly Phe Cys Thr Pro Gly
    105                 110                 115

atc gtc atg agt atg tac aca ctg ctc cgg aat cag ccc gag ccc acc      439
Ile Val Met Ser Met Tyr Thr Leu Leu Arg Asn Gln Pro Glu Pro Thr
120                 125                 130                 135

atg gag gag att gag aat gcc ttc caa gga aat ctg tgc cgc tgc aca      487
Met Glu Glu Ile Glu Asn Ala Phe Gln Gly Asn Leu Cys Arg Cys Thr
                140                 145                 150

ggc tac aga ccc atc ctc cag ggc ttc cgg acc ttt gcc agg gat ggt      535
Gly Tyr Arg Pro Ile Leu Gln Gly Phe Arg Thr Phe Ala Arg Asp Gly
            155                 160                 165

gga tgc tgt gga gga gat ggg aat aat cca aat tgc tgc atg aac cag      583
Gly Cys Cys Gly Gly Asp Gly Asn Asn Pro Asn Cys Cys Met Asn Gln
        170                 175                 180

aag aaa gac cac tca gtc agc ctc tcg cca tct tta ttc aaa cca gag      631
Lys Lys Asp His Ser Val Ser Leu Ser Pro Ser Leu Phe Lys Pro Glu
    185                 190                 195

gag ttc acg ccc ctg gat cca acc cag gag ccc att ttt ccc cca gag      679
Glu Phe Thr Pro Leu Asp Pro Thr Gln Glu Pro Ile Phe Pro Pro Glu
200                 205                 210                 215

ttg ctg agg ctg aaa gac act cct cgg aag cag ctg cga ttt gaa ggg      727
Leu Leu Arg Leu Lys Asp Thr Pro Arg Lys Gln Leu Arg Phe Glu Gly
                220                 225                 230

gag cgt gtg acg tgg ata cag gcc tca acc ctc aag gag ctg ctg gac      775
Glu Arg Val Thr Trp Ile Gln Ala Ser Thr Leu Lys Glu Leu Leu Asp
            235                 240                 245

ctc aag gct cag cac cct gac gcc aag ctg gtc gtg ggg aac acg gag      823
Leu Lys Ala Gln His Pro Asp Ala Lys Leu Val Val Gly Asn Thr Glu
        250                 255                 260

att ggc att gag atg aag ttc aag aat atg ctg ttt cct atg att gtc      871
Ile Gly Ile Glu Met Lys Phe Lys Asn Met Leu Phe Pro Met Ile Val
    265                 270                 275

tgc cca gcc tgg atc cct gag ctg aat tcg gta gaa cat gga ccc gac      919
Cys Pro Ala Trp Ile Pro Glu Leu Asn Ser Val Glu His Gly Pro Asp
280                 285                 290                 295

ggt atc tcc ttt gga gct gct tgc ccc ctg agc att gtg gaa aaa acc      967
Gly Ile Ser Phe Gly Ala Ala Cys Pro Leu Ser Ile Val Glu Lys Thr
                300                 305                 310

ctg gtg gat gct gtt gct aag ctt cct gcc caa aag aca gag gtg ttc     1015
Leu Val Asp Ala Val Ala Lys Leu Pro Ala Gln Lys Thr Glu Val Phe
```

```
            315                 320                 325

aga ggg gtc ctg gag cag ctg cgc tgg ttt gct ggg aag caa gtc aag     1063
Arg Gly Val Leu Glu Gln Leu Arg Trp Phe Ala Gly Lys Gln Val Lys
        330                 335                 340

tct gtg gcg tcc gtt gga ggg aac atc atc act gcc agc ccc atc tcc     1111
Ser Val Ala Ser Val Gly Gly Asn Ile Ile Thr Ala Ser Pro Ile Ser
    345                 350                 355

gac ctc aac ccc gtg ttc atg gcc agt ggg gcc aag ctg aca ctt gtg     1159
Asp Leu Asn Pro Val Phe Met Ala Ser Gly Ala Lys Leu Thr Leu Val
360                 365                 370                 375

tcc aga ggc acc agg aga act gtc cag atg gac cac acc ttc ttc cct     1207
Ser Arg Gly Thr Arg Arg Thr Val Gln Met Asp His Thr Phe Phe Pro
                380                 385                 390

ggc tac aga aag acc ctg ctg agc ccg gag gag ata ctg ctc tcc ata     1255
Gly Tyr Arg Lys Thr Leu Leu Ser Pro Glu Glu Ile Leu Leu Ser Ile
            395                 400                 405

gag atc ccc tac agc agg gag ggg gag tat ttc tca gca ttc aag cag     1303
Glu Ile Pro Tyr Ser Arg Glu Gly Glu Tyr Phe Ser Ala Phe Lys Gln
        410                 415                 420

gcc tcc cgg aga gaa gat gac att gcc aag gta acc agt ggc atg aga     1351
Ala Ser Arg Arg Glu Asp Asp Ile Ala Lys Val Thr Ser Gly Met Arg
    425                 430                 435

gtt tta ttc aag cca gga acc aca gag gta cag gag ctg gcc ctt tgc     1399
Val Leu Phe Lys Pro Gly Thr Thr Glu Val Gln Glu Leu Ala Leu Cys
440                 445                 450                 455

tat ggt gga atg gcc aac aga acc atc tca gcc ctc aag acc act cag     1447
Tyr Gly Gly Met Ala Asn Arg Thr Ile Ser Ala Leu Lys Thr Thr Gln
                460                 465                 470

agg cag ctt tcc aag ctc tgg aag gag gag ctg ctg cag gac gtg tgt     1495
Arg Gln Leu Ser Lys Leu Trp Lys Glu Glu Leu Leu Gln Asp Val Cys
            475                 480                 485

gca gga ctg gca gag gag ctg cat ctg cct ccc gat gcc cct ggt ggc     1543
Ala Gly Leu Ala Glu Glu Leu His Leu Pro Pro Asp Ala Pro Gly Gly
        490                 495                 500

atg gtg gac ttc cgg tgc acc ctc acc ctc agc ttc ttc ttc aag ttc     1591
Met Val Asp Phe Arg Cys Thr Leu Thr Leu Ser Phe Phe Phe Lys Phe
    505                 510                 515

tac ctg aca gtc ctt cag aag ctg ggc caa gag aac ctg gaa gac aag     1639
Tyr Leu Thr Val Leu Gln Lys Leu Gly Gln Glu Asn Leu Glu Asp Lys
520                 525                 530                 535

tgt ggt aaa ctg gac ccc act ttc gcc agt gca act tta ctg ttt cag     1687
Cys Gly Lys Leu Asp Pro Thr Phe Ala Ser Ala Thr Leu Leu Phe Gln
                540                 545                 550

aaa gac ccc cca gcc gat gtc cag ctc ttc caa gag gtg ccc aag ggt     1735
Lys Asp Pro Pro Ala Asp Val Gln Leu Phe Gln Glu Val Pro Lys Gly
            555                 560                 565

cag tct gag gag gac atg gtg ggc cgg ccc ctg ccc cac ctg gca gcg     1783
Gln Ser Glu Glu Asp Met Val Gly Arg Pro Leu Pro His Leu Ala Ala
        570                 575                 580

gac atg cag gcc tct ggt gag gcc gtg tac tgt gac gac att cct cgc     1831
Asp Met Gln Ala Ser Gly Glu Ala Val Tyr Cys Asp Asp Ile Pro Arg
    585                 590                 595

tac gag aat gag ctg tct ctc cgg ctg gtc acc agc acc cgg gcc cac     1879
Tyr Glu Asn Glu Leu Ser Leu Arg Leu Val Thr Ser Thr Arg Ala His
600                 605                 610                 615

gcc aag atc aag tcc ata gat aca tca gaa gct aag aag gtt cca ggg     1927
Ala Lys Ile Lys Ser Ile Asp Thr Ser Glu Ala Lys Lys Val Pro Gly
                620                 625                 630

ttt gtt tgt ttc att tcc gct gat gat gtt cct ggg agt aac ata act     1975
```

-continued

```
Phe Val Cys Phe Ile Ser Ala Asp Asp Val Pro Gly Ser Asn Ile Thr
            635                 640                 645

gga att tgt aat gat gag aca gtc ttt gcg aag gat aag gtt act tgt      2023
Gly Ile Cys Asn Asp Glu Thr Val Phe Ala Lys Asp Lys Val Thr Cys
        650                 655                 660

gtt ggg cat atc att ggt gct gtg gtt gct gac acc ccg gaa cac aca      2071
Val Gly His Ile Ile Gly Ala Val Val Ala Asp Thr Pro Glu His Thr
    665                 670                 675

cag aga gct gcc caa ggg gtg aaa atc acc tat gaa gaa cta cca gcc      2119
Gln Arg Ala Ala Gln Gly Val Lys Ile Thr Tyr Glu Glu Leu Pro Ala
680                 685                 690                 695

att atc aca att gag gat gct ata aag aac aac tcc ttt tat gga cct      2167
Ile Ile Thr Ile Glu Asp Ala Ile Lys Asn Asn Ser Phe Tyr Gly Pro
                700                 705                 710

gag ctg aag atc gag aaa ggg gac cta aag aag ggg ttt tcc gaa gca      2215
Glu Leu Lys Ile Glu Lys Gly Asp Leu Lys Lys Gly Phe Ser Glu Ala
            715                 720                 725

gat aat gtt gtg tca ggg gag ata tac atc ggt ggc caa gag cac ttc      2263
Asp Asn Val Val Ser Gly Glu Ile Tyr Ile Gly Gly Gln Glu His Phe
        730                 735                 740

tac ctg gag act cac tgc acc att gct gtt cca aaa ggc gag gca ggg      2311
Tyr Leu Glu Thr His Cys Thr Ile Ala Val Pro Lys Gly Glu Ala Gly
    745                 750                 755

gag atg gag ctc ttt gtg tct aca cag aac acc atg aag acc cag agc      2359
Glu Met Glu Leu Phe Val Ser Thr Gln Asn Thr Met Lys Thr Gln Ser
760                 765                 770                 775

ttt gtt gca aaa atg ttg ggg gtt cca gca aac cgg att gtg gtt cga      2407
Phe Val Ala Lys Met Leu Gly Val Pro Ala Asn Arg Ile Val Val Arg
                780                 785                 790

gtg aag aga atg gga gga ggc ttt gga ggc aag gag acc cgg agc act      2455
Val Lys Arg Met Gly Gly Gly Phe Gly Gly Lys Glu Thr Arg Ser Thr
            795                 800                 805

gtg gtg tcc acg gca gtg gcc ctg gct gca tat aag acc ggc cgc cct      2503
Val Val Ser Thr Ala Val Ala Leu Ala Ala Tyr Lys Thr Gly Arg Pro
        810                 815                 820

gtg cga tgc atg ctg gac cgt gat gag gac atg ctg ata act ggt ggc      2551
Val Arg Cys Met Leu Asp Arg Asp Glu Asp Met Leu Ile Thr Gly Gly
    825                 830                 835

aga cat ccc ttc ctg gcc aga tac aag gtt ggc ttc atg aag act ggg      2599
Arg His Pro Phe Leu Ala Arg Tyr Lys Val Gly Phe Met Lys Thr Gly
840                 845                 850                 855

aca gtt gtg gct ctt gag gtg gac cac ttc agc aat gtg ggg aac acc      2647
Thr Val Val Ala Leu Glu Val Asp His Phe Ser Asn Val Gly Asn Thr
                860                 865                 870

cag gat ctc tct cag agt att atg gaa cga gct tta ttc cac atg gac      2695
Gln Asp Leu Ser Gln Ser Ile Met Glu Arg Ala Leu Phe His Met Asp
            875                 880                 885

aac tgc tat aaa atc ccc aac atc cgg ggc act ggg cgg ctg tgc aaa      2743
Asn Cys Tyr Lys Ile Pro Asn Ile Arg Gly Thr Gly Arg Leu Cys Lys
        890                 895                 900

acc aac ctt ccc tcc aac acg gcc ttc cgg ggc ttt ggg ggg ccc cag      2791
Thr Asn Leu Pro Ser Asn Thr Ala Phe Arg Gly Phe Gly Gly Pro Gln
    905                 910                 915

ggg atg ctc att gcc gag tgc tgg atg agt gaa gtt gca gtg acc tgt      2839
Gly Met Leu Ile Ala Glu Cys Trp Met Ser Glu Val Ala Val Thr Cys
920                 925                 930                 935

ggg atg cct gca gag gag gtg cgg aga aaa aac ctg tac aaa gaa ggg      2887
Gly Met Pro Ala Glu Glu Val Arg Arg Lys Asn Leu Tyr Lys Glu Gly
                940                 945                 950
```

-continued

```
gac ctg aca cac ttc aac cag aag ctt gag ggt ttc acc ttg ccc aga     2935
Asp Leu Thr His Phe Asn Gln Lys Leu Glu Gly Phe Thr Leu Pro Arg
            955                 960                 965

tgc tgg gaa gaa tgc cta gca agc tct cag tat cat gct cgg aag agt     2983
Cys Trp Glu Glu Cys Leu Ala Ser Ser Gln Tyr His Ala Arg Lys Ser
        970                 975                 980

gag gtt gac aag ttc aac aag gag aat tgt tgg aaa aag aga gga ttg     3031
Glu Val Asp Lys Phe Asn Lys Glu Asn Cys Trp Lys Lys Arg Gly Leu
    985                 990                 995

tgc ata att ccc acc aag ttt gga ata agc ttc aca gtt cct ttt ctg     3079
Cys Ile Ile Pro Thr Lys Phe Gly Ile Ser Phe Thr Val Pro Phe Leu
1000                1005                1010                1015

aat cag gca gga gcc cta ctt cat gtg tac aca gat ggc tct gtg ctg     3127
Asn Gln Ala Gly Ala Leu Leu His Val Tyr Thr Asp Gly Ser Val Leu
                1020                1025                1030

ctg acc cac ggg ggg act gag atg ggc caa ggc ctt cat acc aaa atg     3175
Leu Thr His Gly Gly Thr Glu Met Gly Gln Gly Leu His Thr Lys Met
            1035                1040                1045

gtc cag gtg gcc agt aga gct ctg aaa atc ccc acc tct aag att tat     3223
Val Gln Val Ala Ser Arg Ala Leu Lys Ile Pro Thr Ser Lys Ile Tyr
        1050                1055                1060

atc agc gag aca agc act aac act gtg ccc aac acc tct ccc acg gct     3271
Ile Ser Glu Thr Ser Thr Asn Thr Val Pro Asn Thr Ser Pro Thr Ala
    1065                1070                1075

gcc tct gtc agc gct gac ctc aat gga cag gcc gtc tat gcg gct tgt     3319
Ala Ser Val Ser Ala Asp Leu Asn Gly Gln Ala Val Tyr Ala Ala Cys
1080                1085                1090                1095

cag acc atc ttg aaa agg ctg gaa ccc tac aag aag aag aat ccc agt     3367
Gln Thr Ile Leu Lys Arg Leu Glu Pro Tyr Lys Lys Lys Asn Pro Ser
                1100                1105                1110

ggc tcc tgg gaa gac tgg gtc aca gct gcc tac atg gac aca gtg agc     3415
Gly Ser Trp Glu Asp Trp Val Thr Ala Ala Tyr Met Asp Thr Val Ser
            1115                1120                1125

ttg tct gcc act ggg ttt tat aga aca ccc aat ctg ggc tac agc ttt     3463
Leu Ser Ala Thr Gly Phe Tyr Arg Thr Pro Asn Leu Gly Tyr Ser Phe
        1130                1135                1140

gag act aac tca ggg aac ccc ttc cac tac ttc agc tat ggg gtg gct     3511
Glu Thr Asn Ser Gly Asn Pro Phe His Tyr Phe Ser Tyr Gly Val Ala
    1145                1150                1155

tgc tct gaa gta gaa atc gac tgc cta aca gga gat cat aag aac ctc     3559
Cys Ser Glu Val Glu Ile Asp Cys Leu Thr Gly Asp His Lys Asn Leu
1160                1165                1170                1175

cgc aca gat att gtc atg gat gtt ggc tcc agt cta aac cct gcc att     3607
Arg Thr Asp Ile Val Met Asp Val Gly Ser Ser Leu Asn Pro Ala Ile
                1180                1185                1190

gat att gga cag gtg gaa ggg gca ttt gtc cag ggc ctt ggc ctc ttc     3655
Asp Ile Gly Gln Val Glu Gly Ala Phe Val Gln Gly Leu Gly Leu Phe
            1195                1200                1205

acc cta gag gag cta cac tat tcc ccc gag ggg agc ctg cac acc cgt     3703
Thr Leu Glu Glu Leu His Tyr Ser Pro Glu Gly Ser Leu His Thr Arg
        1210                1215                1220

ggc cct agc acc tac aag atc ccg gca ttt ggc agc atc ccc att gag     3751
Gly Pro Ser Thr Tyr Lys Ile Pro Ala Phe Gly Ser Ile Pro Ile Glu
    1225                1230                1235

ttc agg gtg tcc ctg ctc cgc gac tgc ccc aac aag aag gcc atc tat     3799
Phe Arg Val Ser Leu Leu Arg Asp Cys Pro Asn Lys Lys Ala Ile Tyr
1240                1245                1250                1255

gca tcg aag gct gtt gga gag ccg ccc ctc ttc ctg gct gct tct atc     3847
Ala Ser Lys Ala Val Gly Glu Pro Pro Leu Phe Leu Ala Ala Ser Ile
                1260                1265                1270
```

```
ttc ttt gcc atc aaa gat gcc atc cgt gca gct cga gct cag cac aca     3895
Phe Phe Ala Ile Lys Asp Ala Ile Arg Ala Ala Arg Ala Gln His Thr
          1275                1280                1285

ggt aat aac gtg aag gaa ctc ttc cgg cta gac agc cct gcc acc ccg     3943
Gly Asn Asn Val Lys Glu Leu Phe Arg Leu Asp Ser Pro Ala Thr Pro
      1290                1295                1300

gag aag atc cgc aat gcc tgc gtg gac aag ttc acc acc ctg tgt gtc     3991
Glu Lys Ile Arg Asn Ala Cys Val Asp Lys Phe Thr Thr Leu Cys Val
   1305                1310                1315

act ggt gtc cca gaa aac tgc aaa ccc tgg tct gtg agg gtc taa         4036
Thr Gly Val Pro Glu Asn Cys Lys Pro Trp Ser Val Arg Val
1320                1325                1330

agagagagtc ctcagcagag tcttcttgtg ctgcctttgg gcttccatgg agcaggagga   4096

acataccaca gaacatggat ctattaaagt cacagaatga cagacctgtg atttgtcaag   4156

atgggatttg gaagacaagt gaatgcaatg gaagattttg atcaaaaatg taatttgtaa   4216

acacaatgat aagcaaattc aaaactgtta tgcctaaatg gtgaatatgc aattaggatc   4276

atttctgtc tgttttaatc atgtatctgg aatagggtcg ggaagggttt gtgctattcc    4336

ccacttactg gacagcctgt ataacctcaa aaaaaaaaaa aaaaa                   4381


<210> SEQ ID NO 20
<211> LENGTH: 1333
<212> TYPE: PRT
<213> ORGANISM: Homo sapiens

<400> SEQUENCE: 20

Met Thr Ala Asp Lys Leu Val Phe Phe Val Asn Gly Arg Lys Val Val
  1               5                  10                  15

Glu Lys Asn Ala Asp Pro Glu Thr Thr Leu Leu Ala Tyr Leu Arg Arg
            20                  25                  30

Lys Leu Gly Leu Ser Gly Thr Lys Leu Gly Cys Gly Glu Gly Gly Cys
        35                  40                  45

Gly Ala Cys Thr Val Met Leu Ser Lys Tyr Asp Arg Leu Gln Asn Lys
     50                  55                  60

Ile Val His Phe Ser Ala Asn Ala Cys Leu Ala Pro Ile Cys Ser Leu
 65                  70                  75                  80

His His Val Ala Val Thr Thr Val Glu Gly Ile Gly Ser Thr Lys Thr
                85                  90                  95

Arg Leu His Pro Val Gln Glu Arg Ile Ala Lys Ser His Gly Ser Gln
            100                 105                 110

Cys Gly Phe Cys Thr Pro Gly Ile Val Met Ser Met Tyr Thr Leu Leu
        115                 120                 125

Arg Asn Gln Pro Glu Pro Thr Met Glu Glu Ile Glu Asn Ala Phe Gln
    130                 135                 140

Gly Asn Leu Cys Arg Cys Thr Gly Tyr Arg Pro Ile Leu Gln Gly Phe
145                 150                 155                 160

Arg Thr Phe Ala Arg Asp Gly Gly Cys Cys Gly Gly Asp Gly Asn Asn
                165                 170                 175

Pro Asn Cys Cys Met Asn Gln Lys Lys Asp His Ser Val Ser Leu Ser
            180                 185                 190

Pro Ser Leu Phe Lys Pro Glu Glu Phe Thr Pro Leu Asp Pro Thr Gln
        195                 200                 205

Glu Pro Ile Phe Pro Pro Glu Leu Leu Arg Leu Lys Asp Thr Pro Arg
    210                 215                 220
```

-continued

```
Lys Gln Leu Arg Phe Glu Gly Glu Arg Val Thr Trp Ile Gln Ala Ser
225                 230                 235                 240

Thr Leu Lys Glu Leu Leu Asp Leu Lys Ala Gln His Pro Asp Ala Lys
                245                 250                 255

Leu Val Val Gly Asn Thr Glu Ile Gly Ile Glu Met Lys Phe Lys Asn
            260                 265                 270

Met Leu Phe Pro Met Ile Val Cys Pro Ala Trp Ile Pro Glu Leu Asn
        275                 280                 285

Ser Val Glu His Gly Pro Asp Gly Ile Ser Phe Gly Ala Ala Cys Pro
    290                 295                 300

Leu Ser Ile Val Glu Lys Thr Leu Val Asp Ala Val Ala Lys Leu Pro
305                 310                 315                 320

Ala Gln Lys Thr Glu Val Phe Arg Gly Val Leu Glu Gln Leu Arg Trp
                325                 330                 335

Phe Ala Gly Lys Gln Val Lys Ser Val Ala Ser Val Gly Gly Asn Ile
            340                 345                 350

Ile Thr Ala Ser Pro Ile Ser Asp Leu Asn Pro Val Phe Met Ala Ser
        355                 360                 365

Gly Ala Lys Leu Thr Leu Val Ser Arg Gly Thr Arg Arg Thr Val Gln
    370                 375                 380

Met Asp His Thr Phe Phe Pro Gly Tyr Arg Lys Thr Leu Leu Ser Pro
385                 390                 395                 400

Glu Glu Ile Leu Leu Ser Ile Glu Ile Pro Tyr Ser Arg Glu Gly Glu
                405                 410                 415

Tyr Phe Ser Ala Phe Lys Gln Ala Ser Arg Arg Glu Asp Asp Ile Ala
            420                 425                 430

Lys Val Thr Ser Gly Met Arg Val Leu Phe Lys Pro Gly Thr Thr Glu
        435                 440                 445

Val Gln Glu Leu Ala Leu Cys Tyr Gly Gly Met Ala Asn Arg Thr Ile
    450                 455                 460

Ser Ala Leu Lys Thr Thr Gln Arg Gln Leu Ser Lys Leu Trp Lys Glu
465                 470                 475                 480

Glu Leu Leu Gln Asp Val Cys Ala Gly Leu Ala Glu Glu Leu His Leu
                485                 490                 495

Pro Pro Asp Ala Pro Gly Gly Met Val Asp Phe Arg Cys Thr Leu Thr
            500                 505                 510

Leu Ser Phe Phe Phe Lys Phe Tyr Leu Thr Val Leu Gln Lys Leu Gly
        515                 520                 525

Gln Glu Asn Leu Glu Asp Lys Cys Gly Lys Leu Asp Pro Thr Phe Ala
    530                 535                 540

Ser Ala Thr Leu Leu Phe Gln Lys Asp Pro Pro Ala Asp Val Gln Leu
545                 550                 555                 560

Phe Gln Glu Val Pro Lys Gly Gln Ser Glu Glu Asp Met Val Gly Arg
                565                 570                 575

Pro Leu Pro His Leu Ala Ala Asp Met Gln Ala Ser Gly Glu Ala Val
            580                 585                 590

Tyr Cys Asp Asp Ile Pro Arg Tyr Glu Asn Glu Leu Ser Leu Arg Leu
        595                 600                 605

Val Thr Ser Thr Arg Ala His Ala Lys Ile Lys Ser Ile Asp Thr Ser
    610                 615                 620

Glu Ala Lys Lys Val Pro Gly Phe Val Cys Phe Ile Ser Ala Asp Asp
625                 630                 635                 640

Val Pro Gly Ser Asn Ile Thr Gly Ile Cys Asn Asp Glu Thr Val Phe
```

-continued

```
                645                 650                 655

Ala Lys Asp Lys Val Thr Cys Val Gly His Ile Ile Gly Ala Val Val
            660                 665                 670

Ala Asp Thr Pro Glu His Thr Gln Arg Ala Ala Gln Gly Val Lys Ile
        675                 680                 685

Thr Tyr Glu Glu Leu Pro Ala Ile Ile Thr Ile Glu Asp Ala Ile Lys
    690                 695                 700

Asn Asn Ser Phe Tyr Gly Pro Glu Leu Lys Ile Glu Lys Gly Asp Leu
705                 710                 715                 720

Lys Lys Gly Phe Ser Glu Ala Asp Asn Val Val Ser Gly Glu Ile Tyr
                725                 730                 735

Ile Gly Gly Gln Glu His Phe Tyr Leu Glu Thr His Cys Thr Ile Ala
            740                 745                 750

Val Pro Lys Gly Glu Ala Gly Glu Met Glu Leu Phe Val Ser Thr Gln
        755                 760                 765

Asn Thr Met Lys Thr Gln Ser Phe Val Ala Lys Met Leu Gly Val Pro
    770                 775                 780

Ala Asn Arg Ile Val Val Arg Val Lys Arg Met Gly Gly Gly Phe Gly
785                 790                 795                 800

Gly Lys Glu Thr Arg Ser Thr Val Val Ser Thr Ala Val Ala Leu Ala
                805                 810                 815

Ala Tyr Lys Thr Gly Arg Pro Val Arg Cys Met Leu Asp Arg Asp Glu
            820                 825                 830

Asp Met Leu Ile Thr Gly Gly Arg His Pro Phe Leu Ala Arg Tyr Lys
        835                 840                 845

Val Gly Phe Met Lys Thr Gly Thr Val Val Ala Leu Glu Val Asp His
    850                 855                 860

Phe Ser Asn Val Gly Asn Thr Gln Asp Leu Ser Gln Ser Ile Met Glu
865                 870                 875                 880

Arg Ala Leu Phe His Met Asp Asn Cys Tyr Lys Ile Pro Asn Ile Arg
                885                 890                 895

Gly Thr Gly Arg Leu Cys Lys Thr Asn Leu Pro Ser Asn Thr Ala Phe
            900                 905                 910

Arg Gly Phe Gly Gly Pro Gln Gly Met Leu Ile Ala Glu Cys Trp Met
        915                 920                 925

Ser Glu Val Ala Val Thr Cys Gly Met Pro Ala Glu Glu Val Arg Arg
    930                 935                 940

Lys Asn Leu Tyr Lys Glu Gly Asp Leu Thr His Phe Asn Gln Lys Leu
945                 950                 955                 960

Glu Gly Phe Thr Leu Pro Arg Cys Trp Glu Glu Cys Leu Ala Ser Ser
                965                 970                 975

Gln Tyr His Ala Arg Lys Ser Glu Val Asp Lys Phe Asn Lys Glu Asn
            980                 985                 990

Cys Trp Lys Lys Arg Gly Leu Cys Ile Ile Pro Thr Lys Phe Gly Ile
        995                1000                1005

Ser Phe Thr Val Pro Phe Leu Asn Gln Ala Gly Ala Leu Leu His Val
   1010                1015                1020

Tyr Thr Asp Gly Ser Val Leu Leu Thr His Gly Gly Thr Glu Met Gly
1025                1030                1035                1040

Gln Gly Leu His Thr Lys Met Val Gln Val Ala Ser Arg Ala Leu Lys
               1045                1050                1055

Ile Pro Thr Ser Lys Ile Tyr Ile Ser Glu Thr Ser Thr Asn Thr Val
           1060                1065                1070
```

-continued

```
Pro Asn Thr Ser Pro Thr Ala Ala Ser Val Ser Ala Asp Leu Asn Gly
       1075                1080                1085

Gln Ala Val Tyr Ala Ala Cys Gln Thr Ile Leu Lys Arg Leu Glu Pro
   1090                1095                1100

Tyr Lys Lys Lys Asn Pro Ser Gly Ser Trp Glu Asp Trp Val Thr Ala
1105                1110                1115                1120

Ala Tyr Met Asp Thr Val Ser Leu Ser Ala Thr Gly Phe Tyr Arg Thr
               1125                1130                1135

Pro Asn Leu Gly Tyr Ser Phe Glu Thr Asn Ser Gly Asn Pro Phe His
           1140                1145                1150

Tyr Phe Ser Tyr Gly Val Ala Cys Ser Glu Val Glu Ile Asp Cys Leu
       1155                1160                1165

Thr Gly Asp His Lys Asn Leu Arg Thr Asp Ile Val Met Asp Val Gly
   1170                1175                1180

Ser Ser Leu Asn Pro Ala Ile Asp Ile Gly Gln Val Glu Gly Ala Phe
1185                1190                1195                1200

Val Gln Gly Leu Gly Leu Phe Thr Leu Glu Glu Leu His Tyr Ser Pro
               1205                1210                1215

Glu Gly Ser Leu His Thr Arg Gly Pro Ser Thr Tyr Lys Ile Pro Ala
           1220                1225                1230

Phe Gly Ser Ile Pro Ile Glu Phe Arg Val Ser Leu Leu Arg Asp Cys
       1235                1240                1245

Pro Asn Lys Lys Ala Ile Tyr Ala Ser Lys Ala Val Gly Glu Pro Pro
   1250                1255                1260

Leu Phe Leu Ala Ala Ser Ile Phe Phe Ala Ile Lys Asp Ala Ile Arg
1265                1270                1275                1280

Ala Ala Arg Ala Gln His Thr Gly Asn Asn Val Lys Glu Leu Phe Arg
               1285                1290                1295

Leu Asp Ser Pro Ala Thr Pro Glu Lys Ile Arg Asn Ala Cys Val Asp
           1300                1305                1310

Lys Phe Thr Thr Leu Cys Val Thr Gly Val Pro Glu Asn Cys Lys Pro
       1315                1320                1325

Trp Ser Val Arg Val
   1330


<210> SEQ ID NO 21
<211> LENGTH: 573
<212> TYPE: DNA
<213> ORGANISM: Bacillus subtilis
<220> FEATURE:
<221> NAME/KEY: CDS
<222> LOCATION: (1)..(573)
<220> FEATURE:
<223> OTHER INFORMATION: Nucleic Acid encoding tetrahydrofolate
      methyltransferase
<300> PUBLICATION INFORMATION:
<308> DATABASE ACCESSION NUMBER: Z99115/GenBank

<400> SEQUENCE: 21

atg aaa gaa gtt aat aaa gag caa atc gaa caa gct gtt cgt caa att       48
Met Lys Glu Val Asn Lys Glu Gln Ile Glu Gln Ala Val Arg Gln Ile
  1               5                  10                  15

tta gaa gcg atc gga gaa gac ccg aat aga gaa ggg ctt ctt gat act       96
Leu Glu Ala Ile Gly Glu Asp Pro Asn Arg Glu Gly Leu Leu Asp Thr
             20                  25                  30

ccg aaa aga gtc gca aag atg tat gcc gaa gta ttc tcc ggc ttg aat      144
Pro Lys Arg Val Ala Lys Met Tyr Ala Glu Val Phe Ser Gly Leu Asn
         35                  40                  45
```

-continued

```
gaa gat cca aaa gaa cat ttc cag act atc ttc ggt gaa aac cat gag      192
Glu Asp Pro Lys Glu His Phe Gln Thr Ile Phe Gly Glu Asn His Glu
     50                  55                  60

gag ctt gtt ctt gta aaa gat ata gcg ttt cat tct atg tgt gag cat      240
Glu Leu Val Leu Val Lys Asp Ile Ala Phe His Ser Met Cys Glu His
 65                  70                  75                  80

cac ctt gtt ccc ttt tat gga aaa gca cat gtt gca tat atc ccg cga      288
His Leu Val Pro Phe Tyr Gly Lys Ala His Val Ala Tyr Ile Pro Arg
                 85                  90                  95

ggc gga aag gtc aca gga ctc agc aaa ctg gca cgt gcc gtt gaa gcc      336
Gly Gly Lys Val Thr Gly Leu Ser Lys Leu Ala Arg Ala Val Glu Ala
            100                 105                 110

gtt gca aag cgc ccg cag ctt cag gaa cgc atc act tct aca att gca      384
Val Ala Lys Arg Pro Gln Leu Gln Glu Arg Ile Thr Ser Thr Ile Ala
        115                 120                 125

gaa agc atc gta gaa acg ctt gat ccg cat ggc gta atg gta gtg gtt      432
Glu Ser Ile Val Glu Thr Leu Asp Pro His Gly Val Met Val Val Val
    130                 135                 140

gaa gcg gaa cac atg tgc atg acg atg cgc ggt gta aga aaa ccg ggt      480
Glu Ala Glu His Met Cys Met Thr Met Arg Gly Val Arg Lys Pro Gly
145                 150                 155                 160

gcg aaa act gtg act tca gca gtc aga ggc gtt ttt aaa gat gat gcc      528
Ala Lys Thr Val Thr Ser Ala Val Arg Gly Val Phe Lys Asp Asp Ala
                165                 170                 175

gct gcc cgt gca gaa gta ttg gaa cat att aaa cgc cag gac taa          573
Ala Ala Arg Ala Glu Val Leu Glu His Ile Lys Arg Gln Asp
            180                 185                 190


<210> SEQ ID NO 22
<211> LENGTH: 190
<212> TYPE: PRT
<213> ORGANISM: Bacillus subtilis

<400> SEQUENCE: 22

Met Lys Glu Val Asn Lys Glu Gln Ile Glu Gln Ala Val Arg Gln Ile
  1               5                  10                  15

Leu Glu Ala Ile Gly Glu Asp Pro Asn Arg Glu Gly Leu Leu Asp Thr
            20                  25                  30

Pro Lys Arg Val Ala Lys Met Tyr Ala Glu Val Phe Ser Gly Leu Asn
        35                  40                  45

Glu Asp Pro Lys Glu His Phe Gln Thr Ile Phe Gly Glu Asn His Glu
     50                  55                  60

Glu Leu Val Leu Val Lys Asp Ile Ala Phe His Ser Met Cys Glu His
 65                  70                  75                  80

His Leu Val Pro Phe Tyr Gly Lys Ala His Val Ala Tyr Ile Pro Arg
                 85                  90                  95

Gly Gly Lys Val Thr Gly Leu Ser Lys Leu Ala Arg Ala Val Glu Ala
            100                 105                 110

Val Ala Lys Arg Pro Gln Leu Gln Glu Arg Ile Thr Ser Thr Ile Ala
        115                 120                 125

Glu Ser Ile Val Glu Thr Leu Asp Pro His Gly Val Met Val Val Val
    130                 135                 140

Glu Ala Glu His Met Cys Met Thr Met Arg Gly Val Arg Lys Pro Gly
145                 150                 155                 160

Ala Lys Thr Val Thr Ser Ala Val Arg Gly Val Phe Lys Asp Asp Ala
                165                 170                 175

Ala Ala Arg Ala Glu Val Leu Glu His Ile Lys Arg Gln Asp
```

-continued 180 185 190

<210> SEQ ID NO 23
<211> LENGTH: 1971
<212> TYPE: DNA
<213> ORGANISM: Homo sapiens
<220> FEATURE:
<223> OTHER INFORMATION: Human methylenetetrahydrofolate reductase (MTHFR) gene: exons 1-8
<300> PUBLICATION INFORMATION:
<308> DATABASE ACCESSION NUMBER: AF105977/GenBank 1-11

<400> SEQUENCE: 23

```
atggtgaacg aagccagagg aaacagcagc ctcaacccct gcttggaggg cagtgccagc     60
agtggcagtg agagctccaa agatagttcg agatgttcca ccccgggcct ggaccctgag    120
cggcatgaga gactccggga gaagatgagg cggcgattgg aatctggtga caagtggttc    180
tccctggaat tcttccctcc tcgaactgct gagggagctg tcaatctcat ctcaaggttt    240
gaccggatgg cagcaggtgg cccctctac atagacgtga cctggcaccc agcaggtgac    300
cctggctcag acaaggagac ctcctccatg atgatcgcca gcaccgccgt gaactactgt    360
ggcctggaga ccatcctgca catgacctgc tgccgtcagc gcctggagga gatcacgggc    420
catctgcaca aagctaagca gctgggcctg aagaacatca tggcgctgcg gggagaccca    480
ataggtgacc agtgggaaga ggaggaggga ggcttcaact acgcagtgga cctggtgaag    540
cacatccgaa gtgagtttgg tgactacttt gacatctgtg tggcaggtta ccccaaaggc    600
caccccgaag cagggagctt tgaggctgac ctgaagcact tgaaggagaa ggtgtctgcg    660
ggagccgatt tcatcatcac gcagcttttc tttgaggctg acacattctt ccgctttgtg    720
aaggcatgca ccgacatggg catcacttgc cccatcgtcc ccgggatctt tcccatccag    780
ggctaccact cccttcggca gcttgtgaag ctgtccaagc tggaggtgcc acaggagatc    840
aaggacgtga ttgagccaat caaagacaac gatgctgcca tccgcaacta tggcatcgag    900
ctggccgtga gcctgtgcca ggagcttctg gccagtggct tggtgccagg cctccacttc    960
tacaccctca accgcgagat ggctaccaca gaggtgctga agcgcctggg gatgtggact   1020
gaggacccca ggcgtcccct accctgggct ctcagtgccc accccaagcg ccgagaggaa   1080
gatgtacgtc ccatcttctg ggcctccaga ccaaagagtt acatctaccg tacccaggag   1140
tgggacgagt tccctaacgg ccgctggggc aattcctctt cccctgcctt tggggagctg   1200
aaggactact acctcttcta cctgaagagc aagtccccca aggaggagct gctgaagatg   1260
tggggggagg agctgaccag tgaagcaagt gtctttgaag tctttgttct ttacctctcg   1320
ggagaaccaa accggaatgg tcacaaagtg acttgcctgc cctggaacga tgagcccctg   1380
gcggctgaga ccagcctgct gaaggaggag ctgctgcggg tgaaccgcca gggcatcctc   1440
accatcaact cacagcccaa catcaacggg aagccgtcct ccgaccccat cgtgggctgg   1500
ggccccagcg gggctatgt cttccagaag gcctacttag agtttttcac ttcccgcgag   1560
acagcggaag cacttctgca agtgctgaag aagtacgagc tccgggttaa ttaccacctt   1620
gtcaatgtga agggtgaaaa catcaccaat gcccctgaac tgcagccgaa tgctgtcact   1680
tggggcatct tccctgggcg agagatcatc cagcccaccg tagtggatcc cgtcagcttc   1740
atgttctgga aggacgaggc ctttgccctg tggattgagc ggtggggaaa gctgtatgag   1800
gaggagtccc cgtcccgcac catcatccag tacatccacg acaactactt cctggtcaac   1860
ctggtggaca atgacttccc actggacaac tgcctctggc aggtggtgga agacacattg   1920
```

-continued

```
gagcttctca acaggcccac ccagaatgcg agagaaacgg aggctccatg a          1971


<210> SEQ ID NO 24
<211> LENGTH: 656
<212> TYPE: PRT
<213> ORGANISM: Homo sapiens
<220> FEATURE:
<223> OTHER INFORMATION: Human methylenetetrahdrofolate reductase
      (MTHFR) protein sequence
<300> PUBLICATION INFORMATION:
<308> DATABASE ACCESSION NUMBER: AF105977/GenBank 1-11

<400> SEQUENCE: 24

Met Val Asn Glu Ala Arg Gly Asn Ser Ser Leu Asn Pro Cys Leu Glu
  1               5                  10                  15

Gly Ser Ala Ser Ser Gly Ser Glu Ser Ser Lys Asp Ser Ser Arg Cys
             20                  25                  30

Ser Thr Pro Gly Leu Asp Pro Glu Arg His Glu Arg Leu Arg Glu Lys
         35                  40                  45

Met Arg Arg Arg Leu Glu Ser Gly Asp Lys Trp Phe Ser Leu Glu Phe
     50                  55                  60

Phe Pro Pro Arg Thr Ala Glu Gly Ala Val Asn Leu Ile Ser Arg Phe
 65                  70                  75                  80

Asp Arg Met Ala Ala Gly Gly Pro Leu Tyr Ile Asp Val Thr Trp His
                 85                  90                  95

Pro Ala Gly Asp Pro Gly Ser Asp Lys Glu Thr Ser Ser Met Met Ile
            100                 105                 110

Ala Ser Thr Ala Val Asn Tyr Cys Gly Leu Glu Thr Ile Leu His Met
        115                 120                 125

Thr Cys Cys Arg Gln Arg Leu Glu Glu Ile Thr Gly His Leu His Lys
    130                 135                 140

Ala Lys Gln Leu Gly Leu Lys Asn Ile Met Ala Leu Arg Gly Asp Pro
145                 150                 155                 160

Ile Gly Asp Gln Trp Glu Glu Glu Glu Gly Gly Phe Asn Tyr Ala Val
                165                 170                 175

Asp Leu Val Lys His Ile Arg Ser Glu Phe Gly Asp Tyr Phe Asp Ile
            180                 185                 190

Cys Val Ala Gly Tyr Pro Lys Gly His Pro Glu Ala Gly Ser Phe Glu
        195                 200                 205

Ala Asp Leu Lys His Leu Lys Glu Lys Val Ser Ala Gly Ala Asp Phe
    210                 215                 220

Ile Ile Thr Gln Leu Phe Phe Glu Ala Asp Thr Phe Phe Arg Phe Val
225                 230                 235                 240

Lys Ala Cys Thr Asp Met Gly Ile Thr Cys Pro Ile Val Pro Gly Ile
                245                 250                 255

Phe Pro Ile Gln Gly Tyr His Ser Leu Arg Gln Leu Val Lys Leu Ser
            260                 265                 270

Lys Leu Glu Val Pro Gln Glu Ile Lys Asp Val Ile Glu Pro Ile Lys
        275                 280                 285

Asp Asn Asp Ala Ala Ile Arg Asn Tyr Gly Ile Glu Leu Ala Val Ser
    290                 295                 300

Leu Cys Gln Glu Leu Leu Ala Ser Gly Leu Val Pro Gly Leu His Phe
305                 310                 315                 320

Tyr Thr Leu Asn Arg Glu Met Ala Thr Thr Glu Val Leu Lys Arg Leu
                325                 330                 335

Gly Met Trp Thr Glu Asp Pro Arg Arg Pro Leu Pro Trp Ala Leu Ser
```

-continued

```
            340                 345                 350

Ala His Pro Lys Arg Arg Glu Glu Asp Val Arg Pro Ile Phe Trp Ala
        355                 360                 365

Ser Arg Pro Lys Ser Tyr Ile Tyr Arg Thr Gln Glu Trp Asp Glu Phe
    370                 375                 380

Pro Asn Gly Arg Trp Gly Asn Ser Ser Ser Pro Ala Phe Gly Glu Leu
385                 390                 395                 400

Lys Asp Tyr Tyr Leu Phe Tyr Leu Lys Ser Lys Ser Pro Lys Glu Glu
                405                 410                 415

Leu Leu Lys Met Trp Gly Glu Glu Leu Thr Ser Glu Ala Ser Val Phe
            420                 425                 430

Glu Val Phe Val Leu Tyr Leu Ser Gly Glu Pro Asn Arg Asn Gly His
        435                 440                 445

Lys Val Thr Cys Leu Pro Trp Asn Asp Glu Pro Leu Ala Ala Glu Thr
    450                 455                 460

Ser Leu Leu Lys Glu Glu Leu Leu Arg Val Asn Arg Gln Gly Ile Leu
465                 470                 475                 480

Thr Ile Asn Ser Gln Pro Asn Ile Asn Gly Lys Pro Ser Ser Asp Pro
                485                 490                 495

Ile Val Gly Trp Gly Pro Ser Gly Gly Tyr Val Phe Gln Lys Ala Tyr
            500                 505                 510

Leu Glu Phe Phe Thr Ser Arg Glu Thr Ala Glu Ala Leu Leu Gln Val
        515                 520                 525

Leu Lys Lys Tyr Glu Leu Arg Val Asn Tyr His Leu Val Asn Val Lys
    530                 535                 540

Gly Glu Asn Ile Thr Asn Ala Pro Glu Leu Gln Pro Asn Ala Val Thr
545                 550                 555                 560

Trp Gly Ile Phe Pro Gly Arg Glu Ile Ile Gln Pro Thr Val Val Asp
                565                 570                 575

Pro Val Ser Phe Met Phe Trp Lys Asp Glu Ala Phe Ala Leu Trp Ile
            580                 585                 590

Glu Arg Trp Gly Lys Leu Tyr Glu Glu Glu Ser Pro Ser Arg Thr Ile
        595                 600                 605

Ile Gln Tyr Ile His Asp Asn Tyr Phe Leu Val Asn Leu Val Asp Asn
    610                 615                 620

Asp Phe Pro Leu Asp Asn Cys Leu Trp Gln Val Val Glu Asp Thr Leu
625                 630                 635                 640

Glu Leu Leu Asn Arg Pro Thr Gln Asn Ala Arg Glu Thr Glu Ala Pro
                645                 650                 655
```

```
<210> SEQ ID NO 25
<211> LENGTH: 2561
<212> TYPE: DNA
<213> ORGANISM: Escherichia coli
<220> FEATURE:
<221> NAME/KEY: CDS
<222> LOCATION: (1131)..(2399)
<223> OTHER INFORMATION: Escherichia coli nucleic acid encoding
      folypolyglutamate synthetase-dihydrofolate
      synthetase
<300> PUBLICATION INFORMATION:
<308> DATABASE ACCESSION NUMBER: M32445/GenBank

<400> SEQUENCE: 25

ccgcggttcg accacttttt tatccaaagt ttcgggctgt tatgttttaa tgtgcaacat     60

tcatggtctg ttgggggcaa aaatggcatt atgcgtcccc aaagataaaa ctggcatcga    120
```

-continued

```
accaggttca gacagaaagg tccctaatga gctggattga acgaattaaa agcaacatta    180

ctcccacccg caaggcgagc attcctgaag ggtgtggac taagtgtgat agctgcggtc    240

aggttttata ccgcgctgag ctggaacgta atcttgaggt ctgtccgaag tgtgaccatc    300

acatgcgtat gacagcgcgt aatcgcctgc atagcctgtt agatgaagga agccttgtgg    360

agctgggtag cgagcttgag ccgaaagatg tgctgaagtt tcgtgactcc aagaagtata    420

aagaccgtct ggcatctgcg cagaaagaaa ccggcgaaaa agatgcgctg gtggtgatga    480

aaggcactct gtatggaatg ccggttgtcg ctgcggcatt cgagttcgcc tttatgggcg    540

gttcaatggg gtctgttgtg ggtgcacgtt tcgtgcgtgc cgttgagcag gcgctggaag    600

ataactgccc gctgatctgc ttctccgcct ctggtggcgc acgtatgcag gaagcactga    660

tgtcgctgat gcagatggcg aaaacctctg cggcactggc aaaaatgcag gagcgcggct    720

tgccgtacat ctccgtgctg accgacccga cgatgggcgg tgtttctgca agtttcgcca    780

tgctgggcga tctcaacatc gctgaaccga aagcgttaat ggctttgccg gtccgcgtgt    840

tatcgaacag accgttcgcg aaaaaactgc cgcctggatt ccagcgcagt gaattcctga    900

tcgagaaagg cgcgatcgac atgatcgtcc gtcgtccgga aatgcgcctg aaactggcga    960

gcattctggc gaagttgatg aatctgccag cgccgaatcc tgaagcgccg cgtgaaggcg   1020

tagtggtacc cccggtaccg gatcaggaac ctgaggcctg ataactgata agggcagggc   1080

cactggctct gccctttgc tattctcacc gtaacgaatc agcggatacc atg att      1136
                                                        Met Ile
                                                          1

atc aaa cgc act cct caa gcc gcg tcg cct ctg gct tcg tgg ctt tct     1184
Ile Lys Arg Thr Pro Gln Ala Ala Ser Pro Leu Ala Ser Trp Leu Ser
          5                  10                  15

tat ctg gaa aac ctg cac agt aaa act atc gat ctc ggc ctt gag cgc     1232
Tyr Leu Glu Asn Leu His Ser Lys Thr Ile Asp Leu Gly Leu Glu Arg
     20                  25                  30

gtg agc ctg gtc gcg gcg cgt ctt ggc gtc ctg aaa cca gcg cca ttt     1280
Val Ser Leu Val Ala Ala Arg Leu Gly Val Leu Lys Pro Ala Pro Phe
 35                  40                  45                  50

gtg ttt acc gtt gcg ggt acg aat ggc aaa ggc acc acc tgc cgt acg     1328
Val Phe Thr Val Ala Gly Thr Asn Gly Lys Gly Thr Thr Cys Arg Thr
                 55                  60                  65

ctg gag tcg att ctg atg gcg gca ggg tac aaa gtg ggc gtc tac agt     1376
Leu Glu Ser Ile Leu Met Ala Ala Gly Tyr Lys Val Gly Val Tyr Ser
             70                  75                  80

tcg cct cat ctg gtg cgt tat acc gag cgc gta cgt gtg cag ggc cag     1424
Ser Pro His Leu Val Arg Tyr Thr Glu Arg Val Arg Val Gln Gly Gln
         85                  90                  95

gaa ttg ccg gaa tcg gcc cac acc gcc tct ttt gcg gag att gaa tcg     1472
Glu Leu Pro Glu Ser Ala His Thr Ala Ser Phe Ala Glu Ile Glu Ser
    100                 105                 110

gca cgc ggt gat att tcc ctg acc tat ttc gag tac ggt acg ctg tcg     1520
Ala Arg Gly Asp Ile Ser Leu Thr Tyr Phe Glu Tyr Gly Thr Leu Ser
115                 120                 125                 130

gcg ttg tgg ctg ttc aag cag gca caa ctt gac gtg gtg att ctg gaa     1568
Ala Leu Trp Leu Phe Lys Gln Ala Gln Leu Asp Val Val Ile Leu Glu
                135                 140                 145

gta ggg ctg ggc ggt cgt ctg gac gca acc aat att gtc gac gcc gat     1616
Val Gly Leu Gly Gly Arg Leu Asp Ala Thr Asn Ile Val Asp Ala Asp
            150                 155                 160

gtc gcg gta gta acc agt att gcg ctg gat cat acc gac tgg ctg ggt     1664
Val Ala Val Val Thr Ser Ile Ala Leu Asp His Thr Asp Trp Leu Gly
        165                 170                 175
```

```
cca gat cgc gaa agt att ggt cgc gag aaa gca ggc atc ttc cgc agc     1712
Pro Asp Arg Glu Ser Ile Gly Arg Glu Lys Ala Gly Ile Phe Arg Ser
    180                 185                 190

gaa aaa ccg gca att gtc ggt gag ccg gaa atg cct tct acc att gct     1760
Glu Lys Pro Ala Ile Val Gly Glu Pro Glu Met Pro Ser Thr Ile Ala
195                 200                 205                 210

gat gtg gcg cag gaa aaa ggt gca ctg tta caa cgt cgg ggc gtt gag     1808
Asp Val Ala Gln Glu Lys Gly Ala Leu Leu Gln Arg Arg Gly Val Glu
                215                 220                 225

tgg aac tat tcc gtc acc gat cat gac tgg gcg ttt agc gat gct cac     1856
Trp Asn Tyr Ser Val Thr Asp His Asp Trp Ala Phe Ser Asp Ala His
            230                 235                 240

ggc acg ctg gaa aat ctg ccg ttg ccg ctt gtc ccg caa ccg aat gcc     1904
Gly Thr Leu Glu Asn Leu Pro Leu Pro Leu Val Pro Gln Pro Asn Ala
        245                 250                 255

gca aca gcg ctg gcg gca ctg cgt gcc agc ggg ctg gaa gtc agt gaa     1952
Ala Thr Ala Leu Ala Ala Leu Arg Ala Ser Gly Leu Glu Val Ser Glu
    260                 265                 270

aat gcc att cgc gac ggg att gcc agc gca att ttg ccg gga cgt ttc     2000
Asn Ala Ile Arg Asp Gly Ile Ala Ser Ala Ile Leu Pro Gly Arg Phe
275                 280                 285                 290

cag att gtg agc gag tcg cca cgc gtt att ttt gat gtc gcg cat aat     2048
Gln Ile Val Ser Glu Ser Pro Arg Val Ile Phe Asp Val Ala His Asn
                295                 300                 305

cca cat gcg gcg gaa tat ctc acc ggg cgt atg aaa gcg cta ccg aaa     2096
Pro His Ala Ala Glu Tyr Leu Thr Gly Arg Met Lys Ala Leu Pro Lys
            310                 315                 320

aac ggg cgc atg ctg gcg gtt atc ggt atg cta cat gat aaa gat att     2144
Asn Gly Arg Met Leu Ala Val Ile Gly Met Leu His Asp Lys Asp Ile
        325                 330                 335

gcc gga act ctg gcc tgg ttg aaa agc gtg gtt gat gac tgg tat tgt     2192
Ala Gly Thr Leu Ala Trp Leu Lys Ser Val Val Asp Asp Trp Tyr Cys
    340                 345                 350

gcg cca ctg gaa ggg ccg cgc ggt gcc acg gca gaa caa ctg ctt gag     2240
Ala Pro Leu Glu Gly Pro Arg Gly Ala Thr Ala Glu Gln Leu Leu Glu
355                 360                 365                 370

cat ttg ggt aac ggc aaa tca ttt gat agc gtt gcg cag gca tgg gat     2288
His Leu Gly Asn Gly Lys Ser Phe Asp Ser Val Ala Gln Ala Trp Asp
                375                 380                 385

gcc gca atg gcg gac gct aaa gcg gaa gac acc gtg ctg gtg tgt ggt     2336
Ala Ala Met Ala Asp Ala Lys Ala Glu Asp Thr Val Leu Val Cys Gly
            390                 395                 400

tct ttc cac acg gtc gca cat gtc atg gaa gtg att gac gcg agg aga     2384
Ser Phe His Thr Val Ala His Val Met Glu Val Ile Asp Ala Arg Arg
        405                 410                 415

agc ggt ggc aag taa gtttcagaat cggttagtgg gcacgatcgt gctggtggcg     2439
Ser Gly Gly Lys
    420

ctgggggtga ttgtacttcc agggctgctg gacgggcaga aaaaacatta tcaggatgag   2499

ttcgcggcta tcccgctggt gccgaaagcg ggcgatcgtg atgagcctga tatgatgcca   2559

gc                                                                  2561
```

<210> SEQ ID NO 26
<211> LENGTH: 422
<212> TYPE: PRT
<213> ORGANISM: Escherichia coli

<400> SEQUENCE: 26

-continued

```
Met Ile Ile Lys Arg Thr Pro Gln Ala Ala Ser Pro Leu Ala Ser Trp
  1               5                  10                  15

Leu Ser Tyr Leu Glu Asn Leu His Ser Lys Thr Ile Asp Leu Gly Leu
             20                  25                  30

Glu Arg Val Ser Leu Val Ala Ala Arg Leu Gly Val Leu Lys Pro Ala
         35                  40                  45

Pro Phe Val Phe Thr Val Ala Gly Thr Asn Gly Lys Gly Thr Thr Cys
     50                  55                  60

Arg Thr Leu Glu Ser Ile Leu Met Ala Ala Gly Tyr Lys Val Gly Val
 65                  70                  75                  80

Tyr Ser Ser Pro His Leu Val Arg Tyr Thr Glu Arg Val Arg Val Gln
                 85                  90                  95

Gly Gln Glu Leu Pro Glu Ser Ala His Thr Ala Ser Phe Ala Glu Ile
            100                 105                 110

Glu Ser Ala Arg Gly Asp Ile Ser Leu Thr Tyr Phe Glu Tyr Gly Thr
        115                 120                 125

Leu Ser Ala Leu Trp Leu Phe Lys Gln Ala Gln Leu Asp Val Val Ile
    130                 135                 140

Leu Glu Val Gly Leu Gly Gly Arg Leu Asp Ala Thr Asn Ile Val Asp
145                 150                 155                 160

Ala Asp Val Ala Val Val Thr Ser Ile Ala Leu Asp His Thr Asp Trp
                165                 170                 175

Leu Gly Pro Asp Arg Glu Ser Ile Gly Arg Glu Lys Ala Gly Ile Phe
            180                 185                 190

Arg Ser Glu Lys Pro Ala Ile Val Gly Glu Pro Glu Met Pro Ser Thr
        195                 200                 205

Ile Ala Asp Val Ala Gln Glu Lys Gly Ala Leu Leu Gln Arg Arg Gly
    210                 215                 220

Val Glu Trp Asn Tyr Ser Val Thr Asp His Asp Trp Ala Phe Ser Asp
225                 230                 235                 240

Ala His Gly Thr Leu Glu Asn Leu Pro Leu Pro Leu Val Pro Gln Pro
                245                 250                 255

Asn Ala Ala Thr Ala Leu Ala Ala Leu Arg Ala Ser Gly Leu Glu Val
            260                 265                 270

Ser Glu Asn Ala Ile Arg Asp Gly Ile Ala Ser Ala Ile Leu Pro Gly
        275                 280                 285

Arg Phe Gln Ile Val Ser Glu Ser Pro Arg Val Ile Phe Asp Val Ala
    290                 295                 300

His Asn Pro His Ala Ala Glu Tyr Leu Thr Gly Arg Met Lys Ala Leu
305                 310                 315                 320

Pro Lys Asn Gly Arg Met Leu Ala Val Ile Gly Met Leu His Asp Lys
                325                 330                 335

Asp Ile Ala Gly Thr Leu Ala Trp Leu Lys Ser Val Val Asp Asp Trp
            340                 345                 350

Tyr Cys Ala Pro Leu Glu Gly Pro Arg Gly Ala Thr Ala Glu Gln Leu
        355                 360                 365

Leu Glu His Leu Gly Asn Gly Lys Ser Phe Asp Ser Val Ala Gln Ala
    370                 375                 380

Trp Asp Ala Ala Met Ala Asp Ala Lys Ala Glu Asp Thr Val Leu Val
385                 390                 395                 400

Cys Gly Ser Phe His Thr Val Ala His Val Met Glu Val Ile Asp Ala
                405                 410                 415

Arg Arg Ser Gly Gly Lys
```

```
           420


<210> SEQ ID NO 27
<211> LENGTH: 564
<212> TYPE: DNA
<213> ORGANISM: Cricetulus sp.
<220> FEATURE:
<221> NAME/KEY: CDS
<222> LOCATION: (1)..(564)
<223> OTHER INFORMATION: Chinese hamster dihydrofalate reductase cDNA
<300> PUBLICATION INFORMATION:
<308> DATABASE ACCESSION NUMBER: M37124/GenBank

<400> SEQUENCE: 27

atg gtt cga ccg ctg aac tgc atc gtc gcc gtg tcc cag aat atg ggc       48
Met Val Arg Pro Leu Asn Cys Ile Val Ala Val Ser Gln Asn Met Gly
  1               5                  10                  15

atc ggc aag aac gga gac ttt ccc tgg cca atg ctc agg aac gaa ttc       96
Ile Gly Lys Asn Gly Asp Phe Pro Trp Pro Met Leu Arg Asn Glu Phe
             20                  25                  30

aag tac ttc caa aga atg acc acc acc tcc tca gtg gaa ggt aaa cag      144
Lys Tyr Phe Gln Arg Met Thr Thr Thr Ser Ser Val Glu Gly Lys Gln
         35                  40                  45

aac ctg gtg att atg ggc cgg aaa acc tgg ttc tcc att cct gag aag      192
Asn Leu Val Ile Met Gly Arg Lys Thr Trp Phe Ser Ile Pro Glu Lys
     50                  55                  60

aat cga cct tta aag gac aga att aat ata gtt ctc agt aga gag ctc      240
Asn Arg Pro Leu Lys Asp Arg Ile Asn Ile Val Leu Ser Arg Glu Leu
 65                  70                  75                  80

aag gaa cca cca caa gga gct cat ttt ctt gcc aaa agt ctg gac gat      288
Lys Glu Pro Pro Gln Gly Ala His Phe Leu Ala Lys Ser Leu Asp Asp
                 85                  90                  95

gcc tta aaa ctt att gaa caa cca gag tta gca gat aaa gtg gac atg      336
Ala Leu Lys Leu Ile Glu Gln Pro Glu Leu Ala Asp Lys Val Asp Met
            100                 105                 110

gtt tgg ata gtt gga ggc agt tcc gtt tac aag gaa gcc atg aat cag      384
Val Trp Ile Val Gly Gly Ser Ser Val Tyr Lys Glu Ala Met Asn Gln
        115                 120                 125

cca ggc cat ctc aga ctc ttt gtg aca agg atc atg cag gaa ttt gaa      432
Pro Gly His Leu Arg Leu Phe Val Thr Arg Ile Met Gln Glu Phe Glu
    130                 135                 140

agt gac acg ttc ttc cca gaa att gat ttg gag aaa tat aaa ctt ctc      480
Ser Asp Thr Phe Phe Pro Glu Ile Asp Leu Glu Lys Tyr Lys Leu Leu
145                 150                 155                 160

cca gag tac cca ggg gtc ctt tct gaa gtc cag gag gaa aaa ggc atc      528
Pro Glu Tyr Pro Gly Val Leu Ser Glu Val Gln Glu Glu Lys Gly Ile
                165                 170                 175

aag tat aaa ttt gaa gtc tat gag aag aaa ggc taa                      564
Lys Tyr Lys Phe Glu Val Tyr Glu Lys Lys Gly
            180                 185


<210> SEQ ID NO 28
<211> LENGTH: 187
<212> TYPE: PRT
<213> ORGANISM: Cricetulus sp.

<400> SEQUENCE: 28

Met Val Arg Pro Leu Asn Cys Ile Val Ala Val Ser Gln Asn Met Gly
  1               5                  10                  15

Ile Gly Lys Asn Gly Asp Phe Pro Trp Pro Met Leu Arg Asn Glu Phe
             20                  25                  30

Lys Tyr Phe Gln Arg Met Thr Thr Thr Ser Ser Val Glu Gly Lys Gln
```

-continued

```
        35                  40                  45

Asn Leu Val Ile Met Gly Arg Lys Thr Trp Phe Ser Ile Pro Glu Lys
     50                  55                  60

Asn Arg Pro Leu Lys Asp Arg Ile Asn Ile Val Leu Ser Arg Glu Leu
 65                  70                  75                  80

Lys Glu Pro Pro Gln Gly Ala His Phe Leu Ala Lys Ser Leu Asp Asp
                 85                  90                  95

Ala Leu Lys Leu Ile Glu Gln Pro Glu Leu Ala Asp Lys Val Asp Met
            100                 105                 110

Val Trp Ile Val Gly Gly Ser Ser Val Tyr Lys Glu Ala Met Asn Gln
        115                 120                 125

Pro Gly His Leu Arg Leu Phe Val Thr Arg Ile Met Gln Glu Phe Glu
    130                 135                 140

Ser Asp Thr Phe Phe Pro Glu Ile Asp Leu Glu Lys Tyr Lys Leu Leu
145                 150                 155                 160

Pro Glu Tyr Pro Gly Val Leu Ser Glu Val Gln Glu Glu Lys Gly Ile
                165                 170                 175

Lys Tyr Lys Phe Glu Val Tyr Glu Lys Lys Gly
            180                 185


<210> SEQ ID NO 29
<211> LENGTH: 942
<212> TYPE: DNA
<213> ORGANISM: Homo sapiens
<220> FEATURE:
<223> OTHER INFORMATION: Human thymidylate synthase gene: exons 1-8
<300> PUBLICATION INFORMATION:
<308> DATABASE ACCESSION NUMBER: D00596/GenBank

<400> SEQUENCE: 29

atgcctgtgg ccggctcgga gctgccgcgc cggcccttgc cccccgccgc acaggagcgg     60

gacgccgagc cgcgtccgcc gcacggggag ctgcagtacc tggggcagat ccaacacatc    120

ctccgctgcg gcgtcaggaa ggacgaccgc acgggcaccg gcaccctgtc ggtattcggc    180

atgcaggcgc gctacagcct gagagatgaa ttccctctgc tgacaaccaa acgtgtgttc    240

tggaagggtg ttttggagga gttgctgtgg tttatcaagg gatccacaaa tgctaaagag    300

ctgtcttcca agggagtgaa aatctgggat gccaatggat cccgagactt tttggacagc    360

ctgggattct ccaccagaga agaaggggac ttgggcccag tttatggctt ccagtggagg    420

cattttgggg cagaatacag agatatggaa tcagattatt caggacaggg agttgaccaa    480

ctgcaaagag tgattgacac catcaaaacc aaccctgacg acagaagaat catcatgtgc    540

gcttggaatc caagagatct tcctctgatg gcgctgcctc catgccatgc cctctgccag    600

ttctatgtgg tgaacagtga gctgtcctgc cagctgtacc agagatcggg agacatgggc    660

ctcggtgtgc ctttcaacat cgccagctac gccctgctca cgtacatgat tgcgcacatc    720

acgggcctga agccaggtga ctttatacac actttgggag atgcacatat ttacctgaat    780

cacatcgagc cactgaaaat tcagcttcag cgagaaccca gacctttccc aaagctcagg    840

attcttcgaa aagttgagaa aattgatgac ttcaaagctg aagactttca gattgaaggg    900

tacaatccgc atccaactat taaaatggaa atggctgttt ag                       942


<210> SEQ ID NO 30
<211> LENGTH: 313
<212> TYPE: PRT
<213> ORGANISM: Homo sapiens
<220> FEATURE:
```

<223> OTHER INFORMATION: Human thymidylate synthase protein sequence
<300> PUBLICATION INFORMATION:
<308> DATABASE ACCESSION NUMBER: D00596/GenBank

<400> SEQUENCE: 30

```
Met Pro Val Ala Gly Ser Glu Leu Pro Arg Arg Pro Leu Pro Pro Ala
  1               5                  10                  15

Ala Gln Glu Arg Asp Ala Glu Pro Arg Pro Pro His Gly Glu Leu Gln
             20                  25                  30

Tyr Leu Gly Gln Ile Gln His Ile Leu Arg Cys Gly Val Arg Lys Asp
         35                  40                  45

Asp Arg Thr Gly Thr Gly Thr Leu Ser Val Phe Gly Met Gln Ala Arg
     50                  55                  60

Tyr Ser Leu Arg Asp Glu Phe Pro Leu Leu Thr Thr Lys Arg Val Phe
 65                  70                  75                  80

Trp Lys Gly Val Leu Glu Glu Leu Leu Trp Phe Ile Lys Gly Ser Thr
                 85                  90                  95

Asn Ala Lys Glu Leu Ser Ser Lys Gly Val Lys Ile Trp Asp Ala Asn
            100                 105                 110

Gly Ser Arg Asp Phe Leu Asp Ser Leu Gly Phe Ser Thr Arg Glu Glu
        115                 120                 125

Gly Asp Leu Gly Pro Val Tyr Gly Phe Gln Trp Arg His Phe Gly Ala
    130                 135                 140

Glu Tyr Arg Asp Met Glu Ser Asp Tyr Ser Gly Gln Gly Val Asp Gln
145                 150                 155                 160

Leu Gln Arg Val Ile Asp Thr Ile Lys Thr Asn Pro Asp Asp Arg Arg
                165                 170                 175

Ile Ile Met Cys Ala Trp Asn Pro Arg Asp Leu Pro Leu Met Ala Leu
            180                 185                 190

Pro Pro Cys His Ala Leu Cys Gln Phe Tyr Val Val Asn Ser Glu Leu
        195                 200                 205

Ser Cys Gln Leu Tyr Gln Arg Ser Gly Asp Met Gly Leu Gly Val Pro
    210                 215                 220

Phe Asn Ile Ala Ser Tyr Ala Leu Leu Thr Tyr Met Ile Ala His Ile
225                 230                 235                 240

Thr Gly Leu Lys Pro Gly Asp Phe Ile His Thr Leu Gly Asp Ala His
                245                 250                 255

Ile Tyr Leu Asn His Ile Glu Pro Leu Lys Ile Gln Leu Gln Arg Glu
            260                 265                 270

Pro Arg Pro Phe Pro Lys Leu Arg Ile Leu Arg Lys Val Glu Lys Ile
        275                 280                 285

Asp Asp Phe Lys Ala Glu Asp Phe Gln Ile Glu Gly Tyr Asn Pro His
    290                 295                 300

Pro Thr Ile Lys Met Glu Met Ala Val
305                 310
```

<210> SEQ ID NO 31
<211> LENGTH: 2344
<212> TYPE: DNA
<213> ORGANISM: Homo sapiens
<220> FEATURE:
<221> NAME/KEY: CDS
<222> LOCATION: (9)..(2252)
<220> FEATURE:
<223> OTHER INFORMATION: Human cholesterol esterase cDNA
<300> PUBLICATION INFORMATION:
<308> DATABASE ACCESSION NUMBER: M85201/GenBank

```
<400> SEQUENCE: 31

agaggctg atg ctc acc atg ggg cgc ctg caa ctg gtt gtg ttg ggc ctc      50
         Met Leu Thr Met Gly Arg Leu Gln Leu Val Val Leu Gly Leu
           1               5                  10

acc tgc tgc tgg gca gtg gcg agt gcc gcg aag ctg ggc gcc gtg tac       98
Thr Cys Cys Trp Ala Val Ala Ser Ala Ala Lys Leu Gly Ala Val Tyr
 15                  20                  25                  30

aca gaa ggt ggg ttc gtg gaa ggc gtc aat aag aag ctc ggc ctc ctg      146
Thr Glu Gly Gly Phe Val Glu Gly Val Asn Lys Lys Leu Gly Leu Leu
                 35                  40                  45

ggt gac tct gtg gac atc ttc aag ggc atc ccc ttc gca gct ccc acc      194
Gly Asp Ser Val Asp Ile Phe Lys Gly Ile Pro Phe Ala Ala Pro Thr
             50                  55                  60

aag gcc ctg gaa aat cct cag cca cat cct ggc tgg caa ggg acc ctg      242
Lys Ala Leu Glu Asn Pro Gln Pro His Pro Gly Trp Gln Gly Thr Leu
         65                  70                  75

aag gcc aag aac ttc aag aag aga tgc ctg cag gcc acc atc acc cag      290
Lys Ala Lys Asn Phe Lys Lys Arg Cys Leu Gln Ala Thr Ile Thr Gln
     80                  85                  90

gac agc acc tac ggg gat gaa gac tgc ctg tac ctc aac att tgg gtg      338
Asp Ser Thr Tyr Gly Asp Glu Asp Cys Leu Tyr Leu Asn Ile Trp Val
 95                 100                 105                 110

ccc cag ggc agg aag caa gtc tcc cgg gac ctg ccc gtt atg atc tgg      386
Pro Gln Gly Arg Lys Gln Val Ser Arg Asp Leu Pro Val Met Ile Trp
                115                 120                 125

atc tat gga ggc gcc ttc ctc atg ggg tcc ggc cat ggg gcc aac ttc      434
Ile Tyr Gly Gly Ala Phe Leu Met Gly Ser Gly His Gly Ala Asn Phe
            130                 135                 140

ctc aac aac tac ctg tat gac ggc gag gag atc gcc aca cgc gga aac      482
Leu Asn Asn Tyr Leu Tyr Asp Gly Glu Glu Ile Ala Thr Arg Gly Asn
        145                 150                 155

gtc atc gtg gtc acc ttc aac tac cgt gtc ggc ccc ctt ggg ttc ctc      530
Val Ile Val Val Thr Phe Asn Tyr Arg Val Gly Pro Leu Gly Phe Leu
    160                 165                 170

agc act ggg gac gcc aat ctg cca ggt aac tat ggt ctt cgg gat cag      578
Ser Thr Gly Asp Ala Asn Leu Pro Gly Asn Tyr Gly Leu Arg Asp Gln
175                 180                 185                 190

cac atg gcc att gct tgg gtg aag agg aat atc gcg gcc ttc ggg ggg      626
His Met Ala Ile Ala Trp Val Lys Arg Asn Ile Ala Ala Phe Gly Gly
                195                 200                 205

gac ccc aac aac atc acg ctc ttc ggg gag tct gct gga ggt gcc agc      674
Asp Pro Asn Asn Ile Thr Leu Phe Gly Glu Ser Ala Gly Gly Ala Ser
            210                 215                 220

gtc tct ctg cag acc ctc tcc ccc tac aac aag ggc ctc atc cgg cga      722
Val Ser Leu Gln Thr Leu Ser Pro Tyr Asn Lys Gly Leu Ile Arg Arg
        225                 230                 235

gcc atc agc cag agc ggc gtg gcc ctg agt ccc tgg gtc atc cag aaa      770
Ala Ile Ser Gln Ser Gly Val Ala Leu Ser Pro Trp Val Ile Gln Lys
    240                 245                 250

aac cca ctc ttc tgg gcc aaa aag gtg gct gag aag gtg ggt tgc cct      818
Asn Pro Leu Phe Trp Ala Lys Lys Val Ala Glu Lys Val Gly Cys Pro
255                 260                 265                 270

gtg ggt gat gcc gcc agg atg gcc cag tgt ctg aag gtt act gat ccc      866
Val Gly Asp Ala Ala Arg Met Ala Gln Cys Leu Lys Val Thr Asp Pro
                275                 280                 285

cga gcc ctg acg ctg gcc tat aag gtg ccg ctg gca ggc ctg gag tac      914
Arg Ala Leu Thr Leu Ala Tyr Lys Val Pro Leu Ala Gly Leu Glu Tyr
            290                 295                 300

ccc atg ctg cac tat gtg ggc ttc gtc cct gtc att gat gga gac ttc      962
```

-continued

```
Pro Met Leu His Tyr Val Gly Phe Val Pro Val Ile Asp Gly Asp Phe
        305                 310                 315

atc ccc gct gac ccg atc aac ctg tac gcc aac gcc gcc gac atc gac     1010
Ile Pro Ala Asp Pro Ile Asn Leu Tyr Ala Asn Ala Ala Asp Ile Asp
    320                 325                 330

tat ata gca ggc acc aac aac atg gac ggc cac atc ttc gcc agc atc     1058
Tyr Ile Ala Gly Thr Asn Asn Met Asp Gly His Ile Phe Ala Ser Ile
335                 340                 345                 350

gac atg cct gcc atc aac aag ggc aac aag aaa gtc acg gag gag gac     1106
Asp Met Pro Ala Ile Asn Lys Gly Asn Lys Lys Val Thr Glu Glu Asp
                355                 360                 365

ttc tac aag ctg gtc agt gag ttc aca atc acc aag ggg ctc aga ggc     1154
Phe Tyr Lys Leu Val Ser Glu Phe Thr Ile Thr Lys Gly Leu Arg Gly
            370                 375                 380

gcc aag acg acc ttt gat gtc tac act gag tcc tgg gcc cag gac cca     1202
Ala Lys Thr Thr Phe Asp Val Tyr Thr Glu Ser Trp Ala Gln Asp Pro
        385                 390                 395

tcc cag gag aat aag aag aag act gtg gtg gac ttt gag acc gat gtc     1250
Ser Gln Glu Asn Lys Lys Lys Thr Val Val Asp Phe Glu Thr Asp Val
    400                 405                 410

ctc ttc ctg gtg ccc acc gag att gcc cta gcc cag cac aga gcc aat     1298
Leu Phe Leu Val Pro Thr Glu Ile Ala Leu Ala Gln His Arg Ala Asn
415                 420                 425                 430

gcc aag agt gcc aag acc tac gcc tac ctg ttt tcc cat ccc tct cgg     1346
Ala Lys Ser Ala Lys Thr Tyr Ala Tyr Leu Phe Ser His Pro Ser Arg
                435                 440                 445

atg ccc gtc tac ccc aaa tgg gtg ggg gcc gac cat gca gat gac att     1394
Met Pro Val Tyr Pro Lys Trp Val Gly Ala Asp His Ala Asp Asp Ile
            450                 455                 460

cag tac gtt ttc ggg aag ccc ttc gcc acc ccc acg ggc tac cgg ccc     1442
Gln Tyr Val Phe Gly Lys Pro Phe Ala Thr Pro Thr Gly Tyr Arg Pro
        465                 470                 475

caa gac agg aca gtc tct aag gcc atg atc gcc tac tgg acc aac ttt     1490
Gln Asp Arg Thr Val Ser Lys Ala Met Ile Ala Tyr Trp Thr Asn Phe
    480                 485                 490

gcc aaa aca ggg gac ccc aac atg ggc gac tcg gct gtg ccc aca cac     1538
Ala Lys Thr Gly Asp Pro Asn Met Gly Asp Ser Ala Val Pro Thr His
495                 500                 505                 510

tgg gaa ccc tac act acg gaa aac agc ggc tac ctg gag atc acc aag     1586
Trp Glu Pro Tyr Thr Thr Glu Asn Ser Gly Tyr Leu Glu Ile Thr Lys
                515                 520                 525

aag atg ggc agc agc tcc atg aag cgg agc ctg aga acc aac ttc ctg     1634
Lys Met Gly Ser Ser Ser Met Lys Arg Ser Leu Arg Thr Asn Phe Leu
            530                 535                 540

cgc tac tgg acc ctc acc tat ctg gcg ctg ccc aca gtg acc gac cag     1682
Arg Tyr Trp Thr Leu Thr Tyr Leu Ala Leu Pro Thr Val Thr Asp Gln
        545                 550                 555

gag gcc acc cct gtg ccc ccc aca ggg gac tcc gag gcc act ccc gtg     1730
Glu Ala Thr Pro Val Pro Pro Thr Gly Asp Ser Glu Ala Thr Pro Val
    560                 565                 570

ccc ccc acg ggt gac tcc gag acc gcc ccc gtg ccg ccc acg ggt gac     1778
Pro Pro Thr Gly Asp Ser Glu Thr Ala Pro Val Pro Pro Thr Gly Asp
575                 580                 585                 590

tcc ggg gcc ccc ccc gtg ccg ccc acg ggt gac tcc ggg gcc ccc ccc     1826
Ser Gly Ala Pro Pro Val Pro Pro Thr Gly Asp Ser Gly Ala Pro Pro
                595                 600                 605

gtg ccg ccc acg ggt gac tcc ggg gcc ccc ccc gtg ccg ccc acg ggt     1874
Val Pro Pro Thr Gly Asp Ser Gly Ala Pro Pro Val Pro Pro Thr Gly
            610                 615                 620
```

-continued

```
gac tcc ggg gcc ccc ccc gtg ccg ccc acg ggt gac tcc ggg gcc ccc      1922
Asp Ser Gly Ala Pro Pro Val Pro Pro Thr Gly Asp Ser Gly Ala Pro
        625                 630                 635

ccc gtg ccg ccc acg ggt gac tcc ggg gcc ccc ccc gtg ccg ccc acg      1970
Pro Val Pro Pro Thr Gly Asp Ser Gly Ala Pro Pro Val Pro Pro Thr
    640                 645                 650

ggt gac tcc ggc gcc ccc ccc gtg ccg ccc acg ggt gac gcc ggg ccc      2018
Gly Asp Ser Gly Ala Pro Pro Val Pro Pro Thr Gly Asp Ala Gly Pro
655                 660                 665                 670

ccc ccc gtg ccg ccc acg ggt gac tcc ggc gcc ccc ccc gtg ccg ccc      2066
Pro Pro Val Pro Pro Thr Gly Asp Ser Gly Ala Pro Pro Val Pro Pro
                675                 680                 685

acg ggt gac tcc ggg gcc ccc ccc gtg acc ccc acg ggt gac tcc gag      2114
Thr Gly Asp Ser Gly Ala Pro Pro Val Thr Pro Thr Gly Asp Ser Glu
            690                 695                 700

acc gcc ccc gtg ccg ccc acg ggt gac tcc ggg gcc ccc tgt gcc cca      2162
Thr Ala Pro Val Pro Pro Thr Gly Asp Ser Gly Ala Pro Cys Ala Pro
        705                 710                 715

cgg gtg act ctg agg ctg ccc ctg tgc ccc cca cag atg act cca agg      2210
Arg Val Thr Leu Arg Leu Pro Leu Cys Pro Pro Gln Met Thr Pro Arg
    720                 725                 730

aag ctc aga tgc ctg cag tca ata ggt ttt agc gtc cca tga              2252
Lys Leu Arg Cys Leu Gln Ser Ile Gly Phe Ser Val Pro
735                 740                 745

gccttggtat caagaggcca caagagtggg accccagggg ctcccctccc atcttgagct    2312

cttcctgaat aaagcctcat accctgaaa aa                                   2344


<210> SEQ ID NO 32
<211> LENGTH: 747
<212> TYPE: PRT
<213> ORGANISM: Homo sapiens

<400> SEQUENCE: 32

Met Leu Thr Met Gly Arg Leu Gln Leu Val Val Leu Gly Leu Thr Cys
  1               5                  10                  15

Cys Trp Ala Val Ala Ser Ala Ala Lys Leu Gly Ala Val Tyr Thr Glu
             20                  25                  30

Gly Gly Phe Val Glu Gly Val Asn Lys Lys Leu Gly Leu Leu Gly Asp
         35                  40                  45

Ser Val Asp Ile Phe Lys Gly Ile Pro Phe Ala Ala Pro Thr Lys Ala
     50                  55                  60

Leu Glu Asn Pro Gln Pro His Pro Gly Trp Gln Gly Thr Leu Lys Ala
 65                  70                  75                  80

Lys Asn Phe Lys Lys Arg Cys Leu Gln Ala Thr Ile Thr Gln Asp Ser
                 85                  90                  95

Thr Tyr Gly Asp Glu Asp Cys Leu Tyr Leu Asn Ile Trp Val Pro Gln
            100                 105                 110

Gly Arg Lys Gln Val Ser Arg Asp Leu Pro Val Met Ile Trp Ile Tyr
        115                 120                 125

Gly Gly Ala Phe Leu Met Gly Ser Gly His Gly Ala Asn Phe Leu Asn
    130                 135                 140

Asn Tyr Leu Tyr Asp Gly Glu Glu Ile Ala Thr Arg Gly Asn Val Ile
145                 150                 155                 160

Val Val Thr Phe Asn Tyr Arg Val Gly Pro Leu Gly Phe Leu Ser Thr
                165                 170                 175

Gly Asp Ala Asn Leu Pro Gly Asn Tyr Gly Leu Arg Asp Gln His Met
            180                 185                 190
```

```
Ala Ile Ala Trp Val Lys Arg Asn Ile Ala Ala Phe Gly Gly Asp Pro
        195                 200                 205

Asn Asn Ile Thr Leu Phe Gly Glu Ser Ala Gly Gly Ala Ser Val Ser
    210                 215                 220

Leu Gln Thr Leu Ser Pro Tyr Asn Lys Gly Leu Ile Arg Arg Ala Ile
225                 230                 235                 240

Ser Gln Ser Gly Val Ala Leu Ser Pro Trp Val Ile Gln Lys Asn Pro
                245                 250                 255

Leu Phe Trp Ala Lys Lys Val Ala Glu Lys Val Gly Cys Pro Val Gly
            260                 265                 270

Asp Ala Ala Arg Met Ala Gln Cys Leu Lys Val Thr Asp Pro Arg Ala
        275                 280                 285

Leu Thr Leu Ala Tyr Lys Val Pro Leu Ala Gly Leu Glu Tyr Pro Met
    290                 295                 300

Leu His Tyr Val Gly Phe Val Pro Val Ile Asp Gly Asp Phe Ile Pro
305                 310                 315                 320

Ala Asp Pro Ile Asn Leu Tyr Ala Asn Ala Ala Asp Ile Asp Tyr Ile
                325                 330                 335

Ala Gly Thr Asn Asn Met Asp Gly His Ile Phe Ala Ser Ile Asp Met
            340                 345                 350

Pro Ala Ile Asn Lys Gly Asn Lys Lys Val Thr Glu Glu Asp Phe Tyr
        355                 360                 365

Lys Leu Val Ser Glu Phe Thr Ile Thr Lys Gly Leu Arg Gly Ala Lys
    370                 375                 380

Thr Thr Phe Asp Val Tyr Thr Glu Ser Trp Ala Gln Asp Pro Ser Gln
385                 390                 395                 400

Glu Asn Lys Lys Lys Thr Val Val Asp Phe Glu Thr Asp Val Leu Phe
                405                 410                 415

Leu Val Pro Thr Glu Ile Ala Leu Ala Gln His Arg Ala Asn Ala Lys
            420                 425                 430

Ser Ala Lys Thr Tyr Ala Tyr Leu Phe Ser His Pro Ser Arg Met Pro
        435                 440                 445

Val Tyr Pro Lys Trp Val Gly Ala Asp His Ala Asp Asp Ile Gln Tyr
    450                 455                 460

Val Phe Gly Lys Pro Phe Ala Thr Pro Thr Gly Tyr Arg Pro Gln Asp
465                 470                 475                 480

Arg Thr Val Ser Lys Ala Met Ile Ala Tyr Trp Thr Asn Phe Ala Lys
                485                 490                 495

Thr Gly Asp Pro Asn Met Gly Asp Ser Ala Val Pro Thr His Trp Glu
            500                 505                 510

Pro Tyr Thr Thr Glu Asn Ser Gly Tyr Leu Glu Ile Thr Lys Lys Met
        515                 520                 525

Gly Ser Ser Ser Met Lys Arg Ser Leu Arg Thr Asn Phe Leu Arg Tyr
    530                 535                 540

Trp Thr Leu Thr Tyr Leu Ala Leu Pro Thr Val Thr Asp Gln Glu Ala
545                 550                 555                 560

Thr Pro Val Pro Pro Thr Gly Asp Ser Glu Ala Thr Pro Val Pro Pro
                565                 570                 575

Thr Gly Asp Ser Glu Thr Ala Pro Val Pro Pro Thr Gly Asp Ser Gly
            580                 585                 590

Ala Pro Pro Val Pro Pro Thr Gly Asp Ser Gly Ala Pro Pro Val Pro
        595                 600                 605
```

-continued

```
Pro Thr Gly Asp Ser Gly Ala Pro Pro Val Pro Pro Thr Gly Asp Ser
    610                 615                 620

Gly Ala Pro Pro Val Pro Pro Thr Gly Asp Ser Gly Ala Pro Pro Val
625                 630                 635                 640

Pro Pro Thr Gly Asp Ser Gly Ala Pro Pro Val Pro Pro Thr Gly Asp
                645                 650                 655

Ser Gly Ala Pro Pro Val Pro Pro Thr Gly Asp Ala Gly Pro Pro Pro
            660                 665                 670

Val Pro Pro Thr Gly Asp Ser Gly Ala Pro Pro Val Pro Pro Thr Gly
        675                 680                 685

Asp Ser Gly Ala Pro Pro Val Thr Pro Thr Gly Asp Ser Glu Thr Ala
    690                 695                 700

Pro Val Pro Pro Thr Gly Asp Ser Gly Ala Pro Cys Ala Pro Arg Val
705                 710                 715                 720

Thr Leu Arg Leu Pro Leu Cys Pro Pro Gln Met Thr Pro Arg Lys Leu
                725                 730                 735

Arg Cys Leu Gln Ser Ile Gly Phe Ser Val Pro
            740                 745


<210> SEQ ID NO 33
<211> LENGTH: 1905
<212> TYPE: DNA
<213> ORGANISM: Bos taurus
<220> FEATURE:
<223> OTHER INFORMATION: Bovine pancreatic cholesterol esterase cDNA
<300> PUBLICATION INFORMATION:
<310> PATENT DOCUMENT NUMBER: 08/462,884
<311> PATENT FILING DATE: 1995-06-05
<312> PUBLICATION DATE: 1997-04-29

<400> SEQUENCE: 33

gcctagaggc agacactgac tatggggcgg ctgggagcta gccgtcttgg gccgtcgcct     60

ggctgcttgg cagtagcgag tgcagcgaag ttgggctccg tatacaccga aggcggcttc    120

gtggagggcg tcaacaagaa gctgagcctc tttggcgact ctgttgacat cttcaagggc    180

atccccttcg ctgccgcccc caaggccctg gagaagcccg agcgacaccc cggctggcaa    240

gggaccctga aggccaagag ctttaagaaa cggtgcctgc aggccacgct cacgcaggac    300

agcacctacg gaaatgaaga ctgcctctac ctcaacatct gggtccccca gggcaggaag    360

gaagtctccc acgacctgcc cgtcatgatc tggatctatg gaggcgcctt cctcatgggg    420

gccagccaag ggccaactt tctcagcaac tacctctacg acggggagga gattgccaca    480

cggggcaacg tcatcgtggt cacgttcaac taccgcgttg ggcccctggg ctttctcagc    540

accggggact ccaacctgcc aggtaactat ggcctttggg atcagcacat ggccattgct    600

tgggtgaaga ggaacattga ggccttcgga ggagaccccg acaacatcac cctctttggg    660

gagtcggccg gaggcgccag cgtctctctg cagaccctct ctccctacaa caagggcctc    720

atcaagcgag ccatcagcca gagtggagtg ggtttgtgcc cttgggccat ccagcaggac    780

cccctcttct gggctaaaag gattgcagag aaggtgggct gccccgtgga cgacaccagc    840

aagatggctg ggtgtctgaa gatcactgac ccccgtgccc tgacgctggc ctataagctg    900

cccctgggaa gcacggaata ccccaagctg cactatctgt ccttcgtccc cgtcatcgat    960

ggagacttca tccctgatga ccccgtcaac ctgtacgcca acgccgcgga cgtcgactac   1020

atagcgggca ccaatgacat ggacggccac ctctttgtcg ggatggacgt gccagccatc   1080

aacagcaaca aacaggacgt cacggaggag gacttctata agctggtcag cgggctcacc   1140
```

-continued

```
gtcaccaagg ggctcagagg tgccaatgcc acgtacgagg tgtacaccga gccctgggcc   1200

caggactcat cccaggagac caggaagaag accatggtgg acctggagac tgacatcctc   1260

ttcctgatcc ccacaaagat tgccgtggcc cagcacaaga gccacgccaa gagcgccaac   1320

acctacacct acctgttctc ccaaccgtct cggatgccca tctaccccaa gtggatgggg   1380

gctgaccacg ccgatgacct ccagtatgtc ttcgggaagc ccttcgccac ccccctgggc   1440

taccgggccc aagacaggac tgtgtccaag gccatgattg cctactggac caactttgcc   1500

agaactgggg accctaacac gggccactcg acagtgcccg caaactggga tccctacacc   1560

ctggaagatg acaactacct ggaaatcaac aagcagatgg acagcaactc tatgaagctg   1620

catctgagga ccaactacct gcagttctgg acccagacct accaggccct gcccacggtg   1680

accagcgcgg gggccagcct gctgccccc gaggacaact ctcaggccag ccccgtgccc   1740

ccagcggaca actccggggc tcccaccgaa ccctctgcgg gtgactctga ggtggctcag   1800

atgcctgtcg tcattggttt ctaatgtccg gcctccaggg gccacaggag accccagggc   1860

ccacttccct cccaagtgcc tcctgaataa agcctcaacc atctc                    1905
```

<210> SEQ ID NO 34
<211> LENGTH: 606
<212> TYPE: PRT
<213> ORGANISM: Bos taurus
<220> FEATURE:
<223> OTHER INFORMATION: Bovine pancreatic cholesterol esterase protein sequence
<300> PUBLICATION INFORMATION:
<310> PATENT DOCUMENT NUMBER: 08/462,884
<311> PATENT FILING DATE: 1995-06-05
<312> PUBLICATION DATE: 1997-04-29

<400> SEQUENCE: 34

```
Ala Arg Gln Thr Leu Thr Met Gly Arg Leu Gly Ala Ser Arg Leu Gly
1               5                   10                  15

Pro Ser Pro Gly Cys Leu Ala Val Ala Ser Ala Ala Lys Leu Gly Ser
            20                  25                  30

Val Tyr Thr Glu Gly Gly Phe Val Glu Gly Val Asn Lys Lys Leu Ser
        35                  40                  45

Leu Phe Gly Asp Ser Val Asp Ile Phe Lys Gly Ile Pro Phe Ala Ala
    50                  55                  60

Ala Pro Lys Ala Leu Glu Lys Pro Glu Arg His Pro Gly Trp Gln Gly
65                  70                  75                  80

Thr Leu Lys Ala Lys Ser Phe Lys Lys Arg Cys Leu Gln Ala Thr Leu
                85                  90                  95

Thr Gln Asp Ser Thr Tyr Gly Asn Glu Asp Cys Leu Tyr Leu Asn Ile
            100                 105                 110

Trp Val Pro Gln Gly Arg Lys Glu Val Ser His Asp Leu Pro Val Met
        115                 120                 125

Ile Trp Ile Tyr Gly Gly Ala Phe Leu Met Gly Ala Ser Gln Gly Ala
    130                 135                 140

Asn Phe Leu Ser Asn Tyr Leu Tyr Asp Gly Glu Glu Ile Ala Thr Arg
145                 150                 155                 160

Gly Asn Val Ile Val Val Thr Phe Asn Tyr Arg Val Gly Pro Leu Gly
                165                 170                 175

Phe Leu Ser Thr Gly Asp Ser Asn Leu Pro Gly Asn Tyr Gly Leu Trp
            180                 185                 190

Asp Gln His Met Ala Ile Ala Trp Val Lys Arg Asn Ile Glu Ala Phe
        195                 200                 205
```

-continued

```
Gly Gly Asp Pro Asp Asn Ile Thr Leu Phe Gly Glu Ser Ala Gly Gly
    210                 215                 220

Ala Ser Val Ser Leu Gln Thr Leu Ser Pro Tyr Asn Lys Gly Leu Ile
225                 230                 235                 240

Lys Arg Ala Ile Ser Gln Ser Gly Val Gly Leu Cys Pro Trp Ala Ile
                245                 250                 255

Gln Gln Asp Pro Leu Phe Trp Ala Lys Arg Ile Ala Glu Lys Val Gly
            260                 265                 270

Cys Pro Val Asp Asp Thr Ser Lys Met Ala Gly Cys Leu Lys Ile Thr
        275                 280                 285

Asp Pro Arg Ala Leu Thr Leu Ala Tyr Lys Leu Pro Leu Gly Ser Thr
    290                 295                 300

Glu Tyr Pro Lys Leu His Tyr Leu Ser Phe Val Pro Val Ile Asp Gly
305                 310                 315                 320

Asp Phe Ile Pro Asp Asp Pro Val Asn Leu Tyr Ala Asn Ala Ala Asp
                325                 330                 335

Val Asp Tyr Ile Ala Gly Thr Asn Asp Met Asp Gly His Leu Phe Val
            340                 345                 350

Gly Met Asp Val Pro Ala Ile Asn Ser Asn Lys Gln Asp Val Thr Glu
        355                 360                 365

Glu Asp Phe Tyr Lys Leu Val Ser Gly Leu Thr Val Thr Lys Gly Leu
    370                 375                 380

Arg Gly Ala Asn Ala Thr Tyr Glu Val Tyr Thr Glu Pro Trp Ala Gln
385                 390                 395                 400

Asp Ser Ser Gln Glu Thr Arg Lys Lys Thr Met Val Asp Leu Glu Thr
                405                 410                 415

Asp Ile Leu Phe Leu Ile Pro Thr Lys Ile Ala Val Ala Gln His Lys
            420                 425                 430

Ser His Ala Lys Ser Ala Asn Thr Tyr Thr Tyr Leu Phe Ser Gln Pro
        435                 440                 445

Ser Arg Met Pro Ile Tyr Pro Lys Trp Met Gly Ala Asp His Ala Asp
    450                 455                 460

Asp Leu Gln Tyr Val Phe Gly Lys Pro Phe Ala Thr Pro Leu Gly Tyr
465                 470                 475                 480

Arg Ala Gln Asp Arg Thr Val Ser Lys Ala Met Ile Ala Tyr Trp Thr
                485                 490                 495

Asn Phe Ala Arg Thr Gly Asp Pro Asn Thr Gly His Ser Thr Val Pro
            500                 505                 510

Ala Asn Trp Asp Pro Tyr Thr Leu Glu Asp Asp Asn Tyr Leu Glu Ile
        515                 520                 525

Asn Lys Gln Met Asp Ser Asn Ser Met Lys Leu His Leu Arg Thr Asn
    530                 535                 540

Tyr Leu Gln Phe Trp Thr Gln Thr Tyr Gln Ala Leu Pro Thr Val Thr
545                 550                 555                 560

Ser Ala Gly Ala Ser Leu Leu Pro Pro Glu Asp Asn Ser Gln Ala Ser
                565                 570                 575

Pro Val Pro Pro Ala Asp Asn Ser Gly Ala Pro Thr Glu Pro Ser Ala
            580                 585                 590

Gly Asp Ser Glu Val Ala Gln Met Pro Val Val Ile Gly Phe
        595                 600                 605
```

<210> SEQ ID NO 35

```
<211> LENGTH: 2182
<212> TYPE: DNA
<213> ORGANISM: Streptomyces sp.
<220> FEATURE:
<221> NAME/KEY: CDS
<222> LOCATION: (382)..(2025)
<220> FEATURE:
<223> OTHER INFORMATION: Streptomyces A19249 cholesterol oxidase gene
<300> PUBLICATION INFORMATION:
<308> DATABASE ACCESSION NUMBER: U13981/GenBank

<400> SEQUENCE: 35

ggatcctgga gggcatcgcc gccggggtct ccaccatccc cctcgcggcg agcctctacc     60

tcagccggca gggcgtcgag taccacgtga cctgcctgct gcggaagctc aaggtcccaa    120

ccgcgccgca ctggtctccc gcgcctactc catggcgtgc tgaaggtcgg tgcctggcct    180

cccgaggtcg tcgaggactt cgtgaagtga gcgggcaccc cgcccgtccc cgccccgcaa    240

cggcccgttc cgcacaccgg gtgacccgac cccctcggcc cccgacgtcc gccgatctcc    300

cccgacaagt ccccacgccg gaaccccccc gaccggcccc cgatacctct cagtcccctc    360

tcgaagctca ggagcaacag c gtg aac gca cac cag cct ctg tcg cgc cgc      411
                        Val Asn Ala His Gln Pro Leu Ser Arg Arg
                         1               5                  10

cgc atg ctc ggc ctg gcc gcc ttg ggc gcc gcc gca ctc acc ggg cag      459
Arg Met Leu Gly Leu Ala Ala Leu Gly Ala Ala Ala Leu Thr Gly Gln
                15                  20                  25

acc acg atc acc gcg gcc ccc cgc gcg gcc gcc gcc acc gcc ccc ggc      507
Thr Thr Ile Thr Ala Ala Pro Arg Ala Ala Ala Ala Thr Ala Pro Gly
            30                  35                  40

ggc tcc ggc ggc acg ttc gtg ccc gcc gtc gtg atc ggc acc ggc tac      555
Gly Ser Gly Gly Thr Phe Val Pro Ala Val Val Ile Gly Thr Gly Tyr
        45                  50                  55

ggc gcg gcc gtc tcc gcc ctg cgg ctc ggc gag gcc ggg gtc tcc acc      603
Gly Ala Ala Val Ser Ala Leu Arg Leu Gly Glu Ala Gly Val Ser Thr
    60                  65                  70

ctg atg ctg gag atg ggc cag ctg tgg aac cag ccc ggc ccg gac ggc      651
Leu Met Leu Glu Met Gly Gln Leu Trp Asn Gln Pro Gly Pro Asp Gly
 75                  80                  85                  90

aac gtc ttc tgc ggg atg ctc aag ccc gac aag cgc tcc agc tgg ttc      699
Asn Val Phe Cys Gly Met Leu Lys Pro Asp Lys Arg Ser Ser Trp Phe
                95                 100                 105

aag acc cgc acc gag gcc ccg ctc ggc tcc ttc ctc tgg ctc gac ctc      747
Lys Thr Arg Thr Glu Ala Pro Leu Gly Ser Phe Leu Trp Leu Asp Leu
            110                 115                 120

gcc aac cgg gac atc gac ccc tac gcg ggc gtc ctg gac cgg gtc aac      795
Ala Asn Arg Asp Ile Asp Pro Tyr Ala Gly Val Leu Asp Arg Val Asn
        125                 130                 135

ttc gac cag atg tcc gtg tac gtg ggc cgc ggg gtc ggc ggc ggc tcg      843
Phe Asp Gln Met Ser Val Tyr Val Gly Arg Gly Val Gly Gly Gly Ser
    140                 145                 150

ctc gtc aac ggc ggt atg gcc gtc acg ccc cgg cgc tcc tac ttc cag      891
Leu Val Asn Gly Gly Met Ala Val Thr Pro Arg Arg Ser Tyr Phe Gln
155                 160                 165                 170

gag gtg ctg ccc cag gtc gac gcc gac gag atg tac ggc acc tac ttc      939
Glu Val Leu Pro Gln Val Asp Ala Asp Glu Met Tyr Gly Thr Tyr Phe
                175                 180                 185

ccg cgc gcg aac tcc ggc ctg cgg gtc aac aac atc gac aag gac tgg      987
Pro Arg Ala Asn Ser Gly Leu Arg Val Asn Asn Ile Asp Lys Asp Trp
            190                 195                 200

ttc gag cag acc gag tgg tac acg ttc gcg cgc gtt gcc cgt ctg cag     1035
Phe Glu Gln Thr Glu Trp Tyr Thr Phe Ala Arg Val Ala Arg Leu Gln
```

-continued

```
        205                 210                 215

gcc gag aac gcc ggc ctg aag acc acc ttc gtg ccc aac gtc tac gac      1083
Ala Glu Asn Ala Gly Leu Lys Thr Thr Phe Val Pro Asn Val Tyr Asp
    220                 225                 230

tgg gac tac atg cgc ggt gag gcg gac ggc acc aac ccc aag tcc gcg      1131
Trp Asp Tyr Met Arg Gly Glu Ala Asp Gly Thr Asn Pro Lys Ser Ala
235                 240                 245                 250

ctc gcc gcc gag gtc atc tac ggc aac aac cac ggc aag gtc tcc ctc      1179
Leu Ala Ala Glu Val Ile Tyr Gly Asn Asn His Gly Lys Val Ser Leu
                255                 260                 265

gac aag agc tac ctg gcg gcc gcc ctg ggc acc ggc aag gtc acc gtc      1227
Asp Lys Ser Tyr Leu Ala Ala Ala Leu Gly Thr Gly Lys Val Thr Val
            270                 275                 280

gag acc ctg cac cag gtc aag acg atc cgt cag cag aac gac ggc acc      1275
Glu Thr Leu His Gln Val Lys Thr Ile Arg Gln Gln Asn Asp Gly Thr
        285                 290                 295

tac ctg ctg acg gtc gag cag aag gac ccc gac ggc aag ctg ctc ggg      1323
Tyr Leu Leu Thr Val Glu Gln Lys Asp Pro Asp Gly Lys Leu Leu Gly
    300                 305                 310

acc aag gag atc tcc tgc cgc cac ctc ttc ctc ggc gcc ggc agc ctc      1371
Thr Lys Glu Ile Ser Cys Arg His Leu Phe Leu Gly Ala Gly Ser Leu
315                 320                 325                 330

ggc tcc att gaa ctg ctg ctg cgc gcc cgg gag acc ggc acc ctg ccc      1419
Gly Ser Ile Glu Leu Leu Leu Arg Ala Arg Glu Thr Gly Thr Leu Pro
                335                 340                 345

ggc ctc agc tcc gag atc ggc ggc ggc tgg ggc ccc aac ggc aac atc      1467
Gly Leu Ser Ser Glu Ile Gly Gly Gly Trp Gly Pro Asn Gly Asn Ile
            350                 355                 360

atg acc gcc cgc gcc aac cat gtg tgg aac ccc acg ggc agc aag cag      1515
Met Thr Ala Arg Ala Asn His Val Trp Asn Pro Thr Gly Ser Lys Gln
        365                 370                 375

tcg tcg atc ccc gcc ctc ggc atc gac gac tgg gac aac ccc gac aac      1563
Ser Ser Ile Pro Ala Leu Gly Ile Asp Asp Trp Asp Asn Pro Asp Asn
    380                 385                 390

ccc gtc ttc gcc gag ata gcc ccc atg ccg gcg ggc ctc gag acc tgg      1611
Pro Val Phe Ala Glu Ile Ala Pro Met Pro Ala Gly Leu Glu Thr Trp
395                 400                 405                 410

gtc agc ctc tac ctg gcc atc acc aag aac ccg gag cgc ggc acc ttc      1659
Val Ser Leu Tyr Leu Ala Ile Thr Lys Asn Pro Glu Arg Gly Thr Phe
                415                 420                 425

gtc tac gac gcc gcc aag gac cgg gcg gac ctg cgc tgg acc cgg gac      1707
Val Tyr Asp Ala Ala Lys Asp Arg Ala Asp Leu Arg Trp Thr Arg Asp
            430                 435                 440

cag aac gcg ccc gcg gtc gcc gcc gcc aag tcg ctg ttc gac cgc gtc      1755
Gln Asn Ala Pro Ala Val Ala Ala Ala Lys Ser Leu Phe Asp Arg Val
        445                 450                 455

aac aag gcc aac acg acc atc tac cgg tac gac ctc ttc ggc aag cag      1803
Asn Lys Ala Asn Thr Thr Ile Tyr Arg Tyr Asp Leu Phe Gly Lys Gln
    460                 465                 470

atc aag gcg ttc gcc gac gac ttc tgc tac cac ccg ctc ggc ggc tgc      1851
Ile Lys Ala Phe Ala Asp Asp Phe Cys Tyr His Pro Leu Gly Gly Cys
475                 480                 485                 490

gtc ctc ggc aag gcc acc gac aac tac ggc cgc gtc tcc ggg tac aag      1899
Val Leu Gly Lys Ala Thr Asp Asn Tyr Gly Arg Val Ser Gly Tyr Lys
                495                 500                 505

aac ctc tac gtc acc gac ggc tcg ctc atc ccc ggc agc atc ggc gtc      1947
Asn Leu Tyr Val Thr Asp Gly Ser Leu Ile Pro Gly Ser Ile Gly Val
            510                 515                 520

aac ccg ttc gtg acc atc acg gcg ctg gcg gag cgg aac gtc gag cgc      1995
```

-continued

```
Asn Pro Phe Val Thr Ile Thr Ala Leu Ala Glu Arg Asn Val Glu Arg
        525                 530                 535

gtc atc aag gag gac atc gcg ggt tcc tga cgagcgacgg gcggggcgcg      2045
Val Ile Lys Glu Asp Ile Ala Gly Ser
    540                 545

gcatgcgctc cgccccttcg tctcttcgcc ccgcgacgca cgccccgcaa cggtgggcgg   2105

ccgaaccccg aaccgaaagg gaacgcggga acgcttccgt gaactccccg ctcaccgagc   2165

caacagcctg tggatcc                                                  2182


<210> SEQ ID NO 36
<211> LENGTH: 547
<212> TYPE: PRT
<213> ORGANISM: Streptomyces sp.

<400> SEQUENCE: 36

Val Asn Ala His Gln Pro Leu Ser Arg Arg Arg Met Leu Gly Leu Ala
  1               5                  10                  15

Ala Leu Gly Ala Ala Ala Leu Thr Gly Gln Thr Thr Ile Thr Ala Ala
            20                  25                  30

Pro Arg Ala Ala Ala Ala Thr Ala Pro Gly Gly Ser Gly Gly Thr Phe
        35                  40                  45

Val Pro Ala Val Val Ile Gly Thr Gly Tyr Gly Ala Ala Val Ser Ala
     50                  55                  60

Leu Arg Leu Gly Glu Ala Gly Val Ser Thr Leu Met Leu Glu Met Gly
 65                  70                  75                  80

Gln Leu Trp Asn Gln Pro Gly Pro Asp Gly Asn Val Phe Cys Gly Met
                 85                  90                  95

Leu Lys Pro Asp Lys Arg Ser Ser Trp Phe Lys Thr Arg Thr Glu Ala
            100                 105                 110

Pro Leu Gly Ser Phe Leu Trp Leu Asp Leu Ala Asn Arg Asp Ile Asp
        115                 120                 125

Pro Tyr Ala Gly Val Leu Asp Arg Val Asn Phe Asp Gln Met Ser Val
    130                 135                 140

Tyr Val Gly Arg Gly Val Gly Gly Gly Ser Leu Val Asn Gly Gly Met
145                 150                 155                 160

Ala Val Thr Pro Arg Arg Ser Tyr Phe Gln Glu Val Leu Pro Gln Val
                165                 170                 175

Asp Ala Asp Glu Met Tyr Gly Thr Tyr Phe Pro Arg Ala Asn Ser Gly
            180                 185                 190

Leu Arg Val Asn Asn Ile Asp Lys Asp Trp Phe Glu Gln Thr Glu Trp
        195                 200                 205

Tyr Thr Phe Ala Arg Val Ala Arg Leu Gln Ala Glu Asn Ala Gly Leu
    210                 215                 220

Lys Thr Thr Phe Val Pro Asn Val Tyr Asp Trp Asp Tyr Met Arg Gly
225                 230                 235                 240

Glu Ala Asp Gly Thr Asn Pro Lys Ser Ala Leu Ala Ala Glu Val Ile
                245                 250                 255

Tyr Gly Asn Asn His Gly Lys Val Ser Leu Asp Lys Ser Tyr Leu Ala
            260                 265                 270

Ala Ala Leu Gly Thr Gly Lys Val Thr Val Glu Thr Leu His Gln Val
        275                 280                 285

Lys Thr Ile Arg Gln Gln Asn Asp Gly Thr Tyr Leu Leu Thr Val Glu
    290                 295                 300

Gln Lys Asp Pro Asp Gly Lys Leu Leu Gly Thr Lys Glu Ile Ser Cys
```

-continued

```
305                 310                 315                 320

Arg His Leu Phe Leu Gly Ala Gly Ser Leu Gly Ser Ile Glu Leu Leu
                325                 330                 335

Leu Arg Ala Arg Glu Thr Gly Thr Leu Pro Gly Leu Ser Ser Glu Ile
            340                 345                 350

Gly Gly Gly Trp Gly Pro Asn Gly Asn Ile Met Thr Ala Arg Ala Asn
        355                 360                 365

His Val Trp Asn Pro Thr Gly Ser Lys Gln Ser Ser Ile Pro Ala Leu
    370                 375                 380

Gly Ile Asp Asp Trp Asp Asn Pro Asp Asn Pro Val Phe Ala Glu Ile
385                 390                 395                 400

Ala Pro Met Pro Ala Gly Leu Glu Thr Trp Val Ser Leu Tyr Leu Ala
                405                 410                 415

Ile Thr Lys Asn Pro Glu Arg Gly Thr Phe Val Tyr Asp Ala Ala Lys
            420                 425                 430

Asp Arg Ala Asp Leu Arg Trp Thr Arg Asp Gln Asn Ala Pro Ala Val
        435                 440                 445

Ala Ala Ala Lys Ser Leu Phe Asp Arg Val Asn Lys Ala Asn Thr Thr
    450                 455                 460

Ile Tyr Arg Tyr Asp Leu Phe Gly Lys Gln Ile Lys Ala Phe Ala Asp
465                 470                 475                 480

Asp Phe Cys Tyr His Pro Leu Gly Gly Cys Val Leu Gly Lys Ala Thr
                485                 490                 495

Asp Asn Tyr Gly Arg Val Ser Gly Tyr Lys Asn Leu Tyr Val Thr Asp
            500                 505                 510

Gly Ser Leu Ile Pro Gly Ser Ile Gly Val Asn Pro Phe Val Thr Ile
        515                 520                 525

Thr Ala Leu Ala Glu Arg Asn Val Glu Arg Val Ile Lys Glu Asp Ile
    530                 535                 540

Ala Gly Ser
545
```

```
<210> SEQ ID NO 37
<211> LENGTH: 1845
<212> TYPE: DNA
<213> ORGANISM: Brevibacterium sterolicum
<220> FEATURE:
<223> OTHER INFORMATION: Nucleotide sequence encoding cholesterol
      oxidase II
<300> PUBLICATION INFORMATION:
<310> PATENT DOCUMENT NUMBER: 08/460,114
<311> PATENT FILING DATE: 1995-06-02
<312> PUBLICATION DATE: 1997-09-09

<400> SEQUENCE: 37

atgacgctca acgacgagca gttacggctg tcccggcgag gattcctcac cgcgggcgct      60

gcgggcgccg gcgtgctggc agccggcgca ctcggcggct ggaccccggc cttcgccgtc     120

cctgccggtt ccgccggctc cctcggatcg ctcggatcga ccgggccggt cgcgccgctt     180

ccgacgccgc cgaacttccc gaacgacatc gcgctgttcc agcaggcgta ccagaactgg     240

tccaaggaga tcatgctgga cgccacttgg gtctgctcgc ccaagacgcc gcaggatgtc     300

gttcgccttg ccaactgggc gcacgagcac gactacaaga tccgcccgcg cggcgcgatg     360

cacggctgga ccccgctcac cgtggagaag gggccaacg tcgagaaggt gatcctcgcc      420

gacacgatga cgcatctgaa cggcatcacg gtgaacacgg gcggccccgt ggctaccgtc     480

acggccggtg ccggcgccag catcgaggcg atcgtcaccg aactgcagaa gcacgacctc     540
```

-continued

```
ggctgggcca acctgcccgc tccgggtgtg ctgtcgatcg gtggcgccct tgcggtcaac     600

gcgcacggtg cggcgctgcc ggccgtcggc cagaccacgc tgcccggtca cacctacggt     660

tcgctgagca acctggtcac cgagctgacc gcggtcgtct ggaacggcaa cacctacgca     720

ctcgagacgt accagcgcaa cgatcctcgg atcaccccac tgctcaccaa cctcgggcgc     780

tgcttcctga cctcggtgac gatgcaggcc ggccccaact tccgtcagcg gtgccagagc     840

tacaccgaca tcccgtggcg ggaactgttc gcgccgaagg gcgccgacgg ccgcacgttc     900

gagaagttcg tcgcggaatc gggcggcgcc gaggcgatct ggtacccgtt caccgagaag     960

ccgtggatga aggtgtggac ggtctcgccg accaagccgg actcgtcgaa cgaggtcgga    1020

agcctcggct cggcgggctc cctcgtcggc aagcctccgc aggcgcgtga ggtctccggc    1080

ccgtacaact acatcttctc cgacaacctg ccggagccca tcaccgacat gatcggcgcc    1140

atcaacgccg gaaaccccgg aatcgcaccg ctgttcggcc cggcgatgta cgagatcacc    1200

aagctcgggc tggccgcgac gaatgccaac gacatctggg gctggtcgaa ggacgtccag    1260

ttctacatca aggccacgac gttgcgactc accgagggcg gcggcgccgt cgtcacgagc    1320

cgcgccaaca tcgcgaccgt gatcaacgac ttcaccgagt ggttccacga gcgcatcgag    1380

ttctaccgcg cgaagggcga gttcccgctc aacggtccgg tcgagatccg ctgctgcggg    1440

ctcgatcagg cagccgacgt caaggtgccg tcggtgggcc cgccgaccat ctcggcgacc    1500

cgtccgcgtc cggatcatcc ggactgggac gtcgcgatct ggctgaacgt tctcggtgtt    1560

ccgggcaccc ccggcatgtt cgagttctac cgcgagatgg agcagtggat gcggagccac    1620

tacaacaacg acgacgccac cttccggccc gagtggtcga aggggtgggc gttcggtccc    1680

gacccgtaca ccgacaacga catcgtcacg aacaagatgc gcgccaccta catcgaaggt    1740

gtcccgacga ccgagaactg ggacaccgcg cgcgctcggt accaaccagg attcgaccgg    1800

catcgcgtgt tcaccaacgg attcatggac aagctgcttc cgtag                    1845

<210> SEQ ID NO 38
<211> LENGTH: 614
<212> TYPE: PRT
<213> ORGANISM: Brevibacterium sterolicum
<220> FEATURE:
<223> OTHER INFORMATION: Cholesterol oxidase II protein sequence
<300> PUBLICATION INFORMATION:
<310> PATENT DOCUMENT NUMBER: 08/460,114
<311> PATENT FILING DATE: 1995-06-02
<312> PUBLICATION DATE: 1997-09-09

<400> SEQUENCE: 38

Met Thr Leu Asn Asp Glu Gln Leu Arg Leu Ser Arg Arg Gly Phe Leu
  1               5                  10                  15

Thr Ala Gly Ala Ala Gly Ala Gly Val Leu Ala Ala Gly Ala Leu Gly
             20                  25                  30

Gly Trp Thr Pro Ala Phe Ala Val Pro Ala Gly Ser Ala Gly Ser Leu
         35                  40                  45

Gly Ser Leu Gly Ser Thr Gly Pro Val Ala Pro Leu Pro Thr Pro Pro
     50                  55                  60

Asn Phe Pro Asn Asp Ile Ala Leu Phe Gln Gln Ala Tyr Gln Asn Trp
 65                  70                  75                  80

Ser Lys Glu Ile Met Leu Asp Ala Thr Trp Val Cys Ser Pro Lys Thr
                 85                  90                  95

Pro Gln Asp Val Val Arg Leu Ala Asn Trp Ala His Glu His Asp Tyr
            100                 105                 110
```

-continued

```
Lys Ile Arg Pro Arg Gly Ala Met His Gly Trp Thr Pro Leu Thr Val
        115                 120                 125

Glu Lys Gly Ala Asn Val Glu Lys Val Ile Leu Ala Asp Thr Met Thr
    130                 135                 140

His Leu Asn Gly Ile Thr Val Asn Thr Gly Gly Pro Val Ala Thr Val
145                 150                 155                 160

Thr Ala Gly Ala Gly Ala Ser Ile Glu Ala Ile Val Thr Glu Leu Gln
                165                 170                 175

Lys His Asp Leu Gly Trp Ala Asn Leu Pro Ala Pro Gly Val Leu Ser
            180                 185                 190

Ile Gly Gly Ala Leu Ala Val Asn Ala His Gly Ala Ala Leu Pro Ala
        195                 200                 205

Val Gly Gln Thr Thr Leu Pro Gly His Thr Tyr Gly Ser Leu Ser Asn
    210                 215                 220

Leu Val Thr Glu Leu Thr Ala Val Val Trp Asn Gly Asn Thr Tyr Ala
225                 230                 235                 240

Leu Glu Thr Tyr Gln Arg Asn Asp Pro Arg Ile Thr Pro Leu Leu Thr
                245                 250                 255

Asn Leu Gly Arg Cys Phe Leu Thr Ser Val Thr Met Gln Ala Gly Pro
            260                 265                 270

Asn Phe Arg Gln Arg Cys Gln Ser Tyr Thr Asp Ile Pro Trp Arg Glu
        275                 280                 285

Leu Phe Ala Pro Lys Gly Ala Asp Gly Arg Thr Phe Glu Lys Phe Val
    290                 295                 300

Ala Glu Ser Gly Gly Ala Glu Ala Ile Trp Tyr Pro Phe Thr Glu Lys
305                 310                 315                 320

Pro Trp Met Lys Val Trp Thr Val Ser Pro Thr Lys Pro Asp Ser Ser
                325                 330                 335

Asn Glu Val Gly Ser Leu Gly Ser Ala Gly Ser Leu Val Gly Lys Pro
            340                 345                 350

Pro Gln Ala Arg Glu Val Ser Gly Pro Tyr Asn Tyr Ile Phe Ser Asp
        355                 360                 365

Asn Leu Pro Glu Pro Ile Thr Asp Met Ile Gly Ala Ile Asn Ala Gly
    370                 375                 380

Asn Pro Gly Ile Ala Pro Leu Phe Gly Pro Ala Met Tyr Glu Ile Thr
385                 390                 395                 400

Lys Leu Gly Leu Ala Ala Thr Asn Ala Asn Asp Ile Trp Gly Trp Ser
                405                 410                 415

Lys Asp Val Gln Phe Tyr Ile Lys Ala Thr Thr Leu Arg Leu Thr Glu
            420                 425                 430

Gly Gly Gly Ala Val Val Thr Ser Arg Ala Asn Ile Ala Thr Val Ile
        435                 440                 445

Asn Asp Phe Thr Glu Trp Phe His Glu Arg Ile Glu Phe Tyr Arg Ala
    450                 455                 460

Lys Gly Glu Phe Pro Leu Asn Gly Pro Val Glu Ile Arg Cys Cys Gly
465                 470                 475                 480

Leu Asp Gln Ala Ala Asp Val Lys Val Pro Ser Val Gly Pro Pro Thr
                485                 490                 495

Ile Ser Ala Thr Arg Pro Arg Pro Asp His Pro Asp Trp Asp Val Ala
            500                 505                 510

Ile Trp Leu Asn Val Leu Gly Val Pro Gly Thr Pro Gly Met Phe Glu
        515                 520                 525
```

-continued

```
Phe Tyr Arg Glu Met Glu Gln Trp Met Arg Ser His Tyr Asn Asn Asp
    530                 535                 540

Asp Ala Thr Phe Arg Pro Glu Trp Ser Lys Gly Trp Ala Phe Gly Pro
545                 550                 555                 560

Asp Pro Tyr Thr Asp Asn Asp Ile Val Thr Asn Lys Met Arg Ala Thr
                565                 570                 575

Tyr Ile Glu Gly Val Pro Thr Thr Glu Asn Trp Asp Thr Ala Arg Ala
            580                 585                 590

Arg Tyr Gln Pro Gly Phe Asp Arg His Arg Val Phe Thr Asn Gly Phe
        595                 600                 605

Met Asp Lys Leu Leu Pro
    610


<210> SEQ ID NO 39
<211> LENGTH: 1531
<212> TYPE: DNA
<213> ORGANISM: Homo sapiens
<220> FEATURE:
<221> NAME/KEY: CDS
<222> LOCATION: (4)..(1125)
<220> FEATURE:
<223> OTHER INFORMATION: Human 3 beta-hydroxy-5-ene steroid
      dehydrogenase cDNA
<300> PUBLICATION INFORMATION:
<308> DATABASE ACCESSION NUMBER: M27137/GenBank

<400> SEQUENCE: 39

gcc atg acg ggc tgg agc tgc ctt gtg aca gga gca gga ggg ttt ctg       48
    Met Thr Gly Trp Ser Cys Leu Val Thr Gly Ala Gly Gly Phe Leu
      1               5                  10                  15

gga cag agg atc atc cgc ctc ttg gtg aag gag aag gag ctg aag gag       96
Gly Gln Arg Ile Ile Arg Leu Leu Val Lys Glu Lys Glu Leu Lys Glu
                 20                  25                  30

atc agg gtc ttg gac aag gcc ttc gga cca gaa ttg aga gag gaa ttt      144
Ile Arg Val Leu Asp Lys Ala Phe Gly Pro Glu Leu Arg Glu Glu Phe
             35                  40                  45

tct aaa ctc cag aac aag acc aag ctg aca gtg ctg gaa gga gac att      192
Ser Lys Leu Gln Asn Lys Thr Lys Leu Thr Val Leu Glu Gly Asp Ile
         50                  55                  60

ctg gat gag cca ttc ctg aag aga gcc tgc cag gac gtc tcg gtc atc      240
Leu Asp Glu Pro Phe Leu Lys Arg Ala Cys Gln Asp Val Ser Val Ile
     65                  70                  75

atc cac acc gcc tgt atc att gat gtc ttc ggt gtc act cac aga gag      288
Ile His Thr Ala Cys Ile Ile Asp Val Phe Gly Val Thr His Arg Glu
 80                  85                  90                  95

tct atc atg aat gtc aat gtg aaa ggt acc cag ctc ctg tta gag gcc      336
Ser Ile Met Asn Val Asn Val Lys Gly Thr Gln Leu Leu Leu Glu Ala
                100                 105                 110

tgt gtc caa gct agt gtg cca gtc ttc atc tac acc agt agc ata gag      384
Cys Val Gln Ala Ser Val Pro Val Phe Ile Tyr Thr Ser Ser Ile Glu
            115                 120                 125

gta gcc ggg ccc aac tcc tac aag gaa atc atc cag aat ggc cat gaa      432
Val Ala Gly Pro Asn Ser Tyr Lys Glu Ile Ile Gln Asn Gly His Glu
        130                 135                 140

gaa gag cct ctg gaa aac aca tgg ccc gct cca tac cca cac agc aaa      480
Glu Glu Pro Leu Glu Asn Thr Trp Pro Ala Pro Tyr Pro His Ser Lys
    145                 150                 155

aag ctt gct gag aag gct gta ctg gcg gct aac ggg tgg aat ctg aaa      528
Lys Leu Ala Glu Lys Ala Val Leu Ala Ala Asn Gly Trp Asn Leu Lys
160                 165                 170                 175

aac ggc ggc acc ctg tac act tgt gcc tta cga ccc atg tat atc tat      576
```

```
Asn Gly Gly Thr Leu Tyr Thr Cys Ala Leu Arg Pro Met Tyr Ile Tyr
                180                 185                 190

ggg gaa gga agc cga ttc ctt tct gct agt ata aac gag gcc ctg aac      624
Gly Glu Gly Ser Arg Phe Leu Ser Ala Ser Ile Asn Glu Ala Leu Asn
            195                 200                 205

aac aat ggg atc ctg tca agt gtt gga aag ttc tcc act gtt aac cca      672
Asn Asn Gly Ile Leu Ser Ser Val Gly Lys Phe Ser Thr Val Asn Pro
        210                 215                 220

gtc tat gtt ggc aat gtg gcc tgg gcc cac att ctg gcc ttg agg gcc      720
Val Tyr Val Gly Asn Val Ala Trp Ala His Ile Leu Ala Leu Arg Ala
    225                 230                 235

ctg cag gac ccc aag aag gcc cca agc atc cga gga cag ttc tac tat      768
Leu Gln Asp Pro Lys Lys Ala Pro Ser Ile Arg Gly Gln Phe Tyr Tyr
240                 245                 250                 255

atc tca gat gac acg cct cac caa agc tat gat aac ctt aat tac acc      816
Ile Ser Asp Asp Thr Pro His Gln Ser Tyr Asp Asn Leu Asn Tyr Thr
                260                 265                 270

ctg agc aaa gag ttc ggc ctc cgc ctt gat tcc aga tgg agc ttt cct      864
Leu Ser Lys Glu Phe Gly Leu Arg Leu Asp Ser Arg Trp Ser Phe Pro
            275                 280                 285

tta tcc ctg atg tat tgg att ggc ttc ctg ctg gaa ata gtg agc ttc      912
Leu Ser Leu Met Tyr Trp Ile Gly Phe Leu Leu Glu Ile Val Ser Phe
        290                 295                 300

cta ctc agg cca att tac acc tat cga ccg ccc ttc aac cgc cac ata      960
Leu Leu Arg Pro Ile Tyr Thr Tyr Arg Pro Pro Phe Asn Arg His Ile
    305                 310                 315

gtc aca ttg tca aat agc gta ttc acc ttc tct tat aag aag gct cag     1008
Val Thr Leu Ser Asn Ser Val Phe Thr Phe Ser Tyr Lys Lys Ala Gln
320                 325                 330                 335

cga gat ctg gcg tat aag cca ctc tac agc tgg gag gaa gcc aag cag     1056
Arg Asp Leu Ala Tyr Lys Pro Leu Tyr Ser Trp Glu Glu Ala Lys Gln
                340                 345                 350

aaa acg gtg gag tgg gtt ggt tcc ctt gtg gac cgg cac aag gag acc     1104
Lys Thr Val Glu Trp Val Gly Ser Leu Val Asp Arg His Lys Glu Thr
            355                 360                 365

ctg aag tcc aag act cag tga tttaaggatg acagagatgt gcatgtgggt        1155
Leu Lys Ser Lys Thr Gln
        370

attgttagga gatgtcatca agctccaccc tcctggcctc atacagaaag tgacaagggc   1215

acaagctcag gtcctgctgc ctccctttca tacaatggcc aacttattgt attcctcatg   1275

tcatcaaaac ctgcgcagtc attggcccaa caagaaggtt tctgtcctaa tcatatacca   1335

gaggaaagac catgtggttt gctgttacca aatctcagta gctgattctg aacaatttag   1395

ggactctttt aacttgaggg tcgttttgac tactagagct ccatttctac tcttaaatga   1455

gaaaggattt cctttctttt taatcttcca ttccttcaca tagtttgata aaaagatcaa   1515

taaatgtttg aatgtt                                                    1531


<210> SEQ ID NO 40
<211> LENGTH: 373
<212> TYPE: PRT
<213> ORGANISM: Homo sapiens

<400> SEQUENCE: 40

Met Thr Gly Trp Ser Cys Leu Val Thr Gly Ala Gly Gly Phe Leu Gly
  1               5                  10                  15

Gln Arg Ile Ile Arg Leu Leu Val Lys Glu Lys Glu Leu Lys Glu Ile
             20                  25                  30
```

-continued

```
Arg Val Leu Asp Lys Ala Phe Gly Pro Glu Leu Arg Glu Glu Phe Ser
        35                  40                  45

Lys Leu Gln Asn Lys Thr Lys Leu Thr Val Leu Glu Gly Asp Ile Leu
    50                  55                  60

Asp Glu Pro Phe Leu Lys Arg Ala Cys Gln Asp Val Ser Val Ile Ile
65                  70                  75                  80

His Thr Ala Cys Ile Ile Asp Val Phe Gly Val Thr His Arg Glu Ser
                85                  90                  95

Ile Met Asn Val Asn Val Lys Gly Thr Gln Leu Leu Leu Glu Ala Cys
            100                 105                 110

Val Gln Ala Ser Val Pro Val Phe Ile Tyr Thr Ser Ser Ile Glu Val
        115                 120                 125

Ala Gly Pro Asn Ser Tyr Lys Glu Ile Ile Gln Asn Gly His Glu Glu
    130                 135                 140

Glu Pro Leu Glu Asn Thr Trp Pro Ala Pro Tyr Pro His Ser Lys Lys
145                 150                 155                 160

Leu Ala Glu Lys Ala Val Leu Ala Ala Asn Gly Trp Asn Leu Lys Asn
                165                 170                 175

Gly Gly Thr Leu Tyr Thr Cys Ala Leu Arg Pro Met Tyr Ile Tyr Gly
            180                 185                 190

Glu Gly Ser Arg Phe Leu Ser Ala Ser Ile Asn Glu Ala Leu Asn Asn
        195                 200                 205

Asn Gly Ile Leu Ser Ser Val Gly Lys Phe Ser Thr Val Asn Pro Val
    210                 215                 220

Tyr Val Gly Asn Val Ala Trp Ala His Ile Leu Ala Leu Arg Ala Leu
225                 230                 235                 240

Gln Asp Pro Lys Lys Ala Pro Ser Ile Arg Gly Gln Phe Tyr Tyr Ile
                245                 250                 255

Ser Asp Asp Thr Pro His Gln Ser Tyr Asp Asn Leu Asn Tyr Thr Leu
            260                 265                 270

Ser Lys Glu Phe Gly Leu Arg Leu Asp Ser Arg Trp Ser Phe Pro Leu
        275                 280                 285

Ser Leu Met Tyr Trp Ile Gly Phe Leu Leu Glu Ile Val Ser Phe Leu
    290                 295                 300

Leu Arg Pro Ile Tyr Thr Tyr Arg Pro Pro Phe Asn Arg His Ile Val
305                 310                 315                 320

Thr Leu Ser Asn Ser Val Phe Thr Phe Ser Tyr Lys Lys Ala Gln Arg
                325                 330                 335

Asp Leu Ala Tyr Lys Pro Leu Tyr Ser Trp Glu Glu Ala Lys Gln Lys
            340                 345                 350

Thr Val Glu Trp Val Gly Ser Leu Val Asp Arg His Lys Glu Thr Leu
        355                 360                 365

Lys Ser Lys Thr Gln
    370
```

```
<210> SEQ ID NO 41
<211> LENGTH: 2051
<212> TYPE: DNA
<213> ORGANISM: Zea mays
<220> FEATURE:
<221> NAME/KEY: CDS
<222> LOCATION: (40)..(1743)
<223> OTHER INFORMATION: Zea mays glucose-6-phosphate isomerase cDNA
<300> PUBLICATION INFORMATION:
<308> DATABASE ACCESSION NUMBER: U17225/GenBank

<400> SEQUENCE: 41
```

-continued

```
cggcacgagg gcgatcgcta tcgacttgta gcggaagcc atg gcg tcg gca gcg        54
                                           Met Ala Ser Ala Ala
                                             1               5

cta atc tgc ggc acg gag cag tgg aag gcc ctc cag gcg cac gtc ggc      102
Leu Ile Cys Gly Thr Glu Gln Trp Lys Ala Leu Gln Ala His Val Gly
                 10                  15                  20

gcg att cag aag acg cac ctg cgc gac ctg atg gcc gac gcc gac cga      150
Ala Ile Gln Lys Thr His Leu Arg Asp Leu Met Ala Asp Ala Asp Arg
             25                  30                  35

tgc aag gca atg acg gct gag tat gaa ggg atc ttt ctg gat tac tcg      198
Cys Lys Ala Met Thr Ala Glu Tyr Glu Gly Ile Phe Leu Asp Tyr Ser
         40                  45                  50

aga cag cag gcg act ggt gaa acc atg gag aag ctc ctt aaa ttg gct      246
Arg Gln Gln Ala Thr Gly Glu Thr Met Glu Lys Leu Leu Lys Leu Ala
     55                  60                  65

gac gct gcg aag ctc aag gag aag att gag aag atg ttt aaa ggt gaa      294
Asp Ala Ala Lys Leu Lys Glu Lys Ile Glu Lys Met Phe Lys Gly Glu
 70                  75                  80                  85

aag ata aat agc aca gag aac agg tca gtg ctt cat gta gct ctg agg      342
Lys Ile Asn Ser Thr Glu Asn Arg Ser Val Leu His Val Ala Leu Arg
                 90                  95                 100

gct cca aga gat gca gtc ata aac agt gat ggg gtg aat gtg gtc cct      390
Ala Pro Arg Asp Ala Val Ile Asn Ser Asp Gly Val Asn Val Val Pro
            105                 110                 115

gag gtt tgg agt gtt aaa gat aaa atc aag cag ttt tca gag act ttt      438
Glu Val Trp Ser Val Lys Asp Lys Ile Lys Gln Phe Ser Glu Thr Phe
        120                 125                 130

aga agt gga tca tgg gtt gga gca act gga aaa ccg ttg aca aat gtt      486
Arg Ser Gly Ser Trp Val Gly Ala Thr Gly Lys Pro Leu Thr Asn Val
    135                 140                 145

gtg tcg gtt gga ata ggt ggt agc ttt ctt ggc cct cta ttt gtg cat      534
Val Ser Val Gly Ile Gly Gly Ser Phe Leu Gly Pro Leu Phe Val His
150                 155                 160                 165

act gca ctc cag acc gat cca gaa gca gca gaa tgt gca aaa ggc cgg      582
Thr Ala Leu Gln Thr Asp Pro Glu Ala Ala Glu Cys Ala Lys Gly Arg
                170                 175                 180

caa ctg aga ttc ctt gca aat gtt gat cca gtt gac gtt gca cga agc      630
Gln Leu Arg Phe Leu Ala Asn Val Asp Pro Val Asp Val Ala Arg Ser
            185                 190                 195

att aaa gat ttg gat cca gaa acc act ctg gtg gtg gtt gta tca aag      678
Ile Lys Asp Leu Asp Pro Glu Thr Thr Leu Val Val Val Val Ser Lys
        200                 205                 210

aca ttc aca aca gcg gaa aca atg tta aat gct cga act ctt aag gag      726
Thr Phe Thr Thr Ala Glu Thr Met Leu Asn Ala Arg Thr Leu Lys Glu
    215                 220                 225

tgg atc gtt tct tct ctt ggg cca cag gct gtt gcc aaa cat atg att      774
Trp Ile Val Ser Ser Leu Gly Pro Gln Ala Val Ala Lys His Met Ile
230                 235                 240                 245

gct gtc agc act aat ctt aag ctt gtg aag gag ttt gga att gac cca      822
Ala Val Ser Thr Asn Leu Lys Leu Val Lys Glu Phe Gly Ile Asp Pro
                250                 255                 260

aac aat gct ttt gcc ttt tgg gac tgg gtt ggc ggc cgt tat agt gtt      870
Asn Asn Ala Phe Ala Phe Trp Asp Trp Val Gly Gly Arg Tyr Ser Val
            265                 270                 275

tgc agt gct gtt ggc gtt ctg cca tta tct ctt cag tat ggc ttt cca      918
Cys Ser Ala Val Gly Val Leu Pro Leu Ser Leu Gln Tyr Gly Phe Pro
        280                 285                 290

att gtc cag aaa ttt ttg gag gga gct tcc agc att gac aac cac ttc      966
Ile Val Gln Lys Phe Leu Glu Gly Ala Ser Ser Ile Asp Asn His Phe
```

-continued

```
    295                 300                 305

tac tca tct tca ttt gag aaa aat ata cct gta ctt ctt ggt ttg ctg     1014
Tyr Ser Ser Ser Phe Glu Lys Asn Ile Pro Val Leu Leu Gly Leu Leu
310                 315                 320                 325

agt gtg tgg aat gtt tca ttt ctt ggt tat cca gct agg gca ata ttg     1062
Ser Val Trp Asn Val Ser Phe Leu Gly Tyr Pro Ala Arg Ala Ile Leu
                330                 335                 340

cca tat tct cag gca ctt gag aag ttg gca cca cat ata cag cag ctt     1110
Pro Tyr Ser Gln Ala Leu Glu Lys Leu Ala Pro His Ile Gln Gln Leu
            345                 350                 355

agc atg gag agt aac ggg aag ggt gtt tcc att gat ggc gcc caa ctt     1158
Ser Met Glu Ser Asn Gly Lys Gly Val Ser Ile Asp Gly Ala Gln Leu
        360                 365                 370

tcc ttt gag aca ggt gaa att gat ttt ggt gaa cct gga act aat ggc     1206
Ser Phe Glu Thr Gly Glu Ile Asp Phe Gly Glu Pro Gly Thr Asn Gly
    375                 380                 385

cag cac agc ttc tat caa tta atc cat cag gga agg gtt atc cct tgc     1254
Gln His Ser Phe Tyr Gln Leu Ile His Gln Gly Arg Val Ile Pro Cys
390                 395                 400                 405

gac ttt att ggt gtt gtt aaa agt cag cag cct gtt tac ttg aaa ggg     1302
Asp Phe Ile Gly Val Val Lys Ser Gln Gln Pro Val Tyr Leu Lys Gly
                410                 415                 420

gaa act gtg agt aat cat gat gag ctt atg tcc aat ttc ttt gcc caa     1350
Glu Thr Val Ser Asn His Asp Glu Leu Met Ser Asn Phe Phe Ala Gln
            425                 430                 435

cct gat gct ctt gct tat gga aag act cct gaa cag ttg cac agt gag     1398
Pro Asp Ala Leu Ala Tyr Gly Lys Thr Pro Glu Gln Leu His Ser Glu
        440                 445                 450

aaa gtt cca gaa aat ctt atc cct cat aag act ttt aag ggc aac cgg     1446
Lys Val Pro Glu Asn Leu Ile Pro His Lys Thr Phe Lys Gly Asn Arg
    455                 460                 465

cca tca cta agt ttg ctt ctg cct aca cta tcc gca tat gag gtt gga     1494
Pro Ser Leu Ser Leu Leu Leu Pro Thr Leu Ser Ala Tyr Glu Val Gly
470                 475                 480                 485

cag ctt tta tcc atc tat gag cac cgg att gca gtt cag ggc ttc ata     1542
Gln Leu Leu Ser Ile Tyr Glu His Arg Ile Ala Val Gln Gly Phe Ile
                490                 495                 500

tgg gga att aac tca ttt gac cag tgg gga gtg gag cta ggg aag tca     1590
Trp Gly Ile Asn Ser Phe Asp Gln Trp Gly Val Glu Leu Gly Lys Ser
            505                 510                 515

ctc gct tct caa gtg agg aaa cag ctg cat gga acc cgg atg gaa gga     1638
Leu Ala Ser Gln Val Arg Lys Gln Leu His Gly Thr Arg Met Glu Gly
        520                 525                 530

aag cct gtt gag ggt ttt aac cac agc act tca agt ttg ctt gca cga     1686
Lys Pro Val Glu Gly Phe Asn His Ser Thr Ser Ser Leu Leu Ala Arg
    535                 540                 545

tat ctt gct gtc aag cca tcc acc ccg tat gat act acc gtg ctg ccg     1734
Tyr Leu Ala Val Lys Pro Ser Thr Pro Tyr Asp Thr Thr Val Leu Pro
550                 555                 560                 565

aag gtg taa ttactcagtt gtttttgaca tgccaattgc tgagttctga             1783
Lys Val

cttggcaagg ttgagcataa gtctttcttc atttgggagt tatcacagag ccagtttggc   1843

agtgctgtag ttttggttta cctactcttt gtagaagaaa agtgaagagt ggatattatg   1903

gaaccaaata tatacctacg gcagcacgca gcatgatgaa acatatttaa aaaatttggg   1963

tgctctacca catgcccgtg gaataaaacg gatgtaaact cagtgcactt ataacaccct   2023

aattgtggtt ttgtttgtgg ttcaaaaa                                      2051
```

```
<210> SEQ ID NO 42
<211> LENGTH: 567
<212> TYPE: PRT
<213> ORGANISM: Zea mays

<400> SEQUENCE: 42

Met Ala Ser Ala Ala Leu Ile Cys Gly Thr Glu Gln Trp Lys Ala Leu
  1               5                  10                  15

Gln Ala His Val Gly Ala Ile Gln Lys Thr His Leu Arg Asp Leu Met
             20                  25                  30

Ala Asp Ala Asp Arg Cys Lys Ala Met Thr Ala Glu Tyr Glu Gly Ile
         35                  40                  45

Phe Leu Asp Tyr Ser Arg Gln Gln Ala Thr Gly Glu Thr Met Glu Lys
     50                  55                  60

Leu Leu Lys Leu Ala Asp Ala Ala Lys Leu Lys Glu Lys Ile Glu Lys
 65                  70                  75                  80

Met Phe Lys Gly Glu Lys Ile Asn Ser Thr Glu Asn Arg Ser Val Leu
                 85                  90                  95

His Val Ala Leu Arg Ala Pro Arg Asp Ala Val Ile Asn Ser Asp Gly
            100                 105                 110

Val Asn Val Val Pro Glu Val Trp Ser Val Lys Asp Lys Ile Lys Gln
        115                 120                 125

Phe Ser Glu Thr Phe Arg Ser Gly Ser Trp Val Gly Ala Thr Gly Lys
    130                 135                 140

Pro Leu Thr Asn Val Val Ser Val Gly Ile Gly Gly Ser Phe Leu Gly
145                 150                 155                 160

Pro Leu Phe Val His Thr Ala Leu Gln Thr Asp Pro Glu Ala Ala Glu
                165                 170                 175

Cys Ala Lys Gly Arg Gln Leu Arg Phe Leu Ala Asn Val Asp Pro Val
            180                 185                 190

Asp Val Ala Arg Ser Ile Lys Asp Leu Asp Pro Glu Thr Thr Leu Val
        195                 200                 205

Val Val Val Ser Lys Thr Phe Thr Thr Ala Glu Thr Met Leu Asn Ala
    210                 215                 220

Arg Thr Leu Lys Glu Trp Ile Val Ser Ser Leu Gly Pro Gln Ala Val
225                 230                 235                 240

Ala Lys His Met Ile Ala Val Ser Thr Asn Leu Lys Leu Val Lys Glu
                245                 250                 255

Phe Gly Ile Asp Pro Asn Asn Ala Phe Ala Phe Trp Asp Trp Val Gly
            260                 265                 270

Gly Arg Tyr Ser Val Cys Ser Ala Val Gly Val Leu Pro Leu Ser Leu
        275                 280                 285

Gln Tyr Gly Phe Pro Ile Val Gln Lys Phe Leu Glu Gly Ala Ser Ser
    290                 295                 300

Ile Asp Asn His Phe Tyr Ser Ser Ser Phe Glu Lys Asn Ile Pro Val
305                 310                 315                 320

Leu Leu Gly Leu Leu Ser Val Trp Asn Val Ser Phe Leu Gly Tyr Pro
                325                 330                 335

Ala Arg Ala Ile Leu Pro Tyr Ser Gln Ala Leu Glu Lys Leu Ala Pro
            340                 345                 350

His Ile Gln Gln Leu Ser Met Glu Ser Asn Gly Lys Gly Val Ser Ile
        355                 360                 365

Asp Gly Ala Gln Leu Ser Phe Glu Thr Gly Glu Ile Asp Phe Gly Glu
    370                 375                 380
```

```
Pro Gly Thr Asn Gly Gln His Ser Phe Tyr Gln Leu Ile His Gln Gly
385                 390                 395                 400

Arg Val Ile Pro Cys Asp Phe Ile Gly Val Val Lys Ser Gln Gln Pro
                405                 410                 415

Val Tyr Leu Lys Gly Glu Thr Val Ser Asn His Asp Glu Leu Met Ser
            420                 425                 430

Asn Phe Phe Ala Gln Pro Asp Ala Leu Ala Tyr Gly Lys Thr Pro Glu
        435                 440                 445

Gln Leu His Ser Glu Lys Val Pro Glu Asn Leu Ile Pro His Lys Thr
    450                 455                 460

Phe Lys Gly Asn Arg Pro Ser Leu Ser Leu Leu Leu Pro Thr Leu Ser
465                 470                 475                 480

Ala Tyr Glu Val Gly Gln Leu Leu Ser Ile Tyr Glu His Arg Ile Ala
                485                 490                 495

Val Gln Gly Phe Ile Trp Gly Ile Asn Ser Phe Asp Gln Trp Gly Val
            500                 505                 510

Glu Leu Gly Lys Ser Leu Ala Ser Gln Val Arg Lys Gln Leu His Gly
        515                 520                 525

Thr Arg Met Glu Gly Lys Pro Val Glu Gly Phe Asn His Ser Thr Ser
    530                 535                 540

Ser Leu Leu Ala Arg Tyr Leu Ala Val Lys Pro Ser Thr Pro Tyr Asp
545                 550                 555                 560

Thr Thr Val Leu Pro Lys Val
                565
```

```
<210> SEQ ID NO 43
<211> LENGTH: 2731
<212> TYPE: DNA
<213> ORGANISM: Homo sapiens
<220> FEATURE:
<221> NAME/KEY: CDS
<222> LOCATION: (459)..(1856)
<220> FEATURE:
<223> OTHER INFORMATION: Human glucokinase cDNA
<300> PUBLICATION INFORMATION:
<308> DATABASE ACCESSION NUMBER: M90299/GenBank

<400> SEQUENCE: 43

ccgagcggcg cctgagcccc agggaagcag gctaggatgt gagagacaca gtcacctgca     60

gcctaattac tcaaaagctg tccccaggtc acagaaggga gaggacattt cccactgaat    120

ctgtctgaag gacactaagc cccacagctc aacacaacca ggagagaaag cgctgaggac    180

gccacccaag cgcccagcaa tggccctgcc tggagaacat ccaggctcag tgaggaaggg    240

tccagaaggg aatgcttgcc gactcgttgg agaacaatga aaaggaggaa actgtgactg    300

aacctcaaac cccaaaccag cccgaggaga accacattct cccagggacc cagggcgggc    360

cgtgacccct gcggcggaga agccttggat atttccactt cagaagccta ctggggaagg    420

ctgaggggtc ccagctcccc acgctggctg ctgtgcag atg ctg gac gac aga gcc    476
                                          Met Leu Asp Asp Arg Ala
                                            1               5

agg atg gag gcc gcc aag aag gag aag gta gag cag atc ctg gca gag      524
Arg Met Glu Ala Ala Lys Lys Glu Lys Val Glu Gln Ile Leu Ala Glu
            10                  15                  20

ttc cag ctg cag gag gag gac ctg aag aag gtg atg aga cgg atg cag      572
Phe Gln Leu Gln Glu Glu Asp Leu Lys Lys Val Met Arg Arg Met Gln
        25                  30                  35

aag gag atg gac cgc ggc ctg agg ctg gag acc cat gaa gag gcc agt      620
```

-continued

```
Lys Glu Met Asp Arg Gly Leu Arg Leu Glu Thr His Glu Glu Ala Ser
     40                  45                  50

gtg aag atg ctg ccc acc tac gtg cgc tcc acc cca gaa ggc tca gaa      668
Val Lys Met Leu Pro Thr Tyr Val Arg Ser Thr Pro Glu Gly Ser Glu
 55                  60                  65                  70

gtc ggg gac ttc ctc tcc ctg gac ctg ggt ggc act aac ttc agg gtg      716
Val Gly Asp Phe Leu Ser Leu Asp Leu Gly Gly Thr Asn Phe Arg Val
                 75                  80                  85

atg ctg gtg aag gtg gga gaa ggt gag gag ggg cag tgg agc gtg aag      764
Met Leu Val Lys Val Gly Glu Gly Glu Glu Gly Gln Trp Ser Val Lys
             90                  95                 100

acc aaa cac cag atg tac tcc atc ccc gag gac gcc atg acc ggc act      812
Thr Lys His Gln Met Tyr Ser Ile Pro Glu Asp Ala Met Thr Gly Thr
        105                 110                 115

gct gag atg ctc ttc gac tac atc tct gag tgc atc tcc gac ttc ctg      860
Ala Glu Met Leu Phe Asp Tyr Ile Ser Glu Cys Ile Ser Asp Phe Leu
    120                 125                 130

gac aag cat cag atg aaa cac aag aag ctg ccc ctg ggc ttc acc ttc      908
Asp Lys His Gln Met Lys His Lys Lys Leu Pro Leu Gly Phe Thr Phe
135                 140                 145                 150

tcc ttt cct gtg agg cac gaa gac atc gat aag ggc atc ctt ctc aac      956
Ser Phe Pro Val Arg His Glu Asp Ile Asp Lys Gly Ile Leu Leu Asn
                155                 160                 165

tgg acc aag ggc ttc aag gcc tca gga gca gaa ggg aac aat gtc gtg     1004
Trp Thr Lys Gly Phe Lys Ala Ser Gly Ala Glu Gly Asn Asn Val Val
            170                 175                 180

ggg ctt ctg cga gac gct atc aaa cgg aga ggg gac ttt gaa atg gat     1052
Gly Leu Leu Arg Asp Ala Ile Lys Arg Arg Gly Asp Phe Glu Met Asp
        185                 190                 195

gtg gtg gca atg gtg aat gac acg gtg gcc acg atg atc tcc tgc tac     1100
Val Val Ala Met Val Asn Asp Thr Val Ala Thr Met Ile Ser Cys Tyr
    200                 205                 210

tac gaa gac cat cag tgc gag gtc ggc atg atc gtg ggc acg ggc tgc     1148
Tyr Glu Asp His Gln Cys Glu Val Gly Met Ile Val Gly Thr Gly Cys
215                 220                 225                 230

aat gcc tgc tac atg gag gag atg cag aat gtg gag ctg gtg gag ggg     1196
Asn Ala Cys Tyr Met Glu Glu Met Gln Asn Val Glu Leu Val Glu Gly
                235                 240                 245

gac gag ggc cgc atg tgc gtc aat acc gag tgg ggc gcc ttc ggg gac     1244
Asp Glu Gly Arg Met Cys Val Asn Thr Glu Trp Gly Ala Phe Gly Asp
            250                 255                 260

tcc ggc gag ctg gac gag ttc ctg ctg gag tat gac cgc ctg gtg gac     1292
Ser Gly Glu Leu Asp Glu Phe Leu Leu Glu Tyr Asp Arg Leu Val Asp
        265                 270                 275

gag agc tct gca aac ccc ggt cag cag ctg tat gag aag ctc ata ggt     1340
Glu Ser Ser Ala Asn Pro Gly Gln Gln Leu Tyr Glu Lys Leu Ile Gly
    280                 285                 290

ggc aag tac atg ggc gag ctg gtg cgg ctt gtg ctg ctc agg ctc gtg     1388
Gly Lys Tyr Met Gly Glu Leu Val Arg Leu Val Leu Leu Arg Leu Val
295                 300                 305                 310

gac gaa aac ctg ctc ttc cac ggg gag gcc tcc gag cag ctg cgc aca     1436
Asp Glu Asn Leu Leu Phe His Gly Glu Ala Ser Glu Gln Leu Arg Thr
                315                 320                 325

cgc gga gcc ttc gag acg cgc ttc gtg tcg cag gtg gag agc gac acg     1484
Arg Gly Ala Phe Glu Thr Arg Phe Val Ser Gln Val Glu Ser Asp Thr
            330                 335                 340

ggc gac cgc aag cag atc tac aac atc ctg agc acg ctg ggg ctg cga     1532
Gly Asp Arg Lys Gln Ile Tyr Asn Ile Leu Ser Thr Leu Gly Leu Arg
        345                 350                 355
```

```
ccc tcg acc acc gac tgc gac atc gtg cgc cgc gcc tgc gag agc gtg     1580
Pro Ser Thr Thr Asp Cys Asp Ile Val Arg Arg Ala Cys Glu Ser Val
    360                 365                 370

tct acg cgc gct gcg cac atg tgc tcg gcg ggg ctg gcg ggc gtc atc     1628
Ser Thr Arg Ala Ala His Met Cys Ser Ala Gly Leu Ala Gly Val Ile
375                 380                 385                 390

aac cgc atg cgc gag agc cgc agc gag gac gta atg cgc atc act gtg     1676
Asn Arg Met Arg Glu Ser Arg Ser Glu Asp Val Met Arg Ile Thr Val
                395                 400                 405

ggc gtg gat ggc tcc gtg tac aag ctg cac ccc agc ttc aag gag cgg     1724
Gly Val Asp Gly Ser Val Tyr Lys Leu His Pro Ser Phe Lys Glu Arg
            410                 415                 420

ttc cat gcc agc gtg cgc agg ctg acg ccc agc tgc gag atc acc ttc     1772
Phe His Ala Ser Val Arg Arg Leu Thr Pro Ser Cys Glu Ile Thr Phe
        425                 430                 435

atc gag tcg gag gag ggc agt ggc cgg ggc gcg gcc ctg gtc tcg gcg     1820
Ile Glu Ser Glu Glu Gly Ser Gly Arg Gly Ala Ala Leu Val Ser Ala
    440                 445                 450

gtg gcc tgt aag aag gcc tgt atg ctg ggc cag tga gagcagtggc          1866
Val Ala Cys Lys Lys Ala Cys Met Leu Gly Gln
455                 460                 465

cgcaagcgca gggaggatgc cacagcccca cagcacccag gctccatggg gaagtgctcc   1926

ccacacgtgc tcgcagcctg gcggggcagg aggcctggcc ttgtcaggac ccaggccgcc   1986

tgccataccg ctggggaaca gagcgggcct cttccctcag tttttcggtg ggacagcccc   2046

agggccctaa cggggggtgcg gcaggagcag gaacagagac tctggaagcc ccccaccttt  2106

ctcgctggaa tcaatttccc agaagggagt tgctcactca ggactttgat gcatttccac   2166

actgtcagag ctgttggcct cgcctgggcc caggctctgg gaaggggtgc cctctggatc   2226

ctgctgtggc ctcacttccc tgggaactca tcctgtgtgg ggaggcagct ccaacagctt   2286

gaccagacct agacctgggc caaaagggca ggccaggggc tgctcatcac ccagtcctgg   2346

ccatttttctt gcctgaggct caagaggccc agggagcaat gggagggggc tccatggagg  2406

aggtgtccca agctttgaat accccccaga gaccttttct ctcccatacc atcactgagt   2466

ggcttgtgat tctgggatgg accctcgcag caggtgcaag agacagagcc cccaagcctc   2526

tgccccaagg ggcccacaaa ggggagaagg gccagcccta catcttcagc tcccatagcg   2586

ctggctcagg aagaaacccc aagcagcatt cagcacaccc caagggacaa ccccatcata   2646

tgacatgcca ccctctccat gcccaaccta agattgtgtg ggttttttaa ttaaaaatgt   2706

taaaagtttt aaacatgaaa aaaaa                                         2731


<210> SEQ ID NO 44
<211> LENGTH: 465
<212> TYPE: PRT
<213> ORGANISM: Homo sapiens

<400> SEQUENCE: 44

Met Leu Asp Asp Arg Ala Arg Met Glu Ala Ala Lys Lys Glu Lys Val
  1               5                  10                  15

Glu Gln Ile Leu Ala Glu Phe Gln Leu Gln Glu Glu Asp Leu Lys Lys
             20                  25                  30

Val Met Arg Arg Met Gln Lys Glu Met Asp Arg Gly Leu Arg Leu Glu
         35                  40                  45

Thr His Glu Glu Ala Ser Val Lys Met Leu Pro Thr Tyr Val Arg Ser
     50                  55                  60

Thr Pro Glu Gly Ser Glu Val Gly Asp Phe Leu Ser Leu Asp Leu Gly
```

-continued

```
65                  70                  75                  80

Gly Thr Asn Phe Arg Val Met Leu Val Lys Val Gly Glu Gly Glu Glu
                85                  90                  95

Gly Gln Trp Ser Val Lys Thr Lys His Gln Met Tyr Ser Ile Pro Glu
            100                 105                 110

Asp Ala Met Thr Gly Thr Ala Glu Met Leu Phe Asp Tyr Ile Ser Glu
        115                 120                 125

Cys Ile Ser Asp Phe Leu Asp Lys His Gln Met Lys His Lys Lys Leu
    130                 135                 140

Pro Leu Gly Phe Thr Phe Ser Phe Pro Val Arg His Glu Asp Ile Asp
145                 150                 155                 160

Lys Gly Ile Leu Leu Asn Trp Thr Lys Gly Phe Lys Ala Ser Gly Ala
                165                 170                 175

Glu Gly Asn Asn Val Val Gly Leu Leu Arg Asp Ala Ile Lys Arg Arg
            180                 185                 190

Gly Asp Phe Glu Met Asp Val Val Ala Met Val Asn Asp Thr Val Ala
        195                 200                 205

Thr Met Ile Ser Cys Tyr Tyr Glu Asp His Gln Cys Glu Val Gly Met
    210                 215                 220

Ile Val Gly Thr Gly Cys Asn Ala Cys Tyr Met Glu Glu Met Gln Asn
225                 230                 235                 240

Val Glu Leu Val Glu Gly Asp Glu Gly Arg Met Cys Val Asn Thr Glu
                245                 250                 255

Trp Gly Ala Phe Gly Asp Ser Gly Glu Leu Asp Glu Phe Leu Leu Glu
            260                 265                 270

Tyr Asp Arg Leu Val Asp Glu Ser Ser Ala Asn Pro Gly Gln Gln Leu
        275                 280                 285

Tyr Glu Lys Leu Ile Gly Gly Lys Tyr Met Gly Glu Leu Val Arg Leu
    290                 295                 300

Val Leu Leu Arg Leu Val Asp Glu Asn Leu Leu Phe His Gly Glu Ala
305                 310                 315                 320

Ser Glu Gln Leu Arg Thr Arg Gly Ala Phe Glu Thr Arg Phe Val Ser
                325                 330                 335

Gln Val Glu Ser Asp Thr Gly Asp Arg Lys Gln Ile Tyr Asn Ile Leu
            340                 345                 350

Ser Thr Leu Gly Leu Arg Pro Ser Thr Thr Asp Cys Asp Ile Val Arg
        355                 360                 365

Arg Ala Cys Glu Ser Val Ser Thr Arg Ala Ala His Met Cys Ser Ala
    370                 375                 380

Gly Leu Ala Gly Val Ile Asn Arg Met Arg Glu Ser Arg Ser Glu Asp
385                 390                 395                 400

Val Met Arg Ile Thr Val Gly Val Asp Gly Ser Val Tyr Lys Leu His
                405                 410                 415

Pro Ser Phe Lys Glu Arg Phe His Ala Ser Val Arg Arg Leu Thr Pro
            420                 425                 430

Ser Cys Glu Ile Thr Phe Ile Glu Ser Glu Glu Gly Ser Gly Arg Gly
        435                 440                 445

Ala Ala Leu Val Ser Ala Val Ala Cys Lys Lys Ala Cys Met Leu Gly
    450                 455                 460

Gln
465
```

<210> SEQ ID NO 45

```
<211> LENGTH: 2788
<212> TYPE: DNA
<213> ORGANISM: Aspergillus niger
<220> FEATURE:
<221> NAME/KEY: CDS
<222> LOCATION: (486)..(2303)
<220> FEATURE:
<223> OTHER INFORMATION: Aspergillus niger glucose oxidase cDNA

<400> SEQUENCE: 45

gaattcggta ttctcggcat ggccaaagtc ggtatccctt ggcgccacga tgatttgcgt     60

ccaggattcg tatagttcct cgtccacgag ctgcctaccg tcagcgtgag gcagtgagct    120

aatatggggc caataagcca ctacgaggat gacatggcct ctacagaacg agagacgcag    180

aggatcagga cgccaatcct gcgctccacc tgtctaagga ttcgcttttg gactatccag    240

ggattatggc ttcggattat tgtattcggg ataccgacgg ctgagcacac ggaggatgag    300

gttcagctca cggcccctat cagtatgcat tatgaggatg gcttcttgga aagcagagga    360

attggattat cgaacaagtt ggttctggac cattgactcg agcgtataag taacctcgtt    420

cggtcctcct gtcaccttct gatcagcaac cagcctttcc tctctcattc cctcatctgc    480

ccatc atg cag act ctc ctt gtg agc tcg ctt gtg gtc tcc ctc gct gcg    530
      Met Gln Thr Leu Leu Val Ser Ser Leu Val Val Ser Leu Ala Ala
        1               5                  10                  15

gcc ctg cca cac tac atc agg agc aat ggc att gaa gcc agc ctc ctg      578
Ala Leu Pro His Tyr Ile Arg Ser Asn Gly Ile Glu Ala Ser Leu Leu
                 20                  25                  30

act gat ccc aag gat gtc tcc ggc cgc acg gtc gac tac atc atc gct      626
Thr Asp Pro Lys Asp Val Ser Gly Arg Thr Val Asp Tyr Ile Ile Ala
             35                  40                  45

ggt gga ggt ctg act gga ctc acc acc gct gct cgt ctg acg gag aac      674
Gly Gly Gly Leu Thr Gly Leu Thr Thr Ala Ala Arg Leu Thr Glu Asn
         50                  55                  60

ccc aac atc agt gtg ctc gtc atc gaa agt ggc tcc tac gag tcg gac      722
Pro Asn Ile Ser Val Leu Val Ile Glu Ser Gly Ser Tyr Glu Ser Asp
     65                  70                  75

aga ggt cct atc att gag gac ctg aac gcc tac ggc gac atc ttt ggc      770
Arg Gly Pro Ile Ile Glu Asp Leu Asn Ala Tyr Gly Asp Ile Phe Gly
 80                  85                  90                  95

agc agt gta gac cac gcc tac gag acc gtg gag ctc gct acc aac aat      818
Ser Ser Val Asp His Ala Tyr Glu Thr Val Glu Leu Ala Thr Asn Asn
                100                 105                 110

caa acc gcg ctg atc cgc tcc gga aat ggt ctc ggt ggc tct act cta      866
Gln Thr Ala Leu Ile Arg Ser Gly Asn Gly Leu Gly Gly Ser Thr Leu
            115                 120                 125

gtg aat ggt ggc acc tgg act cgc ccc cac aag gca cag gtt gac tct      914
Val Asn Gly Gly Thr Trp Thr Arg Pro His Lys Ala Gln Val Asp Ser
        130                 135                 140

tgg gag act gtc ttt gga aat gag ggc tgg aac tgg gac aat gtg gcc      962
Trp Glu Thr Val Phe Gly Asn Glu Gly Trp Asn Trp Asp Asn Val Ala
    145                 150                 155

gcc tac tcc ctc cag gct gag cgt gct cgc gca cca aat gcc aaa cag     1010
Ala Tyr Ser Leu Gln Ala Glu Arg Ala Arg Ala Pro Asn Ala Lys Gln
160                 165                 170                 175

atc gct gct ggc cac tac ttc aac gca tcc tgc cat ggt gtt aat ggt     1058
Ile Ala Ala Gly His Tyr Phe Asn Ala Ser Cys His Gly Val Asn Gly
                180                 185                 190

act gtc cat gcc gga ccc cgc gac acc ggc gat gac tat tct ccc atc     1106
Thr Val His Ala Gly Pro Arg Asp Thr Gly Asp Asp Tyr Ser Pro Ile
            195                 200                 205
```

-continued

```
gtc aag gct ctc atg agc gct gtc gaa gac cgg ggc gtt ccc acc aag      1154
Val Lys Ala Leu Met Ser Ala Val Glu Asp Arg Gly Val Pro Thr Lys
        210                 215                 220

aaa gac ttc gga tgc ggt gac ccc cat ggt gtg tcc atg ttc ccc aac      1202
Lys Asp Phe Gly Cys Gly Asp Pro His Gly Val Ser Met Phe Pro Asn
    225                 230                 235

acc ttg cac gaa gac caa gtg cgc tcc gat gcc gct cgc gaa tgg cta      1250
Thr Leu His Glu Asp Gln Val Arg Ser Asp Ala Ala Arg Glu Trp Leu
240                 245                 250                 255

ctt ccc aac tac caa cgt ccc aac ctg caa gtc ctg acc gga cag tat      1298
Leu Pro Asn Tyr Gln Arg Pro Asn Leu Gln Val Leu Thr Gly Gln Tyr
                260                 265                 270

gtt ggt aag gtg ctc ctt agc cag aac ggc acc acc cct cgt gcc gtt      1346
Val Gly Lys Val Leu Leu Ser Gln Asn Gly Thr Thr Pro Arg Ala Val
            275                 280                 285

ggc gtg gaa ttc ggc acc cac aag ggc aac acc cac aac gtt tac gct      1394
Gly Val Glu Phe Gly Thr His Lys Gly Asn Thr His Asn Val Tyr Ala
        290                 295                 300

aag cac gag gtc ctc ctg gcc gcg ggc tcc gct gtc tct ccc aca atc      1442
Lys His Glu Val Leu Leu Ala Ala Gly Ser Ala Val Ser Pro Thr Ile
    305                 310                 315

ctc gaa tat tcc ggt atc gga atg aag tcc atc ctg gag ccc ctt ggt      1490
Leu Glu Tyr Ser Gly Ile Gly Met Lys Ser Ile Leu Glu Pro Leu Gly
320                 325                 330                 335

atc gac acc gtc gtt gac ctg ccc gtc ggc ttg aac ctg cag gac cag      1538
Ile Asp Thr Val Val Asp Leu Pro Val Gly Leu Asn Leu Gln Asp Gln
                340                 345                 350

acc acc gct acc gtc cgc tcc cgc atc acc tct gct ggt gca gga cag      1586
Thr Thr Ala Thr Val Arg Ser Arg Ile Thr Ser Ala Gly Ala Gly Gln
            355                 360                 365

gga cag gcc gct tgg ttc gcc acc ttc aac gag acc ttt ggt gac tat      1634
Gly Gln Ala Ala Trp Phe Ala Thr Phe Asn Glu Thr Phe Gly Asp Tyr
        370                 375                 380

tcc gaa aag gca cac gag ctg ctc aac acc aag ctg gag cag tgg gcc      1682
Ser Glu Lys Ala His Glu Leu Leu Asn Thr Lys Leu Glu Gln Trp Ala
    385                 390                 395

gaa gag gcc gtc gcc cgt ggc gga ttc cac aac acc acc gcc ttg ctc      1730
Glu Glu Ala Val Ala Arg Gly Gly Phe His Asn Thr Thr Ala Leu Leu
400                 405                 410                 415

atc cag tac gag aac tac cgc gac tgg att gtc aac cac aac gtc gcg      1778
Ile Gln Tyr Glu Asn Tyr Arg Asp Trp Ile Val Asn His Asn Val Ala
                420                 425                 430

tac tcg gaa ctc ttc ctc gac act gcc gga gta gcc agc ttc gat gtg      1826
Tyr Ser Glu Leu Phe Leu Asp Thr Ala Gly Val Ala Ser Phe Asp Val
            435                 440                 445

tgg gac ctt ctg ccc ttc acc cga gga tac gtt cac atc ctc gac aag      1874
Trp Asp Leu Leu Pro Phe Thr Arg Gly Tyr Val His Ile Leu Asp Lys
        450                 455                 460

gac ccc tac ctt cac cac ttc gcc tac gac cct cag tac ttc ctc aac      1922
Asp Pro Tyr Leu His His Phe Ala Tyr Asp Pro Gln Tyr Phe Leu Asn
    465                 470                 475

gag ctg gac ctg ctc ggt cag gct gcc gct act caa ctg gcc cgc aac      1970
Glu Leu Asp Leu Leu Gly Gln Ala Ala Ala Thr Gln Leu Ala Arg Asn
480                 485                 490                 495

atc tcc aac tcc ggt gcc atg cag acc tac ttc gct ggg gag act atc      2018
Ile Ser Asn Ser Gly Ala Met Gln Thr Tyr Phe Ala Gly Glu Thr Ile
                500                 505                 510

ccc ggt gat aac ctc gcg tat gat gcc gat ttg agc gcc tgg act gag      2066
Pro Gly Asp Asn Leu Ala Tyr Asp Ala Asp Leu Ser Ala Trp Thr Glu
            515                 520                 525
```

```
tac atc ccg tac cac ttc cgt cct aac tac cat ggc gtg ggt act tgc     2114
Tyr Ile Pro Tyr His Phe Arg Pro Asn Tyr His Gly Val Gly Thr Cys
        530                 535                 540

tcc atg atg ccg aag gag atg ggc ggt gtt gtt gat aat gct gcc cgt     2162
Ser Met Met Pro Lys Glu Met Gly Gly Val Val Asp Asn Ala Ala Arg
    545                 550                 555

gtg tat ggt gtg cag gga ctg cgt gtc att gat ggt tct att cct cct     2210
Val Tyr Gly Val Gln Gly Leu Arg Val Ile Asp Gly Ser Ile Pro Pro
560                 565                 570                 575

acg caa atg tcg tcc cat gtc atg acg gtg ttc tat gcc atg gcg cta     2258
Thr Gln Met Ser Ser His Val Met Thr Val Phe Tyr Ala Met Ala Leu
                580                 585                 590

aaa att tcg gat gct atc ttg gaa gat tat gct tcc atg cag tga         2303
Lys Ile Ser Asp Ala Ile Leu Glu Asp Tyr Ala Ser Met Gln
            595                 600                 605

gtggtatgat ggggatatga gtgaggatat taggggatgg tacttagatg ctggggaggt   2363

ataatcatag attggataga attggtaggt tacatagaca ggttacatga atagacgttc   2423

gttatatgtg agcagacatt actaccaaac aagggcattg ttcagttagt cgaacgatag   2483

tcatatgttt tgtacgggaa gaaagtttca ctaattatta agcaaacgga tcaggggttg   2543

ccagctaaaa tacaatcatc cgatgttcta ttttcttcaa attgatcgac cagtcagtta   2603

atgaatgcat gagagcaact ctgcgcatcc tctagctatc tagtcaataa taagcatgtt   2663

gtttaagatg aaacaccgcc atagacatat tctgttgctg gtgaagcaag ccctcgctaa   2723

atatgctgat aacttcctat gccagtagaa tattttccca ctctgctgcg cgctctcaaa   2783

agctt                                                               2788
```

<210> SEQ ID NO 46
<211> LENGTH: 605
<212> TYPE: PRT
<213> ORGANISM: Aspergillus niger

<400> SEQUENCE: 46

```
Met Gln Thr Leu Leu Val Ser Ser Leu Val Val Ser Leu Ala Ala Ala
  1               5                  10                  15

Leu Pro His Tyr Ile Arg Ser Asn Gly Ile Glu Ala Ser Leu Leu Thr
             20                  25                  30

Asp Pro Lys Asp Val Ser Gly Arg Thr Val Asp Tyr Ile Ile Ala Gly
         35                  40                  45

Gly Gly Leu Thr Gly Leu Thr Thr Ala Ala Arg Leu Thr Glu Asn Pro
     50                  55                  60

Asn Ile Ser Val Leu Val Ile Glu Ser Gly Ser Tyr Glu Ser Asp Arg
 65                  70                  75                  80

Gly Pro Ile Ile Glu Asp Leu Asn Ala Tyr Gly Asp Ile Phe Gly Ser
                 85                  90                  95

Ser Val Asp His Ala Tyr Glu Thr Val Glu Leu Ala Thr Asn Asn Gln
            100                 105                 110

Thr Ala Leu Ile Arg Ser Gly Asn Gly Leu Gly Gly Ser Thr Leu Val
        115                 120                 125

Asn Gly Gly Thr Trp Thr Arg Pro His Lys Ala Gln Val Asp Ser Trp
    130                 135                 140

Glu Thr Val Phe Gly Asn Glu Gly Trp Asn Trp Asp Asn Val Ala Ala
145                 150                 155                 160

Tyr Ser Leu Gln Ala Glu Arg Ala Arg Ala Pro Asn Ala Lys Gln Ile
                165                 170                 175
```

```
Ala Ala Gly His Tyr Phe Asn Ala Ser Cys His Gly Val Asn Gly Thr
            180                 185                 190

Val His Ala Gly Pro Arg Asp Thr Gly Asp Asp Tyr Ser Pro Ile Val
        195                 200                 205

Lys Ala Leu Met Ser Ala Val Glu Asp Arg Gly Val Pro Thr Lys Lys
    210                 215                 220

Asp Phe Gly Cys Gly Asp Pro His Gly Val Ser Met Phe Pro Asn Thr
225                 230                 235                 240

Leu His Glu Asp Gln Val Arg Ser Asp Ala Ala Arg Glu Trp Leu Leu
                245                 250                 255

Pro Asn Tyr Gln Arg Pro Asn Leu Gln Val Leu Thr Gly Gln Tyr Val
            260                 265                 270

Gly Lys Val Leu Leu Ser Gln Asn Gly Thr Thr Pro Arg Ala Val Gly
        275                 280                 285

Val Glu Phe Gly Thr His Lys Gly Asn Thr His Asn Val Tyr Ala Lys
    290                 295                 300

His Glu Val Leu Leu Ala Ala Gly Ser Ala Val Ser Pro Thr Ile Leu
305                 310                 315                 320

Glu Tyr Ser Gly Ile Gly Met Lys Ser Ile Leu Glu Pro Leu Gly Ile
                325                 330                 335

Asp Thr Val Val Asp Leu Pro Val Gly Leu Asn Leu Gln Asp Gln Thr
            340                 345                 350

Thr Ala Thr Val Arg Ser Arg Ile Thr Ser Ala Gly Ala Gly Gln Gly
        355                 360                 365

Gln Ala Ala Trp Phe Ala Thr Phe Asn Glu Thr Phe Gly Asp Tyr Ser
    370                 375                 380

Glu Lys Ala His Glu Leu Leu Asn Thr Lys Leu Glu Gln Trp Ala Glu
385                 390                 395                 400

Glu Ala Val Ala Arg Gly Gly Phe His Asn Thr Thr Ala Leu Leu Ile
                405                 410                 415

Gln Tyr Glu Asn Tyr Arg Asp Trp Ile Val Asn His Asn Val Ala Tyr
            420                 425                 430

Ser Glu Leu Phe Leu Asp Thr Ala Gly Val Ala Ser Phe Asp Val Trp
        435                 440                 445

Asp Leu Leu Pro Phe Thr Arg Gly Tyr Val His Ile Leu Asp Lys Asp
    450                 455                 460

Pro Tyr Leu His His Phe Ala Tyr Asp Pro Gln Tyr Phe Leu Asn Glu
465                 470                 475                 480

Leu Asp Leu Leu Gly Gln Ala Ala Ala Thr Gln Leu Ala Arg Asn Ile
                485                 490                 495

Ser Asn Ser Gly Ala Met Gln Thr Tyr Phe Ala Gly Glu Thr Ile Pro
            500                 505                 510

Gly Asp Asn Leu Ala Tyr Asp Ala Asp Leu Ser Ala Trp Thr Glu Tyr
        515                 520                 525

Ile Pro Tyr His Phe Arg Pro Asn Tyr His Gly Val Gly Thr Cys Ser
    530                 535                 540

Met Met Pro Lys Glu Met Gly Gly Val Val Asp Asn Ala Ala Arg Val
545                 550                 555                 560

Tyr Gly Val Gln Gly Leu Arg Val Ile Asp Gly Ser Ile Pro Pro Thr
                565                 570                 575

Gln Met Ser Ser His Val Met Thr Val Phe Tyr Ala Met Ala Leu Lys
            580                 585                 590
```

-continued

```
Ile Ser Asp Ala Ile Leu Glu Asp Tyr Ala Ser Met Gln
        595                 600                 605
```

<210> SEQ ID NO 47
<211> LENGTH: 2386
<212> TYPE: DNA
<213> ORGANISM: Cladosporium oxysporum
<220> FEATURE:
<223> OTHER INFORMATION: Nucleic Acid encoding glucose oxidase
<300> PUBLICATION INFORMATION:
<310> PATENT DOCUMENT NUMBER: 08/746,257
<311> PATENT FILING DATE: 1996-11-07
<312> PUBLICATION DATE: 1999-03-09

<400> SEQUENCE: 47

```
caacgtcact gctgaggctg tgacacctct ggccgagcca atccgcacaa cgtgctcgcc     60

cacgaacgcc aacacggacc ctgatgttat ctttttgaag atgacaatac cctgccaagc    120

acataagtct gccctaatga tccatcgaga cagacatctt catgacattt cgttgaggtc    180

aagccaagca agacggtgcg tgagcacgtt gcatactacg tactcgcaac cgcacgtatt    240

gcgatactgt gctctttgag aaagacataa gtagacggta gcagaatcgc atttccgggc    300

ttcctttcct cagcatccac caactcagac tcgcctcatc ttgagccatc atgtacaaac    360

ccatcgcgct ttccactcta ctcgctgttg cctcacaggc actgccacac caatctcgag    420

ccgagagcgc ccacgcaatt acagcagacg tctcccaagt ctcaaacaag accttcgact    480

acatcgtctg tggaggcggg ctcacaggct tagtcgtcgc aagccgcttg tccgaagatc    540

caaacatctc cgttctggtg atcgagggtg gcaacgacga ccacgaagac cctcgggtta    600

acgacgtgag gacttacgga caagccttcg agaccgaact cgactatggc ctcaaatcca    660

cttcagttcc atggcagaac aacaccggtc tcctgcttgt cgcaggcaag actcttggtg    720

ggagtggcag catcaacggc gccagctgga ccaaaggcga caagactcag tatgatctcc    780

tccccggttt gactggcgac gattcctggt ccttcgacgc cctcaacgag atcatgctca    840

gtattgagga cttccacacc ccaactgagg accaagtagc caaaggtgct gcatttgaag    900

gagagtttca tggacgcgag ggcaatgttc aagtgtcctt ccctgcgggc atgtttggca    960

gcatacagca accagctctg gaggcatccg ctctcgtctg gaagggcatg aagaaagttg   1020

ccgacttcgc ggccggtatc acgactggtg cgaccatgat tcccaacatg cttgaggcca   1080

atgagtccca gaaccgctcc tcacctttca cggtttacgc caagcagcaa acacaagagc   1140

gcgataactt catcatcctc acgggacacc gtgtgatctc tctcaactgg cgcgagggct   1200

ccgaaatgat cgccgatggc gtcagcttcc aggcatgccg tgactgcaaa atccacaagg   1260

ccaagacaaa gcgagaagtg cttcttgctg gcggctcttt gcaaagccca cagctacttg   1320

agctttctgg agtaggcaac ccgatgtac tggcagccgc cgccgtgccg ctcaaattgg    1380

cgtctccaaa cgttggcaaa aacatgcaag agcaaaccaa gaacaccctc tggttcgatc   1440

ccgtcaacac cgagttcgat ggttctggac cacccaacgc catctctttc ccgaatgtcg   1500

atcagttgtt caggaataac agcgccacca tgtacaagaa catcatgtct ggcctcaagc   1560

aatactcaga agacctggcc gctaccggca cggtgaccaa cgccacagcc acccaccaga   1620

tcctcgaagc acaggtcgac aacctctggc acaaccttgt aggcgccgcc gaaatcttct   1680

tcgtgacatc acccgccacc ggccaagtcg gcgtcgacct ctggaacctg atcgttttgt   1740

cgcgtggcta tgtgcacatc acctcaaact cctcatggga tcacccagaa atcgagcctt   1800

cctacttcgg tcaccaattc gacctcgacg tccaactagc agcgaccaag cagtcgcgcg   1860
```

-continued

```
aagtcttcca gaccgaccct ctagctcctc tcgtcagcgc tgagactttc ccgggccttg   1920

aagccgtgcc gcaaggcgca gaagatcagg tctgggagca gtgggtcaaa gccaccttca   1980

cctctgtctg gcactacatc gcaaccttgg gtatgatgaa ggaggaactt ggaggcgtcg   2040

tggacagcag attgaaggtc tacggtattg agaatgtgcg tgctgtggat gctagcgtgt   2100

tgccgattca gctttcggcg catcttagtt cttcgctgta tggcattgct gagaaggctg   2160

cgaagatgat caaggaggat cagagggcgt gattagcgtt ctaaaacaat catgatagca   2220

tgtttgagtg gcatgctcat tgcagctctg ggcggaattt tgtggctctg ctaataagga   2280

gtccttggct taagtatgca ctcacaccaa cattttatct acatcgctta gtagcgatga   2340

tgtacgaatc cacatccaat cagtccaatc atcgtataag tctgtc                  2386
```

<210> SEQ ID NO 48
<211> LENGTH: 613
<212> TYPE: PRT
<213> ORGANISM: Cladosporium oxysporum
<220> FEATURE:
<223> OTHER INFORMATION: Glucose oxidase protein sequence
<300> PUBLICATION INFORMATION:
<310> PATENT DOCUMENT NUMBER: 08/746,257
<311> PATENT FILING DATE: 1996-11-07
<312> PUBLICATION DATE: 1999-03-09

<400> SEQUENCE: 48

```
Met Tyr Lys Pro Ile Ala Leu Ser Thr Leu Leu Ala Val Ala Ser Gln
  1               5                  10                  15

Ala Leu Pro His Gln Ser Arg Ala Glu Ser Ala His Ala Ile Thr Ala
             20                  25                  30

Asp Val Ser Gln Val Ser Asn Lys Thr Phe Asp Tyr Ile Val Cys Gly
         35                  40                  45

Gly Gly Leu Thr Gly Leu Val Val Ala Ser Arg Leu Ser Glu Asp Pro
     50                  55                  60

Asn Ile Ser Val Leu Val Ile Glu Gly Gly Asn Asp Asp His Glu Asp
 65                  70                  75                  80

Pro Arg Val Asn Asp Val Arg Thr Tyr Gly Gln Ala Phe Glu Thr Glu
                 85                  90                  95

Leu Asp Tyr Gly Leu Lys Ser Thr Ser Val Pro Trp Gln Asn Asn Thr
            100                 105                 110

Gly Leu Leu Leu Val Ala Gly Lys Thr Leu Gly Gly Ser Gly Ser Ile
        115                 120                 125

Asn Gly Ala Ser Trp Thr Lys Gly Asp Lys Thr Gln Tyr Asp Leu Leu
    130                 135                 140

Pro Gly Leu Thr Gly Asp Asp Ser Trp Ser Phe Asp Ala Leu Asn Glu
145                 150                 155                 160

Ile Met Leu Ser Ile Glu Asp Phe His Thr Pro Thr Glu Asp Gln Val
                165                 170                 175

Ala Lys Gly Ala Ala Phe Glu Gly Glu Phe His Gly Arg Glu Gly Asn
            180                 185                 190

Val Gln Val Ser Phe Pro Ala Gly Met Phe Gly Ser Ile Gln Gln Pro
        195                 200                 205

Ala Leu Glu Ala Ser Ala Leu Val Trp Lys Gly Met Lys Lys Val Ala
    210                 215                 220

Asp Phe Ala Ala Gly Ile Thr Thr Gly Ala Thr Met Ile Pro Asn Met
225                 230                 235                 240

Leu Glu Ala Asn Glu Ser Gln Asn Arg Ser Ser Pro Phe Thr Val Tyr
                245                 250                 255
```

```
Ala Lys Gln Gln Thr Gln Glu Arg Asp Asn Phe Ile Ile Leu Thr Gly
            260                 265                 270

His Arg Val Ile Ser Leu Asn Trp Arg Glu Gly Ser Glu Met Ile Ala
        275                 280                 285

Asp Gly Val Ser Phe Gln Ala Cys Arg Asp Cys Lys Ile His Lys Ala
    290                 295                 300

Lys Thr Lys Arg Glu Val Leu Leu Ala Gly Gly Ser Leu Gln Ser Pro
305                 310                 315                 320

Gln Leu Leu Glu Leu Ser Gly Val Gly Asn Pro Asp Val Leu Ala Ala
                325                 330                 335

Ala Ala Val Pro Leu Lys Leu Ala Ser Pro Asn Val Gly Lys Asn Met
            340                 345                 350

Gln Glu Gln Thr Lys Asn Thr Leu Trp Phe Asp Pro Val Asn Thr Glu
        355                 360                 365

Phe Asp Gly Ser Gly Pro Pro Asn Ala Ile Ser Phe Pro Asn Val Asp
    370                 375                 380

Gln Leu Phe Arg Asn Asn Ser Ala Thr Met Tyr Lys Asn Ile Met Ser
385                 390                 395                 400

Gly Leu Lys Gln Tyr Ser Glu Asp Leu Ala Ala Thr Gly Thr Val Thr
                405                 410                 415

Asn Ala Thr Ala Thr His Gln Ile Leu Glu Ala Gln Val Asp Asn Leu
            420                 425                 430

Trp His Asn Leu Val Gly Ala Ala Glu Ile Phe Phe Val Thr Ser Pro
        435                 440                 445

Ala Thr Gly Gln Val Gly Val Asp Leu Trp Asn Leu Ile Val Leu Ser
    450                 455                 460

Arg Gly Tyr Val His Ile Thr Ser Asn Ser Ser Trp Asp His Pro Glu
465                 470                 475                 480

Ile Glu Pro Ser Tyr Phe Gly His Gln Phe Asp Leu Asp Val Gln Leu
                485                 490                 495

Ala Ala Thr Lys Gln Ser Arg Glu Val Phe Gln Thr Asp Pro Leu Ala
            500                 505                 510

Pro Leu Val Ser Ala Glu Thr Phe Pro Gly Leu Glu Ala Val Pro Gln
        515                 520                 525

Gly Ala Glu Asp Gln Val Trp Glu Gln Trp Val Lys Ala Thr Phe Thr
    530                 535                 540

Ser Val Trp His Tyr Ile Ala Thr Leu Gly Met Met Lys Glu Glu Leu
545                 550                 555                 560

Gly Gly Val Val Asp Ser Arg Leu Lys Val Tyr Gly Ile Glu Asn Val
                565                 570                 575

Arg Ala Val Asp Ala Ser Val Leu Pro Ile Gln Leu Ser Ala His Leu
            580                 585                 590

Ser Ser Ser Leu Tyr Gly Ile Ala Glu Lys Ala Ala Lys Met Ile Lys
        595                 600                 605

Glu Asp Gln Arg Ala
    610
```

<210> SEQ ID NO 49
<211> LENGTH: 947
<212> TYPE: DNA
<213> ORGANISM: Homo sapiens
<220> FEATURE:
<221> NAME/KEY: CDS
<222> LOCATION: (16)..(801)
<220> FEATURE:

```
<223> OTHER INFORMATION: Human short-chain alcohol dehydrogenase cDNA
<300> PUBLICATION INFORMATION:
<308> DATABASE ACCESSION NUMBER: U73514/GenBank

<400> SEQUENCE: 49

gtggccggcg acaag atg gca gca gcg tgt cgg agc gtg aag ggc ctg gtg      51
                 Met Ala Ala Ala Cys Arg Ser Val Lys Gly Leu Val
                   1               5                  10

gcg gta ata acc gga gga gcc tcg ggc ctg ggc ctg gcc acg gcg gag       99
Ala Val Ile Thr Gly Gly Ala Ser Gly Leu Gly Leu Ala Thr Ala Glu
         15                  20                  25

cga ctt gtg ggg cag gga gcc tct gct gtg ctt ctg gac ctg ccc aac      147
Arg Leu Val Gly Gln Gly Ala Ser Ala Val Leu Leu Asp Leu Pro Asn
     30                  35                  40

tcg ggt ggg gag gcc caa gcc aag aag tta gga aac aac tgc gtt ttc      195
Ser Gly Gly Glu Ala Gln Ala Lys Lys Leu Gly Asn Asn Cys Val Phe
 45                  50                  55                  60

gcc cca gcc gac gtg acc tct gag aag gat gtg caa aca gct ctg gct      243
Ala Pro Ala Asp Val Thr Ser Glu Lys Asp Val Gln Thr Ala Leu Ala
                 65                  70                  75

cta gca aaa gga aag ttt ggc cgt gtg gat gta gct gtc aac tgt gca      291
Leu Ala Lys Gly Lys Phe Gly Arg Val Asp Val Ala Val Asn Cys Ala
             80                  85                  90

ggc atc gcg gtg gct agc aag acg tac aac tta aag aag ggc cag acc      339
Gly Ile Ala Val Ala Ser Lys Thr Tyr Asn Leu Lys Lys Gly Gln Thr
         95                 100                 105

cat acc ttg gaa gac ttc cag cga gtt ctt gat gtg aat ctc atg ggc      387
His Thr Leu Glu Asp Phe Gln Arg Val Leu Asp Val Asn Leu Met Gly
    110                 115                 120

acc ttc aat gtg atc cgc ctg gtg gct ggt gag atg ggc cag aat gaa      435
Thr Phe Asn Val Ile Arg Leu Val Ala Gly Glu Met Gly Gln Asn Glu
125                 130                 135                 140

cca gac cag gga ggc caa cgt ggg gtc atc atc aac act gcc agt gtg      483
Pro Asp Gln Gly Gly Gln Arg Gly Val Ile Ile Asn Thr Ala Ser Val
                145                 150                 155

gct gcc ttc gag ggt cag gtt gga caa gct gca tac tct gct tcc aag      531
Ala Ala Phe Glu Gly Gln Val Gly Gln Ala Ala Tyr Ser Ala Ser Lys
            160                 165                 170

ggg gga ata gtg ggc atg aca ctg ccc att gct cgg gat ctg gct ccc      579
Gly Gly Ile Val Gly Met Thr Leu Pro Ile Ala Arg Asp Leu Ala Pro
        175                 180                 185

ata ggt atc cgg gtg atg acc att gcc cca ggt ctg ttt ggc acc cca      627
Ile Gly Ile Arg Val Met Thr Ile Ala Pro Gly Leu Phe Gly Thr Pro
    190                 195                 200

ctg ctg acc agc ctc cca gag aaa gtg tgc aac ttc ttg gcc agc caa      675
Leu Leu Thr Ser Leu Pro Glu Lys Val Cys Asn Phe Leu Ala Ser Gln
205                 210                 215                 220

gtg ccc ttc cct agc cga ctg ggt gac cct gct gag tat gct cac ctc      723
Val Pro Phe Pro Ser Arg Leu Gly Asp Pro Ala Glu Tyr Ala His Leu
                225                 230                 235

gta cag gcc atc atc gag aac cca ttc ctc aat gga gag gtc atc cgg      771
Val Gln Ala Ile Ile Glu Asn Pro Phe Leu Asn Gly Glu Val Ile Arg
            240                 245                 250

ctg gat ggg gcc att cgt atg cag cct tga agggagaagg cagagaaaac        821
Leu Asp Gly Ala Ile Arg Met Gln Pro
        255                 260

acacgctcct ctgcccttcc tttccctggg gtactactct ccagcttggg aggaagccca    881

gtagccattt tgtaactgcc taccagtcgc cctctgtgcc taataaagtc tctttttctc    941

acagag                                                               947
```

<210> SEQ ID NO 50
<211> LENGTH: 261
<212> TYPE: PRT
<213> ORGANISM: Homo sapiens

<400> SEQUENCE: 50

```
Met Ala Ala Ala Cys Arg Ser Val Lys Gly Leu Val Ala Val Ile Thr
  1               5                  10                  15

Gly Gly Ala Ser Gly Leu Gly Leu Ala Thr Ala Glu Arg Leu Val Gly
             20                  25                  30

Gln Gly Ala Ser Ala Val Leu Leu Asp Leu Pro Asn Ser Gly Gly Glu
         35                  40                  45

Ala Gln Ala Lys Lys Leu Gly Asn Asn Cys Val Phe Ala Pro Ala Asp
     50                  55                  60

Val Thr Ser Glu Lys Asp Val Gln Thr Ala Leu Ala Leu Ala Lys Gly
 65                  70                  75                  80

Lys Phe Gly Arg Val Asp Val Ala Val Asn Cys Ala Gly Ile Ala Val
                 85                  90                  95

Ala Ser Lys Thr Tyr Asn Leu Lys Lys Gly Gln Thr His Thr Leu Glu
            100                 105                 110

Asp Phe Gln Arg Val Leu Asp Val Asn Leu Met Gly Thr Phe Asn Val
        115                 120                 125

Ile Arg Leu Val Ala Gly Glu Met Gly Gln Asn Glu Pro Asp Gln Gly
    130                 135                 140

Gly Gln Arg Gly Val Ile Ile Asn Thr Ala Ser Val Ala Ala Phe Glu
145                 150                 155                 160

Gly Gln Val Gly Gln Ala Ala Tyr Ser Ala Ser Lys Gly Gly Ile Val
                165                 170                 175

Gly Met Thr Leu Pro Ile Ala Arg Asp Leu Ala Pro Ile Gly Ile Arg
            180                 185                 190

Val Met Thr Ile Ala Pro Gly Leu Phe Gly Thr Pro Leu Leu Thr Ser
        195                 200                 205

Leu Pro Glu Lys Val Cys Asn Phe Leu Ala Ser Gln Val Pro Phe Pro
    210                 215                 220

Ser Arg Leu Gly Asp Pro Ala Glu Tyr Ala His Leu Val Gln Ala Ile
225                 230                 235                 240

Ile Glu Asn Pro Phe Leu Asn Gly Glu Val Ile Arg Leu Asp Gly Ala
                245                 250                 255

Ile Arg Met Gln Pro
            260
```

<210> SEQ ID NO 51
<211> LENGTH: 1966
<212> TYPE: DNA
<213> ORGANISM: Homo sapiens
<220> FEATURE:
<221> NAME/KEY: CDS
<222> LOCATION: (19)..(1143)
<220> FEATURE:
<223> OTHER INFORMATION: Human alcohol dehydrogenase cDNA
<300> PUBLICATION INFORMATION:
<308> DATABASE ACCESSION NUMBER: U09623/GenBank

<400> SEQUENCE: 51

```
cgggactttt tctgactg atg ggc act gct gga aaa gtt att aaa tgc aaa       51
                    Met Gly Thr Ala Gly Lys Val Ile Lys Cys Lys
                      1               5                  10
```

-continued

```
gca gct gtg ctt tgg gag cag aag caa ccc ttc tcc att gag gaa ata       99
Ala Ala Val Leu Trp Glu Gln Lys Gln Pro Phe Ser Ile Glu Glu Ile
             15                  20                  25

gaa gtt gcc cca cca aag act aaa gaa gtt cgc att aag att ttg gcc      147
Glu Val Ala Pro Pro Lys Thr Lys Glu Val Arg Ile Lys Ile Leu Ala
         30                  35                  40

aca gga atc tgt cgc aca gat gac cat gtg ata aaa gga aca atg gtg      195
Thr Gly Ile Cys Arg Thr Asp Asp His Val Ile Lys Gly Thr Met Val
     45                  50                  55

tcc aag ttt cca gtg att gtg gga cat gag gca act ggg att gta gag      243
Ser Lys Phe Pro Val Ile Val Gly His Glu Ala Thr Gly Ile Val Glu
 60                  65                  70                  75

agc att gga gaa gga gtg act aca gtg aaa cca ggt gac aaa gtc atc      291
Ser Ile Gly Glu Gly Val Thr Thr Val Lys Pro Gly Asp Lys Val Ile
                 80                  85                  90

cct ctc ttt ctg cca caa tgt aga gaa tgc aat gct tgt cgc aac cca      339
Pro Leu Phe Leu Pro Gln Cys Arg Glu Cys Asn Ala Cys Arg Asn Pro
             95                 100                 105

gat ggc aac ctt tgc att agg agc gat att act ggt cgt gga gta ctg      387
Asp Gly Asn Leu Cys Ile Arg Ser Asp Ile Thr Gly Arg Gly Val Leu
        110                 115                 120

gct gat ggc acc acc aga ttt aca tgc aag ggc aaa cca gta cac cac      435
Ala Asp Gly Thr Thr Arg Phe Thr Cys Lys Gly Lys Pro Val His His
    125                 130                 135

ttc atg aac acc agt aca ttt acc gag tac aca gtg gtg gat gaa tct      483
Phe Met Asn Thr Ser Thr Phe Thr Glu Tyr Thr Val Val Asp Glu Ser
140                 145                 150                 155

tct gtt gct aag att gat gat gca gct cct cct gag aaa gtc tgt tta      531
Ser Val Ala Lys Ile Asp Asp Ala Ala Pro Pro Glu Lys Val Cys Leu
                160                 165                 170

att ggc tgt ggg ttt tcc act gga tat ggc gct gct gtt aaa act ggc      579
Ile Gly Cys Gly Phe Ser Thr Gly Tyr Gly Ala Ala Val Lys Thr Gly
            175                 180                 185

aag gtc aaa cct ggt tcc act tgc gtc gtc ttt ggc ctg gga gga gtt      627
Lys Val Lys Pro Gly Ser Thr Cys Val Val Phe Gly Leu Gly Gly Val
        190                 195                 200

ggc ctg tca gtc atc atg ggc tgt aag tca gct ggt gca tct agg atc      675
Gly Leu Ser Val Ile Met Gly Cys Lys Ser Ala Gly Ala Ser Arg Ile
    205                 210                 215

att ggg att gac ctc aac aaa gac aaa ttt gag aag gcc atg gct gta      723
Ile Gly Ile Asp Leu Asn Lys Asp Lys Phe Glu Lys Ala Met Ala Val
220                 225                 230                 235

ggt gcc act gag tgt atc agt ccc aag gac tct acc aaa ccc atc agt      771
Gly Ala Thr Glu Cys Ile Ser Pro Lys Asp Ser Thr Lys Pro Ile Ser
                240                 245                 250

gag gtg ctg tca gaa atg aca ggc aac aac gtg gga tac acc ttt gaa      819
Glu Val Leu Ser Glu Met Thr Gly Asn Asn Val Gly Tyr Thr Phe Glu
            255                 260                 265

gtt att ggg cat ctt gaa acc atg att gat gcc ctg gca tcc tgc cac      867
Val Ile Gly His Leu Glu Thr Met Ile Asp Ala Leu Ala Ser Cys His
        270                 275                 280

atg aac tat ggg acc agc gtg gtt gta gga gtt cct cca tca gcc aag      915
Met Asn Tyr Gly Thr Ser Val Val Val Gly Val Pro Pro Ser Ala Lys
    285                 290                 295

atg ctc acc tat gac ccg atg ttg ctc ttc act gga cgc aca tgg aag      963
Met Leu Thr Tyr Asp Pro Met Leu Leu Phe Thr Gly Arg Thr Trp Lys
300                 305                 310                 315

gga tgt gtc ttt gga ggt ttg aaa agc aga gat gat gtc cca aaa cta     1011
Gly Cys Val Phe Gly Gly Leu Lys Ser Arg Asp Asp Val Pro Lys Leu
                320                 325                 330
```

```
gtg act gag ttc ctg gca aag aaa ttt gac ctg gac cag ttg ata act     1059
Val Thr Glu Phe Leu Ala Lys Lys Phe Asp Leu Asp Gln Leu Ile Thr
            335                 340                 345

cat gtt tta cca ttt aaa aaa atc agt gaa gga ttt gag ctg ctc aat     1107
His Val Leu Pro Phe Lys Lys Ile Ser Glu Gly Phe Glu Leu Leu Asn
        350                 355                 360

tca gga caa agc att cga acg gtc ctg acg ttt tga gatccaaagt          1153
Ser Gly Gln Ser Ile Arg Thr Val Leu Thr Phe
    365                 370

ggcaggaggt ctgtgttgtc atggtgaact ggagtttctc ttgtgagagt tccctcatct   1213

gaaatcatgt atctgtctca caaatacaag cataagtaga agatttgttg aagacataga   1273

acccttataa agaattatta acctttataa acatttaaag tcttgtgagc acctgggaat   1333

tagtataata acaatgttaa tatttttgat ttacattttg taaggctata attgtatctt   1393

ttaagaaaac atacacttgg atttctatgt tgaaatggag atttttaaga gttttaacca   1453

gctgctgcag atatataact caaaacagat atagcgtata aagatatagt aaatgcatct   1513

cccagagtaa tattcactta acacattgaa actattattt tttagatttg aatataaatg   1573

tattttttaa acacttgtta tgagttaact tggattacat tttgaaatca gttcattcca   1633

tgatgcatat tactggatta gattaagaaa gacagaaaag attaagggac gggcacattt   1693

ttcaacgatt aagaatcatc attacataac ttggtgaaac tgaaaaagta tatcatatgg   1753

gtacacaagg ctatttgcca gcatatatta atattttaga aaatattcct tttgtaatac   1813

tgaatataaa catagagcta gagtcatatt atcatactta tcataatgtt caatttgata   1873

cagtagaatt gcaagtccct aagtccctat tcactgtgct tagtagtgac tccatttaat   1933

aaaaagtgtt tttagttttt aacaactaaa ccg                                1966


<210> SEQ ID NO 52
<211> LENGTH: 374
<212> TYPE: PRT
<213> ORGANISM: Homo sapiens

<400> SEQUENCE: 52

Met Gly Thr Ala Gly Lys Val Ile Lys Cys Lys Ala Ala Val Leu Trp
  1               5                  10                  15

Glu Gln Lys Gln Pro Phe Ser Ile Glu Glu Ile Glu Val Ala Pro Pro
            20                  25                  30

Lys Thr Lys Glu Val Arg Ile Lys Ile Leu Ala Thr Gly Ile Cys Arg
        35                  40                  45

Thr Asp Asp His Val Ile Lys Gly Thr Met Val Ser Lys Phe Pro Val
     50                  55                  60

Ile Val Gly His Glu Ala Thr Gly Ile Val Glu Ser Ile Gly Glu Gly
 65                  70                  75                  80

Val Thr Thr Val Lys Pro Gly Asp Lys Val Ile Pro Leu Phe Leu Pro
                 85                  90                  95

Gln Cys Arg Glu Cys Asn Ala Cys Arg Asn Pro Asp Gly Asn Leu Cys
            100                 105                 110

Ile Arg Ser Asp Ile Thr Gly Arg Gly Val Leu Ala Asp Gly Thr Thr
        115                 120                 125

Arg Phe Thr Cys Lys Gly Lys Pro Val His His Phe Met Asn Thr Ser
    130                 135                 140

Thr Phe Thr Glu Tyr Thr Val Val Asp Glu Ser Ser Val Ala Lys Ile
145                 150                 155                 160
```

-continued

```
Asp Asp Ala Ala Pro Pro Glu Lys Val Cys Leu Ile Gly Cys Gly Phe
                165                 170                 175

Ser Thr Gly Tyr Gly Ala Ala Val Lys Thr Gly Lys Val Lys Pro Gly
            180                 185                 190

Ser Thr Cys Val Val Phe Gly Leu Gly Gly Val Gly Leu Ser Val Ile
        195                 200                 205

Met Gly Cys Lys Ser Ala Gly Ala Ser Arg Ile Ile Gly Ile Asp Leu
    210                 215                 220

Asn Lys Asp Lys Phe Glu Lys Ala Met Ala Val Gly Ala Thr Glu Cys
225                 230                 235                 240

Ile Ser Pro Lys Asp Ser Thr Lys Pro Ile Ser Glu Val Leu Ser Glu
                245                 250                 255

Met Thr Gly Asn Asn Val Gly Tyr Thr Phe Glu Val Ile Gly His Leu
            260                 265                 270

Glu Thr Met Ile Asp Ala Leu Ala Ser Cys His Met Asn Tyr Gly Thr
        275                 280                 285

Ser Val Val Val Gly Val Pro Pro Ser Ala Lys Met Leu Thr Tyr Asp
    290                 295                 300

Pro Met Leu Leu Phe Thr Gly Arg Thr Trp Lys Gly Cys Val Phe Gly
305                 310                 315                 320

Gly Leu Lys Ser Arg Asp Asp Val Pro Lys Leu Val Thr Glu Phe Leu
                325                 330                 335

Ala Lys Lys Phe Asp Leu Asp Gln Leu Ile Thr His Val Leu Pro Phe
            340                 345                 350

Lys Lys Ile Ser Glu Gly Phe Glu Leu Leu Asn Ser Gly Gln Ser Ile
        355                 360                 365

Arg Thr Val Leu Thr Phe
    370


<210> SEQ ID NO 53
<211> LENGTH: 2277
<212> TYPE: DNA
<213> ORGANISM: Homo sapiens
<220> FEATURE:
<221> NAME/KEY: CDS
<222> LOCATION: (3)..(1127)
<220> FEATURE:
<223> OTHER INFORMATION: Human class III alcohol dehydrogenase (ADH5)
      chi subunit cDNA
<300> PUBLICATION INFORMATION:
<308> DATABASE ACCESSION NUMBER: M30471/GenBank

<400> SEQUENCE: 53

ac atg gcg aac gag gtt atc aag tgc aag gct gca gtt gct tgg gag        47
   Met Ala Asn Glu Val Ile Lys Cys Lys Ala Ala Val Ala Trp Glu
     1               5                  10                  15

gct gga aag cct ctc tcc ata gag gag ata gag gtg gca ccc cca aag       95
Ala Gly Lys Pro Leu Ser Ile Glu Glu Ile Glu Val Ala Pro Pro Lys
                 20                  25                  30

gct cat gaa gtt cga atc aag atc att gcc act gcg gtt tgc cac acc      143
Ala His Glu Val Arg Ile Lys Ile Ile Ala Thr Ala Val Cys His Thr
             35                  40                  45

gat gcc tat acc ctg agt gga gct gat cct gag ggt tgt ttt cca gtg      191
Asp Ala Tyr Thr Leu Ser Gly Ala Asp Pro Glu Gly Cys Phe Pro Val
         50                  55                  60

atc ttg gga cat gaa ggt gct gga att gtg gaa agt gtt ggt gag gga      239
Ile Leu Gly His Glu Gly Ala Gly Ile Val Glu Ser Val Gly Glu Gly
     65                  70                  75

gtt act aag ctg aag gcg ggt gac act gtc atc cca ctt tac atc cca      287
```

-continued

```
Val Thr Lys Leu Lys Ala Gly Asp Thr Val Ile Pro Leu Tyr Ile Pro
 80                 85                  90                  95

cag tgt gga gaa tgc aaa ttt tgt cta aat cct aaa act aac ctt tgc      335
Gln Cys Gly Glu Cys Lys Phe Cys Leu Asn Pro Lys Thr Asn Leu Cys
                100                 105                 110

cag aag ata aga gtc act caa ggg aaa gga tta atg cca gat ggt acc      383
Gln Lys Ile Arg Val Thr Gln Gly Lys Gly Leu Met Pro Asp Gly Thr
            115                 120                 125

agc aga ttt act tgc aaa gga aag aca att ttg cat tac atg gga acc      431
Ser Arg Phe Thr Cys Lys Gly Lys Thr Ile Leu His Tyr Met Gly Thr
        130                 135                 140

agc aca ttt tct gaa tac aca gtt gtg gct gat atc tct gtt gct aaa      479
Ser Thr Phe Ser Glu Tyr Thr Val Val Ala Asp Ile Ser Val Ala Lys
    145                 150                 155

ata gat cct tta gca cct ttg gat aaa gtc tgc ctt cta ggt tgt ggc      527
Ile Asp Pro Leu Ala Pro Leu Asp Lys Val Cys Leu Leu Gly Cys Gly
160                 165                 170                 175

att tca acc ggt tat ggt gct gct gtg aac act gcc aag ttg gag cct      575
Ile Ser Thr Gly Tyr Gly Ala Ala Val Asn Thr Ala Lys Leu Glu Pro
                180                 185                 190

ggc tct gtt tgt gcc gtc ttt ggt ctg gga gga gtc gga ttg gca gtt      623
Gly Ser Val Cys Ala Val Phe Gly Leu Gly Gly Val Gly Leu Ala Val
            195                 200                 205

atc atg ggc tgt aaa gtg gct ggt gct tcc cgg atc att ggt gtg gac      671
Ile Met Gly Cys Lys Val Ala Gly Ala Ser Arg Ile Ile Gly Val Asp
        210                 215                 220

atc aat aaa gat aaa ttt gca agg gcc aaa gag ttt gga gcc act gaa      719
Ile Asn Lys Asp Lys Phe Ala Arg Ala Lys Glu Phe Gly Ala Thr Glu
    225                 230                 235

tgt att aac cct cag gat ttt agt aaa ccc atc cag gaa gtg ctc att      767
Cys Ile Asn Pro Gln Asp Phe Ser Lys Pro Ile Gln Glu Val Leu Ile
240                 245                 250                 255

gag atg acc gat gga gga gtg gac tat tcc ttt gaa tgt att ggt aat      815
Glu Met Thr Asp Gly Gly Val Asp Tyr Ser Phe Glu Cys Ile Gly Asn
                260                 265                 270

gtg aag gtc atg aga gca gca ctt gag gca tgt cac aag ggc tgg ggc      863
Val Lys Val Met Arg Ala Ala Leu Glu Ala Cys His Lys Gly Trp Gly
            275                 280                 285

gtc agc gtc gtg gtt gga gta gct gct tca ggt gaa gaa att gcc act      911
Val Ser Val Val Val Gly Val Ala Ala Ser Gly Glu Glu Ile Ala Thr
        290                 295                 300

cgt cca ttc cag ctg gta aca ggt cgc aca tgg aaa ggc act gcc ttt      959
Arg Pro Phe Gln Leu Val Thr Gly Arg Thr Trp Lys Gly Thr Ala Phe
    305                 310                 315

gga gga tgg aag agt gta gaa agt gtc cca aag ttg gtg tct gaa tat     1007
Gly Gly Trp Lys Ser Val Glu Ser Val Pro Lys Leu Val Ser Glu Tyr
320                 325                 330                 335

atg tcc aaa aag ata aaa gtt gat gaa ttt gtg act cac aat ctg tct     1055
Met Ser Lys Lys Ile Lys Val Asp Glu Phe Val Thr His Asn Leu Ser
                340                 345                 350

ttt gat gaa atc aac aaa gcc ttt gaa ctg atg cat tct gga aag agc     1103
Phe Asp Glu Ile Asn Lys Ala Phe Glu Leu Met His Ser Gly Lys Ser
            355                 360                 365

att cga act gtt gta aag att taa ttcaaaagag aaaaataatg tccatcctgt    1157
Ile Arg Thr Val Val Lys Ile
        370

cgtgatgtga taggagcagc ttaacaggca gggagaagcg cctccaacct cacagcctcg   1217

tagagcttca cagctactcc agaaaatagg gttatgtgtg tcattcatga atctctataa   1277
```

-continued

```
tcaaggacaa ggataattca gtcatgaacc tgttttctgg atgctcctcc acataaataa   1337

ttgctagttt attaaggaat attttaacat aataaaagta atttctacat ttgtgtggaa   1397

attgtcttgt tttatgctgt catcattgtc acggttgtct gccattatct tcattctgca   1457

agggaaaggg aaaggaagca gggcagtggt gggtgtctga aacctcagaa acataacgtt   1517

gaacttttaa gggtctcagt ccccgttgat taaagaacag atcctagcca tcagtgacaa   1577

agttaatcag gacccaagtc tgcttctgtg atattatctt gaagggaggt actgtgcctt   1637

gttcatacct gtaccccaaa ttcctaggat gcatctgcct tcaggggca ctaaaatgta    1697

ttattgaaac agcattctgg gcttaaatag gtgtatgtat gtgttggttg tgactgtact   1757

attctagtat agtgaactac atactgaata tccaagttct cagcacctac ttttgtcaaa   1817

tcttaacatt ttgccacttc gagatcacat tgccttcctc ccctccaaga ggtaacaatt   1877

atccacaatt tgatgtttat cattcctgtg ttgttgtact ttcactgtgt ataacctaaa   1937

ccatctactc tttagtactg ttttatatat ttttaagcct catacttgct cattctacag   1997

ctttttcac tcattattgt ataattatat ctgaagctct cgttcattaa ttttagtcct    2057

gtgtagcaga attcaattac gggaaactac cataatttat ctgttctcca gtccagttga   2117

aggcatgaag ttgttgccag tttctgtatt ataacactgt agtggaacat tcttctgcat   2177

tgggctactc gcgtgttacc taagacgtat cacagaataa acacatttag ccttatagac   2237

attgccaaat tgctcttcaa agtaaatgtg agtttttgtg                         2277
```

```
<210> SEQ ID NO 54
<211> LENGTH: 374
<212> TYPE: PRT
<213> ORGANISM: Homo sapiens

<400> SEQUENCE: 54

Met Ala Asn Glu Val Ile Lys Cys Lys Ala Ala Val Ala Trp Glu Ala
  1               5                  10                  15

Gly Lys Pro Leu Ser Ile Glu Glu Ile Glu Val Ala Pro Pro Lys Ala
             20                  25                  30

His Glu Val Arg Ile Lys Ile Ile Ala Thr Ala Val Cys His Thr Asp
         35                  40                  45

Ala Tyr Thr Leu Ser Gly Ala Asp Pro Glu Gly Cys Phe Pro Val Ile
     50                  55                  60

Leu Gly His Glu Gly Ala Gly Ile Val Glu Ser Val Gly Glu Gly Val
 65                  70                  75                  80

Thr Lys Leu Lys Ala Gly Asp Thr Val Ile Pro Leu Tyr Ile Pro Gln
                 85                  90                  95

Cys Gly Glu Cys Lys Phe Cys Leu Asn Pro Lys Thr Asn Leu Cys Gln
            100                 105                 110

Lys Ile Arg Val Thr Gln Gly Lys Gly Leu Met Pro Asp Gly Thr Ser
        115                 120                 125

Arg Phe Thr Cys Lys Gly Lys Thr Ile Leu His Tyr Met Gly Thr Ser
    130                 135                 140

Thr Phe Ser Glu Tyr Thr Val Val Ala Asp Ile Ser Val Ala Lys Ile
145                 150                 155                 160

Asp Pro Leu Ala Pro Leu Asp Lys Val Cys Leu Leu Gly Cys Gly Ile
                165                 170                 175

Ser Thr Gly Tyr Gly Ala Ala Val Asn Thr Ala Lys Leu Glu Pro Gly
            180                 185                 190

Ser Val Cys Ala Val Phe Gly Leu Gly Gly Val Gly Leu Ala Val Ile
```

-continued

```
        195                 200                 205

Met Gly Cys Lys Val Ala Gly Ala Ser Arg Ile Ile Gly Val Asp Ile
    210                 215                 220

Asn Lys Asp Lys Phe Ala Arg Ala Lys Glu Phe Gly Ala Thr Glu Cys
225                 230                 235                 240

Ile Asn Pro Gln Asp Phe Ser Lys Pro Ile Gln Glu Val Leu Ile Glu
                245                 250                 255

Met Thr Asp Gly Gly Val Asp Tyr Ser Phe Glu Cys Ile Gly Asn Val
            260                 265                 270

Lys Val Met Arg Ala Ala Leu Glu Ala Cys His Lys Gly Trp Gly Val
        275                 280                 285

Ser Val Val Val Gly Val Ala Ala Ser Gly Glu Glu Ile Ala Thr Arg
    290                 295                 300

Pro Phe Gln Leu Val Thr Gly Arg Thr Trp Lys Gly Thr Ala Phe Gly
305                 310                 315                 320

Gly Trp Lys Ser Val Glu Ser Val Pro Lys Leu Val Ser Glu Tyr Met
                325                 330                 335

Ser Lys Lys Ile Lys Val Asp Glu Phe Val Thr His Asn Leu Ser Phe
            340                 345                 350

Asp Glu Ile Asn Lys Ala Phe Glu Leu Met His Ser Gly Lys Ser Ile
        355                 360                 365

Arg Thr Val Val Lys Ile
    370


<210> SEQ ID NO 55
<211> LENGTH: 1618
<212> TYPE: DNA
<213> ORGANISM: Homo sapiens
<220> FEATURE:
<221> NAME/KEY: CDS
<222> LOCATION: (31)..(1158)
<223> OTHER INFORMATION: Human class I alcohol dehydrogenase  beta-1
      subunit cDNA
<300> PUBLICATION INFORMATION:
<308> DATABASE ACCESSION NUMBER: M24317/GenBank

<400> SEQUENCE: 55

ctgctggtgg gcagagaaga cagaaacgac atg agc aca gca gga aaa gta atc      54
                                 Met Ser Thr Ala Gly Lys Val Ile
                                   1               5

aaa tgc aaa gca gct gtg cta tgg gag gta aag aaa ccc ttt tcc att      102
Lys Cys Lys Ala Ala Val Leu Trp Glu Val Lys Lys Pro Phe Ser Ile
     10                  15                  20

gag gat gtg gag gtt gca cct cct aag gct tat gaa gtt cgc att aag      150
Glu Asp Val Glu Val Ala Pro Pro Lys Ala Tyr Glu Val Arg Ile Lys
 25                  30                  35                  40

atg gtg gct gta gga atc tgt cgc aca gat gac cac gtg gtt agt ggc      198
Met Val Ala Val Gly Ile Cys Arg Thr Asp Asp His Val Val Ser Gly
                 45                  50                  55

aac ctg gtg acc ccc ctt cct gtg att tta ggc cat gag gca gcc ggc      246
Asn Leu Val Thr Pro Leu Pro Val Ile Leu Gly His Glu Ala Ala Gly
             60                  65                  70

atc gtg gag agt gtt gga gaa ggg gtg act aca gtc aaa cca ggt gat      294
Ile Val Glu Ser Val Gly Glu Gly Val Thr Thr Val Lys Pro Gly Asp
         75                  80                  85

aaa gtc atc ccg ctc ttt act cct cag tgt gga aaa tgc aga gtt tgt      342
Lys Val Ile Pro Leu Phe Thr Pro Gln Cys Gly Lys Cys Arg Val Cys
     90                  95                 100

aaa aac ccg gag agc aac tac tgc ttg aaa aat gat cta ggc aat cct      390
```

-continued

```
Lys Asn Pro Glu Ser Asn Tyr Cys Leu Lys Asn Asp Leu Gly Asn Pro
105                 110                 115                 120

cgg ggg acc ctg cag gat ggc acc agg agg ttc acc tgc agg ggg aag      438
Arg Gly Thr Leu Gln Asp Gly Thr Arg Arg Phe Thr Cys Arg Gly Lys
                125                 130                 135

ccc att cac cac ttc ctt ggc acc agc acc ttc tcc cag tac acg gtg      486
Pro Ile His His Phe Leu Gly Thr Ser Thr Phe Ser Gln Tyr Thr Val
            140                 145                 150

gtg gat gag aat gca gtg gcc aaa att gat gca gcc tcg ccc ctg gag      534
Val Asp Glu Asn Ala Val Ala Lys Ile Asp Ala Ala Ser Pro Leu Glu
        155                 160                 165

aaa gtc tgc ctc att ggc tgt gga ttc tcg act ggt tat ggg tct gca      582
Lys Val Cys Leu Ile Gly Cys Gly Phe Ser Thr Gly Tyr Gly Ser Ala
    170                 175                 180

gtt aac gtt gcc aag gtc acc cca ggc tct acc tgt gct gtg ttt ggc      630
Val Asn Val Ala Lys Val Thr Pro Gly Ser Thr Cys Ala Val Phe Gly
185                 190                 195                 200

ctg gga ggg gtc ggc cta tct gct gtt atg ggc tgt aaa gca gct gga      678
Leu Gly Gly Val Gly Leu Ser Ala Val Met Gly Cys Lys Ala Ala Gly
                205                 210                 215

gca gcc aga atc att gcg gtg gac atc aac aag gac aaa aaa gca aag      726
Ala Ala Arg Ile Ile Ala Val Asp Ile Asn Lys Asp Lys Lys Ala Lys
            220                 225                 230

gcc aaa gag ttg ggt gcc act gaa tgc atc aac cct caa gac tac aag      774
Ala Lys Glu Leu Gly Ala Thr Glu Cys Ile Asn Pro Gln Asp Tyr Lys
        235                 240                 245

aaa ccc atc cag gaa gtg cta aag gaa atg act gat gga ggt gtg gat      822
Lys Pro Ile Gln Glu Val Leu Lys Glu Met Thr Asp Gly Gly Val Asp
    250                 255                 260

ttt tcg ttt gaa gtc atc ggt cgg ctt gac acc atg atg gct tcc ctg      870
Phe Ser Phe Glu Val Ile Gly Arg Leu Asp Thr Met Met Ala Ser Leu
265                 270                 275                 280

tta tgt tgt cat gag gca tgt ggc aca agc gtc atc gta ggg gta cct      918
Leu Cys Cys His Glu Ala Cys Gly Thr Ser Val Ile Val Gly Val Pro
                285                 290                 295

cct gct tcc cag aac ctc tca ata aac cct atg ctg cta ctg act gga      966
Pro Ala Ser Gln Asn Leu Ser Ile Asn Pro Met Leu Leu Leu Thr Gly
            300                 305                 310

cgc acc tgg aag ggg gct gtt tat ggt ggc ttt aag agt aaa gaa ggt     1014
Arg Thr Trp Lys Gly Ala Val Tyr Gly Gly Phe Lys Ser Lys Glu Gly
        315                 320                 325

atc cca aaa ctt gtg gct gat ttt atg gct aag aag ttt tca ctg gat     1062
Ile Pro Lys Leu Val Ala Asp Phe Met Ala Lys Lys Phe Ser Leu Asp
    330                 335                 340

gcg tta ata acc cat gtt tta cct ttt gaa aaa ata aat gaa gga ttt     1110
Ala Leu Ile Thr His Val Leu Pro Phe Glu Lys Ile Asn Glu Gly Phe
345                 350                 355                 360

gac ctg ctt cac tct ggg aaa agt atc cgt acc gtc ctg acg ttt tga     1158
Asp Leu Leu His Ser Gly Lys Ser Ile Arg Thr Val Leu Thr Phe
                365                 370                 375

ggcaatagag atgccttccc ctgtagcagt cttcagcctc ctctacccta caagatctgg   1218

agcaacagct aggaaatatc attaattcag ctcttcagag atgttatcaa taaattacac   1278

atgggggctt tccaaagaaa tggaaattga tgggaaatta tttttcagga aatttaaaa    1338

ttcaagtgag aagtaaataa agtgttgaac atcagctggg gaattgaagc caacaaacct   1398

tccttcttaa ccattctact gtgtcacctt tgccattgag gaaaaatatt cctgtgactt   1458

cttgcatttt tggtatcttc ataatcttta gtcatcgaat cccagtggag gggacccttt   1518
```

-continued

```
tacttgccct gaacatacac atgctgggcc attgtgattg aagtcttcta actctgtctc   1578

agttttcact gtcgacattt tcctttttct aataaaaatg                         1618


<210> SEQ ID NO 56
<211> LENGTH: 375
<212> TYPE: PRT
<213> ORGANISM: Homo sapiens

<400> SEQUENCE: 56

Met Ser Thr Ala Gly Lys Val Ile Lys Cys Lys Ala Ala Val Leu Trp
  1               5                  10                  15

Glu Val Lys Lys Pro Phe Ser Ile Glu Asp Val Glu Val Ala Pro Pro
             20                  25                  30

Lys Ala Tyr Glu Val Arg Ile Lys Met Val Ala Val Gly Ile Cys Arg
         35                  40                  45

Thr Asp Asp His Val Val Ser Gly Asn Leu Val Thr Pro Leu Pro Val
     50                  55                  60

Ile Leu Gly His Glu Ala Ala Gly Ile Val Glu Ser Val Gly Glu Gly
 65                  70                  75                  80

Val Thr Thr Val Lys Pro Gly Asp Lys Val Ile Pro Leu Phe Thr Pro
                 85                  90                  95

Gln Cys Gly Lys Cys Arg Val Cys Lys Asn Pro Glu Ser Asn Tyr Cys
            100                 105                 110

Leu Lys Asn Asp Leu Gly Asn Pro Arg Gly Thr Leu Gln Asp Gly Thr
        115                 120                 125

Arg Arg Phe Thr Cys Arg Gly Lys Pro Ile His His Phe Leu Gly Thr
    130                 135                 140

Ser Thr Phe Ser Gln Tyr Thr Val Val Asp Glu Asn Ala Val Ala Lys
145                 150                 155                 160

Ile Asp Ala Ala Ser Pro Leu Glu Lys Val Cys Leu Ile Gly Cys Gly
                165                 170                 175

Phe Ser Thr Gly Tyr Gly Ser Ala Val Asn Val Ala Lys Val Thr Pro
            180                 185                 190

Gly Ser Thr Cys Ala Val Phe Gly Leu Gly Gly Val Gly Leu Ser Ala
        195                 200                 205

Val Met Gly Cys Lys Ala Ala Gly Ala Ala Arg Ile Ile Ala Val Asp
    210                 215                 220

Ile Asn Lys Asp Lys Lys Ala Lys Ala Lys Glu Leu Gly Ala Thr Glu
225                 230                 235                 240

Cys Ile Asn Pro Gln Asp Tyr Lys Lys Pro Ile Gln Glu Val Leu Lys
                245                 250                 255

Glu Met Thr Asp Gly Gly Val Asp Phe Ser Phe Glu Val Ile Gly Arg
            260                 265                 270

Leu Asp Thr Met Met Ala Ser Leu Leu Cys Cys His Glu Ala Cys Gly
        275                 280                 285

Thr Ser Val Ile Val Gly Val Pro Pro Ala Ser Gln Asn Leu Ser Ile
    290                 295                 300

Asn Pro Met Leu Leu Leu Thr Gly Arg Thr Trp Lys Gly Ala Val Tyr
305                 310                 315                 320

Gly Gly Phe Lys Ser Lys Glu Gly Ile Pro Lys Leu Val Ala Asp Phe
                325                 330                 335

Met Ala Lys Lys Phe Ser Leu Asp Ala Leu Ile Thr His Val Leu Pro
            340                 345                 350

Phe Glu Lys Ile Asn Glu Gly Phe Asp Leu Leu His Ser Gly Lys Ser
```

-continued 355 360 365

Ile Arg Thr Val Leu Thr Phe
370 375

<210> SEQ ID NO 57
<211> LENGTH: 906
<212> TYPE: DNA
<213> ORGANISM: Aspergillus flavus
<220> FEATURE:
<223> OTHER INFORMATION: Urate oxidase cDNA
<300> PUBLICATION INFORMATION:
<310> PATENT DOCUMENT NUMBER: 08/314,586
<311> PATENT FILING DATE: 1994-09-28
<312> PUBLICATION DATE: 1996-07-30

<400> SEQUENCE: 57
atgtctgcgg taaaagcagc gcgctacggc aaggacaatg ttcgcgtcta caaggttcac 60
aaggacgaga agaccggtgt ccagacggtg tacgagatga ccgtctgtgt gcttctggag 120
ggtgagattg agacctctta caccaaggcc gacaacagcg tcattgtcgc aaccgactcc 180
attaagaaca ccatttacat caccgccaag cagaaccccg ttactcctcc cgagctgttc 240
ggctccatcc tgggcacaca cttcattgag aagtacaacc acatccatgc cgctcacgtc 300
aacattgtct gccaccgctg gacccggatg gacattgacg gcaagccaca ccctcactcc 360
ttcatccgcg acagcgagga gaagcggaat gtgcaggtgg acgtggtcga gggcaagggc 420
atcgatatca agtcgtctct gtccggcctg accgtgctga agagcaccaa ctcgcagttc 480
tggggcttcc tgcgtgacga gtacaccaca cttaaggaga cctgggaccg tatcctgagc 540
accgacgtcg atgccacttg gcagtggaag aatttcagtg gactccagga ggtccgctcg 600
cacgtgccta agttcgatgc tacctgggcc actgctcgcg aggtcactct gaagactttt 660
gctgaagata acagtgccag cgtgcaggcc actatgtaca agatggcaga gcaaatcctg 720
gcgcgccagc agctgatcga gactgtcgag tactcgttgc ctaacaagca ctatttcgaa 780
atcgacctga gctggcacaa gggcctccaa aacaccggca agaacgccga ggtcttcgct 840
cctcagtcgg accccaacgg tctgatcaag tgtaccgtcg gccggtcctc tctgaagtct 900
aaattg 906

<210> SEQ ID NO 58
<211> LENGTH: 302
<212> TYPE: PRT
<213> ORGANISM: Aspergillus flavus
<220> FEATURE:
<223> OTHER INFORMATION: Urate oxidase protein sequence
<300> PUBLICATION INFORMATION:
<310> PATENT DOCUMENT NUMBER: 08/314,586
<311> PATENT FILING DATE: 1994-09-28
<312> PUBLICATION DATE: 1996-07-30

<400> SEQUENCE: 58

Met Ser Ala Val Lys Ala Ala Arg Tyr Gly Lys Asp Asn Val Arg Val
1 5 10 15

Tyr Lys Val His Lys Asp Glu Lys Thr Gly Val Gln Thr Val Tyr Glu
20 25 30

Met Thr Val Cys Val Leu Leu Glu Gly Glu Ile Glu Thr Ser Tyr Thr
35 40 45

Lys Ala Asp Asn Ser Val Ile Val Ala Thr Asp Ser Ile Lys Asn Thr
50 55 60

Ile Tyr Ile Thr Ala Lys Gln Asn Pro Val Thr Pro Pro Glu Leu Phe
65 70 75 80

-continued

```
Gly Ser Ile Leu Gly Thr His Phe Ile Glu Lys Tyr Asn His Ile His
                 85                  90                  95

Ala Ala His Val Asn Ile Val Cys His Arg Trp Thr Arg Met Asp Ile
            100                 105                 110

Asp Gly Lys Pro His Pro His Ser Phe Ile Arg Asp Ser Glu Glu Lys
        115                 120                 125

Arg Asn Val Gln Val Asp Val Val Glu Gly Lys Gly Ile Asp Ile Lys
    130                 135                 140

Ser Ser Leu Ser Gly Leu Thr Val Leu Lys Ser Thr Asn Ser Gln Phe
145                 150                 155                 160

Trp Gly Phe Leu Arg Asp Glu Tyr Thr Thr Leu Lys Glu Thr Trp Asp
                165                 170                 175

Arg Ile Leu Ser Thr Asp Val Asp Ala Thr Trp Gln Trp Lys Asn Phe
            180                 185                 190

Ser Gly Leu Gln Glu Val Arg Ser His Val Pro Lys Phe Asp Ala Thr
        195                 200                 205

Trp Ala Thr Ala Arg Glu Val Thr Leu Lys Thr Phe Ala Glu Asp Asn
    210                 215                 220

Ser Ala Ser Val Gln Ala Thr Met Tyr Lys Met Ala Glu Gln Ile Leu
225                 230                 235                 240

Ala Arg Gln Gln Leu Ile Glu Thr Val Glu Tyr Ser Leu Pro Asn Lys
                245                 250                 255

His Tyr Phe Glu Ile Asp Leu Ser Trp His Lys Gly Leu Gln Asn Thr
            260                 265                 270

Gly Lys Asn Ala Glu Val Phe Ala Pro Gln Ser Asp Pro Asn Gly Leu
        275                 280                 285

Ile Lys Cys Thr Val Gly Arg Ser Ser Leu Lys Ser Lys Leu
    290                 295                 300
```

<210> SEQ ID NO 59
<211> LENGTH: 999
<212> TYPE: DNA
<213> ORGANISM: Bacillus sp.
<220> FEATURE:
<223> OTHER INFORMATION: Uricase cDNA
<300> PUBLICATION INFORMATION:
<310> PATENT DOCUMENT NUMBER: 08/469,649
<311> PATENT FILING DATE: 1995-06-06
<312> PUBLICATION DATE: 1998-03-17

<400> SEQUENCE: 59

```
atgaccaaac acaaagaaag agtgatgtat tatggaaaag gtgacgtatt tgcttatcgc     60

acctatttaa aaccacttac tggagttaga acgattcctg aatctccatt ttccggtcga    120

gatcatattc tttttggagt aaatgtaaaa atctcagtag gaggaacaaa attgctgacc    180

tcctttacga aaggggataa cagcttagtc gttgcaacag actcgatgaa aaactttata    240

caaaaacatt tagctagtta tacaggaaca acgatagaag gtttttttaga atatgtagct    300

acttcttttt tgaagaaata ttctcatatt gaaaagattt cgttgatagg agaggaaatt    360

ccctttgaaa caacttttgc agtaaagaat ggaaatagag cagctagtga gctagtattt    420

aaaaaatcac gaaatgaata tgccaccgct tatttgaata tggttcgtaa tgaagataac    480

accctaaaca ttactgaaca acaaagcgga cttgctggtc ttcaattaat aaaagtcagc    540

ggaaattcct ttgtcggttt tattcgtgac gaatacacaa ctcttccaga ggattcaaac    600

cgccctctat ttgtttactt aaacatcaaa tggaagtaca aaaacacgga agactcattt    660
```

-continued

```
ggaacgaatc cagaaaatta tgttgcagct gaacaaattc gcgacatcgc cacttccgta    720

tttcatgaaa ccgagacgct ttccatccaa catttaattt atttaatcgg ccgcagaata    780

ttagaaagat tccctcaact tcaagaagtt tacttcgaat ctcaaaatca tacatgggat    840

aaaatagtgg aggaaattcc tgaatcagaa gggaaagtat atacagaacc gcgaccgcca    900

tatggatttc aatgctttac tgtcacccaa gaagacttgc cacacgaaaa cattcttatg    960

ttctctgatg aacccgatca taaaggagca cttaaatga                           999


<210> SEQ ID NO 60
<211> LENGTH: 332
<212> TYPE: PRT
<213> ORGANISM: Bacillus sp.
<220> FEATURE:
<223> OTHER INFORMATION: Uricase protein sequence

<400> SEQUENCE: 60

Met Thr Lys His Lys Glu Arg Val Met Tyr Tyr Gly Lys Gly Asp Val
  1               5                  10                  15

Phe Ala Tyr Arg Thr Tyr Leu Lys Pro Leu Thr Gly Val Arg Thr Ile
             20                  25                  30

Pro Glu Ser Pro Phe Ser Gly Arg Asp His Ile Leu Phe Gly Val Asn
         35                  40                  45

Val Lys Ile Ser Val Gly Gly Thr Lys Leu Leu Thr Ser Phe Thr Lys
     50                  55                  60

Gly Asp Asn Ser Leu Val Val Ala Thr Asp Ser Met Lys Asn Phe Ile
 65                  70                  75                  80

Gln Lys His Leu Ala Ser Tyr Thr Gly Thr Thr Ile Glu Gly Phe Leu
                 85                  90                  95

Glu Tyr Val Ala Thr Ser Phe Leu Lys Lys Tyr Ser His Ile Glu Lys
            100                 105                 110

Ile Ser Leu Ile Gly Glu Glu Ile Pro Phe Glu Thr Thr Phe Ala Val
        115                 120                 125

Lys Asn Gly Asn Arg Ala Ala Ser Glu Leu Val Phe Lys Lys Ser Arg
    130                 135                 140

Asn Glu Tyr Ala Thr Ala Tyr Leu Asn Met Val Arg Asn Glu Asp Asn
145                 150                 155                 160

Thr Leu Asn Ile Thr Glu Gln Gln Ser Gly Leu Ala Gly Leu Gln Leu
                165                 170                 175

Ile Lys Val Ser Gly Asn Ser Phe Val Gly Phe Ile Arg Asp Glu Tyr
            180                 185                 190

Thr Thr Leu Pro Glu Asp Ser Asn Arg Pro Leu Phe Val Tyr Leu Asn
        195                 200                 205

Ile Lys Trp Lys Tyr Lys Asn Thr Glu Asp Ser Phe Gly Thr Asn Pro
    210                 215                 220

Glu Asn Tyr Val Ala Ala Glu Gln Ile Arg Asp Ile Ala Thr Ser Val
225                 230                 235                 240

Phe His Glu Thr Glu Thr Leu Ser Ile Gln His Leu Ile Tyr Leu Ile
                245                 250                 255

Gly Arg Arg Ile Leu Glu Arg Phe Pro Gln Leu Gln Glu Val Tyr Phe
            260                 265                 270

Glu Ser Gln Asn His Thr Trp Asp Lys Ile Val Glu Glu Ile Pro Glu
        275                 280                 285

Ser Glu Gly Lys Val Tyr Thr Glu Pro Arg Pro Pro Tyr Gly Phe Gln
    290                 295                 300
```

-continued

```
Cys Phe Thr Val Thr Gln Glu Asp Leu Pro His Glu Asn Ile Leu Met
305                 310                 315                 320

Phe Ser Asp Glu Pro Asp His Lys Gly Ala Leu Lys
                325                 330


<210> SEQ ID NO 61
<211> LENGTH: 936
<212> TYPE: DNA
<213> ORGANISM: Papio hamadryas
<220> FEATURE:
<221> NAME/KEY: CDS
<222> LOCATION: (11)..(925)
<220> FEATURE:
<223> OTHER INFORMATION: Baboon urate oxidase cDNA
<300> PUBLICATION INFORMATION:
<308> DATABASE ACCESSION NUMBER: M27694/GenBnak

<400> SEQUENCE: 61

ccagaagaaa atg gcc gac tac cat aac aac tat aaa aag aat gat gaa        49
           Met Ala Asp Tyr His Asn Asn Tyr Lys Lys Asn Asp Glu
             1               5                  10

ttg gag ttt gtc cga act ggc tat ggg aag gat atg gta aaa gtt ctc       97
Leu Glu Phe Val Arg Thr Gly Tyr Gly Lys Asp Met Val Lys Val Leu
     15                  20                  25

cat att cag cga gat gga aaa tat cac agc att aaa gag gtg gca act      145
His Ile Gln Arg Asp Gly Lys Tyr His Ser Ile Lys Glu Val Ala Thr
 30                  35                  40                  45

tca gtg caa ctt act ctg agt tcc aaa aaa gat tac ctg cat gga gat      193
Ser Val Gln Leu Thr Leu Ser Ser Lys Lys Asp Tyr Leu His Gly Asp
                 50                  55                  60

aat tca gat atc atc cct aca gac acc atc aag aac aca gtt cat gtc      241
Asn Ser Asp Ile Ile Pro Thr Asp Thr Ile Lys Asn Thr Val His Val
             65                  70                  75

ttg gca aag ttt aag gga atc aaa agc ata gaa gcc ttt ggt gtg aat      289
Leu Ala Lys Phe Lys Gly Ile Lys Ser Ile Glu Ala Phe Gly Val Asn
         80                  85                  90

att tgt gag tat ttt ctt tct tct ttt aac cat gta atc cga gct caa      337
Ile Cys Glu Tyr Phe Leu Ser Ser Phe Asn His Val Ile Arg Ala Gln
     95                 100                 105

gtc tac gtg gaa gaa atc cct tgg aag cgt ctt gaa aag aat gga gtt      385
Val Tyr Val Glu Glu Ile Pro Trp Lys Arg Leu Glu Lys Asn Gly Val
110                 115                 120                 125

aag cat gtc cat gca ttt att cac act ccc act gga aca cac ttc tgt      433
Lys His Val His Ala Phe Ile His Thr Pro Thr Gly Thr His Phe Cys
                130                 135                 140

gaa gtt gaa caa ctg aga agt gga ccc ccc gtc att act tct gga atc      481
Glu Val Glu Gln Leu Arg Ser Gly Pro Pro Val Ile Thr Ser Gly Ile
            145                 150                 155

aaa gac ctc aag gtc ttg aaa aca aca cag tct gga ttt gaa ggt ttc      529
Lys Asp Leu Lys Val Leu Lys Thr Thr Gln Ser Gly Phe Glu Gly Phe
        160                 165                 170

atc aag gac cag ttc acc acc ctc cct gag gtg aag gac cga tgc ttt      577
Ile Lys Asp Gln Phe Thr Thr Leu Pro Glu Val Lys Asp Arg Cys Phe
    175                 180                 185

gcc acc caa gtg tac tgc aag tgg cgc tac cac cag tgc agg gat gtg      625
Ala Thr Gln Val Tyr Cys Lys Trp Arg Tyr His Gln Cys Arg Asp Val
190                 195                 200                 205

gac ttc gag gct acc tgg ggc acc att cgg gac ctt gtc ctg gag aaa      673
Asp Phe Glu Ala Thr Trp Gly Thr Ile Arg Asp Leu Val Leu Glu Lys
                210                 215                 220

ttt gct ggg ccc tat gac aaa ggc gag tac tca ccc tct gtg cag aag      721
Phe Ala Gly Pro Tyr Asp Lys Gly Glu Tyr Ser Pro Ser Val Gln Lys
```

-continued

```
            225                 230                 235

acc ctc tat gat atc cag gtg ctc tcc ctg agc cga gtt cct gag ata      769
Thr Leu Tyr Asp Ile Gln Val Leu Ser Leu Ser Arg Val Pro Glu Ile
        240                 245                 250

gaa gat atg gaa atc agc ctg cca aac att cac tac ttc aat ata gac      817
Glu Asp Met Glu Ile Ser Leu Pro Asn Ile His Tyr Phe Asn Ile Asp
    255                 260                 265

atg tcc aaa atg ggt ctg atc aac aag gaa gag gtc ttg ctg cca tta      865
Met Ser Lys Met Gly Leu Ile Asn Lys Glu Glu Val Leu Leu Pro Leu
270                 275                 280                 285

gac aat cca tat gga aaa att act ggt aca gtc aag agg aag ttg tct      913
Asp Asn Pro Tyr Gly Lys Ile Thr Gly Thr Val Lys Arg Lys Leu Ser
                290                 295                 300

tca aga ctg tga cattgtggcc a                                         936
Ser Arg Leu


<210> SEQ ID NO 62
<211> LENGTH: 304
<212> TYPE: PRT
<213> ORGANISM: Papio hamadryas

<400> SEQUENCE: 62

Met Ala Asp Tyr His Asn Asn Tyr Lys Lys Asn Asp Glu Leu Glu Phe
  1               5                  10                  15

Val Arg Thr Gly Tyr Gly Lys Asp Met Val Lys Val Leu His Ile Gln
             20                  25                  30

Arg Asp Gly Lys Tyr His Ser Ile Lys Glu Val Ala Thr Ser Val Gln
         35                  40                  45

Leu Thr Leu Ser Ser Lys Lys Asp Tyr Leu His Gly Asp Asn Ser Asp
     50                  55                  60

Ile Ile Pro Thr Asp Thr Ile Lys Asn Thr Val His Val Leu Ala Lys
 65                  70                  75                  80

Phe Lys Gly Ile Lys Ser Ile Glu Ala Phe Gly Val Asn Ile Cys Glu
                 85                  90                  95

Tyr Phe Leu Ser Ser Phe Asn His Val Ile Arg Ala Gln Val Tyr Val
            100                 105                 110

Glu Glu Ile Pro Trp Lys Arg Leu Glu Lys Asn Gly Val Lys His Val
        115                 120                 125

His Ala Phe Ile His Thr Pro Thr Gly Thr His Phe Cys Glu Val Glu
    130                 135                 140

Gln Leu Arg Ser Gly Pro Pro Val Ile Thr Ser Gly Ile Lys Asp Leu
145                 150                 155                 160

Lys Val Leu Lys Thr Thr Gln Ser Gly Phe Glu Gly Phe Ile Lys Asp
                165                 170                 175

Gln Phe Thr Thr Leu Pro Glu Val Lys Asp Arg Cys Phe Ala Thr Gln
            180                 185                 190

Val Tyr Cys Lys Trp Arg Tyr His Gln Cys Arg Asp Val Asp Phe Glu
        195                 200                 205

Ala Thr Trp Gly Thr Ile Arg Asp Leu Val Leu Glu Lys Phe Ala Gly
    210                 215                 220

Pro Tyr Asp Lys Gly Glu Tyr Ser Pro Ser Val Gln Lys Thr Leu Tyr
225                 230                 235                 240

Asp Ile Gln Val Leu Ser Leu Ser Arg Val Pro Glu Ile Glu Asp Met
                245                 250                 255

Glu Ile Ser Leu Pro Asn Ile His Tyr Phe Asn Ile Asp Met Ser Lys
            260                 265                 270
```

```
Met Gly Leu Ile Asn Lys Glu Glu Val Leu Leu Pro Leu Asp Asn Pro
        275                 280                 285

Tyr Gly Lys Ile Thr Gly Thr Val Lys Arg Lys Leu Ser Ser Arg Leu
    290                 295                 300


<210> SEQ ID NO 63
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide used for site-directed mutagenesis
      of Human SAH hydrolase (mutant K426D)
<220> FEATURE:
<221> NAME/KEY: mutation
<222> LOCATION: (10)..(12)
<223> OTHER INFORMATION: Codon change from AAG to GAG
<300> PUBLICATION INFORMATION:
<308> DATABASE ACCESSION NUMBER: Z99115/GenBank

<400> SEQUENCE: 63

ggccccttcg agccggatca ctaccgc                                          27


<210> SEQ ID NO 64
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide used for site-directed mutagenesis
      of Human SAH hydrolase (Mutant K186A)
<220> FEATURE:
<221> NAME/KEY: mutation
<222> LOCATION: (13)..(15)
<223> OTHER INFORMATION: Codon change from AAG to GCC

<400> SEQUENCE: 64

gacttcgtca ccgccagcaa gtttggg                                          27


<210> SEQ ID NO 65
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide used for site-directed mutagenesis
      of Human SAH hydrolase (mutant F302S)
<220> FEATURE:
<221> NAME/KEY: mutation
<222> LOCATION: (13)..(15)
<223> OTHER INFORMATION: Codon change from TTT-TCT

<400> SEQUENCE: 65

aacattggac actctgacgt ggagatc                                          27


<210> SEQ ID NO 66
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide used for site-directed mutagenesis
      of Human SAH hydrolase (mutant H301D)
<220> FEATURE:
<221> NAME/KEY: mutation
<222> LOCATION: (13)..(15)
<223> OTHER INFORMATION: Codon change from CAC to GAC

<400> SEQUENCE: 66
```

```
tgtaacattg gagactttga cgtggag                                          27


<210> SEQ ID NO 67
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide used for site-directed mutagenesis
      of Human SAH hydrolase (mutant H353S)
<220> FEATURE:
<221> NAME/KEY: mutation
<222> LOCATION: (13)..(15)
<223> OTHER INFORMATION: Codon change from CAC to TCC

<400> SEQUENCE: 67

tgtgccatgg gctcccccag cttcgtg                                          27


<210> SEQ ID NO 68
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide used for site-directed mutagenesis
      of Human SAH hydrolase (mutant R343A)
<220> FEATURE:
<221> NAME/KEY: mutation
<222> LOCATION: (13)..(15)
<223> OTHER INFORMATION: Codon change from CGG to GCG

<400> SEQUENCE: 68

ctggccgagg gtgcgctggt caacctg                                          27


<210> SEQ ID NO 69
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide used for site-directed mutagenesis
      of Human SAH hydrolase (mutant D190A)
<220> FEATURE:
<221> NAME/KEY: mutation
<222> LOCATION: (13)..(15)
<223> OTHER INFORMATION: Codon change from GAC to GCC

<400> SEQUENCE: 69

aagagcaagt ttgccaacct ctatggc                                          27


<210> SEQ ID NO 70
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide used for site-directed mutagenesis
      of Human SAH hydrolase (mutant F82A)
<220> FEATURE:
<221> NAME/KEY: mutation
<222> LOCATION: (13)..(15)
<223> OTHER INFORMATION: Codon change from TTC to GCC

<400> SEQUENCE: 70

agctgcaaca tcgcctccac ccaggac                                          27


<210> SEQ ID NO 71
<211> LENGTH: 27
<212> TYPE: DNA
<213> ORGANISM: Artificial Sequence
```

```
<220> FEATURE:
<223> OTHER INFORMATION: Description of Artificial Sequence:
      Oligonucleotide used for site-directed mutagenesis
      of Human SAH hydrolase (mutant N181D)
<220> FEATURE:
<221> NAME/KEY: mutation
<222> LOCATION: (13)..(15)
<223> OTHER INFORMATION: Codon change from AAT to GAC

<400> SEQUENCE: 71

aacctctatg gcgaccggga gtccctc                                    27


<210> SEQ ID NO 72
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide used for site-directed mutagenesis
      of Human SAH hydrolase (mutant R431A)
<220> FEATURE:
<221> NAME/KEY: mutation
<222> LOCATION: (13)..(15)
<223> OTHER INFORMATION: Codon change from CGC to GCC

<400> SEQUENCE: 72

ccggatcact acgcctactg agaattc                                    27


<210> SEQ ID NO 73
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide used for site-directed mutagenesis
      of Human SAH hydrolase (mutant K426R)
<220> FEATURE:
<221> NAME/KEY: mutation
<222> LOCATION: (13)..(15)
<223> OTHER INFORMATION: Codon change from AAG to CGC

<400> SEQUENCE: 73

tgtgatggct tccgcccgga tcactac                                    27


<210> SEQ ID NO 74
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide used for site-directed mutagenesis
      of Human SAH hydrolase (mutant C195S)
<220> FEATURE:
<221> NAME/KEY: mutation
<222> LOCATION: (13)..(15)
<223> OTHER INFORMATION: Codon change from TGC to TCC

<400> SEQUENCE: 74

aacctctatg gctcccggga gtccctc                                    27


<210> SEQ ID NO 75
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide used for site-directed mutagenesis
      of Human SAH hydrolase (mutant: deletion 432)
```

-continued

```
<220> FEATURE:
<221> NAME/KEY: mutation
<222> LOCATION: (13)..(15)
<223> OTHER INFORMATION: Codon change from ATC to TGA

<400> SEQUENCE: 75

gatcactacc gctgatgaga attcgag                                    27
```

METHODS AND COMPOSITIONS FOR ASSAYING ANALYTES

FIELD OF THE INVENTION

The present invention relates to compositions and methods for assaying analytes, preferably, small molecule analytes. More particularly, assay methods that employ, in place of antibodies, modified enzymes that retain binding affinity or have enhanced binding affinity, but that have attenuated catalytic activity, are provided. The modified enzymes are also provided.

BACKGROUND OF THE INVENTION

Methods for assaying analytes have wide applications. Many analytes including small molecule analytes are essential components and/or participants of biological systems and processes. Methods for assaying these analytes can be used in monitoring the biological systems/processes, or prognosis or diagnosis of diseases or disorders caused by deficiencies and/or imbalances of the analytes. For instances, homocysteine (Hcy), a thiolated amino acid; folic acid, an organic acid; and cholesterol, a lipid are all important prognostic and diagnostic markers for a wide range of cardiovascular diseases. Vitamins are important prognostic and diagnostic markers for various vitamin deficient diseases or disorders. Glucose, a monosaccharide, is a diagnostic marker for numerous glycemic conditions such as diabetic mellitus. Ethanol, an alcohol, is important in monitoring liquor consumption and potential liver damages. Bile acids or bile salts are important prognostic and diagnostic markers for certain cancers such as colon cancer. Monitoring uric acid is important because abnormally high concentration of uric acid is the diagnostic marker and cause of hyperuricemia leading to gout, which is very painful and can damage the kidney. In addition to these prognostic and diagnostic uses, methods for assaying analytes have applications in other agricultural, industrial or environmental protection processes where determining the presence, location and amount of the analytes is critical.

Assays for Homocysteine

Homocysteine (Hcy) is a thiol-containing amino acid formed from methionine during S-adenosylmethionine-dependent transmethylation reactions. Intracellular Hcy is remethylated to methionine, or is irreversibly catabolized in a series of reactions to form cysteine. Intracellular Hcy is exported into extracellular fluids such as blood and urine, and circulates mostly in oxidized form, and mainly bound to plasma protein (Refsum et al., *Annu. Rev. Medicine*, 49:31–62 (1998)). The amount of Hcy in plasma and urine reflects the balance between Hcy production and utilization. This balance may be perturbed by clinical states characterized by genetic disorders of enzymes involved in Hcy transsulfuration and remethylation (e.g., cystathionine β-synthase and $N^{5,10}$-methylenetetrahydrofolate reductase or dietary deficiency of vitamins (e.g., vitamin $B_6$, $B_{12}$ and folate) involved in Hcy metabolism (Baual, et al., *Cleveland Clinic Journal of Medicine*, 64:543–549 (1997)). In addition, plasma Hcy levels may also be perturbed by some medications such as anti-folate drugs (e.g., methotrexate) used for treatments of cancer or arthritis (Foody, et al., *Clinician Reviews*, 8:203–210 (1998)).

Severe cases of homocysteinemia are caused by homozygous defects in genes encoding for enzymes involved in Hcy metabolisms. In such cases, a defect in an enzyme involved in either Hcy remethylation or transsulfuration leads to as much as 50-fold elevations of Hcy in the blood and urine.

The classic form of such a disorder, congenital homocystemia (Hcymia), is caused by homozygous defects in the gene encoding cystathionine β-synthase (CBS). These individuals suffer from thromboembolic complications at an early age, which result in stroke, myocardial infarction, renovascular hypertension, intermittent claudication, mesenteric ischemic, and pulmonary embolism. Such patients may also exhibit mental retardation and other abnormalities resembling ectopia lensis and skeletal deformities (Perry T., Homocysteine: Selected aspects in Nyham W. L. ed. *Hertable disorders of amino acid metabolism*. New York, John Wiley & Sons, pp. 419–451 (1974)). It is also known that elevated Hcy levels in pregnant women is related to birth defects of children with neurotube closures (Scott et al., "The etiology of neural tube defects" in Graham, I., Refsum, H., Rosenberg, I. H., and Ureland P. M. ed. "*Homocysteine metabolism: from basic science to clinical medicine*" Kluwer Academic Publishers, Boston, pp. 133–136 (1995)). Thus, the diagnostic utility of Hcy determinations has been well documented in these clinical conditions.

It has been demonstrated that even mild or moderately elevated levels of Hcy also increase the risk of atherosclerosis of the coronary, cerebral and peripheral arteries and cardiovascular disease (Boushey, et al., *JAMA*, 274:1049–1057 (1995)). The prevalence of Hcymia was shown to be 42%, 28%, and 30% among patients with cerebral vascular disease, peripheral vascular disease and cardiovascular disease, respectively (Moghadasian, et al., *Arch. Intern. Med.*, 157:2299–2307 (1997)). A meta-analysis of 27 clinical studies calculated that each increase of 5 $\mu$M in Hcy level increases the risk for coronary artery disease by 60% in men and by 80% in women, which is equivalent to an increase of 20 $mg \cdot dl^{-1}$ (0.5 $mmol \cdot dl^{-1}$) in plasma cholesterol, suggesting that Hcy, as a risk factor, is as strong as cholesterol in general population. Results from these clinical studies concluded that hyperhomocysteinemia is an emerging new independent risk factor for cardiovascular disease, and may be accountable for half of all cardiovascular patients who do not have any of the established cardiovascular risk factors (e.g., hypertension, hypercholesterolemia, cigarette smoking, diabetes mellitus, marked obesity and physical activity).

Mild homocysteinemia is mainly caused by heterozygosity of enzyme defects. A common polymorphism in the gene for methylenetetrahydrofolate reductase appears to influence the sensitivity of homocysteine levels to folic acid deficiency (Boers, et al., *J. Inher. Metab. Dis.*, 20:301–306 (1997)). Moreover, plasma homocysteine levels are also significantly increased in heart and renal transplant patients (Ueland, et al., *J. Lab. Clin. Med.*, 114:473–501 (1989)), Alzheimer patients (Jacobsen, et al., *Clin. Chem.*, 44:2238–2239 (1998)), as well as in patients of non-insulin-dependent diabetes mellitus (Ducloux, et al., *Nephrol. Dial. Transplantl*, 13:2890–2893 (1998)). The accumulating evidence linking elevated homocysteine with cardiovascular disease has prompted the initiation of double-blind, randomized and placebo controlled multicenter clinical trials to demonstrate the efficacy of lowering plasma Hcy in preventing or halting the progress of vascular disease (Diaz-Arrastia, et al., *Arch. Neurol*, 55:1407–1408 (1998)).

Determination of plasma homocysteine levels may become a common clinical practice in the near future. Today, cardiologists have already started to recommend their patients to examine their homocysteine levels especially for those who have family history in cardiovascular disease, or who have cardiovascular problem but with normal levels of cholesterol and other risk factors, and those who are older than 60 years-old.

The assay of total Hcy in plasma or serum is complicated by the fact that 70% of plasma Hcy is protein-bound, 20–30% exists as free symmetric or mostly asymmetric mixed disulfides, free reduced Hcy exists in only trace amounts (Stehouwer, et al., *Kidney International*, 55308–314 (1999)). As a risk factor for cardiovascular disease, the determination of total plasma Hcy levels (reduced, oxidized and protein-bound) has been recommended in clinical setting(Hornberger, et al., *American J. of Public Health*, 88:61–67 (1998)). Since 1982, several methods for determining total plasma Hcy have been described (Mansoor, et al., *Anal. BioChem.*, 200:218–229 (1992); Steir, et al., *Arch. Intern. Med.*, 158:1301–1306 (1998); Ueland, et al., *Clin. Chem.*, 39:1764–1779 01993); and Ueland, et al., "Plasma homocysteine and cardiovascular disease" in Francis, R. B. Jr. eds. *Atherosclerotic Cardiovascular Disease, Hemostasis, and Endothelial Function*. New York, Marcel Dokker, pp. 183–236 (1992); see, also, Ueland, et al., "Plasma homocysteine and cardiovascular disease" in Francis, R. B. Jr. eds. *Atherosclerotic Cardiovascular Disease, Hemostasis, and Endothelial Function*. New York, Marcel Dokker, pp. 183–236 (1992)). Most of these methods require sophisticated chromatographic techniques such as HPLC, capillary gas chromatography, or mass spectrometry (GC/MS) to directly or indirectly (e.g., enzymatic conversion of Hcy to SAH (S-adenosylhomocysteine) by SAH hydrolase followed by HPLC or TLC separation) measure Hcy. Radioenzymatic conversion of Hcy to radiolabelled SAH by SAH hydrolase prior to TLC separation has also been used. A feature common to all these methods includes the following four steps: (1) reduction of oxidized Hcy to reduced Hcy; (2) precolumn derivatization or enzymic conversion to SAH; (3) chromatographic separation; and (4) detection of the Hcy derivative or SAH. In these assays, chromatographic separation is the common key step of the prior art methods which are often time-consuming and cumbersome to perform. More particularly, these methods require highly specialized and sophisticated equipment and well-trained analytic specialists. The use of such equipment is generally not well accepted in routine clinical laboratory practice.

Immunoassays for Hcy that use a monoclonal antibody against SAH (Araki, et al., *J. Chromatog.*, 422:43–52 (1987) are known. These assays are based upon conversion of Hcy to SAH, which is then detected by a monoclonal antibody. Monoclonal antibody against albumin-bound Hcy has been developed for determination of albumin-bound Hcy (Stabler, et al., *J. Clin. Invest.*, 81:466–474 (1988)), which is the major fraction of total plasma Hcy. Other immmological protocols are also available (see, e.g., U.S. Pat. No. 5,885,767 and U.S. Pat. No. 5,631,127). Though immunoassays avoid a time-consuming chromatographic separation step and are amenable to automation, production of monoclonal antibody are expensive, somewhat unpredictable, and often require secondary or even tertiary antibodies for detection.

Despite the importance and wide applications of methods for assaying analytes, currently available methods for assaying analytes suffer from several deficiencies. First, for many analytes, specific binding partners are not readily available and this lack of specific binding partner often compromises the specificity of the assay method. Although such deficiency may be overcome by generating antibodies for macromolecule analytes, generating antibodies, especially monoclonal antibodies with the desired specificity and uniformity, is often time consuming and expensive. In addition, for many small molecule analytes, the option of generating antibodies is often not available because small molecules are poor antigens. Generation of antibodies against small molecules usually requires conjugation of the small molecules to macromolecules, and this often makes the antibody screening more tedious and laborious. Second, many methods for assaying analytes, especially small molecule analytes, involve chemical derivations and chromatographic separation can be time consuming. Third, many such assay methods use sophisticated and expensive analytical equipment such as HPLCs and GC/MS.

Therefore, it is an object herein to provide quick and simple and assays that address these deficiencies. It is also an object herein to provide such an assay for quantifying and/or detecting homocysteine in body fluids and body tissues.

SUMMARY OF THE INVENTION

Assays, particularly assays that are based on immunoassay formats, but that employ mutant analyte-binding enzymes that, substantially retain binding affinity or have enhanced binding affinity for desired analytes or an immediate analyte enzymatic conversion products but have attenuated catalytic activity, are provided. In place of antibodies, these assys use modified enzymes that retain binding affinity or having enhanced binding affinity, but have attenuated catalytic activity. These methods are designated substrate trapping methods; and the modified enzymes, are designated as "substrate trapping enzymes." The substrate trapping enzymes (also designated pseudoantibodies) and methods for preparing them are also provided. These substrate trapping enzymes are intended to replace antibodies, monoclonal, polyclonal or any mixture thereof, in reactions, methods, assays and processess in which an antibody (polyclonal, monoclonal or specific binding fragment thereof) is a reactant. They can also act as competitive inhibitors with analytes for binding to entities such as receptors and other anti-ligands and other analytes. Hence, they can be used in competitive binding assays in place of, for example, receptor agonists or modulators of receptor activity.

Any process or method, particularly immunoassays or assays in which an antibody aids in detection of a target analyte, can be modified as described herein, by substituting a substrate trapping enzyme for the antibody used in the process or method. The substrate trapping enzymes can be prepared by any method known to those of skill in the art by which the catalytic activity of an enzyme is substantially attenuated or eliminated, without affecting or without substantially reducing the binding affinity of the resulting modified enzyme for an analyte.

The methods are particularly useful for detecting analytes indicative of metabolic conditions, inborn errors of metabolism, such as hypothyroidism, galactosemia, phenylketonuria (PKU), and maple syrup urine disease; disease markers, such as glucose levels, cholesterol levels, Hcy levels and other such parameters in body fluid and tissue samples from mammals, including humans. The methods also include methods for detecting contanimants in food, for testing foods to quantitate certain nutrients, for screening blood. The assays readily can be automated.

Accordingly, methods in which an antibody is a reactant, wherein the improvement is replacement of the antibody with a substrate trapping enzymes as defined herein, are provided. The methods may also rely on competitive binding of the modified enzyme for a target analyte.

In another embodiment, a method is provided for assaying an analyte, preferably a small molecule analyte, in a sample by: a) contacting the sample with a mutant analyte-binding enzyme, the mutant enzyme substantially retains its binding affinity or has enhanced binding affinity for the analyte or an immediate analyte enzymatic conversion product but has attenuated catalytic activity; and b) detecting binding between the analyte or the immediate analyte enzymatic conversion product and the mutant analyte-binding enzyme.

The small molecule analyte to be assayed can be any analyte, including organic and inorganic molecules. Typically the small molecule to be assayed has a molecular weight that is about or less than 10,000 daltons. Preferably, the small molecule has a molecular weight that is about or less than 5,000 dalton.

Inorganic molecules include, but are not limited to, an inorganic ion such as a sodium, a potassium, a magnesium, a calcium, a chlorine, an iron, a copper, a zinc, a manganese, a cobalt, an iodine, a molybdenum, a vanadium, a nickel, a chromium, a fluorine, a silicon, a tin, a boron or an arsenic ion. Organic molecules include, but are not limited to, an amino acid, a peptide, typically containing less than about 10 amino acids, a nucleoside, a nucleotide, an oligonucleotide, typically containing less than about 10 nucleotides, a vitamin, a monosaccharide, an oligosaccharide containing less than 10 monosaccharides or a lipid.

The amino acids, include, but are not limited to, D- or L-amino-acids, including the building blocks of naturally-occurring peptides and protiens including Ala (A), Arg (R), Asn (N), Asp (D), Cys (C), Gln (Q), Glu (E), Gly (G), His (H), Ile (I), Leu (L), Lys (K), Met (M), Phe (F), Pro (P) Ser (S), Thr (T), Trp (W), Tyr (Y) and Val (V).

Nucleosides, include, but but are not limited to, adenosine, guanosine, cytidine, thymidine and uridine. Nucleotides include, but are not limited to, AMP, GMP, CMP, UMP, ADP, GDP, CDP, UDP, ATP, GTP, CTP, UTP, dAMP, dGMP, dCMP, dTMP, dADP, dGDP, dCDP, dTDP, dATP, dGTP, dCTP and dTTP.

Vitamins, include, but are not limited to, water-soluble vitamins such as thiamine, riboflavin, nicotinic acid, pantothenic acid, pyridoxine, biotin, folate, vitamin $B_{12}$ and ascorbic acid, fat-soluble vitamins such as vitamin A, vitamin D, vitamin E, and vitamin K.

Monosaccharides, include but are not limited to, D- or L-monosaccharides. Monosaccharides include, but are not limited to, triose, such as glyceraldehyde, tetroses such as erythrose and threose, pentoses such as ribose, arabinose, xylose, lyxose and ribulose, hexoses such as allose, altrose, glucose, mannose, gulose, idose, galactose, talose and fructose and heptose such as sedoheptulose.

Lipids, include, but are not limited to, triacylglycerols such as tristearin, tripalmitin and triolein, waxes, phosphoglycerides such as phosphatidylethanolamine, phosphatidylcholine, phosphatidylserine, phosphatidylinositol and cardiolipin, sphingolipids such as sphingomyelin, cerebrosides and gangliosides, sterols such as cholesterol and stigmasterol and sterol fatty acid esters. The fatty acids can be saturated fatty acids such as lauric acid, myristic acid, palmitic acid, stearic acid, arachidic acid and lignoceric acid, or can be unsaturated fatty acids such as palmitoleic acid, oleic acid, linoleic acid, linolenic acid and arachidonic acid.

In an exemplary embodiment, mutant S-adenosylhomocysteine (SAH) hydrolases, substantially retaining binding affinity or having enhanced binding affinity for homocysteine (Hcy) or SAH but having attenuated catalytic activity, are provided. Also provided are methods, combinations, kits and articles of manufacture for assaying analytes, preferably small molecule analytes such as inorganic ions, amino acids (e.g., homocysteine), peptides, nucleosides, nucleotides, oligonucleotides, vitamins, monosaccharides (e.g., glucose), oligosaccharides, lipids (e.g., cholesterol), organic acids (e.g., folate species, bile acids and uric acids).

In another embodiment, provided herein are purified mutant SAH hydrolases, the mutant SAH hydrolases substantially retain their binding affinity or have enhanced binding affinity for homocysteine (Hcy) or SAH but have attenuated catalytic activity.

Examples of such mutant SAH hydrolases include those in which the the attenuated catalytic activity is caused by mutation(s) in the mutant SAH hydrolase's binding site for $NAD^+$, or mutation(s) in the mutant SAH hydrolase's catalytic site or a combination thereof; those that have attenuated 5'-hydrolytic activity but substantially retain the 3'-oxidative activity; those that irreversibly bind SAH; those that have a Km for SAH that is about or less than 10.0 $\mu$M; those that have a Kcat for SAH that is about or less than 0.1 $S^{-1}$; those that have one or more insertional, deletional or point mutations; those that are derived from the sequence of amino acids set forth in SEQ ID No. 1 or encoded by the sequence of nucleotides set forth in SEQ ID No.2 and have one or, preferably at least two or more mutations selected from Phe302 to Ser (F302S), Lys186 to Ala (K186A), His301 to Asp (H301D), His353 to Ser (H353S), Arg343 to Ala (R343A), Asp190 to Ala (D190A), Phe82 to Ala (F82A), Thr157 to Leu (T157L), Cys195 to Asp (C195D), Asn181 to Asp (N181D), and deletion of Tyr432 (Δ432); or those that are derived from the sequence of amino acids set forth in SEQ ID No. 1 or encoded by the sequence of nucleotides set forth in SEQ ID No. 2 and have a combination of Arg431 to Ala (R431A) and Lys426 to Arg (K426R) mutations; or any that hybridize under conditions of low, more preferably moderate, most preferably high, stringency along their full-length and have a Km at least about 10%, more preferably at least about 50% of the Km of the wildtype enzyme for the analayte or substrate, but having substantially attenuated catalytic activity to the coding portion of the sequence of nucleotides set forth in SEQ ID No. 1 or encoding the sequence of amino acids set forth in SEQ ID No. 2.

Isolated nucleic acid fragments encoding the above-described mutant SAH hydrolases, preferably in the form of plasmid or expression vectors, are also provided. Recombinant host cells, especially recombinant bacterial cells, yeast cells, fungal cells, plant cells, insect cells and animal cells, containing the plasmids or vectors are further provided. Methods for producing the mutant SAH hydrolases using the recombinant host cells are further provided.

Assays for Homocysteine and Metabolically Related Analytes

Assays for homocysteine, which as noted above, is a risk factor for cardiovascular disease and other diseases, are provided herein.

Homocysteine

In these embodiments, the small molecule to be assayed is homocysteine (Hcy) and the mutant analyte-binding enzymes are mutant Hcy-binding enzymes that substantially retain their binding affinity or that have enhanced binding affinity for Hcy or an immediate Hcy enzymatic conversion product but have attenuated catalytic activity.

Mutant Hcy-binding enzymes that can be used in the assay include those in which the attenuated catalytic activity is caused by mutation in the mutant enzyme's binding site for its co-enzyme or for a non-Hcy substrate, or mutation in the mutant enzyme's catalytic site or a combination thereof.

In another embodiment, the mutant enzyme is a mutant cystathionine β-synthase and the attenuated catalytic activity is caused by mutation in the mutant cystathionine β-synthase's catalytic site, its binding site for pyridoxal 5'-phosphate or L-serine, or a combination thereof.

In another embodiment, the mutant enzyme is a mutant methionine synthase and the attenuated catalytic activity is caused by mutation in the mutant methionine synthase's catalytic site, its binding site for vitamin $B_{12}$ or 5-methyltetrahydrofolate (5-$CH_3$-THF), or a combination thereof. More preferably, the mutant methionine synthase is an *E. coli.* methionine synthase, the mutant methionine synthase has one or more of the following mutations: His759Gly, Asp757Glu, Asp757Asn, and Ser801Ala.

In another embodiment, the mutant enzyme is a mutant methioninase and the attenuated catalytic activity is caused by mutation in the mutant methionine synthase's catalytic site, its binding site for a compound with the formulae of R'SH, in which R'SH is a substituted thiol, where R is preferably alkyl, preferably lower alkyl (1 to 6 carbons, preferably 1 to 3 carbons, in a straight or branched chain), heteraryl, where the heteroatom is O, S or N, or aryl, which is substituted, such as with alkyl, preferably lower alkyl, or hal, or unsubstituted, preferably aryl or heteraryl with one ring or two to three fused rings, preferably with about 4 to 7 members in each ring, or combinations of any of the above.

In a preferred embodiment, the mutant enzyme is a mutant SAH hydrolase, where the mutant SAH hydrolase substantially retains its binding affinity or has enhanced binding affinity for Hcy or SAH but has attenuated catalytic activity. Examples of such mutant SAH hydrolases that can be used in the assay include those in which the attenuated catalytic activity is caused by mutation(s) in the mutant SAH hydrolase's binding site for $NAD^+$, or mutation(s) in the mutant SAH hydrolase's catalytic site or a combination thereof; those that have attenuated 5'-hydrolytic activity but substantially retains its 3'-oxidative activity; those that irreversibly bind SAH; those that have a Km for SAH that is about or less than 10.0 $\mu$M; those that have a Kcat for SAH that is about or less than 0.1 $S^{-1}$; those that have one or more insertional, deletional or point mutation; those that are derived from the sequence of amino acids set forth in SEQ ID No. 1 or encoded by the sequence of nucleotides set forth in SEQ ID No. 2 but have one or more of the following mutations: Phe302 to Ser (F302S), Lys186 to Ala (K186A), His301 to Asp (H301D), His353 to Ser (H353S), Arg343 to Ala (R343A), Asp190 to Ala (D190A), Phe82 to Ala (F82A), Thr157 to Leu (T157L), Cys195 to Asp (C195D), Asn181 to Asp (N181D), and deletion of Tyr432 (Δ432); or those that are derived from a sequence of amino acids set forth in SEQ ID No. 1 or encoded by the sequence of nucleotides set forth in SEQ ID No. 2 and have a combination of Arg431 to Ala (R431A) and Lys426 to Arg (K426R) mutations or any that hybridize under conditions of low, more preferably moderate, most preferably high, stringency along their full-length and have a Km at least about 10%, more preferably at least about 50% of the Km of the wildtype enzyme for the analayte or substrate, but having substantially attenuated catalytic activity.

In one embodiment that uses a mutant SAH hydrolase, oxidized Hcy in the sample is converted into reduced Hcy prior to the contact between the sample and the mutant SAH hydrolase. The oxidized Hcy in the sample is converted into reduced Hcy by a reducing agent, such as, but are not limited to, tri-n-butyphosphine (TBP), β-ME, DTT, dithioerythritol, thioglycolic acid, glutathione, tris(2-carbxyethyl)phosphine, sodium cyanoborohydride, $NaBH_4$, $KBH_4$ and free metals.

In another embodiment that uses a mutant SAH hydrolase, prior to the contact between the sample and the mutant SAH hydrolase, the Hcy in the sample is converted into SAH. More preferably, the Hcy in the sample is converted into SAH by a wild-type SAH hydrolase. Also more preferably, the SAH in the sample is contacted with the mutant SAH hydrolase in the presence of a SAH hydrolase catalysis inhibitor, such as, but are not limited to, neplanocin A or thimersol.

In another embodiment that uses a mutant SAH hydrolase, prior to the contact between the SAH and the mutant SAH hydrolase, free adenosine is removed or degraded. More preferably, free adenosine is degraded by combined effect of adenosine deaminase, purine nucleoside phosphorylase and xanthine oxidase.

In another embodiment that uses a mutant SAH hydrolase, the SAH is contacted with the mutant SAH hydrolase in the presence of a labelled SAH or a derivative or an analog thereof, whereby the amount of the labeled SAH bound to the mutant SAH hydrolase inversely relates to amount of the SAH in the sample. More preferably, the labelled SAH derivative or analog is a fluorescence labelled adenosyl-cysteine.

In another embodiment that uses a mutant SAH hydrolase, the mutant SAH hydrolase is labelled mutant SAH hydrolase. More preferably, the mutant SAH hydrolase is labelled by fluorescence.

In still another embodiment, the mutant enzyme is a mutant betaine-homocysteine methyltransferase and the attenuated catalytic activity is caused by mutation in the mutant betaine-homocysteine methyltransferase's binding site for betaine, its catalytic site, or a combination thereof.

In another embodiment, the Hcy assay is performed in combination with assays for other analytes associated with cardiovasicular disease and/or regulation of Hcy levels, such as assays for cholesterol and/or folic acid.

Folate

In another embodiment, the mutant enzyme is a mutant methionine synthase. In this embodiment, the folate species can be a 5,-methyltetrahydrofolate, the mutant folate-species-binding enzyme is a mutant methionine synthase, and the attenuated catalytic activity of the mutant methionine synthase is caused by mutation in its catalytic site, its binding site for vitamin $B_{12}$, Hcy, or a combination thereof.

In another embodiment, the folate species is tetrahydrofolate, the mutant folate-species-binding enzyme is a mutant tetrahydrofolate methyltransferase, and the attenuated catalytic activity of the mutant tetrahydrofolate methyltransferase is caused by mutation in its catalytic site, its binding site for serine, or a combination thereof.

In still another embodiment, the folate species is 5,10,-methylene tetrahydrofolate, the mutant folate-species-binding enzyme is a mutant methylenetetrahydrofolate reductase, and the attenuated catalytic activity of the methylenetetrahydrofolate reductase is caused by mutation in its catalytic site.

In yet another embodiment, the folate species is 5,10,-methylene tetrahydrofolate, the mutant folate-species-binding enzyme is a mutant folypolyglutamate synthase, and the attenuated catalytic activity of the folypolyglutamate synthase is caused by mutation in its catalytic site, its binding site for ATP, L-glutamate, $Mg^{2+}$, or a combination thereof. In yet another preferred embodiment, the folate species is dihydrofolate, the mutant folate-species-binding enzyme is a mutant dihydrofolate reductase, and the attenuated catalytic activity of the mutant dihydrofolate reductase is caused by mutation in its catalytic site, its binding site for NADPH, or a combination thereof. More preferably, the mutant dihydrofolate reductase is a *Lactobacillus casei* dihydrofolate reductase having the Arg43Ala or Trp21His mutation (Basran et al., *Protein Eng.*, 10(7):815–26 91997)).

In yet another embodiment, the folate species is 5,10,-methylene tetrahydrofolate (5,10-methylene-$FH_4$), the mutant folate-species-binding enzyme is a mutant thymidylate synthase, and the attenuated catalytic activity of the mutant thymidylate synthase is caused by mutation in its catalytic site, its binding site for dUMP, or a combination thereof. More preferably, the mutant thymidylate synthase is a human thymidylate synthase having a mutation selected from of Tyr6His, Glu214Ser, Ser216Ala, Ser216Leu, Asn229Ala and His199X, where X is any amino acid that is not His (Schiffer et al., *Biochemistry*, 34(50):16279–87 (1995); Steadman et al., *Biochemistry*, 37:7089–7095 (1998); Williams et al., *Biochemistry*, 37(20):7096–102 (1998); Finer-Moore et al., *J. Mol. Biol.*, 276(1):113–29 (1998); and Finer-Moore et al., *Biochemistry*, 35(16):5125–36 (1996)). Also more preferably, the mutant thymidylate synthase is an *E. coli* thymidylate synthase having an Arg126Glu mutation (Strop et al., *Protein Sci.*, 6(12):2504–11 (1997)) or a *Lactobacillus casei* thymidylate synthase having a V316Am mutation (Carreras et al., *Biochemistry*, 31 (26):6038–44 (1992)).

Cholesterol

In another embodiment, the analyte is cholesterol and the mutant analyte-binding enzyme is a mutant cholesterol-binding enzyme, where the mutant enzyme substantially retains its binding affinity or has enhanced binding affinity for cholesterol but has attenuated catalytic activity. In a preferred embodiment, the mutant cholesterol-binding enzyme is a mutant cholesterol esterase, and the attenuated catalytic activity of the mutant cholesterol esterase is caused by mutation in its catalytic site, its binding site for $H_2O$ or a combination thereof. More preferably, the cholesterol esterase is a pancreatic cholesterol esterase having a Ser194Thr or Ser194Ala mutation (DiPersio et al., *J. Biol. Chem.*, 265(28):16801–6 (1990)). In another preferred embodiment, the mutant cholesterol-binding enzyme is a mutant cholesterol oxidase, and the attenuated catalytic activity of the mutant cholesterol oxidase is caused by mutation in its catalytic site, its binding site for $O_2$ or a combination thereof. More preferably, the cholesterol oxidase is a *Brevibacterium sterolicum* cholesterol oxidase having a His447Asn or His447Gln mutation (Yue et al., *Biochemistry*, 38(14):4277–86 (1999)).

Bile Acid (salt)

In still another specific embodiment, the small molecule analyte is a bile acid (salt) and the mutant analyte-binding enzyme is a mutant bile-acid (salt)-binding enzyme, the mutant enzyme substantially retains its binding affinity or has enhanced binding affinity for the bile acid (salt) but has attenuated catalytic activity. Preferably, the mutant bile-acid (salt)-binding enzyme is a mutant 3-α-hydroxy steroid dehydrogenase, and the attenuated catalytic activity of the mutant 3-α-hydroxy steroid dehydrogenase is caused by mutation in its catalytic site, its binding site for $NAD^+$ or a combination thereof.

Assays for Disorders Associated with Glucose Metabolism

In yet another specific embodiment, the small molecule analyte is glucose and the mutant analyte-binding enzyme is a mutant glucose-binding enzyme, the mutant enzyme substantially retains its binding affinity or has enhanced binding affinity for glucose but has attenuated catalytic activity. Preferably, the mutant glucose-binding enzyme is a *Clostridium thermosulfurogenes* glucose isomerase having a mutation selected from His101Phe, His101Glu, His101Gln, His101Asp and His101Asn (Lee et al., *J. Biol. Chem.*, 265(31):19082–90 (1990)). Also preferably, the mutant glucose-binding enzyme is a mutant hexokinase or glucokinase, and the attenuated catalytic activity of the mutant hexokinase or glucokinase is caused by mutation in its catalytic site, its binding site for ATP or $Mg^{2+}$, or a combination thereof. Further preferably, the mutant glucose-binding enzyme is a mutant glucose oxidase, and the attenuated catalytic activity of the mutant glucose oxidase is caused by mutation in its catalytic site, its binding site for $H_2O$ or $O_2$, or a combination thereof. Any disorders associated with glucose metabolism may be monitored or assessed.

Ethanol

In yet another specific embodiment, the small molecule analyte is ethanol and the mutant analyte-binding enzyme is a mutant ethanol-binding enzyme, the mutant enzyme substantially retains its binding affinity or has enhanced binding affinity for ethanol but has attenuated catalytic activity. Preferably, the mutant ethanol-binding enzyme is a mutant alcohol dehydrogenase, and the attenuated catalytic activity of the mutant alcohol dehydrogenase is caused by mutation in its catalytic site, its binding site for $NAD^+$ or $Zn^{2+}$, or a combination thereof. More preferably, the mutant alcohol dehydrogenase is a human liver alcohol dehydrogenase having a His51Gln mutation (Ehrig et al., *Biochemistry*, 30(4):1062–8 (1991)). Also more preferably, the mutant alcohol dehydrogenase is a horse liver alcohol dehydrogenase having a Phe93Trp or Val203Ala mutation (Bahnson et al., *Proc. Natl. Acad. Sci.*, 94(24):12797–802 (1997); Colby et al., *Biochemistry*, 37(26):9295–304 (1998)).

Assays for Disorders, Such as Gout, Associated with Uric Acid Acid Metabolism

In another exemplary embodiment, the small molecule analyte is uric acid and the mutant analyte-binding enzyme is a mutant uric-acid-binding enzyme, the mutant enzyme substantially retains its binding affinity or has enhanced binding affinity for uric acid but has attenuated catalytic activity. Preferably, the mutant uric-acid-binding enzyme is a mutant urate oxidase, and the attenuated catalytic activity of the mutant urate oxidase is caused by mutation in its catalytic site, its binding site for $O_2$, $H_2O$, or copper ion, or a combination thereof. More preferably, the mutant urate oxidase is a rat urate oxidase having a mutation selected from H127Y, H129Y and F131S (Chu et al., *Ann. N.Y. Acad. Sci.*, 804:781–6 (1996)).

In all embodiments, the sample being assayed typically is a body fluid or tissue, including, but are not limited to blood, urine, cerebral spinal fluid, synovial fluid, amniotic fluid, and tissue samples, such as biopsied tissues. Preferably, the body fluid is blood or urine. More preferably, the blood sample is further separated into a plasma or sera fraction.

Further provided herein are combinations that include: a) a mutant analyte-binding enzyme, the mutant enzyme substantially retains its binding affinity or has enhanced binding affinity for the analyte or an immediate analyte enzymatic conversion product but has attenuated catalytic activity; and b) reagents and or other means for detecting binding between the analyte or the immediate analyte enzymatic conversion product with the mutant analyte-binding enzyme. Preferably, binding between the analyte or the immediate analyte enzymatic conversion product with the mutant analyte-binding enzyme is detected using a labelled analyte, a labelled immediate analyte enzymatic conversion product, or a derivative or an analog thereof, or a labelled mutant analyte-binding enzyme. Also preferably, the combination where the analyte is Hcy further also includes reagents for detecting cholesterol and/or folic acid.

Finally, kits and articles of manufacture that include the above combinations and optionally instructions for performing the assay of interest are provided. Articles of manufacture that contain the mutant enzymes with a label indicating the assay in which the enzyme is used, and also packaging material that contains the enzyme.

Particular compositions, combinations, kits and articles of manufacture for assaying analytes, preferably small molecule analytes, are described in the sections and subsections that follow.

DETAILED DESCRIPTION OF THE INVENTION

A. DEFINITIONS

Figure 1:
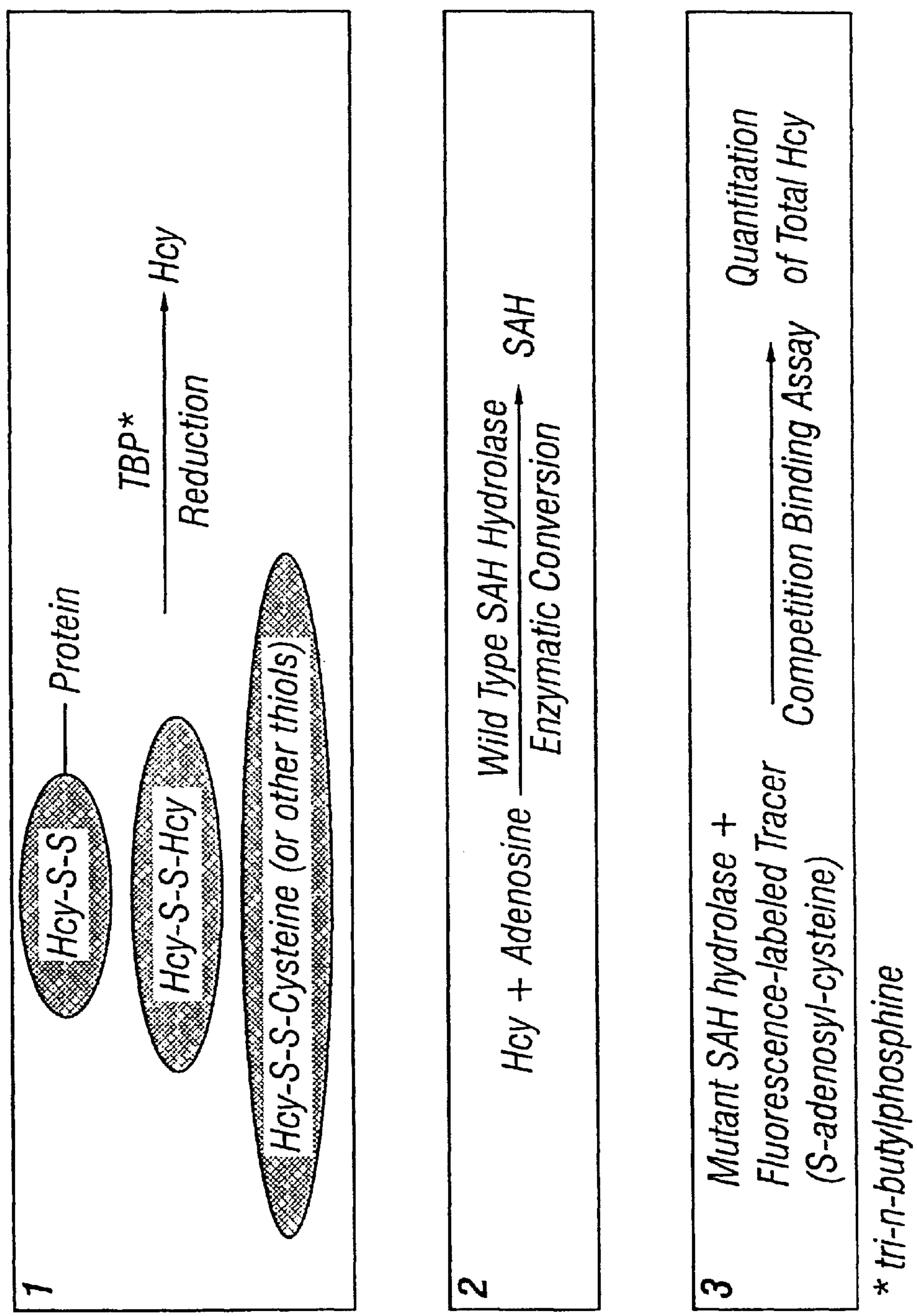
FIG. 1 depicts Hcy assay using wild type and mutant SAH hydrolase.

Unless defined otherwise, all technical and scientific terms used herein have the same meaning as is commonly understood by one of ordinary skill in the art to which this invention belongs. All patents, applications, published applications and other publications and sequences from GenBank and other data bases referred to herein are incorporated by reference in their entirety.

As used herein, "analyte" refers to a molecule that can specifically bind to an enzyme, either as a co-enzyme, a co-factor or a substrate.

As used herein, "enzyme" refers to a protein specialized to catalyze or promote a specific metabolic reaction. Generally, enzymes are catalysts, but for purposes herein, such "enzymes" include those that would be modified during a reaction. Since the enzymes are modifed to eliminate or substantially eliminate catalytic activity, they will not be so-modified during a reaction.

As used herein, "analyte-binding enzyme" refers to an enzyme that uses the analyte as its co-enzyme, co-factor, or its sole or one of its substrates. For instance, "Hcy-binding enzyme" refers to an enzyme that uses Hcy as its co-enzyme, co-factor, or its sole or one of its substrates. Examples of Hcy-binding enzymes include SAH hydrolase, cystathionine β-synthase, methionine synthase, betaine-homocysteine methyltrans-ferase and methioninase. It is intended to encompass analyte-binding enzyme with conservative amino acid substitutions that do not substantially alter its activity. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al. *Molecular Biology of the Gene*, 4th Edition, 1987, The Bejacmin/Cummings Pub. co., p.224).

Such substitutions are preferably made in accordance with those set forth in TABLE 1 as follows:

TABLE 1

| Original residue | Conservative substitution |
|---|---|
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions are also permissible and may be determined empirically or in accord with known conservative substitutions.

As used herein, the "amino acids," which occur in the various amino acid sequences appearing herein, are identified according to their well-known, three-letter or one-letter abbreviations. The nucleotides, which occur in the various DNA fragments, are designated with the standard single-letter designations used routinely in the art.

As used herein, "a mutant analyte-binding enzyme" (used interchangeably with "modified enzyme" and "substrate trapping enzyme" that substantially retains its binding affinity or has enhanced binding affinity for the analyte or an immediate analyte enzymatic conversion product" refers to a mutant form of analyte-binding enzyme that retains sufficient binding affinity for the analyte to be detected in the process or method, particularly assay, of interest. Typically this is at least about 10%, preferably at least about 50% binding affinity for the analyte or an immediate analyte enzymatic conversion product, compared to its wildtype counterpart. Preferably, such mutant analyte-binding enzyme retains 60%, 70%, 80%, 90%, 100% binding affinity for the analyte or an immediate analyte enzymatic conversion product compared to its wildtype counterpart, or has a higher binding affinity than its wildtype counterpart. Such mutant analyte-binding enzyme is herein referred to as a "substrate trapping enzyme", i.e., a molecule that specifically binds to a selected analyte or target molecule, but does not catalyze conversion thereof.

As used herein, "immediate analyte enzymatic conversion product" refers to a product derived from the analyte by catalysis of a single analyte-binding enzyme. For example, the "immediate Hcy enzymatic conversion product" of SAH hydrolase is SAH. The "immediate Hcy enzymatic conversion product" of cystathionine β-synthase is cystathionine. The "immediate Hcy enzymatic conversion product" of methionine synthase and betaine-homocysteine methyltransferase is methionine.

As used herein the term "assessing" is intended to includes quantitative and qualitative determination in the sense of obtaining an absolute value for the amount or concentration of the analyte, e.g., a homocysteine co-substrate, present in the sample, and also of obtaining an index, ratio, percentage, visual or other value indicative of the level of analyte in the sample. Assessment may be direct or indirect and the chemical species actually detected need not of course be the analyte itself but may for example be a derivative thereof or some further substance.

As used herein, "attenuated catalytic activity" refers to a mutant analyte-binding enzyme that retain sufficiently reduced catalytic activity to be useful as a "pseudo-antibody", i e, a molecule used in place of antibody in immunoassay formats. The precise reduction in catalytic activity for use in the assays can be empirically determined for each assay. Typically, the enzyme will restain less than about 50% of one of its catalytic activities or less than 50% of its overall catalytic activities compared to its wildtype counterpart. Preferably, a mutant analyte-binding enzyme retains less than 40%, 30%, 20%, 10%, 1%, 0.1%, or 0.01% of one of its catalytic activities or its overall catalytic activities compared to its wildtype counterpart. More preferably, a mutant analyte-binding enzyme lacks detectable level of one of its catalytic activities or its overall catalytic activities compared to its wildtype counterpart. In instances in which catalytic activity is retained and/or a further reduction thereof is desired, the contacting step can be effected in the presence of a catalysis inhibitor. Such inhibitors, include, but are not limited to, heavy metals, chelators or other agents that bind to a co-factor required for catalysis, but not for binding, and other such agents.

As used herein, "macromolecule" refers to a molecule that, without attaching to another molecule, is capable of generating an antibody that specifically binds to the macromolecule.

As used herein, "small molecule" refers to a molecule that, without forming homo-aggregates or without attaching to a macromolecule or adjuvant, is incapable of generating an antibody that specifically binds to the small molecule. Preferably, the small molecule has a molecule weight that is about or less than 10,000 daltons. More preferably, the small molecule has a molecule weight that is about or less than 5,000 dalton.

As used herein, "inorganic molecule" refers to a molecule that does not contain hydrocarbon group(s).

As used herein, "organic molecule" refers to a molecule that contains hydrocarbon group(s).

As used herein, "vitamin" refers to a trace organic substance required in certain biological species. Most vitamins function as components of certain coenzymes.

As used herein, "biomolecule" refers to an organic compound normally present as an essential component of living organisms.

As used herein, "lipid" refers to water-insoluble, oily or greasy organic substances that are extractable from cells and tissues by nonpolar solvents, such as chloroform or ether.

As used herein, "homocysteine" (Hcy) refers to a compound with the following molecular formula: $HSCH_2CH_2CH(NH_2)COOH$. Biologically, Hcy is produced by demethylation of methionine and is an intermediate in the biosynthesis of cysteine from methionine. The term "Hcy" encompasses free Hcy (in the reduced form) and conjugated Hcy (in the oxidized form). Hcy can conjugate with proteins, peptides, itself or other thiols through disulfide bond.

As used herein, "SAH hydrolase" refers to an ubiquitous eukaryotic enzyme, which is also found in some prokaryotes, which catalyzes hydrolysis of SAH to Ado and Hcy. SAH hydrolase also catalyzes the formation of SAH from Ado and Hcy. The co-enzyme of SAH hydrolase is $NAD^+$/NADH. SAH hydrolase has several catalytic activities. In the hydrolytic direction, the first step involves oxidation of the 3'-hydroxyl group of SAH (3'-oxidative activity) by enzyme-bound $NAD^+$ (E-$NAD^+$), followed by β-elimination of L-Hcy to give 3'-keto-4',5'-didehydro-5'-deoxy-Ado. Michael addition of water to the 5'-position to this tightly bound intermediate (5'-hydrolytic activity) affords 3'-keto-Ado, which is then reduced by enzyme-bound NADH (E-NADH) to Ado (3'-reduction activity). It is intended to encompass SAH hydrolase with conservative amino acid substitutions that do not substantially alter its activity.

As used herein, "SAH hydrolase catalysis inhibitor" refers to an agent that inhibits one or all of SAH hydrolase catalytic activities, e.g., 3'-oxidative activity, 5'-hydrolytic activity, or 3'-reduction activity, while not affecting SAH hydrolase's binding affinity for Hcy and/or SAH.

As used herein, "cystathionine β-synthase" refers to an enzyme that irreversibly catalyzes the formation of cystathionine from Hcy and serine. The co-enzyme of cystathionine β-synthase is pyridoxal 5'-phosphate. It is intended to encompass cystathionine β-synthase with conservative amino acid substitutions that do not substantially alter its activity.

As used herein, "methionine synthase" refers to an enzyme that irreversibly catalyzes the formation of methionine from Hcy and 5-methyltetrahydrofolate (5-$CH_3$-THF). The co-enzyme of cystathionine β-synthase is vitamin $B_{12}$. It is intended to encompass methionine synthase with conservative amino acid substitutions that do not substantially alter its activity.

As used herein, "betaine-homocysteine methyltransferase" refers to an enzyme that irreversibly catalyzes the formation of methionine and dimethyl-glycine from Hcy and betaine. It is intended to encompass betaine-homocysteine methyltransferase with conservative amino acid substitutions that do not substantially alter its activity.

As used herein, "methioninase" refers to an enzyme which catalyzes α, β- and α, ⌈-eliminations from S-substituted amino acids and also catalyzes a variety of β- and ⌈-exchange reactions, according to the following equations: $RSCH_2CH(NH_2)COOH$+R'SH in equilibrium $R'SCH_2CH(NH_2)COOH$+RSH (β-exchange) and $RSCH_2CH_2CH(NH_2)COOH$+R'SH in equilibrium $R'SCH_2CH_2CH(NH_2)COOH$+RSH (⌈-exchange), where R'SH represents an alkanethiol or a substituted thiol (Ito et al., *J. Biochem*., (Tokyo) 80(6):1327–34 (1976)). In particular, R and R' independently are selected preferably from alkyl, aryl, alkynyl, cycloalkly, heteroaryl, alkenyl, amino acids, proteins and other suitable moieties or mixtures thereof. R and R' typically contain less than about 50 atoms, are substituted or unsubstituted, the carbon chains can be straight or branched or cyclized, heteroatoms include S, N, O; the aryl and heteraryl or other cyclic groups can include one ring or two or more fused rings, each ring preferably containing from 3 to 7, more preferably 4 to 6, members.

As used herein, "adenosine deaminase" refers to an enzyme that catalyzes the deamination of adenosine to form inosine. It is intended to encompass adenosine deaminase with conservative amino acid substitutions that do not substantially alter its activity.

As used herein, "purine nucleoside phosphorylase" refers to an enzyme that catalyzes the formation of hypoxanthine and D-ribose from inosine and water. It is intended to encompass purine nucleoside phosphorylase with conservative amino acid substitutions that do not substantially alter its activity.

As used herein, "xanthine oxidase" refers to an enzyme that catalyzes the conversion of hypoxanthine to uric acid via xanthine. It is intended to encompass xanthine oxidase with conservative amino acid substitutions that do not substantially alter its activity.

As used herein, "folate species" refers to folate or folic acid, which is chemically N-[4-[[2-amino-1,4-dihydro-4- oxo-6-pteridinyl)methyl]amino]-benzxoyl]-L-glutamic acid, or a derivative thereof. Examples of folate derivatives include, but are not limited to, dihydrofolate, tetrahydrofolate, 5,-methyl-tetrahydrofolate and 5,10-methylene tetrahydrofolate.

As used herein, "tetrahydrofolate methyltransferase" refers to an enzyme that catalyzes the formation of 5,10-methylene tetrahydrofolate and glycine from tetrahydrofolate and serine. It is intended to encompass tetrahydrofolate methyltransferase with conservative amino acid substitutions that do not substantially alter its activity.

As used herein, "methylenetetrahydrofolate reductase" refers to an enzyme that catalyzes the formation of 5,-methyl-tetrahydrofolate from 5,10-methylene tetrahydrofolate. It is intended to encompass methylenetetrahydrofolate reductase with conservative amino acid substitutions that do not substantially alter its activity.

As used herein, "folypolyglutamate synthase" refers to an enzyme that catalyzes the formation of 5,10-methylenetetrahydrofolate-diglutamate derivative, ADP and Pi from 5,10-methylenetetrahydrofolate, L-glutamate and ATP. The cofactor of folypolyglutamate synthase is $Mg^{2+}$. It is intended to encompass folypolyglutamate synthase with conservative amino acid substitutions that do not substantially alter its activity.

As used herein, "dihydrofolate reductase" refers to an enzyme that catalyzes the formation of tetrahydrofolate and $NADP^+$ from dihydrofolate, NADPH and $H^+$. It is intended to encompass dihydrofolate reductase with conservative amino acid substitutions that do not substantially alter its activity.

As used herein, "thymidylate synthase" refers to an enzyme that catalyzes the formation of dihydrofolate and dTMP from 5,10-methylenetetrahydrofolate and dUMP. It is intended to encompass thymidylate synthase with conservative amino acid substitutions that do not substantially alter its activity.

As used herein, "cholesterol esterase" refers to an enzyme that catalyzes the formation of cholesterol and fatty acids from cholesterolester and $H_2O$. It is intended to encompass cholesterol esterase with conservative amino acid substitutions that do not substantially alter its activity.

As used herein, "cholesterol oxidase" refers to an enzyme that catalyzes the formation of cholesterol-4-en-3-one and $H_2O_2$ from cholesterol and $O_2$. It is intended to encompass cholesterol oxidase with conservative amino acid substitutions that do not substantially alter its activity.

As used herein, "bile acid" refers to acidic sterols synthesized from cholesterol in the liver. Following synthesis, the bile acids are secreted into bile and enter the lumen of the small intestine, where they facilitate absorption of fat-soluble vitamins and cholesterol. In humans, the most abundant bile acid is cholic acid.

As used herein, "bile salt" refers to salt of bile acid. The major human bile salts are sodium glycocholate and sodium taurocholate.

As used herein, "3-α-hydroxy steroid dehydrogenase" refers to an enzyme that catalyzes the 3-oxo-bile-acid, $H^+$ and NADH from 3-α-hydroxy-bile-acid and $NAD^+$. It is intended to encompass 3-α-hydroxy steroid dehydrogenase with conservative amino acid substitutions that do not substantially alter its activity.

As used herein, "glucose isomerase" refers to an enzyme that catalyzes the reversible conversion between D-glucose and D-fructose. It is intended to encompass glucose isomerase with conservative amino acid substitutions that do not substantially alter its activity.

As used herein, "hexokinase or glucokinase" refers to an enzyme that catalyzes the formation of D-glucose 6-phosphate and ADP from α-D-glucose and ATP. The cofactor of hexokinase or glucokinase is $Mg^{2+}$. It is intended to encompass hexokinase or glucokinase with conservative amino acid substitutions that do not substantially alter its activity.

As used herein, "glucose oxidase" refers to an enzyme that catalyzes the formation of gluconic acid and $H_2O_2$ from glucose, $H_2O$ and $O_2$. It is intended to encompass glucose oxidase with conservative amino acid substitutions that do not substantially alter its activity.

As used herein, "alcohol dehydrogenase" refers to an enzyme that catalyzes the formation of acetaldehyde, NADH and $H^+$ from ethanol and $NAD^+$. The cofactor of alcohol dehydrogenase is $Zn^{2+}$. It is intended to encompass alcohol dehydrogenase with conservative amino acid substitutions that do not substantially alter its activity.

As used herein, "urate oxidase or uricase" refers to an enzyme that catalyzes the formation of allantoin and $CO_2$ from uric acid, $O_2$ and $H_2O$. The cofactor of urate oxidase or uricase is copper. It is intended to encompass urate oxidase or uricase with conservative amino acid substitutions that do not substantially alter its activity.

As used herein, "serum" refers to the fluid portion of the blood obtained after removal of the fibrin clot and blood cells, distinguished from the plasma in circulating blood.

As used herein, "plasma" refers to the fluid, noncellular portion of the blood, distinguished from the serum obtained after coagulation.

As used herein, "substantially pure" means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers or isomers. In such instances, further purification might increase the specific activity of the compound.

As used herein, "biological activity" refers to the in vivo activities of a compound or physiological responses that result upon in vivo administration of a compound, composition or other mixture. Biological activity, thus, encompasses therapeutic effects and pharmaceutical activity of such compounds, compositions and mixtures. Biological activities may be observed in vitro systems designed to test or use such activities. Thus, for purposes herein the biological activity of a luciferase is its oxygenase activity whereby, upon oxidation of a substrate, light is produced.

As used herein, a "receptor" refers to a molecule that has an affinity for a given ligand. Receptors may be naturally-occurring or synthetic molecules. Receptors may also be referred to in the art as anti-ligands. As used herein, the receptor and anti-ligand are interchangeable. Receptors can be used in their unaltered state or as aggregates with other species. Receptors may be attached, covalently or noncovalently, or in physical contact with, to a binding member, either directly or indirectly via a specific binding substance or linker. Examples of receptors, include, but are not limited to: antibodies, cell membrane receptors surface receptors and internalizing receptors, monoclonal antibodies and antisera reactive with specific antigenic determinants [such as on viruses, cells, or other materials], drugs, polynucleotides, nucleic acids, peptides, cofactors, lectins, sugars, polysaccharides, cells, cellular membranes, and organelles.

Examples of receptors and applications using such receptors, include but are not restricted to:

a) enzymes: specific transport proteins or enzymes essential to survival of microorganisms, which could serve as targets for antibiotic [ligand] selection;

b) antibodies: identification of a ligand-binding site on the antibody molecule that combines with the epitope of an antigen of interest may be investigated; determination of a sequence that mimics an antigenic epitope may lead to the development of vaccines of which the immunogen is based on one or more of such sequences or lead to the development of related diagnostic agents or compounds useful in therapeutic treatments such as for auto-immune diseases c) nucleic acids: identification of ligand, such as protein or RNA, binding sites;

d) catalytic polypeptides: polymers, preferably polypeptides, that are capable of promoting a chemical reaction involving the conversion of one or more reactants to one or more products; such polypeptides generally include a binding site specific for at least one reactant or reaction intermediate and an active functionality proximate to the binding site, in which the functionality is capable of chemically modifying the bound reactant [see, e.q., U.S. Pat. No. 5,215,899];

e) hormone receptors: determination of the ligands that bind with high affinity to a receptor is useful in the development of hormone replacement therapies; for example, identification of ligands that bind to such receptors may lead to the development of drugs to control blood pressure; and f) opiate receptors: determination of ligands that bind to the opiate receptors in the brain is useful in the development of less-addictive replacements for morphine and related drugs.

As used herein, "antibody" includes antibody fragments, such as Fab fragments, which are composed of a light chain and the variable region of a heavy chain.

As used herein, "humanized antibodies" refer to antibodies that are modified to include "human" sequences of amino acids so that administration to a human will not provoke an immune response. Methods for preparation of such antibodies are known. For example, the hybridoma that expresses the monoclonal antibody is altered by recombinant DNA techniques to express an antibody in which the amino acid composition of the non-variable regions is based on human antibodies. Computer programs have been designed to identify such regions.

As used herein, "production by recombinant" means by using recombinant DNA methods means the use of the well known methods of molecular biology for expressing proteins encoded by cloned DNA.

As used herein, "substantially identical" to a product means sufficiently similar so that the property of interest is sufficiently unchanged so that the substantially identical product can be used in place of the product.

As used herein, "equivalent," when referring to two sequences of nucleic acids means that the two sequences in question encode the same sequence of amino acids or equivalent proteins. It also encompasses those that hybridize under conditions of moderate, preferably high stringency, whereby the encoded protein retains desired properties.

As used herein, when "equivalent" is used in referring to two proteins or peptides, it means that the two proteins or peptides have substantially the same amino acid sequence with only conservative amino acid substitutions [see, e.g., Table 1, above] that do not substantially alter the activity or function of the protein or peptide.

When "equivalent" refers to a property, the property does not need to be present to the same extent [e.g., two peptides can exhibit different rates of the same type of enzymatic activity], but the activities are preferably substantially the same. "Complementary," when referring to two nucleic acid molecules, means that the two sequences of nucleotides are capable of hybridizing, preferably with less than 25%, more preferably with less than 15%, even more preferably with less than 5%, most preferably with no mismatches between opposed nucleotides. Preferably the two molecules will hybridize under conditions of high stringency.

As used herein: "stringency of hybridization" in determining percentage mismatch is as follows:

1) high stringency: 0.1×SSPE, 0.1% SDS, 65° C.;

2) medium stringency: 0.2×SSPE, 0.1% SDS, 50° C. (also referred to as moderate stringency); and 3) low stringency: 1.0×SSPE, 0.1% SDS, 50° C.

It is understood that equivalent stringencies may be achieved using alternative buffers, salts and temperatures.

The term "substantially" identical or homologous or similar varies with the context as understood by those skilled in the relevant art and generally means at least 70%, preferably means at least 80%, more preferably at least 90%, and most preferably at least 95% identity.

As used herein, a "composition" refers to a any mixture of two or more products or compounds. It may be a solution, a suspension, liquid, powder, a paste, aqueous, non-aqueous or any combination thereof.

As used herein, a "combination" refers to any association between two or among more items.

As used herein, "fluid" refers to any composition that can flow. Fluids thus encompass compositions that are in the form of semi-solids, pastes, solutions, aqueous mixtures, gels, lotions, creams and other such compositions.

As used herein, "vector (or plasmid)" refers to discrete elements that are used to introduce heterologous DNA into cells for either expression or replication thereof. Selection and use of such vehicles are well known within the skill of the artisan. An expression vector includes vectors capable of expressing DNAs that are operatively linked with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, "a promoter region or promoter element" refers to a segment of DNA or RNA that controls transcription of the DNA or RNA to which it is operatively linked. The promoter region includes specific sequences that are sufficient for RNA polymerase recognition, binding and transcription initiation. This portion of the promoter region is referred to as the promoter. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated. Exemplary promoters contemplated for use in prokaryotes include the bacteriophage T7 and T3 promoters, and the like.

As used herein, "operatively linked or operationally associated" refers to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or in vitro transcription, it may be necessary to remove, add or alter 5' untranslated portions of the clones to eliminate extra, potential inappropriate alternative translation initiation (i.e., start) codons or other sequences that may interfere with or reduce expression, either at the level of transcription or translation. Alternatively, consensus ribosome binding sites (see, e.g., Kozak, *J. Biol. Chem.*, 266:19867–19870 (1991)) can be inserted immediately 5' of the start codon and may enhance expression. The desirability of (or need for) such modification may be empirically determined.

As used herein, "sample" refers to anything which may contain an analyte for which an analyte assay is desired. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s).

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:1726).

For clarity of disclosure, and not by way of limitation, the detailed description of the invention is divided into the subsections that follow.

B. METHODS FOR ASSAYING ANALYTES

Provided herein are methods for assaying an analyte in a sample. Any assays that employs an antibody as a reagent can be modified as described herein by replacing the antibody with an enzyme that has been modified such that it retains the ability to bind to an analyte of interest but has substantially reduced catalytic activity (i.e., a substrate trapping enzyme).

Assays provided herein include the steps of: a) contacting a sample with a mutant or modified enzyme that binds to the analyte of interest; and b) detecting binding between the analyte or the immediate analyte enzymatic conversion product with the mutant analyte-binding enzyme. The mutant or modified enzyme substantially retains the binding affinity, has enhanced binding affinity of the wildtype or unmodified enzyme for the analyte or an immediate analyte enzymatic conversion product, but has attenuated catalytic activity.

1. Analytes

Any analyte that can specifically bind to an enzyme, either as a co-enzyme, a co-factor or a substrate can be assayed by the presently claimed methods. Analytes can be any molecules, including biological macromolecules and small molecules, ligands, anti-ligands and other species. Preferably, the analyte to be assayed is a small molecule. In one embodiment, the small molecule analyte to be assayed is an inorganic molecule. Preferably, the inorganic molecule is an inorganic ion such as a sodium, a potassium, a magnesium, a calcium, a chlorine, an iron, a copper, a zinc, a manganese, a cobalt, an iodine, a molybdenum, a vanadium, a nickel, a chromium, a fluorine, a silicon, a tin, a boron or an arsenic ion.

In another specific embodiment, the small molecule analyte is an organic molecule. Preferably, the organic molecule to be assayed is an amino acid, a peptide containing less than 10 amino acids, a nucleoside, a nucleotide, an oligonucleotide containing less than 10 nucleotides, a vitamin, a monosaccharide, an oligosaccharide containing less than 10 monosaccharides or a lipid.

Any amino acids can be assayed by the presently claimed methods. For example, a D- and a L-amino-acid can be assayed. In addition, any building blocks of naturally occurring peptides and proteins including Ala (A), Arg (R), Asn (N), Asp (D), Cys (C), Gln (Q), Glu (E), Gly (G), His (H), Ile (I), Leu (L), Lys (K), Met (M), Phe (F), Pro (P) Ser (S), Thr (T), Trp (W), Tyr (Y) and Val (V) can be assayed. Further, any derivatives of the naturally occurring amino acids, e.g., Hcy as a derivative of Cys, can be assayed.

Any nucleosides can be assayed by the presently claimed methods. Examples of such nucleosides include adenosine, guanosine, cytidine, thymidine and uridine.

Any nucleotides can be assayed by the presently claimed methods. Examples of such nucleotides include AMP, GMP, CMP, UMP, ADP, GDP, CDP, UDP, ATP, GTP, CTP, UTP, dAMP, dGMP, dCMP, dTMP, dADP, dGDP, dCDP, dTDP, dATP, dGTP, dCTP and dTTP. In addition, any oligonucleotides containing less than 10 such nucleotides or other nucleotides can be assayed.

Any vitamins can be assayed by the presently claimed methods. For example, water-soluble vitamins such as thiamine, riboflavin, nicotinic acid, pantothenic acid, pyridoxine, biotin, folate, vitamin $B_{12}$ and ascorbic acid can be assayed. Similarly, fat-soluble vitamins such as vitamin A, vitamin D, vitamin E, and vitamin K can be assayed.

Any monosaccharides, whether D- or L-monosaccharides and whether aldoses or ketoses, can be assayed by the presently claimed methods. Examples of monosaccharides include triose such as glyceraldehyde, tetroses such as erythrose and threose, pentoses such as ribose, arabinose, xylose, lyxose and ribulose, hexoses such as allose, altrose, glucose, mannose, gulose, idose, galactose, talose and fructose and heptose such as sedoheptulose.

Any lipids can be assayed by the presently claimed methods. Examples of lipids include triacylglycerols such as tristearin, tripalmitin and triolein, waxes, phosphoglycerides such as phosphatidylethanolamine, phosphatidylcholine, phosphatidylserine, phosphatidylinositol and cardiolipin, sphingolipids such as sphingomyelin, cerebrosides and gangliosides, sterols such as cholesterol and stigmasterol and sterol fatty acid esters. The fatty acids can be saturated fatty acids such as lauric acid, myristic acid, palmitic acid, stearic acid, arachidic acid and lignoceric acid, or can be unsaturated fatty acids such as palmitoleic acid, oleic acid, linoleic acid, linolenic acid and arachidonic acid.

In still another specific embodiment, the small molecule to be assayed has a molecular weight that is about or less than 10,000 dalton. More preferably, the small molecule has a molecular weight that is about or less than 5,000 dalton.

Examples of specific analytes that can be assayed by the presently claimed methods include, but are not limited to, Hcy, folate species, cholesterol, glucose, ethanol and uric acid.

2. Mutant Analyte-binding Enzymes ("substrate trapping enzymes")

Any mutant analyte-binding enzyme that substantially retains its binding affinity or has enhanced binding affinity for the analyte or an immediate analyte enzymatic conversion product but has attenuated catalytic activity can be used in the assay. For example, if Hcy is the analyte to be assayed, mutant Hcy-binding enzymes such as mutant cystathionine β-synthase, mutant methionine synthase, mutant betaine-homocysteine methyltransferase, mutant methioninase and mutant SAH hydrolase can be used.

Mutant enzymes having the desired specificity can be prepared using routine mutagenesis methods. Residues to mutate can be identified by systematically mutating residues to different residues, and identifying those that have the desired reduction in catalytic activity and retention of binding activity for a particular substrate. Alternatively or additionally, mutations may be based upon predicted or known 3-D structures of enzymes, including predicted affects of various mutations (see, e.g., Turner et al. (1998) *Nature Structural Biol.* 5:369–376; Ault-Richié et al. (1994) *J. Biol. Chem.* 269:31472–31478; Yuan et al. (1996) *J. Biol. Chem.* 271:28009–28016; Williams et al. (1998) *Biochemistry* 37:7096; Steadman et al. (1998) *Biochemistry* 37:7089–7095; Finer-Moore et al. (1998) *J. Mol. Biol.* 276:113–129; Strop et al. (1997) *Protein Sci.* 6:2504–2511; Finer-Moore et al. (1996) *Biochemistry* 35:5125–5136; Schiffer et al. (1995) *Biochemistry* 34:16279–16287; Costi et al. (1996) *Biochemistry* 35:3944–3949; Graves et al. (1992) *Biochemistry* 31:15–21; Carreras et al. (1992) *Biochemistry* 31:6038–6044. Such predictions can be maded by those of skill in the art of computational chemistry. Hence, for any selected enzyme, the mutations need to inactivate catalytic activity but retain binding activity can be determined empirically.

a. Nucleic Acids Encoding Analyte-binding Enzymes

Nucleic acids encoding analyte-binding enzymes can be obtained by methods known in the art. Known nucleic acid sequences of analyte-binding enzymes can be used in isolating nucleic acids encoding analyte-binding enzymes from natural or other sources. Alternatively, complete or partial nucleic acids encoding analyte-binding enzymes can be obtained by chemical synthesis according to the known sequences or obtained from commercial or other sources.

Eukaryotic cells and prokaryotic cells can serve as a nucleic acid source for the isolation of nucleic acids encoding analyte-binding enzymes. The DNA can be obtained by standard procedures known in the art from cloned DNA (e.g., a DNA "library"), chemical synthesis, cDNA cloning, or by the cloning of genomic DNA, or fragments thereof, purified from the desired cell (see, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II.). Clones derived from genomic DNA can contain regulatory and intron DNA regions in addition to coding regions; clones derived from cDNA or RNA contain only exon sequences. Whatever the source, the gene is generally molecularly cloned into a suitable vector for propagation of the gene.

In the molecular cloning of the gene from cDNA, cDNA can be generated from total cellular RNA or mRNA by methods that are known in the art. The gene can also be obtained from genomic DNA, where DNA fragments are generated (e.g., using restriction enzymes or by mechanical shearing), some of which will encode the desired gene. The linear DNA fragments can then be separated according to size by standard techniques, including but not limited to, agarose and polyacrylamide gel electrophoresis and column chromatography.

Once the DNA fragments are generated, identification of the specific DNA fragment containing all or a portion of the analyte-binding enzymes gene can be accomplished in a number of ways.

A preferred method for isolating an analyte-binding enzyme gene is by the polymerase chain reaction (PCR), which can be used to amplify the desired analyte-binding enzyme sequence in a genomic or cDNA library or from genomic DNA or cDNA that has not been incorporated into a library. Oligonucleotide primers which hybridize to the analyte-binding enzyme sequences can be used as primers in PCR.

Additionally, a portion of the analyte-binding enzyme (of any species) gene or its specific RNA, or a fragment thereof, can be purified (or an oligonucleotide synthesized) and labeled, the generated DNA fragments may be screened by nucleic acid hybridization to the labeled probe (Benton, W. and Davis, R., 1977, *Science* 196:180; Grunstein, M. And Hogness, D., 1975, *Proc. Natl. Acad. Sci. U.S.A.* 72:3961). Those DNA fragments with substantial homology to the probe will hybridize. The analyte-binding enzyme nucleic acids can be also identified and isolated by expression cloning using, for example, anti-analyte-binding enzyme antibodies for selection.

Alternatives to obtaining the analyte-binding enzyme DNA by cloning or amplification include, but are not limited to, chemically synthesizing the gene sequence itself from the known analyte-binding enzyme nucleotide sequence or making cDNA to the mRNA which encodes the analyte-binding enzyme. Any suitable method known to those of skill in the art may be employed.

Once a clone has been obtained, its identity can be confirmed by nucleic acid sequencing (by methods known in the art) and comparison to known analyte-binding enzyme sequences. DNA sequence analysis can be performed by techniques known in the art, including but not limited to, the method of Maxam and Gilbert (1980, *Meth. Enzymol.* 65:499–560), the Sanger dideoxy method (Sanger, F., et al., 1977, *Proc. Natl. Acad. Sci. U.S.A.* 74:5463), the use of T7 DNA polymerase (Tabor and Richardson, U.S. Pat. No. 4,795,699), use of an automated DNA sequenator (e.g., Applied Biosystems, Foster City, Calif.).

Nucleic acids which are hybridizable to an analyte-binding enzyme nucleic acid, or to a nucleic acid encoding an analyte-binding enzyme derivative can be isolated, by nucleic acid hybridization under conditions of low, high, or medium stringency (Shilo and Weinberg, 1981, *Proc. Natl. Acad. Sci. USA* 78:6789–6792).

b. Selecting and Producing Mutant Analyte-binding Enzymes

Once nucleic acids encoding the analyte-binding enzymes are obtained, these nucleic acids can be mutagenized and screened and/or selected for analyte-binding enzymes that substantially retain their binding affinity or have enhanced binding affinity for the analyte or an immediate analyte enzymatic conversion product but have attenuated catalytic activity. Insertional, deletional or point mutation(s) can be introduced into nucleic acids encoding the analyte-binding enzymes. Techniques for mutagenesis known in the art can be used, including, but not limited to, in vitro site-directed mutagenesis (Hutchinson et al., 1978, *J. Biol. Chem* 253:6551), use of TAB® linkers (Pharmacia), mutation-containing PCR primers, etc. Mutagenesis can be followed by phenotypic testing of the altered gene product.

Site-directed mutagenesis protocols can take advantage of vectors that provide single stranded as well as double stranded DNA, as needed. Generally, the mutagenesis protocol with such vectors is as follows. A mutagenic primer, i.e., a primer complementary to the sequence to be changed, but including one or a small number of altered, added, or deleted bases, is synthesized. The primer is extended in vitro by a DNA polymerase and, after some additional manipulations, the now double-stranded DNA is transfected into bacterial cells. Next, by a variety of methods, the desired mutated DNA is identified, and the desired protein is purified from clones containing the mutated sequence. For longer sequences, additional cloning steps are often required because long inserts (longer than 2 kilobases) are unstable in those vectors. Protocols are known to one skilled in the art and kits for site-directed mutagenesis are widely available from biotechnology supply companies, for example from Amersham Life Science, Inc. (Arlington Heights, Ill.) and Stratagene Cloning Systems (La Jolla, Calif.).

Information regrading the structural-functional relationship of the analyte-binding enzymes can be used in the mutagenesis and selection of analyte-binding enzymes that substantially retain their binding affinity or have enhanced binding affinity for the analyte or an immediate analyte enzymatic conversion product but have attenuated catalytic activity. For example, mutants can be made in the enzyme's binding site for its co-enzyme, co-factor, a non-analyte substrate, or in the mutant enzyme's catalytic site, or a combination thereof.

Once a mutant analyte-binding enzyme with desired properties, i.e., substantially retaining its binding affinity or having enhanced binding affinity for the analyte or an immediate analyte enzymatic conversion product but has attenuated catalytic activity, is identified, such mutant analyte-binding enzyme can be produced by any methods known in the art including recombinant expression, chemical synthesis or a combination thereof. Preferably, the mutant analyte-binding enzyme is obtained by recombinant expression.

For recombinant expression, the mutant analyte-binding enzyme gene or portion thereof is inserted into an appropriate cloning vector for expression in a particular host cell. A large number of vector-host systems known in the art may be used. Possible vectors include, but are not limited to, plasmids or modified viruses, but the vector system must be compatible with the host cells used. Such vectors include, but are not limited to, bacteriophages such as lambda derivatives, or plasmids such as pBR322 or pUC plasmid derivatives or the Bluescript vector (Stratagene). The insertion into a cloning vector can, for example, be accomplished by ligating the DNA fragment into a cloning vector which has complementary cohesive termini. If, however, the complementary restriction sites used to fragment the DNA are not present in the cloning vector, the ends of the DNA molecules can be enzymatically modified. Alternatively, a desired site can be produced by ligating sequences of nucleotides (linkers) onto the DNA termini; these ligated linkers can include specific oligonucleotides encoding restriction endonuclease recognition sequences. Recombinant molecules can be introduced into host cells via transformation, transfection, infection, electroporation, etc., so that many copies of the gene sequence are generated.

In an alternative method, the desired gene can be identified and isolated after insertion into a suitable cloning vector in a "shot gun" approach. Enrichment for the desired gene, for example, by size fractionation, can be done before insertion into the cloning vector.

In specific embodiments, transformation of host cells with recombinant DNA molecules that incorporate the isolated mutant analyte-binding enzyme gene, cDNA, or synthesized DNA sequence enables generation of multiple copies of the gene. Thus, the gene can be obtained in large quantities by growing transformants, isolating the recombinant DNA molecules from the transformants and, when necessary, retrieving the inserted gene from the isolated recombinant DNA.

The nucleotide sequence coding for a mutant analyte-binding enzyme or a functionally active analog or fragment or other derivative thereof, can be inserted into an appropriate expression vector, e.g., a vector which contains the necessary elements for the transcription and translation of the inserted protein-coding sequence. The necessary transcriptional and translational signals can also be supplied by the native mutant analyte-binding enzyme gene and/or its flanking regions. A variety of host-vector systems can be utilized to express the protein-coding sequence. These systems include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, suitable transcription and translation elements can be used.

The methods previously described for the insertion of DNA fragments into a vector can be used to construct expression vectors containing a chimeric gene containing appropriate transcriptional/translational control signals and the protein coding sequences. These methods can include in vitro recombinant DNA and synthetic techniques and in vivo recombinants (genetic recombination). Expression of a nucleic acid sequence encoding a mutant analyte-binding enzyme or peptide fragment can be regulated by a second nucleic acid sequence so that the mutant analyte-binding enzyme or peptide is expressed in a host transformed with the recombinant DNA molecule. For example, expression of a mutant analyte-binding enzyme can be controlled by a promoter/enhancer element as is known in the art. Promoters which can be used to control a mutant analyte-binding enzyme expression include, but are not limited to, the SV40 early promoter region (Bernoist and Chambon, 1981, *Nature* 290:304–310), the promoter contained in the 3' long terminal repeat of Rous sarcoma virus (Yamamoto, et al., 1980, *Cell* 22:787–797), the herpes thymidine kinase promoter (Wagner et al., 1981, *Proc. Natl. Acad. Sci. U.S.A.* 78:1441–1445), the regulatory sequences of the metallothioneine gene (Brinster et al., 1982, *Nature* 296:39–42); prokaryotic expression vectors such as the β-lactamase promoter (Villa-Kamaroff, et al., 1978, *Proc. Natl. Acad. Sci. U.S.A.* 75:3727–3731), or the tac promoter (DeBoer, et al., 1983, *Proc. Natl. Acad. Sci. U.S.A.* 80:21–25); see also "Useful proteins from recombinant bacteria" in *Scientific American*, 1980, 242:74–94; promoter elements from yeast or other fungi such as the Gal 4 promoter, the ADC (alcohol dehydrogenase) promoter, PGK (phosphoglycerol kinase) promoter, alkaline phosphatase promoter, and certain animal transcriptional control regions.

For example, a vector can be used that contains a promoter operably linked to a nucleic acid encoding a mutant analyte-binding enzyme, one or more origins of replication, and, optionally, one or more selectable markers (e.g., an antibiotic resistance gene).

In a specific embodiment, an expression construct is made by subcloning a mutant analyte-binding enzyme coding sequence into the EcoRI restriction site of each of the three pGEX vectors (Glutathione S-Transferase expression vectors; Smith and Johnson, 1988, *Gene* 7:31–40). This allows for the expression of a mutant analyte-binding enzyme product from the subclone in the correct reading frame.

Expression vectors containing a mutant analyte-binding enzyme gene inserts can be identified by three general approaches: (a) nucleic acid hybridization, (b) presence or absence of "marker" gene functions, and (c) expression of inserted sequences. In the first approach, the presence of a mutant analyte-binding enzyme gene inserted in an expression vector can be detected by nucleic acid hybridization using probes containing sequences that are homologous to an inserted mutant analyte-binding enzyme gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of a mutant analyte-binding enzyme gene in the vector. For example, if the mutant analyte-binding enzyme gene is inserted within the marker gene sequence of the vector, recombinants containing the mutant analyte-Ebinding enzyme insert can be identified by the absence of the marker gene function. In the third approach, recombinant expression vectors can be identified by assaying the mutant analyte-binding enzyme product expressed by the recombinant. Such assays can be based, for example, on the physical or functional properties of the mutant analyte-binding enzyme in in vitro assay systems, e.g., binding with anti-mutant analyte-binding enzyme antibody.

Once a particular recombinant DNA molecule is identified and isolated, several methods known in the art can be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain can be chosen which modulates the expression of the inserted sequences, or modifies and processes the gene product in the specific fashion desired. Expression from certain promoters can be elevated in the presence of certain inducers; thus, expression of the genetically engineered mutant analyte-binding enzyme can be controlled. Furthermore, different host cells have characteristic and specific mechanisms for the translational and post-translational processing and modification (e.g., glycosylation, phosphorylation) of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in appropriate animal cells can be used to ensure "native" glycosylation of a heterologous protein. Furthermore, different vector/host expression systems can effect processing reactions to different extents.

3. Sample Collection

Any sample can be assayed for an analyte using the above-described methods. In one embodiment, the sample being assayed is a biological sample from a mammal, particularly a human, such as a biological fluid or a biological tissue. Biological fluids, include, but are not limited to, urine, blood, plasma, serum, saliva, semen, stool, sputum, hair and other keratinous samples, cerebral spinal fluid, tears, mucus and amniotic fluid. Biological tissues contemplated include, but are not limited to, aggregates of cells, usually of a particular kind together with their intercellular substance that form one of the structural materials of a human, animal, plant, bacterial, fungal or viral structure, including connective, epithelium, muscle and nerve tissues, organs, tumors, lymph nodes, arteries and individual cell(s). In one specific embodiment, the body fluid to be assayed is urine. In another specific embodiment, the body fluid to be assayed is blood. Preferably, the blood sample is further separated into a plasma or sera fraction.

Serum or plasma can be recovered from the collected blood by any methods known in the art. In one specific embodiment, the serum or plasma is recovered from the collected blood by centrifugation. Preferably, the centrifugation is conducted in the presence of a sealant having a specific gravity greater than that of the serum or plasma and less than that of the blood corpuscles which will form the lower, whereby upon centrifugation, the sealant forms a separator between the upper serum or plasma layer and the lower blood corpuscle layer. The sealants that can be used in the processes include, but are not limited to, styrene resin powders (Japanese Patent Publication No. 38841/1973), pellets or plates of a hydrogel of a crosslinked polymer of 2-hydroxyethyl methacrylate or acrylamide (U.S. Pat. No. 3,647,070), beads of polystyrene bearing an antithrombus agent or a wetting agent on the surfaces (U.S. Pat. No. 3,464,890) and a silicone fluid (U.S. Pat. Nos. 3,852,194 and 3,780,935). In a preferred embodiment, the sealant is a polymer of unsubstituted alkyl acrylates and/or unsubstituted alkyl methacrylates, the alkyl moiety having not more than 18 carbon atoms, the polymer material having a specific gravity of about 1.03 to 1.08 and a viscosity of about 5,000 to 1,000,000 cps at a shearing speed of about 1 second$^{-1}$ when measured at about 25° C. (U.S. Pat. No. 4,140,631).

In another specific embodiment, the serum or plasma is recovered from the collected blood by filtration. Preferably, the blood is filtered through a layer of glass fibers with an average diameter of about 0.2 to 5$\mu$ and a density of about 0.1 to 0.5 g./cm$^3$, the total volume of the plasma or serum to be separated being at most about 50% of the absorption volume of the glass fiber layer; and collecting the run-through from the glass fiber layer which is plasma or serum (U.S. Pat. No. 4,477,575). Also preferably, the blood is filtered through a layer of glass fibers having an average diameter 0.5 to 2.5$\mu$ impregnated with a polyacrylic ester derivative and polyethylene glycol (U.S. Pat. No. 5,364, 533). More preferably, the polyacrylic ester derivative is poly(butyl acrylate), poly(methyl acrylate) or poly(ethyl acrylate), and (a) poly(butyl acrylate), (b) poly(methyl acrylate) or poly(ethyl acrylate) and (c) polyethylene glycol are used in admixture at a ratio of (10-12):(1-4):(1-4).

In still another specific embodiment, the serum or plasma is recovered from the collected blood by treating the blood with a coagulant containing a lignan skelton having oxygen-containing side chains or rings (U.S. Pat. No. 4,803,153). Preferably, the coagulant contains a lignan skelton having oxygen-containing side chains or rings, e.g., d-sesamin, l-sesamin, paulownin, d-asarinin, l-asarinin, 2α-paulownin, 6α-paulownin, pinoresinol, d-eudesmin, l-pinoresinol β-D- glucoside, l-pinoresinol, l-pinoresinol monomethyl ether β-D-glucoside, epimagnolin, lirioresinol-B, syringaresinol (dl), lirioresinonB-dimethyl ether, phillyrin, magnolin, lirioresinol-A, 2α, 6α-d-sesamin, d-diaeudesmin, lirioresinol-C dimethyl ether (ddiayangambin) and sesamolin. More preferably, the coagulant is used in an amount ranging from about 0.01 to 50 g per 1 l of the blood.

C. METHODS FOR ASSAYING HOMOCYSTEINE

Also provided herein is a method for assaying Hcy in a sample. The method includes at least the steps of: a) contacting the sample with a mutant Hcy-binding enzyme, the mutant enzyme substantially retains its binding affinity or has enhanced binding affinity for Hcy or an immediate Hcy enzymatic conversion product but has attenuated catalytic activity; and b) detecting binding between the Hcy or the immediate Hcy enzymatic conversion product with the mutant Hcy-binding enzyme.

1. Homocysteine Metabolism

Homocysteine is an intermediary amino acid produced when methionine is metabolised to cysteine. There are two routes by which homocysteine produced in the body is rapidly metabolised: (1) condensation with serine to form cystathione or (2) conversion to methionine.

As discussed above, homocysteine levels in biological samples are of clinical significance. Homocysteine plays a role sulfhydryl amino acid metabolism; its accumulation may be indicative of various disorders occurring in these pathways, including in particular inborn errors of metabolism. Thus, for example homocystinuria (an abnormal build-up of homocysteine in the urine) is a disorder of amino acid metabolism resulting from deficiencies in the enzymes cystathione β-synthetase or methyltetrahydrofolic acid methyltransferase, which catalyses the methylation of homocysteine to methionine.

In the second pathway, which is illustrated as follows:

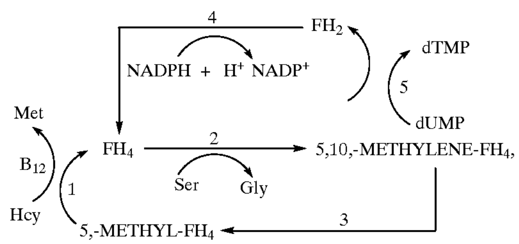

where: 1 is methylene synthase; 2 is tetrahydrofolate ($FH_4$) methyltransferase; 3 is methylenetetrahydrofolate reductase; 4 is dihydrofolate reducatse; 5 is thymidylate synthase; $FH_4$ is tetrahydrofolate and $FH_2$ is dihydrofolate, homocysteine levels are related, among other things, to folate levels and also vitamin $B_{12}$ levels. The various enzymes in these pathways may be assessed and correlated with homocysteine levels.

Sulfhydryl amino acid metabolism is closely linked to that of folic acid and vitamin $B_{12}$ (cobalamin), which act as substrates or co-factors in the various transformations involved. Homocysteine accumulation can be an indicator of malfunction of cobalamin or folate dependent enzymes, or other disorders or diseases related to cobalamin or folate metabolism.

Homocysteine metabolism also may be affected by anti-folate drugs, such as methotrexate, administered to treat a disorders, such as cancer and asthma, since homocysteine conversion to methionine relies on a reaction requiring S-methyl tetrahydrofolate as the methyl donor. Monitoring of homocysteine has therefore also been proposed in the management of malignant disease treatment with anti-folate drugs. More recently, elevated levels of homocysteine in the blood have been correlated with the development of atherosclerosis (see Clarke et al., New Eng. J. Med. 324:1149–1155 (1991)) and even moderate homocysteinemia is a risk factor for cardiac and vascular diseases. Measurement of plasma or blood levels of homocysteine is thus also of importance in the diagnosis and treatment of vascular disease.

2. Mutant Hcy-binding Enzymes

Any mutant Hcy-binding enzymes that substantially retain their binding affinity or have enhanced binding affinity for Hcy or an immediate Hcy enzymatic conversion product but have attenuated catalytic activity can be used in the Hcy assay. Examples of such mutant Hcy-binding enzyme include mutant cystathionine β-synthase, mutant methionine synthase, mutant betaine-homocysteine methyltransferase, mutant methioninase and mutant SAH hydrolase.

a. Nucleic Acids Encoding Hcy-binding Enzymes

Nucleic acids encoding Hcy-binding enzymes can be obtained by methods known in the art. Additional nucleic acid molecules encoding such enzymes are known and the molecules or sequences thereof are publicly available. If the molecules are available they can be used; alternatively the known sequences can be used to obtain clones from selected or desired sources. For example, the nucleic acid sequences of Hcy-binding enzymes, such as cystathionine β-synthase, methionine synthase, betaine-homocysteine methyltransferase, methioninase and SAH hydrolase, can used in isolating nucleic acids encoding Hcy-binding enzymes from natural sources. Alternatively, nucleic acids encoding Hcy-binding enzymes can be obtained by chemical synthesis according to the known sequences.

In one embodiment, the nucleic acid molecules containing sequence of nucleotides with the following GenBank accession Nos. can be used in obtaining nucleic acid encoding SAH hydrolase: AF129871 (*Gossypium hirsutum*); AQ003753 (*Cryptosporidium parvum*); AF105295 (*Alexandrium fundyense*); AA955402 (*Rattus norvegicus*); AA900229 (*Rattus norvegicus*); AA874914 (*Rattus norvegicus*); AA695679 (*Drosophila melanogaster* ovary); AA803942 (*Drosophila melanogaster* ovary; AI187655 (*Manduca sexta* male antennae); U40872 (*Trichomonas vaginalis*); AJ007835 (*Xenopus Laevis*); AF080546 (*Anopheles gambiae*); AI069796 (*T. cruzi epimastigote*); Z97059 (*Arabidopsis thaliana*); AF059581 (*Arabidopsis thaliana*); U82761 (Homo sapiens); AA754430 (*Oryza sativa*); D49804 (*Nicotiana tabacum*); D45204 (*Nicotiana tabacum*); X95636 (*D. melanogaster*); T18277 (endosperm *Zea mays*); R75259 (Mouse brain); Z26881 (*C. roseus*); X12523 (*D. discoideum*); X64391 (*Streptomyces fradiae*); W21772 (Maize Leaf); AH003443 (*Rattus norvegicus*); U14963 (*Rattus norvegicus*); U14962 (*Rattus norvegicus*); U14961 (*Rattus norvegicus*); U14960 (*Rattus norvegicus*); U14959 (*Rattus norvegicus*); U14937 (*Rattus norvegicus*); U14988 (*Rattus norvegicus*); U14987 (*Rattus norvegicus*); U14986 (*Rattus norvegicus*); U14985 (*Rattus norvegicus*); U14984 (*Rattus norvegicus*); U14983 (*Rattus norvegicus*); U14982 (*Rattus norvegicus*); U14981 (*Rattus norvegicus*); U14980 (*Rattus norvegicus*); U14979 (*Rattus norvegicus*); U14978 (*Rattus norvegicus*); U14977 (*Rattus norvegicus*); U14976 (*Rattus norvegicus*); U14975 (*Rattus norvegicus*); L32836 (*Mus musculus*); L35559 (*Xenopus laevis*); Z19779 (Human foetal Adrenals tissue); L23836 (*Rhodobacter capsulatus*); M15185 (Rat); L11872 (*Triticum aestivum*); M19937 (Slime mold (*D. discoideum*); M80630 (*Rhodobacter capsulatus*). Preferably, the nucleic acid moleucles containing nucleotide sequences with the GenBank accession Nos. M61831–61832 can be used in obtaining nucleic acid encoding SAH hydrolase (SEQ ID No. 1; see also Coulter-Karis and Hershfield, *Ann. Hum. Genet*., 53(2):169–175 (1989)). Also preferably, the nucleic acid molecule containing the sequence of nucleotides or encoding the amino acids set forth in SEQ ID No. 3 can be used (see also U.S. Pat. No. 5,854,023).

In another specific embodiment, the nucleic acid molecules containing sequences of nucleotides with the following GenBank accession Nos. can be used in obtaining nucleic acid encoding methionine synthase: Al547373 (Mesembryanthemum crystallinum); Al507856 (COBALAMINE-INDEPENDENT METHIONINE SYNTHASE); A1496185 (COBALAMINE-INDEPENDENT METHIONINE SYNTHASE); Al496016 (COBALAMINE-INDEPENDENT METHIONINE SYNTHASE); A1495904 (COBALAMINE-INDEPENDENT METHIONINE SYNTHASE); Al495702; Al495399; Al461276 (COBALAMINE-INDEPENDENT METHIONINE SYNTHASE); Al460827 (COBALAMINE-INDEPENDENT METHIONINE SYNTHASE); Al460549; Al443293; Al443243 (COBALAMINE-INDEPENDENT METHIONINE SYNTHASE); Al443242 (COBALAMINE-INDEPENDENT METHIONINE SYNTHASE); Al442736 (COBALAMINE-INDEPENDENT METHIONINE SYNTHASE); Al442546; Al442173 (COBALAMINE-INDEPENDENT METHIONINE SYNTHASE); Al442136 (COBALAMINE-INDEPENDENT METHIONINE SYNTHASE); Al441314; Al440982; Al438053; Al416939 (COBALAMINE-INDEPENDENT METHIONINE SYNTHASE); Al416601; Al391967 (*Conidial Neurospora crassa*); AF034214 (*Rattus norvegicus*); U77388 (*Chlamydomonas moewusii*); AF093539 (*Zea mays*); U97200 (*Arabidopsis thaliana*); U36197 (*Chlamydomonas reinhardtii*); AF025794 (Homo sapiens); AJ222785 (*Hordeum vulgare*); Z49150 (*C. blumei kinetoplast met* gene); AB004651 (*Hyphomicrobium methylovorum* gene); AA661438 (Maize Leaf); AA661023 (*Medicago truncatula*); AA660965 (*Medicago truncatula*); AA660880 (*Medicago truncatula*); AA660780 (*Medicago truncatula*); AA660708 (*Medicago truncatula*); AA660643 (*Medicago truncatula*); AA660558 (*Medicago truncatula*); AA660475 (*Medicago truncatula*); AA660444 (*Medicago truncatula*); AA660382 (*Medicago truncatula*); AA660310 (*Medicago truncatula*); AA660241 (*Medicago truncatula*); U75743 (Human); AA389835 (*Arabidopsis thaliana*); U84889 (*Mesembryanthemum crystallinum*); U73338 (Human); AA054818 (Maize Leaf); AA030695 (Maize Leaf); X83499 (*C. roseus*); U15099 (*Saccharomyces cerevisiae* (MET6)); J02804 (*E. coli* speED operon speE and speD genes); M87625 (*Escherichia coli*); J04975 (*E. coli*). Preferably, the nucleic acid molecules containing sequences of nucleotides with GenBank accession Nos. U75743 (SEQ ID No. 4) and U73338 (SEQ ID No. 6) can be used to obtain nucleic acid encoding methionine synthase.

In still another specific embodiment, nucleic acid molecules containing sequences of nucleotides with the following GenBank accession Nos. can be used in obtaining nucleic acid encoding cystathionine β-synthase: Al584826 (Zebrafish L19501); Al566920 (Homo sapiens); Al558544 (Zebrafish); Al529762 (Sugano mouse liver); Al528420 (Sugano mouse liver); Al494445 (Homo sapiens); Al500425 (Homo sapiens); Al421007 (Homo sapiens); Al369768 (Homo sapiens); Al368618 (Homo sapiens); Al312384 (Homo sapiens); Al266220 (Homo sapiens); Al307196 (Homo sapiens); R85449 (Homo sapiens); R84640 (Homo sapiens); Al371928 (Homo sapiens); Al281692 (Homo sapiens); Al198353 (Homo sapiens); Al222601 (Homo sapiens); Al188666 (Soares placenta); Al088293 (Soares Homo sapiens); Al039450 (Homo sapiens); AA995138 (Homo sapiens); Al053744 (Homo sapiens); AA921824 (Homo sapiens); AA876324 (Homo sapiens); AA218777 (neuronal precursor Homo sapiens); AA243110 (neuronal precursor Homo sapiens); AA232188 (neuronal precursor Homo sapiens); AA227066 (neuronal precursor Homo sapiens); AA180443 (HeLa cell Homo sapiens); AA179769 (HeLa cell Homo sapiens); AA620410 (lung carcinoma Homo sapiens); AA173243 (neuroepithelium Homo sapiens); AA173133 (neuroepithelium Homo sapiens); AA811740 (Homo sapiens); AA659341 (Homo sapiens); AA729802 (Homo sapiens); AA063294 (corneal stroma); AA063180 (corneal stroma); AA701200 (fetal liver spleen); AA699637 (fetal liver spleen); AA652920 (Homo sapiens); AA430416 (ovary tumor); AA430367 (ovary tumor); AA642534 (Homo sapiens); AA618538 (Homo sapiens); AA548257 (Homo sapiens); AA554953 (Homo sapiens); AA548561 (Homo sapiens); AA136426 (lung carcinoma); AA136339 (lung carcinoma); AA057714 (corneal stroma); AA260332 (mouse NML *Mus musculus*); AA239916 (mouse NML *Mus musculus*); AA239480 (mouse NML *Mus musculus*); AA096780 (mouse lung); AA105071 (mouse kidney); N76209 (fetal liver spleen); N54505 (fetal liver spleen); AA171542 (neuroepithelium); AA171511 (neuroepithelium); S78267 (human, homocystinuria patient 12, skin fibroblasts); AA057541 (corneal stroma); N50670 (multiple sclerosis); N29067 (melanocyte); T28038 (Human Brain Homo sapiens); H11280 (infant brain); R78956 (placenta); R38394 (infant brain); R35233 (placenta); T91706 (lung); T70457 (liver); T69322 (liver); T69248 (liver); L00972 (Human). Preferably, a nucleic acid molecule containing sequences of nucleotides set forth in SEQ ID No. 8 can be used in obtaining nucleic acid encoding cystathionine β-synthase (see also U.S. Pat. No. 5,523,225).

In yet another specific embodiment, the nucleotide sequences with the following GenBank accession Nos. can be used in obtaining nucleic acid encoding betaine homocysteine S-methyltransferase: Al629131 (Zebrafish); Al601766 (Zebrafish); NM001713 (Homo sapiens); AH007531 (Homo sapiens); AF118378 (Homo sapiens); AF118377 (Homo sapiens); AF118376 (Homo sapiens); AF118375 (Homo sapiens); AF118374 (Homo sapiens); AF118373 (Homo sapiens); AF118372 (Homo sapiens); AF118371 (Homo sapiens); Al550844 (mouse lung); Al529920 (mouse liver); Al529834 (mouse liver); Al529135 (mouse liver); Al527147 (mouse liver); Al527097 (mouse liver); A1497458 (Zebrafish); Al497232 (Zebrafish); Al496988 (Zebrafish); Al496904 (Zebrafish); Al496821 (Zebrafish); Al496747 (Zebrafish); Al471640 (Homo sapiens); AA901407 (*Rattus norvegicus*); Al390284 (mouse); Al244216 (Homo sapiens); Al316045 (mouse liver); Al303938 (mouse liver); Al303911 (mouse liver); Al303222 (mouse liver); Al287146 (mouse liver); Al287008 (mouse liver); Al286878 (mouse liver); Al266927 (mouse liver); Al256283 (mouse liver); Al227233 (mouse liver); Al227053 (mouse liver); U50929 (Human); U53421 (*Sus scrofa*); Al132261 (mouse liver); Al132254 (mouse liver); Al118276 (mouse liver); Al116416 (mouse liver); Al115840 (mouse kidney); Al115838 (mouse kidney); Al048111 (mouse liver); Al043140 (mouse liver); AA989805 (mouse kidney); AA986591 (mouse kidney); AA986590 (mouse kidney); AA985983 (mouse liver); AA755243 (mouse diaphragm); AF038870 (*Rattus norvegicus*); AA693837 (fetal liver); U96133 ((*Rattus norvegicus*). Preferably, the nucleotide sequences with the GenBank accession No. AH007531 can be used in obtaining nucleic acid encoding betaine homocysteine S-methyltransferase (SEQ ID No. 10; see also Garrow, *J. Biol. Chem*., 271(37):22831–8 (1996)).

In yet another specific embodiment, the nucleotide sequences described in U.S. Pat. No. 5,891,704 (SEQ ID No. 11) and the nucleotide sequences with the GenBank Accession No. L43133 (SEQ ID No. 13) (Hori et al., *Cancer Res*., 56(9):2116–22 (1996)) can be used in obtaining nucleic acid encoding methioninase.

b. Selecting and Producing Hcy-binding Enzymes

Once nucleic acids encoding Hcy-binding enzymes are obtained, these nucleic acids can be mutagenized and screened and/or selected for Hcy-binding enzymes that substantially retain their binding affinity or have enhanced binding affinity for Hcy or an immediate Hcy enzymatic conversion product but have attenuated catalytic activity. Insertion, deletion or point mutation(s) can be introduced into nucleic acids encoding Hcy-binding enzymes according to methods known to those of skill in the art, and, particularly, those described in Section C2c herein.

Information regrading the structural-function relationship of the Hcy-binding enzymes can be used in the mutagenesis and selection of Hcy-binding enzymes that substantially retain their binding affinity or have enhanced binding affinity for Hcy or an immediate Hcy enzymatic conversion product but have attenuated catalytic activity. For example, mutants can be made in the enzyme's binding site for its co-enzyme, co-factor, a non-Hcy substrate, or in the mutant enzyme's catalytic site, or a combination thereof.

In one specific embodiment, wherein cystathionine β-synthase is mutagenized, mutants can be made in cystathionine β-synthase's binding site for pyridoxal 5'-phosphate or L-serine, or a combination thereof (Kim et al., *Proc. Nat. Acad. Sci*., 71(2):4821–4825 (1974)). For example, Lys119 of human cystathionine β-synthase can be deleted or mutated, preferably to a non-charged or acidic amino acid residue (Kery et al., *Biochemistry*, 38(9) :2716–24 (1999)).

In another specific embodiment, wherein methionine synthase is mutagenized, mutants can be made in methionine synthase's binding site for vitamin $B_{12}$ or 5-methyltetrahydrofolate (5-$CH_3$-THF), or a combination thereof. For example, Asp946, Glu1097, Arg1134, Ala1136, Gly1138, Tyr1139 and Tyr1189 of human methionine synthase can be deleted or mutated, preferably to a different type of amino acid residue, i.e., Asp and Glu are changed to non-charged or basic residue, Arg is changed to non-charged or acidic residue, Ala and Gly are changed to charged residue or non-charged residue with larger sidechain, and Tyr is charged to residue without an aromatic sidechain (Dixon et al., *Structure*, 4(11):1263–75 (1996)). Preferably, *E. coli*. methionine synthase with amino acid sequence set forth in SEQ ID No. 3, containing His759Gly, Asp757Glu, Asp757Asn, or Ser810Ala is used in the Hcy assay (Amaratunga et al., *Biochemistry*, 35(7):2453–63 (1996))

In still another embodiment, wherein SAH hydrolase is mutagenized, mutants can be made in SAH hydrolase's binding site for $NAD^+$, or mutation(s) in the mutant SAH hydrolase's catalytic site, e.g., the 5'-hydrolytic catalytic site, or a combination thereof.

In yet another embodiment, wherein betaine-homocysteine methyltransferase is mutagenized, mutants can be made in betaine-homocysteine methyltransferase's binding site for $Zn^+$ or betaine. For example, Cys299 and Cys300 of human betaine-homocysteine methyltransferase can be deleted or mutated, preferably to amino acid residue without -SH sidechain, e.g., Serine (Millian and Garrow, *Arch. Biochem. Biophys*., 356(1):93–8 (1998)).

In yet another specific embodiment, wherein methioninase is mutagenized, mutants can be made in methioninase's binding site for R'SH which represents an alkanethiol or a substituted thiol (Ito et al., *J. Biochem*., (Tokyo) 80(6): 1327–34 (1976)).

Once a mutant Hcy-binding enzyme with desired properties, i.e., substantially retaining its binding affinity or having enhanced binding affinity for Hcy or an immediate Hcy enzymatic conversion product but has attenuated catalytic activity, is identified, such mutant Hcy-binding enzyme can be produced by any methods known in the art including recombinant expression, chemical synthesis or a combination thereof as described in Section B. Preferably, the mutant Hcy-binding enzyme is obtained by recombinant expression.

c. Mutant SAH Hydrolase and Nucleic Acids Encoding the Mutant SAH Hydrolase

SAH hydrolase from mammalian sources is a homotetramer of approximate molecular weight of 180–190 KD. The enzyme contains 4 molecules of tightly-bound $NAD^+$ as a co-enzyme. The catalytic mechanism of the enzyme in the hydrolytic direction includes two consecutive reactions, i.e., the 3'-oxidation of the substrate to 3'-keto in concomitant with the reduction of the enzyme-bound $NAD^+$ to NADH, and followed by the 5'-hydrolysis to release the reaction products Hcy and Ado (Refsum, et al., *Clin. Chem*., 31:624–628 (1985)). The C-terminal regions of all known SAH hydrolase are extremely conserved and contain essential amino acid residues to the enzyme catalysis. The crystal structure of human SAH hydrolase in complex with a substrate analog inhibitor was recently determined. This x-ray structure of SAH hydrolase indicates that at least twenty amino acid residues are directly or indirectly interacting with the substrate analog inhibitor and co-enzyme $NAD^+$. Mutations of those amino acid residues that are involve directly or indirectly in the substrate binding and catalysis can readily be made by site-directed mutagenesis, and the sequence of the resulting mutant enzyme can be confirmed by comparing the mutant SAH hydrolase DNA sequence with the sequence of the wild type enzyme to ensure not other mutations are introduced to the specific mutant enzyme.

Provided herein is a substantially purified mutant SAH hydrolase that substantially retains its binding affinity or has enhanced binding affinity for homocysteine (Hcy) or SAH but has attenuated catalytic activity.

In one specific embodiment, the attenuated catalytic activity of the mutant SAH hydrolase is caused by mutation(s) in the mutant SAH hydrolase's binding site for $NAD^+$, or mutation(s) in the mutant SAH hydrolase's catalytic site or a combination thereof.

In another specific embodiment, the mutant SAH hydrolase has attenuated 5'-hydrolytic activity but substantially retains its 3'-oxidative activity.

In still another specific embodiment, the mutant SAH hydrolase irreversibly binds SAH.

In yet another specific embodiment, the mutant SAH hydrolase has a Km for SAH that is about or less than 10.0 $\mu$M. Preferably, the mutant SAH hydrolase has a Km for SAH that is about 1.0 $\mu$M or less than 1.0 $\mu$M.

In yet another specific embodiment, the mutant SAH hydrolase has a Kcat for SAH that is about or less than 0.1 $S^{-1}$.

In yet another specific embodiment, the mutant SAH hydrolase has one or more insertion, deletion or point mutation(s). Preferably, the mutant SAH hydrolase is derived from the sequence of amino acids set forth in SEQ ID No. 1 or encoded by the sequence of nucleotides set forth in SEQ ID No. 2 but has one or more of the following mutations: Phe302 to Ser (F302S), Lys186 to Ala (K186A), His301 to Asp (H301D), His353 to Ser (H353S), Arg343 to Ala (R343A), Asp190 to Ala (D190A), Phe82 to Ala (F82A), Thr157 to Leu (T157L), Cys195 to Asp (C195D), Asn181 to Asp (N181D), and deletion of Tyr432 (Δ432). Also more preferably, the mutant SAH hydrolase is derived sequence of amino acids set forth in SEQ ID No. 1 or encoded by the sequence of nucleotides set forth in SEQ ID No. 2 and has a combination of Arg431 to Ala (R431A) and Lys426 to Arg (K426R) mutations. The nucleic acid molecules contemplated also include those that have conservative amino acid changes, and include those that hybridize along their full length to the coding portion of the sequence of nucleotides set forth in SEQ ID No. 2, under medium stringency, or preferably high stringency, such that the encoded protein retains ability to bind to the sleected analyte without substantial conversion of the analyte.

Also provided herein is an isolated nucleic acid fragment, either DNA or RNA, that includes a sequence of nucleotides encoding a mutant S-adenosylhomocysteine (SAH) hydrolase, the mutant SAH hydrolase substantially retains its binding affinity or has enhanced binding affinity for homocysteine (Hcy) or SAH but has attenuated catalytic activity.

In one specific embodiment, the isolated nucleic acid fragment encodes a mutant SAH hydrolase wherein the attenuated catalytic activity is caused by mutation(s) in the mutant SAH hydrolase's binding site for $NAD^+$, or mutation (s) in the mutant SAH hydrolase's catalytic site or a combination thereof.

In another specific embodiment, the isolated nucleic acid fragment encodes a mutant SAH hydrolase wherein the mutant SAH hydrolase has attenuated 5'-hydrolytic activity but substantially retains its 3'-oxidative activity.

In still another specific embodiment, the isolated nucleic acid fragment encodes a mutant SAH hydrolase wherein the mutant SAH hydrolase irreversibly binds SAH.

In yet another specific embodiment, the isolated nucleic acid fragment encodes a mutant SAH hydrolase wherein the mutant SAH hydrolase has a Km for SAH that is about or less than 10.0 μM. Preferably, the isolated nucleic acid fragment encodes a mutant SAH hydrolase wherein the mutant SAH hydrolase has a Km for SAH that is about 1.0 μM or less than 1.0 μM.

In yet another specific embodiment, the isolated nucleic acid fragment encodes a mutant SAH hydrolase wherein the mutant SAH hydrolase has a Kcat for SAH that is about or less than 0.1 $S^{-1}$.

In yet another specific embodiment, the isolated nucleic acid fragment encodes a mutant SAH hydrolase wherein the mutant SAH hydrolase has one or more insertion, deletion or point mutation(s). Preferably, the isolated nucleic acid fragment encodes a mutant SAH hydrolase wherein the mutant SAH hydrolase is derived from a sequence of nucleotides set forth in SEQ ID No. 1 and has one or more mutation selected from of Phe302 to Ser (F302S), Lys186 to Ala (K186A), His301 to Asp (H301D), His353 to Ser (H353S), Arg343 to Ala (R343A), Asp190 to Ala (D190A), Phe82 to Ala (F82A), Thr157 to Leu (T157L), Cys195 to Asp (C195D), Asn181 to Asp (N181D), and deletion of Tyr432 (Δ432). Also more preferably, the isolated nucleic acid fragment encodes a mutant SAH hydrolase wherein the mutant SAH hydrolase is derived from a sequence of nucleotides set forth in SEQ ID No. 1 and has a combination of Arg431 to Ala (R431A) and Lys426 to Arg (K426R) mutations.

Further provided is a plasmid, including the nucleic acid fragment encoding the above mutant SAH hydrolases. Preferably, the plasmid is an expression vector including a sequence of nucleotides encoding: a) a promoter region; and b) a mutant S-adenosylhomocysteine (SAH) hydrolase, the mutant SAH hydrolase substantially retains its binding affinity or has enhanced binding affinity for homocysteine (Hcy) or SAH but has attenuated catalytic activity. The sequence of nucleotides encoding the mutant SAH hydrolase is operatively linked to the promoter, whereby the mutant SAH hydrolase is expressed. More preferably, the plasmid also includes a selectable marker.

Further provided is a recombinant host cell containing the above plasmid. The recombinant host cell can be any suitable host cell, including, but are not limited to, a bacterial cell, a yeast cell, a fungal cell, a plant cell, an insect cell or an animal cell.

Also provided are methods for producing a mutant SAH hydrolase. The recombinant host cells can be grown or cultured under conditions where by the mutant SAH hydrolase is expressed by the cell. The expressed mutant SAH hydrolase can then be isolated or recovered.

Additional mutant SAH hydrolase that substantially retains its binding affinity or has enhanced binding affinity for homocysteine (Hcy) or SAH, but has attenuated catalytic activity can be produced according to the procedures known to the those of skill in the art, include procedures exemplified herein (see, e.g., Section B). The above-described mutant SAH hydrolases and additional mutant SAH hydrolase that substantially retain binding affinity or have enhanced binding affinity for homocysteine (Hcy) or SAH but have attenuated catalytic activity can be used for assaying Hcy in a sample.

3. Hcy Assays Using Mutant SAH Hydrolase

Figure 2:
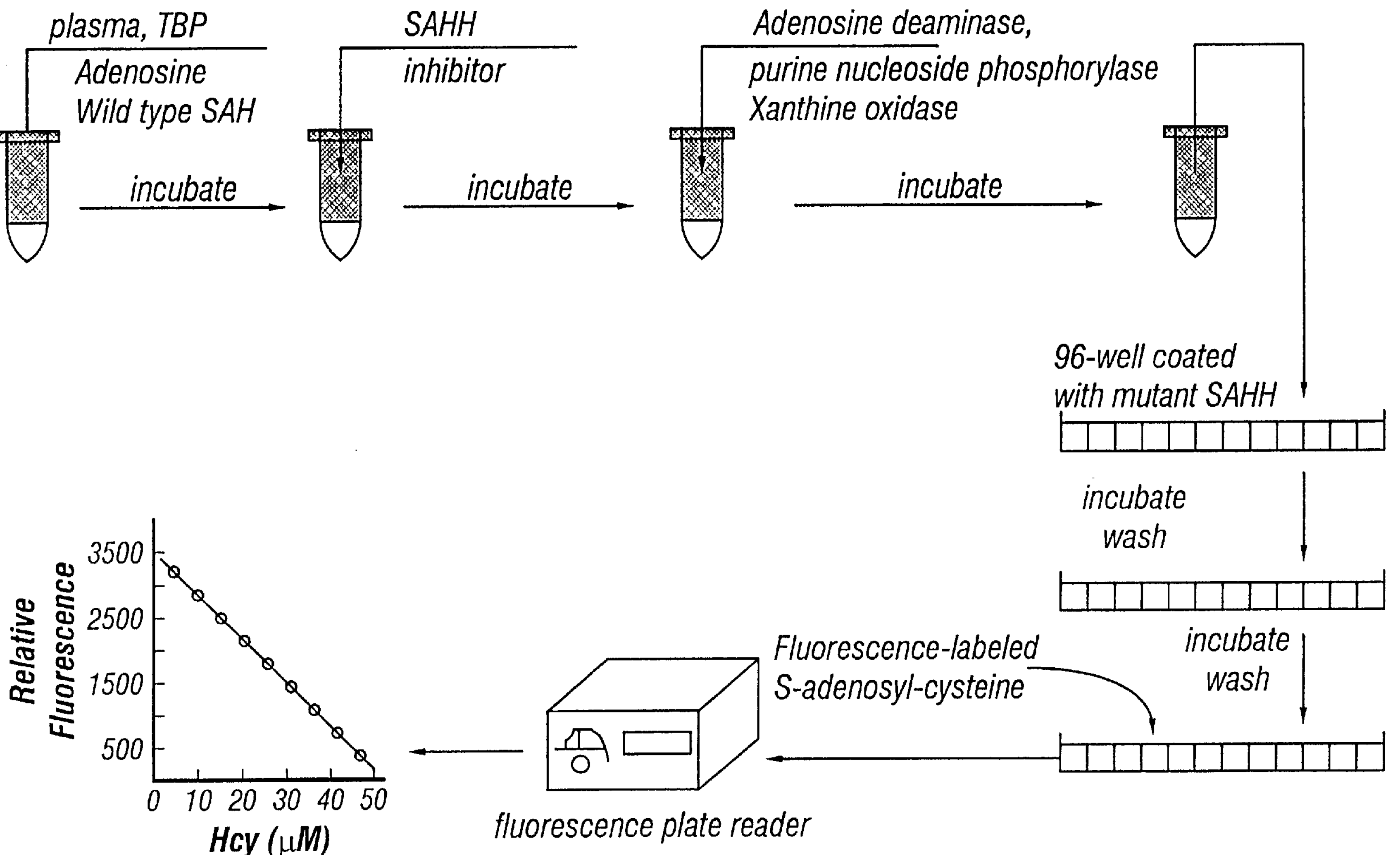
FIG. 2 depicts total plasma Hcy assay procedure with wild type and mutant SAH hydrolase.

In one specific embodiment, the mutant Hcy-binding enzyme used in the Hcy assay is a mutant SAH hydrolase, the mutant SAH hydrolase substantially retains its binding affinity or has enhanced binding affinity for homocysteine (Hcy) or SAH but has attenuated catalytic activity. This assay, described in detail in the EXAMPLES, is depicted in FIG. 1. In this Figure, the homocysteine-containing analyte is reduced to produce Hcy, which, is quantified or detected by binding it to a mutant (substrate trapping) SAH hydrolase; the Hcy is then converted to SAH by reaction with adenosine in the presence of wild type SAH hydrolase. As examplified in the Figure, instead of using a monoclonal antibody to effect quantitation (see, e.g., U.S. Pat. No. 5,885,767 and U.S. Pat. No. 5,631,127). Quantitation is effected using a fluorescence-labeled tracer S-adenosyl cytosine in a competition binding format in which the mutant SAH is used to trap the substrate. Any suitable quantitation assay with any suitable label can be used in the substate trapping method. FIG. 2 depicts an exemplary assay performed in a 96 well format; and FIG. 3 exemplifies preparation of labeling of adenosyl-cysteine with a fluorescent moiety.

In one preferred embodiment, the attenuated catalytic activity in the mutant SAH hydrolase is caused by mutation (s) in the mutant SAH hydrolase's binding site for $NAD^+$, or mutation(s) in the mutant SAH hydrolase's catalytic site or a combination thereof.

In another preferred embodiment, the mutant SAH hydrolase has attenuated 5'-hydrolytic activity but substantially retains its 3'-oxidative activity.

In another preferred embodiment, the mutant SAH hydrolase irreversibly binds SAH.

In still another preferred embodiment, the mutant SAH hydrolase has a Km for SAH that is about or less than 10.0

$\mu$M. More preferably, the mutant SAH hydrolase has a Km for SAH that is about 1.0 $\mu$M or less than 1.0$\mu$M.

In yet another preferred embodiment, the mutant SAH hydrolase has a Kcat for SAH that is about or less than 0.1 $S^{-1}$.

In yet another preferred embodiment, the mutant SAH hydrolase has one or more insertion, deletion or point mutation(s). More preferably, the mutant SAH hydrolase is derived from the sequence of amino acids set forth in SEQ ID No. 1 or encoded by the sequence of nucleotides set forth in SEQ ID No. 2 and has one or more of the following mutations: Phe302 to Ser (F302S), Lys186 to Ala (K186A), His301 to Asp (H301D), His353 to Ser (H353S), Arg343 to Ala (R343A), Asp190 to Ala (D190A), Phe82 to Ala (F82A), Thr157 to Leu (T157L), Cys195 to Asp (C195D), Asn181 to Asp (N181D), and deletion of Tyr432 (Δ432). Also more preferably, the mutant SAH hydrolase is derived from a sequence of amino acids set forth in SEQ ID No. 2 and has a combination of Arg431 to Ala (R431A) and Lys426 to Arg (K426R) mutations.

In yet another preferred embodiment, prior to the contact between the sample and the mutant SAH hydrolase, oxidized Hcy in the sample is converted into reduced Hcy. More preferably, the oxidized Hcy in the sample is converted into reduced Hcy by a reducing agent such as tri-n-butyphosphine (TBP), β-ME, DTT, dithioerythritol, thioglycolic acid, glutathione, tris(2-carbxyethyl)phosphine, sodium cyanoborohydride, $NaBH_4$, $KBH_4$ and free metals.

In yet another preferred embodiment, prior to the contact between the sample and the mutant SAH hydrolase, the Hcy in the sample is converted into SAH. More preferably, the Hcy in the sample is converted into SAH by a wild-type SAH hydrolase. Also more preferably, the SAH is contacted with the mutant SAH hydrolase in the presence of a SAH hydrolase catalysis inhibitor such as neplanocin A or thimersol.

In yet another preferred embodiment, prior to the contact between the SAH and the mutant SAH hydrolase, free adenosine is removed or degraded. More preferably, the free adenosine is degraded by combined effect of adenosine deaminase, purine nucleoside phosphorylase and xanthine oxidase.

Any adenosine deaminase can be used. Preferably, the adenosine deaminase encoded by the nucleic acids having the following GenBank accession Nos. can be used: AF051275 (*Caenorhabditis elegans*); Al573492 (mouse mammary gland); Al462267 (mouse mammary gland); Al429519 (mouse embryo); Al429513 (mouse embryo); Al326688 (*Mus musculus*); Al324114 (mouse placenta); Al322477 (mouse placenta); Al152550 (mouse uterus); U76422 (Human, SEQ ID No. 15; see also Lai et al., *Mol. Cell. Biol.*, 17(5):2413–24 (1997)); U76421 (Human); U76420 (Human); Al120695 (mouse mammary gland); Al049175 (*Mus musculus*); U73107 (*Mus musculus*); AF052506 (*Mus musculus*); AA871919 (Barstead bowel, *Mus musculus*); AA871917 (Barstead bowel, *Mus musculus*); AA871865 (Barstead bowel); AA871752 (Barstead bowel); AA871702 (Barstead bowel); AA871324 (Barstead bowel); AA871189 (Barstead bowel); AA869711 (*Mus musculus*); AA869187 (*Mus musculus*); AA869184 (*Mus musculus*); AA869176 (*Mus musculus*); AA869120 (*Mus musculus*); U75503 (Homo sapiens); AA646698 (mouse mammary gland); AA646681 (mouse mammary gland); AA427106 (mouse mammary gland); D50624 (*Streptomyces virginiae*); AA389303 (mouse embryo); AA389067 (mouse embryo); U88065 (*Xenopus laevis*); AA124740 (*Mus musculus*); U74586 (*Rattus norvegicus*); AA036487 (mouse placenta); AA035873 (mouse placenta); AA030290 (mouse placenta); AA023505 (mouse placenta); AA023331 (mouse placenta); AA111514 (mouse embryo); AA111327 (mouse embryo); AA110493 (mouse embryo); U73185 (*Mus musculus*); AA107590 (mouse embryo); AA102891 (mouse embryo); AA097525 (mouse embryo); AA096642 (mouse embryo); AA087094 (mouse embryo); AA060462 (mouse); U10439 (Human); M13792 (Human); U18942 (*Rattus norvegicus*); K02567 (Human); M10319 (Mouse); M59033 (*E. coli* adenosine). Preferably, the adenosine deaminase encoded by the nucleic acids having the following GenBank accession No. can be used: U76422 (Human, SEQ ID No. 15; see also Lai et al., *Mol. Cell. Biol.*, 17(5):2413–24 (1997)).

Any purine nucleoside phosphorylase can be used. Preferably, the purine nucleoside phosphorylase encoded by the nucleic acids having the following GenBank accession Nos. can be used: U88529 (*E. coli*); U24438 (*E. coli*, SEQ ID No. 17; see also Cornell and Riscoe, *Biochim. Biophys. Acta*, 1396(1):8–14 (1998)); U83703 (*H. pylori*); and M30469 (*E. coli*).

Any xanthine oxidase can be used. Preferably, the xanthine oxidase encoded by the nucleic acids having the following GenBank accession Nos. can be used: AF080548 (*Sinorhizobium meliloti*); and U39487 (Human, SEQ ID No. 19; see also Saksela and Raivio, *Biochem. J.*, 315(1):235–9 (1996)).

In yet another preferred embodiment, the sample containing or suspecting containing SAH is contacted with the mutant SAH hydrolase in the presence of a labelled SAH or a derivative or an analog thereof, whereby the amount of the labeled SAH bound to the mutant SAH hydrolase inversely relates to amount of the SAH in the sample. The SAH, or the derivative or analog thereof, can be labelled by methods known in the art, e.g., to become radioactive, enzymatic, fluorescent, luminescent (including chemo- or bioluminescent) labeled. More preferably, the labelled SAH derivative or analog is a fluorescence labelled adenosylcysteine.

In yet another preferred embodiment, the sample containing or suspected to be containing SAH is contacted with a labelled mutant SAH hydrolase. The mutant SAH hydrolase can be labelled by methods known in the art, e.g., to become radioactive, enzymatic, fluorescent, luminescent (including chemo- or bio-luminescent) labeled. More preferably, the mutant SAH hydrolase is fluorescently labelled. For example, a mutant SAH hydrolase derivided from an SAH hydrolase having sequence of amino acids encoded by the sequence of nucleotides set forth in SEQ ID No. 2 is used and the mutant SAH hydrolase is fluorescently labelled at residue Cys421.

D. METHODS FOR ASSAYING FOLATE SPECIES

Further provided herein is a method for assaying a folate species in a sample. This method includes at least the steps of: a) contacting the sample with a mutant folate-species-binding enzyme, which substantially retains its binding affinity or has enhanced binding affinity for the folate species but has attenuated catalytic activity; and b) detecting binding between the folate species with the mutant folate-species-binding enzyme.

Any mutant folate-species-binding enzymes that substantially retain their binding affinity or have enhanced binding affinity for the folate species but have attenuated catalytic activity can be used in the folate species assay. Examples of such mutant folate-species-binding enzymes include mutant methionine synthase, tetrahydrofolate methyltransferase, methylenetetrahydrofolate reductase, folypolyglutamate synthase, dihydrofolate reductase and thymidylate synthase.

Nucleic acids encoding folate-species-binding enzymes can be obtained by methods known in the art. Where the molecules are available or the sequence known, they can be obtained from publicly available sources. Known nucleic acid sequences of folate-species-binding enzymes, such as methionine synthase, tetrahydrofolate methyltransferase, methylenetetrahydrofolate reductase, folypolyglutamate synthase, dihydrofolate reductase and thymidylate synthase, can be used in isolating nucleic acids encoding folate-species-binding enzymes from natural sources. Alternatively, nucleic acids encoding folate-species-binding enzymes can be obtained by chemical synthesis according to the known sequences.

In specific embodiment, the nucleotide sequences with the following GenBank accession Nos. can be used in obtaining nucleic acid encoding methionine synthase: Al547373 (*Mesembryanthemum crystallinum*); Al507856 (COBALAMINE-INDEPENDENT METHIONINE SYNTHASE); Al496185 (COBALAMINE-INDEPENDENT METHIONINE SYNTHASE); Al496016 (COBALAMINE-INDEPENDENT METHIONINE SYNTHASE); Al495904 (COBALAMINE-INDEPENDENT METHIONINE SYNTHASE); Al495702; Al495399; Al461276 (COBALAMINE-INDEPENDENT METHIONINE SYNTHASE); Al460827 (COBALAMINE-INDEPENDENT METHIONINE SYNTHASE); Al460549; Al443293; Al443243 (COBALAMINE-INDEPENDENT METHIONINE SYNTHASE); Al443242 (COBALAMINE-INDEPENDENT METHIONINE SYNTHASE); Al442736 (COBALAMINE-INDEPENDENT METHIONINE SYNTHASE); Al442546; Al442173 (COBALAMINE-INDEPENDENT METHIONINE SYNTHASE); Al442136 (COBALAMINE-INDEPENDENT METHIONINE SYNTHASE); Al441314; Al440982; Al438053; Al416939 (COBALAMINE-INDEPENDENT METHIONINE SYNTHASE); Al416601; Al391967 (*Conidial Neurospora crassa*); AF034214 (*Rattus norvegicus*); U77388 (*Chlamydomonas moewusii*); AF093539 (*Zea mays*); U97200 (*Arabidopsis thaliana*); U36197 (*Chlamydomonas reinhardtii*); AF025794 (Homo sapiens); AJ222785 (*Hordeum vulgare*); Z49150 (*C. blumei kinetoplast met* gene); AB004651 (*Hyphomicrobium methylovorum* gene); AA661438 (Maize Leaf); AA661023 (*Medicago truncatula*); AA660965 (*Medicago truncatula*); AA660880 (*Medicago truncatula*); AA660780 (*Medicago truncatula*); AA660708 (*Medicago truncatula*); AA660643 (*Medicago truncatula*); AA660558 (*Medicago truncatula*); AA660475 (*Medicago truncatula*); AA660444 (*Medicago truncatula*); AA660382 (*Medicago truncatula*); AA660310 (*Medicago truncatula*); AA660241 (*Medicago truncatula*); U75743 (Human); AA389835 (*Arabidopsis thaliana*); U84889 (*Mesembryanthemum crystallinum*); U73338 (Human); AA054818 (Maize Leaf); AA030695 (Maize Leaf); X83499 (*C. roseus*); U15099 (*Saccharomyces cerevisiae* (MET6)); J02804 (*E. coli* speED operon speE and speD genes); M87625 (*Escherichia coli*); J04975 (*E. coli*). Preferably, the nucleotide sequences with the GenBank accession Nos. U75743 (SEQ ID No. 4) and U73338 (SEQ ID No. 6) can be used for in obtaining nucleic acid encoding methionine synthase.

In another embodiment, the nucleotide sequences with the following GenBank accession Nos. can be used in obtaining nucleic acid encoding tetrahydrofolate methyltransferase: Z99115 (SEQ ID No. 21; see also Kunst et al., *Nature*, 390(6657):249–56 (1997)).

In still another specific embodiment, the nucleotide sequences with the following GenBank accession Nos. can be used in obtaining nucleic acid encoding methylenetetrahydrofolate reductase: AJ237672 (Homo sapiens); AH007491 (*Mus musculus*); AF105998 (*Mus musculus*); AF105997 (*Mus musculus*); AF105996 (*Mus musculus*); AF105995 (*Mus musculus*); AF105994 (*Mus musculus*); AF105993 (*Mus musculus*); AF105992 (*Mus musculus*); AF105991 (*Mus musculus*); AF105990 (*Mus musculus*); AF105989 (*Mus musculus*); AF105988 (*Mus musculus*); AF102543 (*Zymomonas mobilis*); AH007464 (Homo sapiens complete CDs); AF105987 (Homo sapiens); AF105986 (Homo sapiens); AF105985 (Homo sapiens); AF105984 (Homo sapiens); AF105983 (Homo sapiens); AF105982 (Homo sapiens); AF105981 (Homo sapiens); AF105980 (Homo sapiens); AF105979 (Homo sapiens); AF105978 (Homo sapiens); AF105977 (Homo sapiens); Al327505 (mouse); U74302 (*Erwinia carotovora*); AA660667 (*Medicago truncatula*); W11807 (mouse); AA368389 (Placenta I Homo sapiens); AA363389 (Ovary I Homo sapiens); U57049 (*Rattus norvegicus*); X07689 (*X. typhimurium*); and U09806 (Human). Preferably, the nucleotide sequences with the GenBank accession No. AH007464 can be used in obtaining nucleic acid encoding methylenetetrahydrofolate reductase (SEQ ID No. 23; see also Goyette et al., *Mamm. Genome*., 9(8):652–6 (1998)).

In yet another specific embodiment, the nucleotide sequences with the following GenBank accession Nos. can be used in obtaining nucleic acid encoding folypolyglutamate synthase: AL031852 (*S. pombe*); and M32445 (*E. coli*). Preferably, the nucleotide sequences with the GenBank accession No. M32445 can be used in obtaining nucleic acid encoding folypolyglutamate synthase (SEQ ID No. 25; see also Bognar et al., *J. Biol. Chem*., 262(25):12337–43 (1987)).

In yet another specific embodiment, the nucleotide sequences with the following GenBank accession Nos. can be used in obtaining nucleic acid encoding dihydrofolate reductase: AF083501 (*Macaca mulatta rhadinovirus*); AF028812 (*Enterococcus faecalis*); U83347 (Kaposi's sarcoma-associated herpesvirus); U41366 (*Cryptosporidium parvum*); U03885 (*Paramecium tetraurelia*); AF006616 (*Mycobacterium avium*); U71365 (Kaposi's sarcoma-associated herpes-like virus fragment I); AF055727 (*Streptococcus pneumoniae* strain R6); AF055726 (*Streptococcus pneumoniae* strain AP183); AF055725 (*Streptococcus pneumoniae* strain AP13); AF055724 (*Streptococcus pneumoniae* strain AP173); AF055723 (*Streptococcus pneumoniae* strain AP92); AF055722 (*Streptococcus pneumoniae* strain AP71); AF055721 (*Streptococcus pneumoniae* strain AP188); AF055720 (*Streptococcus pneumoniae* strain AP48); AF077008 (*Salmonella typhimurium* plasmid plE1142); AF073488 (*Zea mays*); M12742 (Coliphage T4); U84588 (*Candida albicans*); U12275 (*Plasmodium berghei* ANKA); U12338 (*Pseudomonas aeruginosa*); M18578 (*S. cerevisiae*); J03772 (*Plasmodium falciparum*); L22484 (*Trypanosoma cruzi*); U09476 (Synthetic construct Tn7 (dhfr) gene); U31119 (*Escherichia coli* plasmid pDGO100); L08489 (*Toxoplasma gondii*); M69220 (*E. coli* plasmid pDGO100); L17041 (Synthetic construct); U40997 (*Listeria monocytogenes*); U20781 (*Trypanosoma brucei*); J01609 (*E. coli*); U43152 (*Listeria monocytogenes*); U36276 (Escherichia); U09273 (*Shigella sonnei*); M55264 (*Herpesvirus saimiri*); M20407 (Synthetic mini type II); J05088 (*H. volcanii*); U10186 (*Escherichia coli*); M28071 (*Herpesvirus saimiri*); U12338 (*Pseudomonas aeruginosa* plasmid R1033); M18578 (*S. cerevisiae*); J03772 (*Plasmodium falciparum* (clone HB3)); L22484 (*Trypanosoma cruzi*); U09476 (Synthetic construct); U31119 (*Escherichia coli* plasmid pDGO100); L08489 (*Toxoplasma gondii*); M69220 (*E. coli* plasmid pDGO100); L17041 (Synthetic construct); U40997 (*Listeria monocytogenes*); U20781 (*Trypanosoma brucei*); J01609 (*E. coli*); U43152 (*Listeria monocytogenes*); U36276 (*Escherichia coli*); U09273 (*Shigella sonnei*); M55264 (*Herpesvirus saimiri*); M20407 (Synthetic mini type II); J05088 (*H. volcanii*); U10186 (*Escherichia coli*); M28071 (*Herpesvirus saimiri*); M19237 (*Herpesvirus saimiri*); L26316 (*Mus musculus*); L15311 (Cricetulus sp.); M37124 (Chinese hamster); M19869 (Chinese hamster); M26668 (*Saccharomyces cerevisiae*); M26496 (*Pneumocystis carinii*); M26495 (*P. carinii*); L08594 (*Arabidopsis thaliana*); L08593 (*Arabidopsis thaliana*); K01804 (Bacteriophage T4); M22852 (*C. fasciculata*); M30834 (*P. chabaudi*); J04643 (*P. falciparum*); J03028 (*P. falciparum*); M22159 (*P. falciparum*); M14330 (*L. tropica*); M12734 (Leishmania); K02118 (Plasmid R67 from *E. coli*); J03306 (Plasmid pAZ1 type III); M10922 (*Lactobacillus casei*); M26022 (*Enterobacter aerogenes*); M84522 (*Escherichia coli*); M26023 (*Citrobacter freundii*); and U06861 (*Drosophila melanogaster*). Preferably, the nucleotide sequences with the GenBank accession No. M37124 can be used in obtaining nucleic acid encoding dihydrofolate reductase (SEQ ID No. 27; see also Dicker et al., *J. Biol. Chem.*, 265(14):8317–21 (1990)).

In yet another specific embodiment, the nucleotide sequences with the following GenBank accession Nos. can be used in obtaining nucleic acid encoding thymidylate synthase: AF083501 (*Macaca mulatta rhadinovirus*, thymidylate synthase); AF059506 (*chilo iridescent* virus); Al531067 (*Drosophila melanogaster* Schneider L2 cell); Al515689 (LD *Drosophila melanogaster* embryo; Al514354 (*Drosophila melanogaster* embryo; AB023402 (*Oryza sativa* thyA); Al406263 (*Drosophila melanogaster* head; Al390061 (*Drosophila melanogaster* head; AF099673 (*Caenorhabditis elegans*); AF099672 (*Ascaris suum*); Al297939 (*Drosophila melanogaster* larval-early pupal); Al293665 (*Drosophila melanogaster* larval-early pupal); Al136006 (*Drosophila melanogaster* head); Al258021 (*Drosophila melanogaster* larval-early pupal); D00596 (Homo sapiens); AF029302 (*Rhesus monkey rhadinovirus*); U83348 (Kaposi's sarcoma-associated herpesvirus); U69259 (Synthetic *Plasmodium falciparum*); U12256 (*Filobasidiella neoformans*); U41366 (*Cryptosporidium parvum*); U03885 (*Paramecium tetraurelia*); U86637 (*Neisseria gonorrhoeae*); U71365 (Kaposi's sarcoma-associated herpes-like virus); AF073994 (*Drosophila melanogaster*); AF073488 (*Zea mays*); M12742 (Coliphage T4); U12275 (*Plasmodium berghei* ANKA); J03772 (*Plasmodium falciparum* (clone HB3); L22484 (*Trypanosoma cruzi*); L08489 (*Toxoplasma gondii*); L12138 (Rattus); U20781 (*Trypanosoma brucei*); M29019 (Synthetic Lactobacillus); L31962 (Bacteriophage beta-22); M13190 (*Herpesvirus saimiri*); M14080 (*Herpesvirus saimiri*); M22036 (*Herpesvirus ateles*); M13019 (Mouse); M30774 (Mouse); J04230 (*C. albicans*); L08594 (*Arabidopsis thaliana*); L08593 (*Arabidopsis thaliana*); K01804 (Bacteriophage T4); M30834 (*P. chabaudi*); J04643 (*P. falciparum*); J03028 (*P. falciparum*); M14330 (*L. tropica*); M12734 (Leishmania); M19653 (*L. casei* (thyA)); and M33770 (*L. lactis* (thyA)). Preferably, the nucleotide sequences with the GenBank accession No. D00596 can be used in obtaining nucleic acid encoding thymidylate synthase (SEQ ID No. 29; see also Kaneda et al., *J. Biol. Chem.*, 265(33):20277–84 (1990)).

Once nucleic acids encoding folate-species-binding enzymes are obtained, these nucleic acids can be mutagenized and screened and/or selected for folate-species-binding enzymes that substantially retain their binding affinity or have enhanced binding affinity for the folate species but have attenuated catalytic activity. Insertional, deletional or point mutation(s) can be introduced into nucleic acids encoding folate-species-binding enzymes according to the methods described in Section B.

Information regrading the structural-function relationship of the folate-species-binding enzymes can be used in the mutagenesis and selection of the folate-species-binding enzymes that substantially retain their binding affinity or have enhanced binding affinity for the folate species but have attenuated catalytic activity. For example, mutants can be made in the enzyme's binding site for its co-enzyme, co-factor, a non-folate-species substrate, or in the mutant enzyme's catalytic site, or a combination thereof.

In one specific embodiment, the folate species is 5,-methyltetrahydrofolate, the mutant folate-species-binding enzyme is a mutant methionine synthase, and the attenuated catalytic activity of the mutant methionine synthase is caused by mutation in its catalytic site, its binding site for vitamin $B_{12}$, Hcy, or a combination thereof.

In another specific embodiment, the folate species is tetrahydrofolate, the mutant folate-species-binding enzyme is a mutant tetrahydrofolate methyltransferase, and the attenuated catalytic activity of the mutant tetrahydrofolate methyltransferase is caused by mutation in its catalytic site, its binding site for serine, or a combination thereof.

In still another specific embodiment, the folate species is 5,10,-methylene tetrahydrofolate, the mutant folate-species-binding enzyme is a mutant methylenetetrahydrofolate reductase, and the attenuated catalytic activity of the methylenetetrahydrofolate reductase is caused by mutation in its catalytic site.

In yet another specific embodiment, the folate species is 5,10,-methylene tetrahydrofolate, the mutant folate-species-binding enzyme is a mutant folypolyglutamate synthase, and the attenuated catalytic activity of the folypolyglutamate synthase is caused by mutation in its catalytic site, its binding site for ATP, L-glutamate, $Mg^{2+}$, a combination thereof. ln yet another specific embodiment, the folate species is dihydrofolate, the mutant folate-species-binding enzyme is a mutant dihydrofolate reductase, and the attenuated catalytic activity of the mutant dihydrofolate reductase is caused by mutation in its catalytic site, its binding site for NADPH, or a combination thereof. Preferably, the mutant dihydrofolate reductase is a *Lactobacillus casei* dihydrofolate reductase having an Arg43Ala or Trp21His mutation (Basran et al., *Protein Eng*., 10(7):815–26 91997)).

In yet another specific embodiment, the folate species is 5,10,-methylene tetrahydrofolate, the mutant folate-species-binding enzyme is a mutant thymidylate synthase, and the attenuated catalytic activity of the mutant thymidylate synthase is caused by mutation in its catalytic site, its binding site for dUMP, or a combination thereof. Preferably, the mutant thymidylate synthase is a human thymidylate synthase having a mutation selected from Tyr6His, Glu214Ser, Ser216Ala, Ser216Leu, Asn229Ala and His199X, X being any amino acid that is not His (Schiffer et al., *Biochemistry*, 34(50):16279–87 (1995); Steadman et al., *Biochemistry*, 37:7089–7095 (1998); Williams et al., *Biochemistry*, 37(20):7096–102 (1998); Finer-Moore et al., *J. Mol. Biol*., 276(1):113–29 (1998); and Finer-Moore et al., *Biochemistry*, 35(16):5125–36 (1996)). Also more preferably, the mutant thymidylate synthase is an *E. coli* thymidylate synthase having an Arg126Glu mutation (Strop et al., *Protein Sci.*, 6(12):2504–11 (1997)) or a *Lactobacillus casei* thymidylate synthase having a V316Am mutation (Carreras et al., *Biochemistry*, 31 (26):6038–44 (1992)).

Once a mutant folate-species-binding enzyme with desired properties, i.e., substantially retaining its binding affinity or having enhanced binding affinity for the folate species but has attenuated catalytic activity, is identified, such mutant folate-species-binding enzyme can be produced by any methods known in the art including recombinant expression, chemical synthesis or a combination thereof as described in Section B. Preferably, the mutant folate-species-binding enzyme is obtained by recombinant expression.

E. METHODS FOR ASSAYING CHOLESTEROL

Further provided herein is a method for assaying cholesterol in a sample. This method includes at least the steps of: a) contacting the sample with a mutant cholesterol-binding enzyme, the mutant enzyme substantially retains its binding affinity or has enhanced binding affinity for cholesterol but has attenuated catalytic activity; and b) detecting binding between cholesterol with the mutant cholesterol-binding enzyme.

Any mutant cholesterol-binding enzymes that substantially retain their binding affinity or have enhanced binding affinity for cholesterol but have attenuated catalytic activity can be used in the cholesterol assay. Examples of such mutant cholesterol-binding enzyme include mutant cholesterol esterase and cholesterol oxidase.

Cholesterol-binding Enzymes

Nucleic acids encoding cholesterol-binding enzymes can be obtained by methods known in the art or obtained from public or commerical sources. Known nucleic acid sequences of cholesterol-binding enzymes, such as cholesterol esterase and cholesterol oxidase, can be used in isolating nucleic acids encoding cholesterol-binding enzymes from natural sources. Alternatively, nucleic acids encoding cholesterol-binding enzymes can be obtained by chemical synthesis according to the known sequences.

In one embodiment, the nucleotide sequences with the following GenBank accession Nos. can be used in obtaining nucleic acid encoding cholesterol esterase: Al558069 (Mouse mammary gland); Al465062 (Mouse mammary gland); AA793597 (Mouse diaphragm); AA762311 (Mouse mammary gland); AA759540 (Mouse mammary gland); AA672047 (Mouse mammary gland); AA571290 (Mouse diaphragm); AA537778 (Mouse diaphragm); AA265434 (Mouse); M69157 (Rat pancreatic); U33169 (*Mus musculus*); L46791 (*Rattus norvegicus*); M85201 (Human). Preferably, the nucleotide sequences with the GenBank accession Nos. M85201 (SEQ ID No. 31), nucleotide sequences described in U.S. Pat. No. 5,624,836 (bovine pancreatic cholesterol esterase; SEQ ID No. 33) can be used in obtaining nucleic acid encoding cholesterol esterase.

In another specific embodiment, the nucleotide sequences with the following GenBank accession Nos. can be used in obtaining nucleic acid encoding cholesterol oxidase: E07692; E07691; E03850 (*Brevibacterium sterolicum*); E03828; E03827; D00712 (*B. sterolicum* choB gene); U13981 (Streptomyces A19249 choM gene); and M31939 (Streptomyces A19249 choP gene). Preferably, the nucleotide sequences with the GenBank accession No. U13981 (SEQ ID No. 35; see also Corbin et al., *Appl. Environ. Microbiol.*, 60(12):4239–44 (1994)) and the nucleotide sequence described in U.S. Pat. No. 5,665,560 (SEQ ID No. 37) can be used in obtaining nucleic acid encoding cholesterol oxidase.

Once nucleic acids encoding cholesterol-binding enzymes are obtained, these nucleic acids can be mutagenized and screened and/or selected for cholesterol-binding enzymes that substantially retain their binding affinity or have enhanced binding affinity for cholesterol but have attenuated catalytic activity. Insertion, deletion or point mutation(s) can be introduced into nucleic acids encoding cholesterol-species-binding enzymes according to the methods described in Section B.

Information regrading the structural-function relationship of the cholesterol-binding enzymes can be used in the mutagenesis and selection of the cholesterol-binding enzymes that substantially retain their binding affinity or have enhanced binding affinity for cholesterol but have attenuated catalytic activity. For example, mutants can be made in the enzyme's binding site for its co-enzyme, co-factor, a non-cholesterol substrate, or in the mutant enzyme's catalytic site, or a combination thereof.

In one specific embodiment, the mutant cholesterol-binding enzyme is a mutant cholesterol esterase, and the attenuated catalytic activity of the mutant cholesterol esterase is caused by mutation in its catalytic site, its binding site for $H_2O$ or a combination thereof. Preferably, the cholesterol esterase is a pancreatic cholesterol esterase having a Ser 194Thr or Ser194Ala mutation (DiPersio et al., *J. Biol. Chem.*, 265(28):16801–6 (1990)).

In another specific embodiment, the mutant cholesterol-binding enzyme is a mutant cholesterol oxidase, and the attenuated catalytic activity of the mutant cholesterol oxidase is caused by mutation in its catalytic site, its binding site for $O_2$ or a combination thereof. Preferably, the cholesterol oxidase is a *Brevibacterium sterolicum* cholesterol oxidase having a His447Asn or His447Gln mutation (Yue et al., *Biochemistry*, 38(14):4277–86 (1999)).

Once a mutant cholesterol-binding enzyme with desired properties, i.e., substantially retaining its binding affinity or having enhanced binding affinity for the cholesterol but has attenuated catalytic activity, is identified, such mutant cholesterol-binding enzyme can be produced by any methods known in the art including recombinant expression, chemical synthesis or a combination thereof as described in Section B. Preferably, the mutant cholesterol-binding enzyme is obtained by recombinant expression.

F. HCY ASSAYS IN CONJUNCTION WITH CHOLESTEROL AND/OR FOLIC ACID ASSAY

The Hcy assays described in Section C can be conducted in conjunction with a cholesterol and/or a folic acid assay.

1. Cholesterol Assay

Cholesterol assay can be conducted according to any methods known in the art. For example, the Hcy assays described in Section C can be conducted in conjunction with cholesterol assays described in Section E. In addition, the Hcy assays can be conducted in conjunction with cholesterol assays described in U.S. Pat. Nos. 4,161,425, 4,164,448, 4,188,188, 4,211,531, 5,034,332, 5,047,327, 5,217,873 and 5,593,894.

U.S. Pat. No. 4,161,425 describes cholesterol assay enzymatic reagents for rate determination of cholesterol in a sample to be assayed. The reagents contain cholesterol oxidase, and a buffering agent in an amount to produce a solution having a pH of between about 5.5 and about 8. The reagent acts by neutralizing substantially all oxygen consumption inhibiting effects of inhibiting effects present in the sample to be assayed, such as an alkyldimethylbenzylammonium salt in an amount sufficient to neutralize substantially all oxygen consumption inhibiting effects of inhibiting agents present in the sample to be assayed. U.S. Pat. No. 4,161,425 also describes methods for determining the cholesterol concentration in a cholesterol containing sample by: (a) oxidizing the cholesterol present in the sample in an oxygen saturated aqueous solution by means of a cholesterol assay enzymatic reagent; (b) generating a first electrical signal related to the oxygen concentration; (c) differentiating the first electrical signal to produce an output signal proportional to the instantaneous time rate of change of oxygen concentration; and (d) measuring the output signal to determine the cholesterol concentration. In this method substantially all oxygen consumption inhibiting effects of inhibiting agents in the sample to be assayed are neutralized by including in the cholesterol assay enzymatic reagent a cationic surfactant in an amount sufficient to neutralize substantially all oxygen consumption inhibiting effects of inhibiting agents present in the sample to be assayed, preferably, from about 0.01 to about 0.4 percent by weight of the reagent of a cationic surfactant. The enzymatic agent is cholesterol oxidase and a buffering agent in an amount to produce a solution having a pH of between 5.5 and about 8; in the presence of a sensor which serves to monitor a property or characteristic of oxygen in the solution related to the oxygen concentration thereof;

U.S. Pat. No. 4,164,448 describes diagnostic agents in solid form for the detection and determination of cholesterol and cholesterol esters in body fluids. The agents include a solid carrier having impregnated or embedded therein cholesterol oxidase, a system for the detection of hydrogen peroxide, buffer and from 2 to 30%, based on the total solid diagnostic agent of at least one surface-active compound with lipophilic and hydrophilic properties. U.S. Pat. No. 4,164,448 also describes processes for the activation of analytically pure, detergent-free, storage-stable cholesterol oxidase, recovered from a micro-organism by extraction with a surfactant, for the analytic determination of cholesterol. The processes include removing all traces of the surfactant from the cholesterol oxidase to produce a surfactant-free cholesterol oxidase and then adding to an aqueous solution of the surfactant-free cholesterol oxidase between 0.005% to 0.1% by weight, based on the weight of the aqueous cholesterol oxidase solution, of at least one surface-active compound with lipophilic and hydrophilic properties before use of the cholesterol oxidase.

U.S. Pat. No. 4,188,188 describes compositions for use in a HDL cholesterol separation. The compositions contain heparin, a divalent cation salt having the formula: $CX_2$, where C is selected from Group IIA metals and manganese and X is a halogen, and an inert filler that includes a polysaccharide, a terminal interlocking linear glucose polymer and a vinylpyrrolidone polymer. This patent also describes high density lipoprotein cholesterol assays utilizing heparin/$MnCl_2$ precipitation. In these assays the the serum sample to be assayed is added to a reagent composition as described above. The resulting supernatant is assayed for cholesterol.

U.S. Pat. No. 4,211,531 describes methods of determining cholesterol in a biological sample. The methods include a precipitation step for precipitating protein in the sample, a color forming step for forming in the resulting supernatant a color proportional to the concentration of at least one form of cholesterol in the sample, and a step of determining the depth of color formed. The precipitation step is carried out by means of a reagent that contains colorimetric amounts of propionic acid and ferric ion. U.S. Pat. No. 4,211,531 also describes methods of determining cholesterol in a biological sample using a color forming step in which a reaction mixture including at least a fraction of the serum and a color forming reagent is formed. The depth of color formed is related to the amount of at least one form of cholesterol in the reaction mixture. In these assays, the reaction mixture contains a colorimetric amount of sulfuric acid and propionic acid. U.S. Pat. No. 4,211,531 also describes methods of determining cholesterol in a sample of human serum, by first precipitating protein in the sample by means of a protein precipitation reagent that contains colorimetric amounts of propionic acid and ferric ion to produce a generally protein-free supernatant. Color is then developed in a reaction mixture containing the supernatant and a cholesterol color reagent, which contains colorimetric amounts of propionic acid and sulfuric acid. The depth of color formed is related to the amount of cholesterol in the sample. U.S. Pat. No. 4,211,531 also provides reagent kits for determination of total cholesterol, which include a first container containing a colorimetric amount of ferric chloride and propionic acid and a second container containing a reagent that contains colorimetric amount of propionic acid and sulfuric acid.

U.S. Pat. No. 5,034,332 describes assays for the presence of HDL cholesterol in a blood plasma sample. This method includes the steps of: mixing the sample with a proteinaceous material that is also present in protein H of boar vesicle seminal plasma so as to cause a precipitation of HDL cholesterol bound to the proteinaceous material; and measuring either the amount of cholesterol in a supernatant formed by the mixing step, or the amount of precipitant formed in the mixing step.

U.S. Pat. No. 5,217,873 describes stable cholesterol assay compositions that contain: (a) at least one acidic compound selected from a bile acid and a salt of a bile acid, the total of the acid compound being present in an amount of up to about 5 mM; (b) a nonionic surfactant present in a concentration of from about 0.15 to about 1.5 percent volume by volume; (c) a buffer in a concentration of from 0 to about v (d) cholesterol oxidase in a concentration of at least about 0.02 KIU/I; (e) cholesterol esterase present in a concentration of at least about 0.07 KIU/I; and (f) a chromogen system for determination of hydrogen peroxide, the cholesterol assay solution having a pH of from about 5.5 to about 7.5 and a completion time of less than 10 minutes at 37° C. U.S. Pat. No. 5,217,873 also describes stable total cholesterol chromogen assay compositions containing an aqueous solution have a pH of from about 6.5 to about 7.5 and (a) phenol in a concentration of from about 8 to about 35 mM; (b) a metal salt of cholic acid present in a concentration of from about 0.2 to about 5 mM; (c) a nonionic surfactant present in a concentration of from about 0.2 to about 1.5 percent volume by volume; (d) a phosphate buffer present in a concentration of from about 0.5 to about 30 mM and sufficient to maintain a pH of from about 6 to about 7.5; (e) 4-aminoantipyrine in a concentration up to about 0.3 mM; (f) cholesterol esterase present in a concentration of at least about 0.07 KIU/I; (g) cholesterol oxidase present in a concentration of at least about 0.02 KIU/I; and (h) peroxidase, the amount of peroxidase and 4-aminoantipyrine being sufficient to enable quantitative determination of the amount of hydrogen peroxide formed from oxidation of cholesterol within 10 minutes at 37° C. U.S. Pat. No. 5,217,873 further describes stable total cholesterol chromogen assay compositions containing an aqueous solution of: a) phenol in a concentration of about 17 mM; b) 2,4dichlorophenol present in a concentration of about 0.5 mM; c) a metal salt of cholic acid present in a concentration of up to about 5 mM; d) polyethylene glycol p-isooctylphenyl ether present in a concentration of from about 0.2 to about 0.6 percent volume by volume; e) $KH_2PO_4$ present in a concentration of about 12.5 mM; f) peroxidase present in a concentration of about 30 KIU/I; g)

cholesterol oxidase present in a concentration of at least about 0.05 KIU/I; h) microbial cholesterol esterase present in a concentration of at least about 0.1 KIU/I; and i) 4-aminoantipyrene present in concentration of about 0.3 mM, the stable total cholesterol chromogen assay composition having a pH of from about 6.0 to about 7.5.

U.S. Pat. No. 5,593,894 describes methods for forming a spectrophotometrically active product of cholesterol, such as HDL-C, LDL-C and VLDL-C. The method includes contacting cholesterol with an acyl compound and a perchlorate effective to form a spectrophotometrically active product of the cholesterol, the perchlorate selected from zinc perchlorate, barium perchlorate and perchloric acid. U.S. Pat. No. 5,593,894 also describes methods for determining the amount of cholesterol present in a test sample by contacting a test sample in which cholesterol is present with an acyl compound and a perchlorate effective to form a spectrophotometrically active product with the cholesterol, the perchlorate selected from zinc perchlorate, barium perchlorate and perchloric acid, and evaluating the spectrophotometric activity to determine the amount of the cholesterol present in the sample.

U.S. Pat. No. 5,047,327 describes stable cholesterol assay compositions. These compositions contain a polyhydroxy compound free aqueous solution of: (a) at least one acidic compound selected from a bile acid and a salt of a bile acid, the total of the acidic compound being present in a positive amount of up to about 5 mM; (b) a nonionic surfactant present in a concentration of from about 0.15 to about 1.5 percent volume by volume; (c) a buffer in a concentration of from 0 to about 65 mM; (d) cholesterol oxidase in a concentration of at least about 0.02 KIU/I, (e) microbial cholesterol esterase in a concentration of at least about 0.07 KIU/I; and (f) a chromogen system for determining of hydrogen peroxide; the cholesterol assay solution having a pH of from about 5.5 to about 8.5 a stability of at least 3 days at 41° C. and an essay completion time within 10 minutes at 37° C. U.S. Pat. No. 5,047,327 also describes stable total cholesterol chromagen assay compositions. These compositions are aqueous solutions having a pH of from about 6.5 to about 7.5 and (a) phenol in a concentration of from about 8 to about 35 mM; (b) sodium cholate present in a concentration of from about 0.2 to about 5 mM; (c) a nonionic surfactant present in a concentration of from about 0.15 to about 1.5 percent volume by volume; (d) a buffer present in a concentration of from 0.5 to about 65 mM; (e) 4-aminoantipyrine; (f) microbial cholesterol esterase present in a concentration of at least about 0.07 KIU/I; (g) cholesterol oxidase present in a concentration of at least about 0.02 KIU/I; and (h) peroxidase, the amount of peridase and 4-aminoantipyrine being sufficient to enable quantitative determination of the amount of hydrogen peroxide formed from oxidation of cholesterol within 10 minutes at 37. degree. C., the assay composition having a stability of at least 3 days at 41° C.

2. Folic Acid Assay

Folic acid assay can be conducted according to any methods known in the art. For example, the Hcy assays described in Section C can be conducted in conjunction with folic acid assays described in Section D. In addition, the Hcy assays can be conducted in conjunction with cholesterol assays described in U.S. Pat. Nos. 4,276,280, 4,336,185, 4,337,339, 5,374,560 and 5,800,979.

U.S. Pat. No. 4,276,280 describes derivatives of folic acid wherein the α-carboxyl group of the glutamyl moiety is substituted with a radical which is capable of being radioiodinated, such as, substituted and unsubstituted tyrosyl and histidyl. The radioiodinated derivatives can be employed as tracers for the assay of folates.

U.S. Pat. No. 4,336,185 describes protein conjugates and iodinated conjugates of folic acid and its salts, esters and amides which retain the ability to competitively bind on a binding protein, such as folic acid binding globulin or on an antibody which is specific to folic acid. The compounds are useful in analysis of body fluids such as blood serum, blood plasma, urine and the like, to assay for the presence of folic acid by competitive protein binding assay (CPSA) or by radioimmunoassay (RIA) procedures.

U.S. Pat. No. 4,337,339 describes that folic acid derivatives, such as radiolabeled pteroyltyrosine, are conveniently synthesized from either pteroic acid or by the direct condensation of 6-formylpterin with p-aminobenzoyltyrosine methyl ester. The radioiodinated derivatives are particularly useful in competitive protein binding and radioimmuno-assays of folate compounds.

U.S. Pat. No. 5,374,560 describes methods for detecting a deficiency of cobalamin or folic acid in warm-blooded animals, by: assaying a body fluid for an elevated level of cystathionine; and correlating an elevated level of cystathionine in the body fluid with a likelihood of a deficiency of cobalamin or folic acid. U.S. Pat. No. 5,374,560 also describes methods for detecting a deficiency of cobalamin in warm-blooded animals, by: assaying a body fluid for an elevated level of 2-methylcitric acid I or 2-methylcitric acid II or; and correlating an elevated level of 2-methylcitric acid I or 2-methylcitric acid II or in the body fluid with a likelihood of a deficiency of cobalamin. U.S. Pat. No. 5,374,560 further describes methods for detecting a deficiency of cobalamin or folic acid in warm-blooded animals and for distinguishing between a deficiency of cobalamin and a deficiency of folic acid, by: assaying a first body fluid from the warm-blooded animal for an elevated level of cystathionine; correlating an elevated level of cystathionine in the body fluid with a likelihood of a deficiency of cobalamin or folic acid; assaying a second body fluid from the warm-blooded animal having an elevated level of cystathionine in the first body fluid correlating with a likelihood of a deficiency of cobalamin or folic acid, for an elevated level of 2-methylcitric acid I or 2-methylcitric acid II or; and correlating an elevated level of 2-methylcitric acid I or 2-methylcitric acid II or in the second body fluid with a likelihood of a deficiency of cobalamin but a likelihood of a deficiency of folic acid. U.S. Pat. No. 5,374,560 further describes methods for detecting a deficiency of cobalamin or folic acid in warm-blooded animals, by: assaying a first body fluid for an elevated level of cystathionine; assaying a second body fluid for an elevated level of homocysteine; and correlating an elevated level of cystathionine and homocysteine with a likelihood of a deficiency of cobalamin or folic acid.

U.S. Pat. No. 5,800,979 describes methods for determination of concentration in a body fluid of at least one member of an endogenous folate co-enzyme pool selected from: (1) pool I containing tetrahydro-folate, dihydrofolate and 5,10-methylenetetrahydrofolate; (2) pool II containing 5-methyltetrahydrofolate; and (3) pool III containing 3-formyltetrahydrofolate, 10-formyltetrahydrofolate, 5,10-methyleneyltetrahydrofolate, and 5-formiminotetrahydrofolate. The method includes the steps of: (a) combining a known amount of at least one internal standard folate co-enzyme which is a non-radioactively-labeled stable isotope of a member of the selected folate co-enzyme pool with the body fluid, wherein the internal standard folate coenzyme is recovered from harvested bacterial cells grown on a medium containing non-radioactively-labeled stable isotope paraaminobenzoic acid; (b) at least partially purifying the endogenous and internal standard folate coenzymes from other components in the body fluid in a partial purification step; (c) quantitating the endogenous folate co-enzymes in the purified body fluid of step (b) by gas chromatography/mass spectrometry analysis; and (d) determining the concentration of the selected endogenous folate coenzyme pool by correcting the concentrations of endogenous folate coenzymes quantitated in step (c) for endogenous losses as reflected by losses in the known amount of internal standard folate co-enzyme of step (a).

G. METHODS FOR ASSAYING BILE ACID AND BILE SALTS

Further provided herein is a method for assaying bile acids or bile salts in a sample by: a) contacting the sample with a mutant bile-acid-binding enzyme or bile-salt-binding enzyme, the mutant enzyme substantially retains its binding affinity or has enhanced binding affinity for the bile acid or bile salt but has attenuated catalytic activity; and b) detecting binding between the bile acid or bile salt with the mutant bile-acid-binding enzyme or bile-salt-binding enzyme.

Any mutant bile-acid-binding enzyme or bile-salt-binding enzyme that substantially retain their binding affinity or have enhanced binding affinity for the bile acid or bile salt but have attenuated catalytic activity can be used in the bile acid or bile salt assay. Example of such mutant bile-acid-binding enzyme or bile-salt-binding enzyme includes 3-α-hydroxy steroid dehydrogenase.

Nucleic acids encoding bile-acid-binding enzymes or bile-salt-binding enzymes can be obtained by methods known in the art. Known nucleic acid sequences of bile-acid-binding enzyme or bile-salt-binding enzyme, such as 3-α-hydroxy steroid dehydrogenase, can be used in isolating nucleic acids encoding bile-acid-binding enzymes or bile-salt-binding enzymes from natural sources. Alternatively, nucleic acids encoding bile-acid-binding enzymes or bile-salt-binding enzymes can be obtained by chemical synthesis according to the known sequences.

In one specific embodiment, the nucleotide sequences with the following GenBank accession Nos. can be used in obtaining nucleic acid encoding 3-α-hydroxy steroid dehydrogenase: AA866404 (*Rattus norvegicus*); AA866403 (*Rattus norvegicus*); U34072 (*Mus musculus*); AF064635 (*Mus musculus* putative steroid); AB009304 (*Anas platyrhynchos*); D17310 (Rat); U32426 (*Molluscum contagiosum* virus); L23428 (*Comamonas testosteroni*); M67467 (*Macaca fuscata*); M27137 (Human). Preferably, the nucleotide sequences with the GenBank accession No. M27137 (SEQ ID No. 39; see also The et al., *Mol. Endocrinol*., 3(8):1310–2 (1989)) can be used in obtaining nucleic acid encoding 3-α-hydroxy steroid dehydrogenase.

Once nucleic acids encoding bile-acid-binding enzymes or bile-salt-binding enzymes are obtained, these nucleic acids can be mutagenized and screened and/or selected for bile-acid-binding enzymes or bile-salt-binding enzymes that substantially retain their binding affinity or have enhanced binding affinity for bile acids or bile salts but have attenuated catalytic activity. Insertion, deletion or point mutation(s) can be introduced into nucleic acids encoding bile-acid-binding enzymes or bile-salt-binding enzymes according to the methods described in Section B.

Information regrading the structural-function relationship of the bile-acid-binding enzymes or bile-salt-binding enzymes can be used in the mutagenesis and selection of the bile-acid-binding enzymes or bile-salt-binding enzymes that substantially retain their binding affinity or have enhanced binding affinity for bile acids or bile salts but have attenuated catalytic activity. For example, mutants can be made in the enzyme's binding site for its co-enzyme or for a non-bile-acid or non-bile-salt substrate, or in the mutant enzyme's catalytic site, or a combination thereof.

In one specific embodiment, the mutant bile-acid-binding enzyme is a mutant 3-α-hydroxy steroid dehydrogenase, and the attenuated catalytic activity of the mutant 3-α-hydroxy steroid dehydrogenase is caused by mutation in its catalytic site, its binding site for $NAD^+$ or a combination thereof.

Once a mutant bile-acid-binding enzyme or bile-salt-binding enzyme with desired properties, i.e., substantially retaining its binding affinity or having enhanced binding affinity for the bile acid or bile salt but having attenuated catalytic activity, is identified, such mutant bile-acid-binding enzyme or bile-salt-binding enzyme can be produced by any methods known in the art including recombinant expression, chemical synthesis or a combination thereof as described in Section B. Preferably, the mutant bile-acid-binding enzyme or bile-salt-binding enzyme is obtained by recombinant expression.

H. METHODS FOR ASSAYING GLUCOSE

Further provided herein is a method for assaying glucose in a sample. This method includes at least the steps of: a) contacting the sample with a mutant glucose-binding enzyme, the mutant enzyme substantially retains its binding affinity or has enhanced binding affinity for glucose but has attenuated catalytic activity; and b) detecting binding between glucose with the mutant glucose-binding enzyme.

Any mutant glucose-binding enzymes that substantially retain their binding affinity or have enhanced binding affinity for glucose but have attenuated catalytic activity can be used in the glucose assay. Examples of such mutant glucose-binding enzyme include mutant glucose isomerase, glucokinase, hexokinase and glucose oxidase.

Nucleic acids encoding glucose-binding enzymes can be obtained by methods known in the art. Known nucleic acid sequences of glucose-binding enzymes, such as glucose isomerase, glucokinase, hexokinase and glucose oxidase, can be used in isolating nucleic acids encoding glucose-binding enzymes from natural sources. Alternatively, nucleic acids encoding glucose-binding enzymes can be obtained by chemical synthesis according to the known sequences.

In one specific embodiment, the nucleotide sequences with the following GenBank accession Nos. can be used in obtaining nucleic acid encoding glucose isomerase: AF065160 (*Toxoplasma gondii*); AF050755 (*Giardia intestinalis* (GPI2)); AF050754 (*Giardia intestinalis* (GPI1)); AI117811 (mouse mammary gland); AA636682 (mouse myotubes); AA611494 (mouse irradiated colon); AA529061 (mouse irradiated colon); AA522284 (mouse embryonic region); AA472600 (mouse mammary gland); L27675 (*Drosophila yakuba* isofemale line 4); D13777 (Synechocystis sp.); AA265107 (mouse pooled organs); AA162075 (mouse skin); AA139952 (mouse heart); AA117013 (mouse embryonic region); W36773 (mouse); W16112 (mouse); AA03546 (mouse embryo); W77098 (mouse embryo); W61997 (mouse embryo); W53620 (mouse embryo); U17225 (*Zea mays*); L27685 (*Drosophila yakuba* isofemale line 1); L27684 (*Drosophila yakuba* isofemale line 13); L27683 (*Drosophila yakuba* isofemale line 12); L27682 (*Drosophila yakuba* isofemale line 11); L27681 (*Drosophila yakuba* isofemale line 10); L27680 (*Drosophila yakuba* isofemale line 9); L27679 (*Drosophila yakuba* isofemale line 8); L27678 (*Drosophila yakuba* isofemale line 7); L27677 (*Drosophila yakuba* isofemale line 6); L27676

(*Drosophila yakuba* isofemale line 5); L27555 (*Drosophila melanogaster* isochromosomal line); L27554 (*Drosophila melanogaster* isochromosomal line); L27553 (*Drosophila melanogaster* isochromosomal line); L27674 (*Drosophila yakuba* isofemale line 3); and L27673 (*Drosophila yakuba* isofemale). Preferably, the nucleotide sequences with the GenBank accession No. U17225 (SEQ ID No. 41; see also Lal and Sachs et al., *Plant Physiol*., 108(3):1295–6 (1995)) can be used in obtaining nucleic acid encoding glucose isomerase.

In another specific embodiment, the nucleotide sequences with the following GenBank accession Nos. can be used in obtaining nucleic acid encoding glucokinase: Al386017 (Mouse testis); Al325384 (Mouse embryo); Al323376 (Mouse embryo); Al255715 (Mouse liver mlia); Al196901 (Mouse liver); Al194797 (Mouse liver); Al194643 (Mouse liver); U44834 (*Mycobacterium tuberculosis*); U21919 (*Brucella abortus*); L41631 (*Mus musculus*); Al035808 (Mouse kidney); Al035659 (Mouse liver); AA882226 (Mouse lung); AH005826 (Homo sapiens pancreatic beta cell specific glucokinase (GCK) and major liver specific glucokinase (GCK) genes); AF041022 (Homo sapiens glucokinase); M69051 (Human liver glucokinase (ATP:D-hexose 6-phosphotransferase); AA109998 (Mouse testis); AA014441 (Mouse embryo); L38990 (*Mus musculus*); U22490 (*Escherichia coli*); M24077 (*Saccharomyces cerevisiae*); M90299 (Human); M88011 (Human pancreatic beta-cell); M25807 (Rat); J04218 (Rat); M60615 (*Z. mobilis*). Preferably, the nucleotide sequences with the GenBank accession No. M90299 (SEQ ID No. 43; see also Koranyi et al., *Diabetes*, 41(7):807–11 (1992)) can be used in obtaining nucleic acid encoding glucokinase.

In still another specific embodiment, the nucleotide sequences with the following GenBank accession Nos. can be used in obtaining nucleic acid encoding glucose oxidase: AF012277 (*Penicillium amagasakiense*); U56240 (*Talaromyces flavus*); X16061 (*Aspergillus niger* gox gene); X56443 (*A. niger* god gene); J05242 (*A. niger*); AF012277 (*Penicillium amagasakiense*); U56240 (*Talaromyces flavus*); X16061 (*Aspergillus niger* gox gene); X56443 (*A. niger* god gene); J05242 (*A. niger* glucose). Preferably, the nucleotide sequences with the GenBank accession No. J05242 (SEQ ID No. 45; see also Frederick et al., *J. Biol. Chem*., 265(7):3793–802 (1990)) and the nucleotide sequences described in U.S. Pat. No. 5,879,921 (SEQ ID No. 47) can be used in obtaining nucleic acid encoding glucose oxidase.

Once nucleic acids encoding glucose-binding enzymes are obtained, these nucleic acids can be mutagenized and screened and/or selected for glucose-binding enzymes that substantially retain their binding affinity or have enhanced binding affinity for glucose but have attenuated catalytic activity. Insertion, deletion or point mutation(s) can be introduced into nucleic acids encoding glucose-binding enzymes according to the methods described in Section B.

Information regrading the structural-function relationship of the glucose-binding enzymes can be used in the mutagenesis and selection of the glucose-binding enzymes that substantially retain their binding affinity or have enhanced binding affinity for glucose but have attenuated catalytic activity. For example, mutants can be made in the enzyme's binding site for its co-enzyme, co-factor, non-glucose substrate, or in the mutant enzyme's catalytic site, or a combination thereof.

In one specific embodiment, the mutant glucose-binding enzyme is a *Clostridium thermosulfurogenes* glucose isomerase having a mutation selected from His101Phe, His101Glu, His101Gln, His101Asp and His101Asn (Lee et al., *J. Biol. Chem*., 265(31):19082–90 (1990)). In another specific embodiment, the mutant glucose-binding enzyme is a mutant hexokinase or glucokinase, and the attenuated catalytic activity of the mutant hexokinase or glucokinase is caused by mutation in its catalytic site, its binding site for ATP or $Mg^{2+}$, or a combination thereof. In still another specific embodiment, the mutant glucose-binding enzyme is a mutant glucose kinase, and the attenuated catalytic activity of the mutant glucose kinase is caused by mutation in its catalytic site, its binding site for $H_2O$ or $O_2$, or a combination thereof.

Once a mutant glucose-binding enzyme with desired properties, i.e., substantially retaining its binding affinity or having enhanced binding affinity for glucose but has attenuated catalytic activity, is identified, such mutant glucose-binding enzyme can be produced by any methods known in the art including recombinant expression, chemical synthesis or a combination thereof as described in Section B. Preferably, the mutant glucose-binding enzyme is obtained by recombinant expression.

I. METHODS FOR ASSAYING ETHANOL

Further provided herein is a method for assaying ethanol in a sample. This method includes at least the steps of: a) contacting the sample with a mutant ethanol-binding enzyme, the mutant enzyme substantially retains its binding affinity or has enhanced binding affinity for ethanol but has attenuated catalytic activity; and b) detecting binding between ethanol with the mutant ethanol-binding enzyme.

Any mutant ethanol-binding enzymes that substantially retains their binding affinity or have enhanced binding affinity for ethanol but have attenuated catalytic activity can be used in the ethanol assay. Examples of such mutant ethanol-binding enzyme includes alcohol dehydrogenase.

Nucleic acids encoding ethanol-binding enzymes can be obtained by methods known in the art. Known nucleic acid sequences of ethanol-binding enzymes, such as alcohol dehydrogenase, can be used in isolating nucleic acids encoding ethanol-binding enzymes from natural sources. Alternatively, nucleic acids encoding ethanol-binding enzymes can be obtained by chemical synthesis according to the known sequences.

In one specific embodiment, the nucleotide sequences with the following GenBank accession Nos. can be used for producing mutant nucleic acid molecules encoding alcohol dehydrogenase: Al194923 (mouse liver); U16293 (Human class IV); U73514 (Human short-chain); U09623 (Human); M30471 (Human class II); Z21104 (Human adult Testis tissue); L33179 (Human class IV sigma-1); M24317 (Human class I); M29872 (Human); M81118 (Human); M21692 (Human class I); M12963 (Human class I); M68895 (Human); U07821 (Human); AF044127 (Homo sapiens peroxisomal short-chain); M12272 (Homo sapiens); D00137 (Homo sapiens); L47166 (Homo sapiens); M12271 (Homo sapiens class I); Z21104 (Human adult Testis tissue). In addition, nucleic acid molecules nucleotide, such as those provided in the follwoing U.S. Patents can be used in obtaining and producing mutant nucleic acid encoding alcohol dehydrogenase:

| U.S. Pat. No. | alcohol dehydrogenase |
|---|---|
| 5,908,924 | thermoanaerobacter ethanolicus 39E secondary-alcohol dehydrogenase |
| 5,855,881 | Mammalian alcohol dehydrogenase |

-continued

| U.S. Pat. No. | alcohol dehydrogenase |
|---|---|
| 5,385,833 | Pseudomonas sp. ATCC No. 49794 alcohol dehydrogenase |
| 5,344,777 | membrane-bound alcohol dehydrogenase complex |
| 5,342,767 | *Lactobacillus kefir* alcohol dehydrogenase 5,225,339 |
| 5,162,516 | alcohol dehydrogenase II gene from *Zymomonas mobilis* |

Nucleic acid molecules that include the sequences of sequences with the GenBank accession Nos. U73514 (SEQ ID No. 49), U09623 (SEQ ID No. 51; see also Kedishvili et al., *J. Biol. Chem.*, 270(8):3625–30 (1995)), M30471 (SEQ ID No. 53; see also Sharma et al., *Biochem. Biophys. Res. Commun.*, 164(2):631–7 (1989)) and M24317 (SEQ ID No. 55; see also Xu et al., *Genomics*, 2(3):209–14 (1988); Ikuta et al., *Proc. Natl. Acad. Sci.*, 82(9):2703–7 (1985)) can be used for in obtaining nucleic acid encoding alcohol dehydrogenase.

Once nucleic acids encoding ethanol-binding enzymes are obtained, these nucleic acids can be mutagenized and screened and/or selected for ethanol-binding enzymes that substantially retain their binding affinity or have enhanced binding affinity for ethanol but have attenuated catalytic activity. Insertion, deletion or point mutation(s) can be introduced into nucleic acids encoding ethanol-binding enzymes according to the methods described in Section B.

Information regrading the structural-function relationship of the ethanol-binding enzymes can be used in the mutagenesis and selection of the ethanol-binding enzymes that substantially retain their binding affinity or have enhanced binding affinity for ethanol but have attenuated catalytic activity. For example, mutants can be made in the enzyme's binding site for its co-enzyme, co-factor, non-ethanol substrate, or in the mutant enzyme's catalytic site, or a combination thereof.

In one specific embodiment, the mutant ethanol-binding enzyme is a mutant alcohol dehydrogenase and the attenuated catalytic activity of the mutant alcohol dehydrogenase is caused by mutation in its catalytic site, its binding site for $NAD^+$ or $Zn^{2+}$, or a combination thereof. Preferably, the mutant alcohol dehydrogenase is a human liver alcohol dehydrogenase having a His51Gln mutation (Ehrig et al., *Biochemistry*, 30(4):1062–8 (1991)). Also preferably, the mutant alcohol dehydrogenase is a horse liver alcohol dehydrogenase having a Phe93Trp or Val203Ala mutation (Bahnson et al., *Proc. Natl. Acad. Sci.*, 94(24):12797–802 (1997); Colby et al., *Biochemistry*, 37(26):9295–304 (1998)).

Once a mutant ethanol-binding enzyme with desired properties, i.e., substantially retaining its binding affinity or having enhanced binding affinity for ethanol but having attenuated catalytic activity, is identified, such mutant ethanol-binding enzyme can be produced by any methods known in the art including recombinant expression, chemical synthesis or a combination thereof as described in Section B. Preferably, the mutant ethanol-binding enzyme is obtained by recombinant expression.

J. METHODS FOR ASSAYING URIC ACID

Further provided herein is a method for assaying uric acid in a sample. This method includes at least the stephs of: a) contacting the sample with a mutant uric-acid-binding enzyme, the mutant enzyme substantially retains its binding affinity or has enhanced binding affinity for uric acid but has attenuated catalytic activity; and b) detecting binding between uric acid with the mutant uric-acid-binding enzyme.

Any mutant uric-acid-binding enzymes that substantially retains their binding affinity or have enhanced binding affinity for uric acid but have attenuated catalytic activity can be used in the uric acid assay. Examples of such mutant uric acid-binding enzyme includes urate oxidase or uricase.

Nucleic acids encoding uric-acid-binding enzymes can be obtained by methods known in the art. Known nucleic acid sequences of uric-acid-binding enzymes, such as urate oxidase or uricase, can be used in isolating nucleic acids encoding uric-acid-binding enzymes from natural sources. Alternatively, nucleic acids encoding uric-acid-binding enzymes can be obtained by chemical synthesis according to the known sequences.

In one specific embodiment, the nucleotide sequences with the following GenBank accession Nos. can be used in obtaining nucleic acid encoding urate oxidase or uricase: AB028150 (*Medicago sativa*); AB028149 (*Medicago sativa*); E13225 (*Arthrobacter globiformis*); U72663 (*Phaseolus vulgaris*); D86930; D86929; D32043 (*Candida utilis*); D49974 (Bacillus sp.); M10594 (Soybean nodulin-35 (N-35)); M24396 (Rat); M27695 (Mouse); M27694 (Baboon); and M27697 (Pig). In addition, the nucleotide sequences described in the follwoing U.S. Patent Nos. can be used in obtaining nucleic acid encoding urate oxidase or uricase: 5,541,098 (SEQ ID No. 57) and 5,728,562 (SEQ ID No. 59). Preferably, the nucleotide sequences with the GenBank accession No. M27694 (SEQ ID No. 61; see also Wu et al., *Proc. Natl. Acad. Sci.*, 86(23):9412–6 (1989)) can be used in obtaining nucleic acid encoding urate oxidase or uricase.

Once nucleic acids encoding uric-acid-binding enzymes are obtained, these nucleic acids can be mutagenized and screened and/or selected for uric-acid-binding enzymes that substantially retain their binding affinity or have enhanced binding affinity for uric acid but have attenuated catalytic activity. Insertion, deletion or point mutation(s) can be introduced into nucleic acids encoding uric-acid-binding enzymes according to the methods described in Section B.

Information regrading the structural-function relationship of the uric-acid-binding enzymes can be used in the mutagenesis and selection of the uric-acid-binding enzymes that substantially retain their binding affinity or have enhanced binding affinity for uric acid but have attenuated catalytic activity. For example, mutants can be made in the enzyme's binding site for its co-enzyme, co-factor, non-uric-acid substrate, or in the mutant enzyme's catalytic site, or a combination thereof.

In one specific embodiment, the mutant uric-acid-binding enzyme is a mutant urate oxidase or uricase, and the attenuated catalytic activity of the mutant urate oxidase or uricase is caused by mutation in its catalytic site, its binding site for $O_2$, $H_2O$, or copper ion, or a combination thereof. Preferably, the mutant urate oxidase is a rat urate oxidase having a mutation selected from H127Y, H129Y and F131S (Chu et al., *Ann. N.Y. Acad. Sci.*, 804:781–6 (1996)).

Once a mutant uric-acid-binding enzyme with desired properties, i.e., substantially retaining its binding affinity or having enhanced binding affinity for uric acid but having attenuated catalytic activity, is identified, such mutant uric-acid-binding enzyme can be produced by any methods known in the art including recombinant expression, chemical synthesis or a combination thereof as described in Section B. Preferably, the mutant uric-acid-binding enzyme is obtained by recombinant expression.

K. COMBINATIONS, KITS AND ARTICLES OF MANUFACTURER

Combinations and kits containing such combination are provided. The combination includes: a) a mutant analyte-binding enzyme, the mutant enzyme substantially retains its binding affinity or has enhanced binding affinity for the analyte or an immediate analyte enzymatic conversion product but has attenuated catalytic activity; and b) reagents and/or other means for detecting binding between the analyte or the immediate analyte enzymatic conversion product and the mutant analyte-binding enzyme. Preferably, the analyte to be assayed is Hcy. Also preferably, binding between the Hcy or the immediate Hcy enzymatic conversion product and the mutant Hcy-binding enzyme is detected using a labelled Hcy, a labelled immediate Hcy enzymatic conversion product, a labelled mutant Hcy-binding enzyme, or a derivative or an analog thereof. More preferably, wherein the analyte to be assayed is Hcy, the combination also inlcudes reagents for detecting cholesterol and/or folic acid.

In another embodiment, the kit also includes instructions for assaying an analyte in a sample.

The packages discussed herein in relation to diagnostic systems are those customarily utilized in diagnostic systems. Such packages include glass and plastic, such as polyethylene, polypropylene and polycarbonate, bottles and vials, plastic and plastic-foil laminated envelopes and the like. The packages may also include containers appropriate for use in auto analyzers. The packages typically include instructions for performing the assays.

In still another embodiment, an article of manufacture is provided. The article includes: a) packaging material; b) a mutant analyte-binding enzyme, the mutant enzyme substantially retains its binding affinity or has enhanced binding affinity for the analyte or an immediate analyte enzymatic conversion product but has attenuated catalytic activity; and c) a label indicating that the mutant analyte-binding enzyme and the reagents are for use in assaying the analyte in a sample. The article of manufacture may also include reagents for detecting binding between the analyte or the immediate analyte enzymatic conversion product and the mutant analyte-binding enzyme.

The following examples are included for illustrative purposes only and are not intended to limit the scope of the invention.

EXAMPLE 1

Preparation of Mutant SAH Hydrolase-encoding Nucleic Acid

Human placental SAH hydrolase gene (SEQ ID No. 1) was subcloned into an expression vector pKK223-3 (Pharmacia Biotech, Piscataway, N.J.) at the EcoR I site. pKK223-3 contains the strong tac promoter upstream from the multiple cloning site and the strong rrnB ribosomal terminator downstream for control of protein expression. The SAH hydrolase gene-containing expression vector was transferred into an *E. coli* strain JM109 (Invitrogen, Carlsbad, Calif.). Site-directed mutagenesis of SAH hydrolase was conducted in two ways: 1) single-strand DNA-based M13 method; and 2) double-strand DNA-based PCR method.

Single-strand DNA-based Mutagenesis

Single-strand DNA-based mutagenesis was conducted based on the method described by Taylor et al., *Nucleic Acids Res.*, 13:8765–8785 (1985), which exploits the inability of Ncil to cleave a thio-containing DNA strand. Sculptor™ invitro mutagenesis system RPN1526 (Amersham Life science, UK) was used. The pKK223-3 vector containing the wild type gene of SAH hydrolase was prepared using the method of alkaline lysis followed by plasmid purification using Promega's DNA purification kit (Wizard plus Minipreps, Promega, Madison Wis.). The purified plasmid was digested with EcoR I (Stratagene, La Jolla, Calif.) at 37° C. for 2 hours to obtain the EcoR I fragment by agarose gel electrophoresis followed by DNA purification using Promega DNA purification kit. The purified EcoR I fragment was subcloned into M13 mp 19 DNA (Pharmacia Biotech, Piscataway, N.J.) by T4 DNA ligase (Pharmacia Biotech Piscataway, N.J.). The ligation was conducted in One-phor-All buffer (10 mM tris-Ac, pH 7.5, 10 mM Mg(Ac)2, 50 mM KAc; Pharmacia LKB Biotechnology AB, Uppsala, Sweden) at 4° C. overnight. The ligation product was transferred into TG1 cells (Stratagene, La Jolla, Calif.) by incubation of 10 μl of the M13 with 90 μl of competent TG1 cells at 0° C. for 30 min. and 42° C. for 75 sec. After being chilled to 0° C. for 2 min, 500 μl of 2XYT media was added to the cells and incubated for 10 min. at 37° C. Two hundred μl of growing nontransformed TG1 cells were mixed with the transformed TG1 cells, and to which 2.5 ml of soft agarose LB (42° C.) was added. The cell mixture was immediately poured onto preheated LB agar plates (40° C.), and incubated at 37° C. overnight. Phage clones were picked up for examination of the insertion of SAH hydrolase gene and the orientation through DNA sequencing and restriction enzyme analysis. The selected phage clone was used for preparation of single strand DNA template.

The M13 phage containing the SAH hydrolase gene were incubated with TG1 cells in 3 ml of 2xYT media overnight. One drop of the overnight culture was mixed with growing TG1 cells (in log phase) in 30 ml of 2XYT media. Cells were incubated for 8 hours with shaking. After centrifugation, the supernatant was collected for single-strand template DNA purification. The purification was conducted according to the manufacture's procedure provided by Amersham Life Science.

Design of Primers for Point Mutation

Oligonucleotides (15–30 bases) were synthesized by CruaChem (Sterling, Va.). The sequence of the oligonucleotides were designed to be complementary to the sequence in the region covering both sides of the mutation site. For example, to mutate lys426 to glu426, the oligonucleotides used as primer contained the following sequence: GGCCCCTTC-GAGCCGGATCACTACCGC (SEQ ID No. 63) where GAG codes for glu instead of original (wild type) AAG which codes for lys.

The selection of mutation sites was based on x-ray structure of the substrate binding site and coenzyme binding site of human SAH hydrolase (Turner et al., *Nature Structural Biology*, 5:369–376 (1998)). Amino acid residues such as Thr157, Asp131, His301, Lys186, Asn191, Glu156, Asp190, Phe362, Phe302, Asn181, His353, Glu59, Ser83, His55, Leu54, Cys79, His301, Arg343, Asp303, Leu344, Asn80, Asn346, Asp107 and entire C-terminal residues can be the mutagenesis targets (see Table 2 for particular mutations generated). The coenzyme binding domain contains residues from Tyr193-Asn346.

The oligonucleotides were dissolved in water to a concentration of 5 ng/μl. The oligonucleotide solution was then phosphorylated at the 5'-end using polynucleotide kinase. The phosphorylation reaction mixture contained the following materials: 2.5 μl of oligonucleotides (5 ng/μl), 3 μl of one-phor-all 10× kinase buffer (Pharmacia Biotech), 21.5 μl of water, 2 μof 10 mM ATP, and 1 μl of polynucleotide kinase (100,000 U/ml) (Pharmacia Biotech). The reaction mixture was incubated at 37C for 30 min. followed by heating at 70° C. for 10 min. to inactivate the enzyme.

TABLE 2

Oligonucleotides used for site-directed mutagenesis of human SAH hydrolases

| Mutant | Mutagenic oligonucleotide | Codon Change | SEQ ID |
|---|---|---|---|
| K186A | GACTTCGTCACC**GCC**AGCAAGTTTGGG | AAG → GCC | 64 |
| F302S | AACATTGGACAC**TCT**GACGTGGAGATC | TTT → TCT | 65 |
| H301D | TGTAACATTGGA**GAC**TTTGACGTGGAG | CAC → GAC | 66 |
| H353S | TGTGCCATGGGC**TCC**CCCAGCTTCGTG | CAC → TCC | 67 |
| R343A | CTGGCCGAGGGT**GCG**CTGGTCAACCTG | CGG → GCG | 68 |
| D190A | AAGAGCAAGTTT**GCC**AACCTCTATGGC | GAC → GCC | 69 |
| F82A | AGCTGCAACATC**GCC**TCCACCCAGGAC | TTC → GCC | 70 |
| N181D | AACCTCTATGGC**GAC**CGGGAGTCCCTC | AAT → GAC | 71 |
| R431A | CCGGATCACTAC**GCC**TACTGAGAATTC | CGC → GCC | 72 |
| K426R | TGTGATGGCTTC**CGC**CCGGATCACTAC | AAG → CGC | 73 |
| C195S | AACCTCTATGGC**TCC**CGGGAGTCCCTC | TGC → TCC | 74 |
| Δ432 | GATCACTACCGC**TGA**TGAGAATTCGAG | ATC → TGA | 75 |

The mutagenized codon is underlined, and the nucleotides changed are in boldtace type The 5'-phosphorylated oligonucleotides DNA was annealed with single-stranded DNA (M13 phage containing wild type human SAH hydrolase gene, 1μg/μl) in a ratio of oligonucleotide: template of 2:1 in annealing buffer. The annealing reaction was performed by incubating the annealing mixture at 70° C. for 3 min. followed by 30 min. at 37° C. or followed by transferring the micro centrifuge tube to a 55° C. beaker and then allow to cool to room temperature. To the annealing mixture (17 μl), 19 μl of dNTP A (α-S) mix, 1.5 μl of T7 DNA polymerase (0.8 units), and 2.5 μl of T4 DNA ligase (92.5 units), and 6 μl of water were added. After 10 min. at room temperature and 30 min. at 37° C., the reaction was stopped by heat inactivation at 70° C. for 15 min. To the reaction mixture was added T5 exonuclease (2000 units) and exonuclease buffer to remove single-strand non-mutant DNA at 37° C. for 30 min. followed by 15 min. of heat inactivation at 70° C. Ncil (5 units) was added to the reaction mixture to nicking the non-mutant strand by incubating Ncil at 37° C. for 90 min. The non-mutant strand was digested by adding 160 units of Exonuclease III and incubating at 37° C. for 30 min. followed by heat inactivation. To repolymerize the gaped DNA, dNTP mix B and 3.5 units of DNA polymerase I and 2.5 units of T4 DNA ligase were added to the reaction mixture, and incubated at 37° C. for 1 h.

The M13 plasmid containing the mutated SAH hydrolase gene was then transferred into competent TG 1 host cells by heat shock method or an electroporation method. Ten μl of the mutant M13 plasmid was added to 90 μl of water and mixed with competent TG1 cells in ice for 40 min. The TG1 cells were shocked by incubation at 42° C. for 45 sec. and immediately at 0° C. for 5 min. The transferred TG1 cells were allowed to return to room temperature, and mixed with 200 μl of growing non-transferred TG1 cells (sever as lawn cells). Three ml of molten Htop agar was added and mixed followed by immediate pouring the cells onto a L plate. The plate was incubated in 37° C. for overnight. Phage plaques formed were picked by sterile tooth pick and swirling in a tube containing 3 ml of 2XYT medium. After overnight culture, cells were collected by centrifugation, and the double-strand M13 plasmid from the cells was purified by using Promega DNA purification kit (Wizard plus Minipreps).

The supernatant from centrifugation was used to purify single-strand M13 DNA. The mutation was confirmed by DNA sequencing of the single-strand M13 DNA using Sequenase Version 2.0 (Unites States Biochemical). The double-strand M13 DNA containing correct mutation sequence was selected, and digested with EcoR I. The EcoR I fragment containing the mutant SAH hydrolase gene was purified by agarose electrophoresis followed by gene cleaning using Qlaquick Gel Extraction kit (Qiagen, Valencia, Calif.). The purified EcoR I fragment was subcloned into pKK223-3 expression vector using T4 ligase. Two μl of EcoR 1 treated and 5'-dephosphorylated pKK223-3 vector backbone was incubated with 10 μl of the purified mutant insert DNA in a backbone to insert ratio of 2:1. The ligation reaction was carried out in One-phore-All buffer containing 0.01 M ATP at 16C overnight. The ligated vector containing mutant SAH hydrolase gene was transferred into competent *E. Coli* JM109 cells by heat shock method. The transformed cells were selected against 100 μl/mI ampicillin. Ampicillin-resistant clones were picked and grown in 10 ml of 2xYT medium containing 35 μl/mi ampicillin for 2 hours at 37° C. and then induced with 1 mM isopropyl-1-thio-β-D-galactopyranoside (IPTG) and grown overnight at 37° C. The cells were harvested by centrifugation, and suspended in 0.8 ml of 50 mM Tri-HCl, pH 7.5, containing 2 mM EDTA. Cells were lysed by rapid freezing and thawing. After centrifugation at 13,500 rpm for 1 hour at 4° C., the supernatant was collected for SDS-PAGE analysis for over-expression of SAH hydrolase mutant protein. A heavy protein band at molecular size of 47,000 Da indicates the overexpression of mutant SAH hydrolase protein.

PCR-based Mutagenesis Method

PCR-based mutagenesis was performed using the ExSite PCR-based Site-Directed Mutagenesis Kit (Stratagene, La Jolla, Calif.). The ExSite method uses increased template concentration and <10 PCR cycles. The resulting mixture of template DNA, newly synthesized DNA and hybrid parental/newly synthesized DNA is treated with Dpn I and Pfu DNA polymerase. Dpn I digests the in vivo methylated parental template and hybrid DNA, and Pfu DNA polymerase polishes the ends to create a blunt-ended PCR product. The end-polished PCR product is then intramolecularly ligated together and transformed into *E. coli* cells. The detailed experimental procedure is described as follows:

To a microcentrifuge tube were added 0.5 pmol of template DNA, 2.5 μl of 10× mutagenesis buffers, 1 μl of 25 mM dNTP mix, 15 pmol of each primer, and ddH$_2$O to a final volume of 24 μl. To the reaction mixture was then added 1 μl of ExSite DNA polymerase blend (5 U/μl). The reaction solution was overlayed with 20 μl of mineral oil and thermal cycle the DNA using 7012 amplification cycles. The cycling parameters are listed in Table 3.

TABLE 3

Mutagenesis Cycling Parameters

| Segment | Cycles | Temperature | Time |
|---|---|---|---|
| 1 | 1 | 94° C. | 4 min. |
| | | 50° C. | 2 min. |
| | | 72° C. | 2 min. |

TABLE 3-continued

| Mutagenesis Cycling Parameters | | | |
|---|---|---|---|
| Segment | Cycles | Temperature | Time |
| 2 | 8 | 94° C. | 1 min. |
| | | 56° C. | 2 min. |
| | | 72° C. | 1 min. |
| | | 72° C. | 5 min. |
| 3 | | 72° C. | 5 min. |

Following amplification, the reaction tube was placed on ice for 2 min. to cool the reaction to <37° C. To the reaction tube were added 1 $\mu$l of the Dpn I restriction enzyme (10 U/$\mu$l) and 0.5 $\mu$l of cloned Pfu DNA polymerase (2.5 U/$\mu$l) followed by incubation at 37° C. for 30 min. The reaction was stopped by heating at 72° C. for 30 min. For ligating the product, to the reaction tube were added 100 $\mu$l of $ddH_2O$, 10 $\mu$l of 10× mutagenesis buffer, and 5 $\mu$l of 10 mM rATP. Transfer 10 $\mu$l of the above reaction mixture to a new micocentrifuge tube and add 1 $\mu$l of T4 DNA ligase (4 U/$\mu$l). The ligation was incubated at 37° C. for 1 hour. 2 $\mu$l of the ligated DNA was added to 80$\mu$l of *Epicurian Coli* XL1-Blue supercompetent cells on ice and incubated for 30 min. followed by 45 seconds at 42° C. and 2 min. on ice. The transformed cells were immediately plated on LB-ampicillin agar plates which had been spread with 20$\mu$l of 10% X-gal prepared in DMF and 20$\mu$l of 100 M IPTG in $H_2O$. The plate was incubated overnight at 37° C. The blue colonies were selected as colonies containing the mutagenized plasmid. The selected colonies were further confirmed by DNA sequencing. Protein overexpression and substrate trapping screening were performed as described above.

Double-strand pKK223-3 containing human SAH hydrolase (wild type) was purified from 50 ml of *E. coli* JM109 culture using Promega DNA purification kit (Wizard plus Minipreps). The purified plasmid was annealed with PCR primers containing the desired mutation sequence.

Deletion and insertion mutations were also performed according to the manufacture's protocol using ExSite PCR-based Site-directed Mutagenesis Kit. Double mutations or combinations of mutation and deletion or insertion were carried out using mutated or deleted DNA as template for secondary mutation or deletion using either M13-based mutagenesis or PCR-based mutagenesis methods.

Identification of Substrate Trapping SAH Hydrolase

The cell-free extracts from colonies that inducibly overexpressed mutant SAH hydrolase proteins were chromatographed on a monoQ column (HR5/5) equipped with FPLC system. Proteins were eluted with a linear gradient of NaCl from 0 to 1 M in 10 mM sodium phosphate buffer, pH 7.0 over 35 min. The major protein peak that eluted at the same or close retention time as that of the wild type SAH hydrolase was collected. An aliquot collected mutant SAH hydrolase (1–10 $\mu$g) was incubated with [$^3$H]SAH (10 mCi/mmole, 200 $\mu$M) and 30 $\mu$M of 5, 5'-dithiobis (2-nitrobenzoic acid) (DTNB) at room temperature for 5–30 min.

The reaction solution was filtered through a membrane of molecular weight cut-off at 30,000 by centrifugation. The filtrate was measured at 412 nm for Hcy formation (enzyme activity) and the [$^3$H] radioactivity on the membrane was measured by scintillation counting after membrane washing with 1 ml of 50 mM phosphate buffer, pH 7.0.

The mutant hydrolases that show high radioactivity on the membrane and low O.D. at 412 nm of the filtrate relative to the wild type enzyme were selected as candidates for further characterization including determination of Km or Kd and binding energy ($\Delta$G). Mutant SAH hydrolases with Km value lower than 10 $\mu$M toward SAH and kcat value lower than 0.1 per second were overexpressed in larger quantity (1–2 L of *E. coli* culture) and the enzyme proteins were purified to homogenous as judged by single band on SDA-PAGE.

EXAMPLE 2

Large Scale Overexpression and Purification of Wild Type and Mutant Forms of SAH Hydrolases Purification The cell-free extract of IPTG-induced *E. Coli* JM109 (containing SAH hydrolase gene in pKK223-3 vector) culture was mixed with powder DEAE-cellulose (Sigma, St. Louis, Mo.) equilibrated with 0.1 M sodium phosphate buffer, pH 7.2 containing 1 mM EDTA (buffer A). The cell-free extract and DEAC-cellulose mixture was placed in a funnel and filtrated under vacuum. After washing with 3 volumes of buffer A, the filtrate was precipitated by solid ammonium sulfate (30–60%). The precipitated protein was collected by centrifugation at 13000 rpm, and resuspended in 50 mM sodium phosphate buffer, pH 7.2, containing 1 mM EDTA. The protein was chromatographed through a Sephacryl S-300 size exclusion column (2.5×100 cm) (Pharmacial Biotech, Piscataway, N.J.) followed by a DEAE-Sepharose ion exchange column (2.5×30 cm) eluted by a linear NaCl gradient. The major protein peak from DEAE-Sepharose was examined by SDS-PAGE. In most of the times, this purification procedure gave a single protein band on SDS-PAGE. Sometime, minor bands were observed on SDS-PAGE. In this case, rechromatography on DEAE-Sepharose column was performed to obtain pure protein. SAH hydrolase activity or [$^3$H]SAH binding affinity was also measured to confirm the protein peak.

Storage of the Purified SAH Hydrolase

The purified wild type and mutant SAH hydrolases were dialyzed against 5 mM sodium phosphate buffer, pH 7.0 for 6 hours at 4° C. The protein was then frozen in liquid nitrogen and lyophilized under vacuum. The lyophilized protein was stored at −70° C. The protein was stable for at least 2 years. The purified protein can also be stored in liquid containing 20% of glycerol at −20° C. For wild type enzyme, addition of 5 mole excess of adenosine (Ado) to the 20% glycerol solution stabilizes the enzyme activity even better.

Assays for Enzyme Activity

The assay of SAH hydrolase activity in the hydrolytic direction was performed as described in Yuan et al., *J. Biol Chem.*, 271:28008–28016, 1996). The assay measures the hydrolysis of SAH into Ado and Hcy. The reaction product Hcy was derivatized by thiol specific reagent DTNB for colometric determination at 412 nm. The assay for SAH hydrolase in the synthetic direction was measured by the formation of SAH from substrate Ado and Hcy using HPLC (see, Yuan et al., *J. Biol. Chem.*, 268:17030–17037 (1993). One unit of the enzyme activity was defined as the amount of enzyme that can hydrolyze or synthesize 1 $\mu$mole of SAH/min/mg.

Assay for Binding Affinity (Kd)

For mutant enzyme that completely lacks activity, the binding constant (Kd) values were determined by an equilibrium dialysis technique using [$^3$H] SAH and Spectrum 5-cell Equilibrium Dialyzer) (Spectrum, Houston, Tex.). The membrane disc used had molecular cut-off of 25,000.

EXAMPLE 3

Preparation of Reagents

Preparation of Fluorophore-labeled Ado and SAH Analogs

Method 1

Ado-5'-carboxylic acid (Sigma, St. Louis, Mo.) was derivatized with 9-(hydroxylmethyl)anthracene (HMA) (Fluka, Buchs, Switzerland). To 10 mg of Ado-5'-carboxylic acid dissolved in 100 ml of chloroform (10 min sonication) was added 50 mg 1-hydroxybenzotriazole (HOBT) (Janssen Chimica, Beerse, Belgium). After evaporation to dryness under nitrogen, 300 mg of N-ethyl-N'-(3-dimethylaminopropyl)carbodiimide hydrochloride in 300 ml chloroform and 5 ml of triethylamine were added. The resulting solution was kept at 0° C. for 30 min. To the above reaction mixture was added 200 mg HMA in 100 ml of chloroform. The mixture was allowed to stand at room temperature for 10 min. and then evaporated to dryness under a stream of nitrogen. The residue obtained was dissolved in 10 ml of HPLC mobile phase (methanol-water mixture, 90:10, w/w). One ml of the above solution was injected into a semi-prepative column (Econosphere, C18, 7×300 mm, Alltech, Dearfield, Ill.). The column was eluted with an isocratic method. The flow rate was 2 ml/min. The peaks were monitored at UV260 nm and fluorescence at Ex-365 nm, Em-415 nm. The peaks with UV and fluorescence absorbance were collected as HMA-labeled Ado-5'-ester.

Method 2

Ado-5'caroboxylic acid and 4-bromomethyl-7-methoxycoumarin (Br-Mmc) (Sigma, St. Louis, Mo.) were dissolved in ethyl acetate in a molar ratio of 1:3. The reaction volume was 25 ml. After addition of 2 g of finely powdered $K_2CO_3$ the solution was refluxed for 1 hour using a ml-reluxer. After cooling, the reaction solution was injected into a C18 column (Econosphere, C18, 7×300 mm, Alltech, Dearfield, Ill.) for HPLC separation. The elution was monitored by UV (260 nm) and fluorescence (Em 328 nm and Ex390 nm). The elution was performed in a linear gradient of methanol:water from 20 to 100% over 30 min. The flow rate was 2 ml/min.

Method 3

Figure 3:
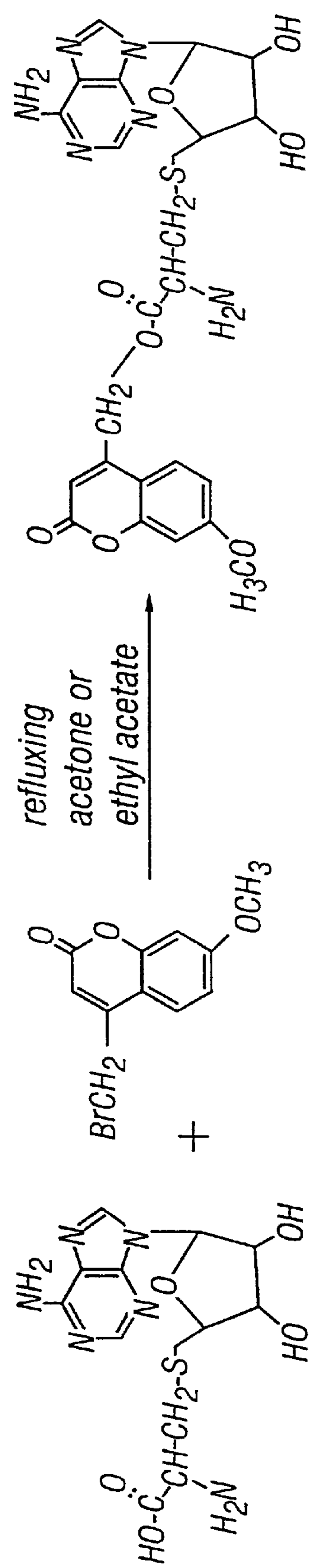
FIG. 3 depicts design and synthesis of fluoresceinated tracer.
Figure 4:
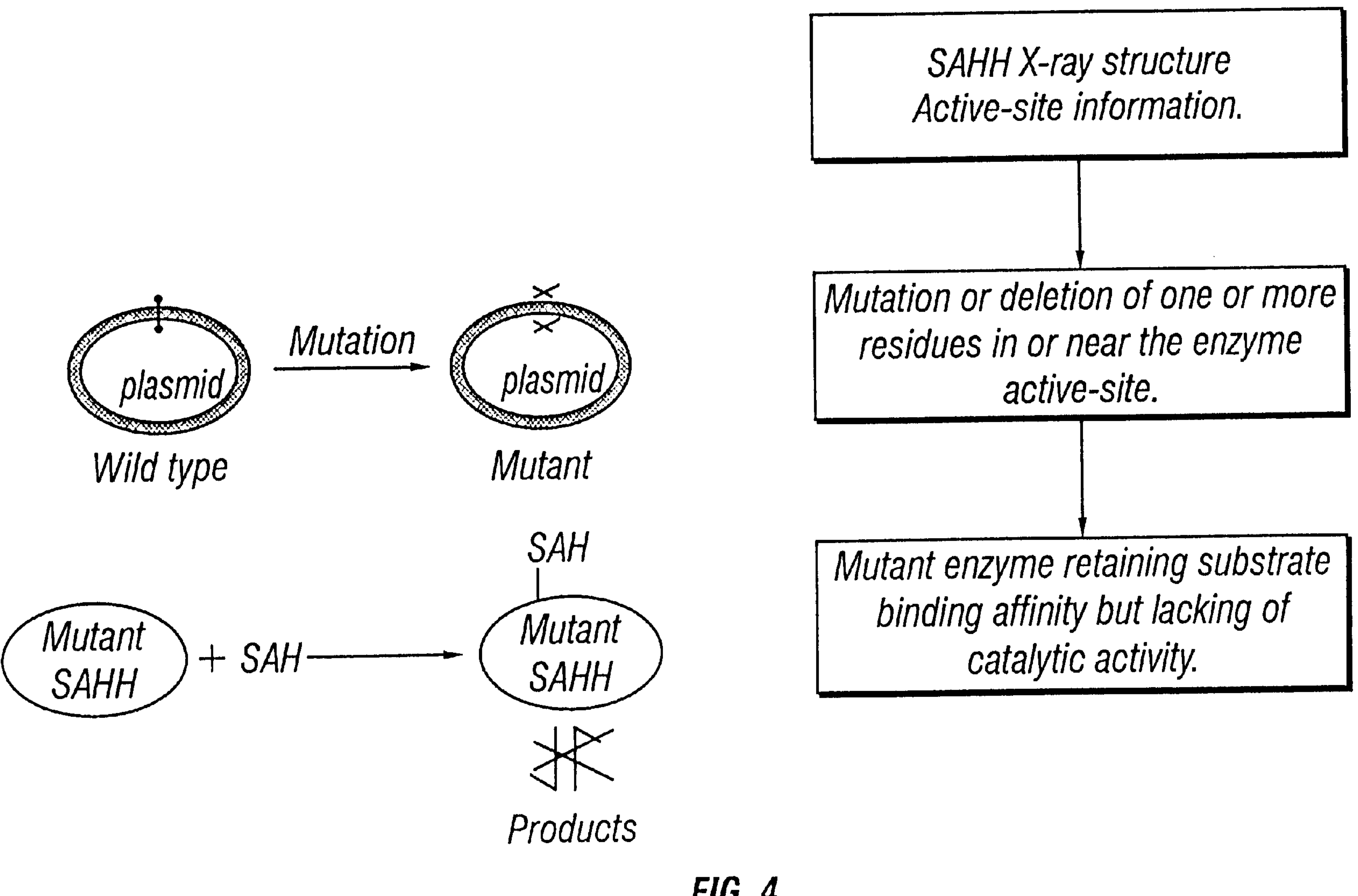
FIG. 4 depicts selection of mutant SAH hydrolase that lacks catalytic activity but retains substrate binding affinity.

This method is depicted in FIG. 3. Adenosyl-L-cysteine (Ado-Cys) and 4-Bromomethyl-7-methoxycoumarin (Br-Mmc) were dissolved in ethyl acetate in a molar ration of 1:3. The final volume was 25 ml (ca, 1 mg Ado-Cys). After addition of 200 mg of finely powdered $K_2CO_3$, the solution was refluxed for 1 hour using a ml-refluxer at 80° C. After cooling, the reaction solution was injected into a C18 column (Econosphere, C18, 7×300 mm, Alltech, Dearfield, Ill.) for separation using HPLC. The fluorescently labeled Ado-Cys was eluted by a linear gradient of methanol; water from 20 to 100% in 30 min. The flow rate was 2 ml/min.

Method 4

Ado-Cys was dissolved in carbonate buffer, pH 9.0 in 1 mM concentration. Fluorescein isotiocyanate (FITC) (PcPierce, Rockford, Ill.) was dissolved in DMSO in 5 mM concentration, and diluted to 1 mM with carbonate buffer, pH 9.0. Equal volumes of Ado-Cys and FITC in carbonate buffer were mixed and incubated in room temperature for 1 our. The Ado-Cys-FITC conjugate was then isolated by HPLC using a C18 column (Econsphere, C18, Alltech, Dearfield, Ill.). The elution was monitored at UV 260 nm and fluorescence at Ex484 nm and Em520 nm. The mobile phases were water and methanol in a linear gradient from 0 to 80% of methanol in 35 min.

Coating Mutant SAH Hydrolase on Microtiter Well (96 well plate)

Mutant SAH hydrolase (F302S) was coated on flat-bottomed 96 well plate (Dynex Technologies, Chantilly, Va.). 200 μl of 20 μg/ml of F302S mutant hydrolase in 50 mM sodium phosphate buffer, pH 7.6. was added to each well. After incubation at 4° C. overnight, the plate was emptied by inversion. After blocking with 0.5% BSA, the plate was then washed three times with 10 mM PBS containing 0.1 NaCl and 0.05% of Tween 20. After inversion and tapping, the plate was stored at 4° C. before use.

Preparation of Standard Samples and Chemical Reagents

1. Construction of a Standard Hcy Curve

Human albumin (Fraction V powder, Sigma) was dissolved in PBS in a protein concentration equal to that of human plasma. To 10 ml of the albumin was added 4 ml of 1% tri-n-butylphosphine (TBP). The mixture was incubated at room temperature for 15 min. followed by gel filtration through a size exclusion column (Sephacryl-S100, 2×90 cm). The albumin protein concentration was normalized to human plasma concentration using protein concentrator (Bio-Rad). The protein concentration was determined by Bradford reagent (Bio-Rad). A series of known concentration of L-homocysteine and L-homocysteine were spiked into the TBP-treated human albumin in a final concentrations ranging from 0 to 50 μM. After incubation at 37° C. for 1 hour, the L-homocysteine spiked albumin and L-homocystine albumin were aliquoted in 70 μl/tube as standard samples, and stored at −20° C. before use.

2. Wild Type SAH Hydrolase Solution

The wild type SAH hydrolase (20 mU/50 μl) was dissolved in 50 mM phosphate buffer, Ph 7.2, containing 1 mM EDTA, 0.25 mM Ado and 1 mg/ml of BSA.

3. Tri-n-butylphosphine (TBP) Solution

Tri-n-btylphosphine (Sigma) was dissolved in dimethylformamide (DMF) to 1% concentration.

4. Fluorophore-labeled Ado-Cys Solution

Br-Mmc-labeled Ado-Cys or FITC-labeled Ado-Cys was dissolved in 50 mM phosphate buffer, pH 7.2, in a concentration of 0.5 mM.

5. SAH Hydrolase Inhibitor Solution

Neplanocin A (natural product), an inhibitor of SAH hydrolase, and a substrate of adenosine deaminase, was dissolved in 50 mM phosphate buffer, pH 7.2. The inhibitor solution (50 μM) was used in an enzyme to inhibitor ratio of 1:1 .5.

6. Multi-enzyme Solution

Adenosine (0.2 U/μl), nucleoside phosphorylase (0.2 U/l) and xanthine oxidase (0.2 U/μl) were dissolved in 50 mM potassium phosphate buffer, pH 7.2. All the enzymes were from Sigma.

7. Washing Solution

The plate washing solution contains of 10 mM PBS, pH 7.2, 0.1 M NaCl, and 0.05% Tween 20.

EXAMPLE 4

Assays of Hcy Using the Mutant SAH Enzyme

Plasma Hcy Assay Procedure 1

Step 1. Conversion of Hcy to SAH

To 50 μl of plasma sample in microcentrifuge tube or in uncoated 96-well plate was added 20 μl of 1% TBP and 50 μl of the wild type SAH hydrolase solution. After incubation at 25° C. for 15 min, 20μl of the enzyme inhibitor solution was added to the reaction mixture, and incubated for 10 min. to inactivate SAH hydrolase.

Step 2. Removal of Remaining Ado and Enzyme Inhibitor

To the solution in Step 1 was added 30 μl of the multi-enzyme solution, and incubated for 15 min at room temperature.

Step 3. Trapping the Formed SAH onto the Mutant SAH Hydrolase

150 μl solution in Step 2 was transferred to a microtiter well pre-coated with mutant SAH hydrolase. After 30 min. incubation at room temperature, the solution was emptied by inversion.

Step 4. Washing

The plate from Step 3 was washed three times with the washing solution followed by inversion and tapping.

Step 5. Binding of Fluorophore-labeled Ado-Cys to the Mutant Enzyme

100 μl of the fluorophore-labeled Ado-Cys or fluorophore-labeled Ado-5' ester was added to the microtiter well in Step 4. After 20 min. incubation at room temperature, the plate was washed three times with the washing solution.

Step 6. Detection of the Mutant SAH Hydrolase-bound Fluorophore-labeled Ado-Cys

To the microtiter well from Step 5, 200 μl of 50 mM phosphate buffer, pH 7.2, was added, and the plate was read for fluorescence using a plate reader (Molecular Devices, fmax). The plasma Hcy concentration was calculated from the standard curve constructed under the same conditions.

Alternative Hcy Assay

Alternatively, the Hcy assay can also be performed by pre-coating SAH on microtiter well, and using fluorophore-labeled mutant SAH hydrolase for competition binding assay. The details are described as follows:

1. Pre-coating SAH on Microtiter Well

SAH was conjugated to polylysine by activate the carboxylic group of SAH with $PCl_3$ at 50° C. The SAH-polylysine conjugate was purified by HPLC, and dissolved in 0.1 M carbonate buffer, pH 9.6. 300 μl of 100 μg/ml SAH-polylysine solution was added to each well, and incubated at 37° C. for 6 hours. The plate was then washed three times with washing solution containing 10 mM PBS, 0.1 M NaCl and 0.05% Tween 20. After inversion and tapping, the plate was stored at 4° C. before use.

2. Fluorophore-labeled Mutant SAH Hydrolase

Mutant SAH hydrolase (e.g., F302S) was specifically fluorescence labels on Cys421, an non-essential cysteine residue which is located on the surface of the protein that is not involved in substrate binding and catalysis. Cys421 residue is readily accessible by thiol reactive molecules, and can be modified without effect the binding affinity of the enzyme. Thiol specific reactive probes such as 7-diethylamino-3(4'-maleimidylphenyl)-4-methylcoumarin (CPM) can specifically label protein thiols. Mutant SAH hydrolase (F302S) (0.5 mg/ml) in 50 mM phosphate buffer, pH 7.2, was incubated with 2 mM of adenine to protect other thiols in the substrate binding site, followed by addition of CPM to final concentration of 50 μM. The reaction mixture was incubated at room temperature for 30 min. followed by gel filtration on a size exclusion column (Sephacryl S-300, 4.5 mm×60 cm) to remove adenine and excess CPM. The CPM-labeled F302S mutant SAH hydrolase (2 mg/ml) was kept in 50 mM phosphate buffer containing 20% glycerol at −20° C. The comparison of Km (SAH) and Kcat (SAH) for wild type and mutant F302S is shown below in Table 4.

TABLE 4

Comparison of kinetic constants between mutant and wild type SAH hydrolases

| Enzyme | Km (SAH) | Kcat (SAH) |
| --- | --- | --- |
| wild type | 7.9 μM | 3.8 $S^{-1}$ |
| F302S | 1.0 μM | 0.1 $S^{-1}$ |

Plasma Hcy Assay Procedure 2

Step 1. Conversion of Hcy to SAH

To 50 μl of plasma sample in microcentrifuge tube or in uncoated 96-well plate was added 20 μl of 1% TBP and 50 μl of the enzyme inhibitor solution was added to the reaction mixture, and incubated for 10 min. to inactivate SAH hydrolase.

Step 2. Removal of Remaining Ado and Enzyme Inhibitor

To the solution in Step 1 was added 30 μl of the multi-enzyme solution, and incubated for 15 min. at room temperature.

Step 3. Competition Binding of SAH to the Mutant SAH Hydrolase

One hundred μl of the solution from Step 2 was transferred to a microtiter well pre-coated with polylysine-SAH conjugate to which 150 μl of the fluorophore-labeled mutant SAH hydrolase was added. After incubation at room temperature for 30 min., the plate was inverted and tapped followed by three times of washing with the washing solution.

Step 4. Detection of the Fluorophore-labeled Mutant SAH Hydrolase Bound to the Microtiter Well To the plate from Step 3 was added 200 μl of 10 nM PBS, and the plate was read by a plate reader (Molecular Devices, fmax) at Ex390 nm and Em460 nm. The plasma concentration of Hcy was calculated from the standard curve constructed under the same conditions with the standard samples.

EXAMPLE 5

Determination of Folate Contents in Serum and Erythrocytes

Sample Preparation

Serum folate, which exists primarily as methyltetrahydrofolic acid (Me-THF) is readily determined by a Me-THF-trapping enzyme such as mutant forms of thymidylate synthase, methionine synthase, dihydrofolate reductase, or folylpolyglutamate synthetase. In contrast, erythrocyte folate exists as polyglutamate derivatives and have to be treated with conjugase to convert folylpolyglutamates to folate before quantitation with mutant folate trapping enzyme. Different forms of folates are converted to one form using folate interconverting enzymes including dihydrofolate reductase, tetrahydrofolate methyltransferase, methylenetetrahydrofolate reductase, thymidylate synthase, methionine synthase Any one of these enzymes can be chosen for preparation of a folate trapping enzymeusing, for example site-directed mutagenesis of nucleic acid that encodes the enzyme.

Preparation of Folate Trapping Enzymes a. Mutation of Thymidylate Synthase

Glutamine 214 of human thymidylate synthase is highly conserved in all thymidylate synthases and is postulated to interact with nucleotide ligands that bind at the active site. Mutation of Glu214 to serine results in attenuated catalytic activity of the enzyme but retains substrate binding ability. Residue Asn229 is involved in formation of hydrogen bonds to constrain the orientation of dUMP in binary complexes with dUMP, and in ternary complexes with dUMP and cofactor 5,10-methylenetetrahydrofolate. Mutation of Asn229 to Ala results in a 2000-fold decrease in the Kcat of the enzyme with a modest increase in Km and Kd. In addition, mutation of His199 to any other amino acid results reduced catalytic activity of the enzyme. The C-terminal residues of thymidylate synthase are involved in the enzyme catalysis. Mutation of these residues results in attenuated enzyme activity, but retains the substrate or cofactor binding affinity.

b. Mutation of Dihydrofolate Reductase

Mutation of Arg43 to Ala or Trp2l to His results in a folate-trapping enzyme.

c. Mutation of Folylpolyglutamate Synthetase

The C-terminal domain (aa's 300–425) of folypolyglutamate synthetase is involved in the folate-binding site of the enzyme. Mutation of Gln421 to Ser leads to an interruption of hydrophobic interactions in the C-terminal domain and results in decreased catalytic activity, but substantially retains substrate-binding ability of the enzyme.

Binding of Folate to Folate Trapping Enzyme

Folate in serum is incubated with a folate trapping enzyme, such as Asn229-thymidylate synthase, which has been precoated on a 96-well plate. After 30 minutes of incubation at room temperature, the plate is washed three times with PBS buffer. Fluorescein-labeled folate is then added to the plate as competitor tracer. The plate is incubated for another 30 min at room temperature.

Detection of Bound Folate

Alter being washed for three times with PBS buffer, the plate is read, using an excitation wavelength Ex of 492 nm and an Em at 515 nm with a fluorescence plate reader. The folate content in serum is calculated based on a folate standard curve prepared and tested under the same conditions using known concentrations of folate.

Since modifications will be apparent to those of skill in this art, it is intended that this invention be limited only by the scope of the appended claims.

What is claimed is:

1. A method for assaying homocysteine (Hcy) in a sample, which method comprises:

a) contacting the sample with a mutant S-adenosylhomocysteine (SAH) hydrolase comprising the amino acid sequence set forth in SEQ ID No. 1 and comprising one or more mutations selected from the group consisting of Phe302 to Ser (F302S), Lys186 to Ala (K186A), His301 to Asp (H301D), His353 to Ser (H353S), Arg343 to Ala (R343A), Asp190 to Ala (D190A), Phe82 to Ala (F82A), Thr157 to Leu (T157L), Asn181 to Asp (N181D), deletion of Tyr432 (Δ432) and a double mutation of Arg431 to Ala (R431 A) and Lys426 to Arg (K426R); and b) detecting binding between Hcy, S-adenosylhomocysteine (SAH) or adenosine with said mutant SAH hydrolase, whereby the presence or amount of Hcy in the sample is assessed.

2. The method of claim 1, wherein prior to the contact between the sample and the mutant SAH hydrolase, oxidized or conjugated Hcy in the sample is converted into reduced Hcy.

3. The method of claim 1, wherein prior to the contact between the sample and the mutant SAH hydrolase, the Hcy in the sample is converted into SAH.

4. The method of claim 3, wherein the Hcy in the sample is converted into SAH by a wild-type SAH hydrolase.

5. The method of claim 4, wherein the SAH is contacted with the mutant SAH hydrolase in the presence of a SAH hydrolase catalysis inhibitor.

6. The method of claim 1, wherein the SAH is contacted with the mutant SAH hydrolase in the presence of a labeled SAH or a derivative or an analog thereof, whereby the amount of the labeled SAH bound to the mutant SAH hydrolase inversely relates to the amount of SAH in the sample.

7. The method of claim 6, wherein the labeled SAH derivative or analog is a fluorescently labeled.

8. The method of claim 1, wherein the mutant SAH hydrolase is a labeled mutant SAH hydrolase.

9. The method of claim 8, wherein the labeled mutant SAH hydrolase is a fluorescence-labeled or enzymatically labeled mutant SAH hydrolase.

10. The method of claim 1, wherein the sample is a body fluid or a biological tissue.

11. The method of claim 10, wherein the body fluid is selected from the group consisting of urine, blood, plasma, serum, saliva, semen, stool, sputum, cerebral spinal fluid, tears, mucus and amniotic fluid.

12. The method of claim 10, wherein the body fluid is blood.

13. The method of claim 12, wherein the blood sample is further separated into a plasma or serum fraction.

14. The method of claim 10, wherein the biological tissue is selected from the group consisting of connective tissue, epithelium tissue, muscle tissue, nerve tissue, organs, tumors, lymph nodes, arteries and individual cell(s).

15. The method of claim 6, wherein the labeled SAH, or a derivative or an analog thereof, is immobilized.

16. The method of claim 1, wherein the mutant SAH hydrolase is immobilized.

* * * * *